US006872815B1

(12) United States Patent
Subramaniam et al.

(10) Patent No.: US 6,872,815 B1
(45) Date of Patent: Mar. 29, 2005

(54) NUCLEIC ACID SEQUENCES TO PROTEINS INVOLVED IN TOCOPHEROL SYNTHESIS

(75) Inventors: Sai S. Subramaniam, Framingham, MA (US); Steven C. Slater, Acton, MA (US); Katherine Karberg, Cambridge, MA (US); Ridong Chen, Maryland Heights, MO (US); Henry E. Valentin, Cambridge, MA (US); Yun-Hua Huang Wong, Chesterfield, MO (US)

(73) Assignee: Calgene LLC, Davis, CA (US)

( * ) Notice: Subject to any disclaimer, the term of this patent is extended or adjusted under 35 U.S.C. 154(b) by 148 days.

(21) Appl. No.: 09/688,069

(22) Filed: Oct. 14, 2000

(51) Int. Cl.⁷ .................. C12N 15/11; C12N 15/31; C12N 15/79; C12N 15/82

(52) U.S. Cl. .............. 536/23.7; 536/23.1; 536/23.2
(58) Field of Search .................. 536/23.1, 23.2, 536/23.7; 435/183, 243, 7.4

(56) References Cited

U.S. PATENT DOCUMENTS

| | | | |
|---|---|---|---|
| 4,727,219 A | 2/1988 | Brar et al. | |
| 5,304,478 A | 4/1994 | Bird et al. | |
| 5,429,939 A | 7/1995 | Misawa et al. | |
| 5,432,069 A | 7/1995 | Grüninger et al. | |
| 5,545,816 A | 8/1996 | Ausich et al. | |
| 5,618,988 A | 4/1997 | Hauptmann et al. | |
| 5,684,238 A | 11/1997 | Ausich et al. | |
| 5,693,507 A | 12/1997 | Daniell et al. | |
| 5,750,865 A | 5/1998 | Bird et al. | |
| 5,792,903 A | 8/1998 | Hirschberg et al. | |
| 5,876,964 A | 3/1999 | Croteau et al. | |
| 5,908,940 A | 6/1999 | Lane et al. | |
| 6,281,017 B1 | 8/2001 | Croteau et al. | |
| 6,303,365 B1 | 10/2001 | Martin et al. | |
| 6,541,259 B1 * | 4/2003 | Lassner et al. | 435/468 |
| 2002/0069426 A1 | 6/2002 | Boronat et al. | |
| 2002/0108148 A1 | 8/2002 | Boronat et al. | |
| 2003/0148300 A1 | 8/2003 | Valentin et al. | |
| 2003/0150015 A1 | 8/2003 | Norris et al. | |
| 2003/0154513 A1 | 8/2003 | van Eenennaam et al. | |
| 2003/0166205 A1 | 9/2003 | van Eenennaam et al. | |
| 2003/0170833 A1 | 9/2003 | Lassner et al. | |
| 2003/0176675 A1 | 9/2003 | Valentin et al. | |
| 2003/0213017 A1 | 11/2003 | Valentin et al. | |
| 2004/0018602 A1 | 1/2004 | Lassner et al. | |
| 2004/0045051 A1 | 3/2004 | Norris et al. | |

FOREIGN PATENT DOCUMENTS

| | | | |
|---|---|---|---|
| CA | 2339519 | 2/2000 | |
| CA | 2343919 | 3/2000 | |
| CA | 2372332 | 11/2000 | |
| DE | 198 35 219 A1 | 8/1998 | |
| EP | 0531639 A2 | 3/1993 | |
| EP | 0 674 000 | 9/1995 | ............ C12N/9/10 |
| EP | 0 723 017 A2 | 7/1996 | |
| EP | 0 763 542 | 3/1997 | ......... C07K/14/195 |
| EP | 1 033 405 | 9/2000 | ............ C12N/15/29 |
| EP | 1 063 297 | 12/2000 | ............ C12N/15/82 |
| FR | 2 778 527 | 11/1999 | |
| GB | 560529 | 4/1944 | |
| WO | WO 91/02059 | 2/1991 | |
| WO | WO 91/09128 | 6/1991 | |
| WO | WO 91/13078 | 9/1991 | |
| WO | WO 93/18158 | 9/1993 | |
| WO | WO 94/11516 | 5/1994 | |
| WO | WO 94/12014 | 6/1994 | |
| WO | WO 94/18337 | 8/1994 | |
| WO | WO 95/08914 | 4/1995 | |
| WO | WO 95/18220 | 7/1995 | |
| WO | WO 95/23863 | 9/1995 | |
| WO | WO 95/34668 | 12/1995 | |
| WO | WO 96/02650 | 2/1996 | |
| WO | WO 96/06172 | 2/1996 | |
| WO | WO 96/13149 | 5/1996 | |
| WO | WO 96/13159 | 5/1996 | |
| WO | WO 96/36717 A3 | 11/1996 | |
| WO | WO 96/36717 A2 | 11/1996 | |
| WO | WO 96/38567 | 12/1996 | |
| WO | WO 97/17447 | 5/1997 | |
| WO | 97/27285 | 7/1997 | ............ C12N/1/20 |
| WO | WO 97/49816 | 12/1997 | |
| WO | WO 98/04685 | 2/1998 | |
| WO | 98/06862 | 2/1998 | ............ C12N/15/82 |
| WO | WO 98/18910 | 5/1998 | |
| WO | WO 99/04021 | 1/1999 | |
| WO | 99/04622 | 2/1999 | ............ A01H/5/00 |
| WO | WO 99/04622 | 2/1999 | |
| WO | 99/06580 | 2/1999 | ........... C12N/15/82 |
| WO | 99/07867 | 2/1999 | ........... C12N/15/82 |
| WO | WO 99/11757 | 3/1999 | |
| WO | WO 99/19460 | 4/1999 | |
| WO | WO 99/55889 | 11/1999 | |
| WO | WO 99/58649 | 11/1999 | |
| WO | 00/01650 | 1/2000 | ............ C07C/45/41 |
| WO | WO 00/08169 | 2/2000 | |
| WO | WO 00/08187 | 2/2000 | |
| WO | WO 00/10380 | 3/2000 | |
| WO | WO 00/11165 | 3/2000 | |
| WO | 00/14207 | 3/2000 | ............ C12N/9/10 |
| WO | WO 00/17233 | 3/2000 | |
| WO | 00/22150 | 4/2000 | ........... C12N/15/82 |
| WO | WO 00/28005 | 5/2000 | |
| WO | WO 00/32757 A2 | 6/2000 | |
| WO | WO 00/32757 A3 | 6/2000 | |

(Continued)

OTHER PUBLICATIONS

Broun et al. Science vol. 282 Nov. 13, 1998.*
Doerks et al., TIG, 14: 248–250 1998.*

(Continued)

Primary Examiner—David T. Fox
Assistant Examiner—Russell Kallis
(74) Attorney, Agent, or Firm—Fulbright & Jaworski L.L.P.

(57) ABSTRACT

Nucleic acid sequences and methods are provided for producing plants and seeds having altered tocopherol content and compositions. The methods find particular use in increasing the tocopherol levels in plants, and in providing desirable tocopherol compositions in a host plant cell.

5 Claims, 40 Drawing Sheets

FOREIGN PATENT DOCUMENTS

| WO | WO 00/34448 | 6/2000 | |
|---|---|---|---|
| WO | WO 00/42205 A3 | 7/2000 | |
| WO | WO 00/42205 A2 | 7/2000 | |
| WO | WO 00/46346 | 8/2000 | |
| WO | 00/61771 | 10/2000 | ........... C12N/15/82 |
| WO | WO 00/63389 | 10/2000 | |
| WO | 00/63391 | 10/2000 | |
| WO | WO 00/65036 A3 | 11/2000 | |
| WO | WO 00/65036 A2 | 11/2000 | |
| WO | 00/68393 | 11/2000 | ........... C12N/15/54 |
| WO | WO 01/04330 | 1/2001 | |
| WO | WO 01/09341 | 2/2001 | |
| WO | WO 01/12827 | 2/2001 | |
| WO | 01/21650 | 3/2001 | ........... C07K/14/00 |
| WO | WO 01/21650 | 3/2001 | |
| WO | WO 01/44276 | 6/2001 | |
| WO | WO 01/62781 | 8/2001 | |
| WO | WO 01/79472 | 10/2001 | |
| WO | WO 01/88169 A2 | 11/2001 | |
| WO | WO 01/88169 A3 | 11/2001 | |
| WO | WO 02/00901 A1 | 1/2002 | |
| WO | WO 02/26933 | 4/2002 | |
| WO | WO 02/29022 | 4/2002 | |
| WO | WO 02/31173 | 4/2002 | |
| WO | WO 02/33060 | 4/2002 | |
| WO | WO 02/46441 | 6/2002 | |
| WO | WO 02/072848 | 9/2002 | |
| WO | WO 02/089561 | 11/2002 | |
| WO | WO 03/034812 | 5/2003 | |
| WO | WO 03/047547 | 6/2003 | |

OTHER PUBLICATIONS

Smith et al. Nature Biotechnology 15:1222–1223, Nov. 1997.*

Bork et al. TIG 12, 10:425–427, Oct. 1996.*

Porfirova et al. PNAS Sep., 17, 2002, vol. 99, No. 19, pp. 12495–12500.*

Porfirova et al., "Isolation of an Arabidopsis mutant lacking vitamin E and identification of a cyclase essential for all tocopherol biosynthesis," *PNAS*, 99(19):12495–12500 (2002).

Bevan et al., Database EMBL, Accession No. AL035394 (Feb. 9, 1999) (XP 002153686).

Desprez et al., Database EMBL, Accession No. Z34566 (Jun. 25, 1994) (XP 002169121).

Gaubier et al., "A Chlorophyll Synthetase Gene from *Arabidopsis thaliana*," *Mol. Gen. Genet.*, 249:58–64 (1995).

Gaubier et al., Database EMBL Accession No. Z38833 (Nov. 1, 1996) (XP 002169117).

Kaneko et al., Database TREMBL, Accession No. P73726 (Feb. 1, 1997) (XP 002169263).

Kaneko et al., Database TREMBL, Accession No. P73727 (Feb. 1, 1997) (XP 002169264).

Kaneko et al., Database TREMBL, Accession No. P73962 (Jul. 15, 1998) (XP 002169129).

Kuntz et al., "Identification of a cDNA for the Plastid–Located Geranylgeranyl Pyrophosphate Synthase from Capsicum annuum: Correlative Increase in Enzyme Activity and Transcript Level during Fruit Ripening," *The Plant Journal*, 2(1):25–34 (1992).

Li et al., "Identification of a Maize Endosperm–Specific cDNA Encoding Farnesyl Pyrophosphate Synthetase," *Gene*, 171:193–196 (1996).

Lin et al., Database EMBL, Accession No. AC003672 (Dec. 11, 1997) (XP 002153688).

Lin et al., Database EMBL, Accession No. AC003673 (Dec. 11, 1997) (XP 002153685).

Lin et al., Database EMBL, Accession No. AC004077 (Feb. 3, 1998) (XP 002169118).

Lopez et al., "Sequence of the bchG Gene from *Chloroflexus aurantiacus*: Relationship between Chlorophyll Synthase and Other Polyprenyltransferases," *Journal of Bacteriology*, 178(11):3369–3373 (1996).

Malakhov et al., Database TREMBL, Accession No. Q55207 (Nov. 1, 1996) (XP 002169125).

Murata et al., Database EMBL, Accession No. D13960 (Mar. 28, 1996) (XP 00 2169124).

Newman et al., Database EMBL, Accession No. T44803 (Feb. 4, 1995) (XP 002169120).

Newman et al., Database EMBL, Accession No. R30625 (Aug. 11, 1995) (XP 002153690).

Norris et al., "Genetic Dissection of Carotenoid Synthesis in Arabidopsis Defines Plastoquinone as an Essential Component of Phytoene Desaturation," *The Plant Cell*, 7:2139–2149 (1995).

Oster et al., "The G4 Gene of *Arabidopsis thaliana* Encodes a Chlorophyll Synthase of Etiolated Plants," *Bot. Acta*, 110:420–423 (1997).

Oster et al., Database Biosis, Accession No. PREV199800047824 (Oct. 1997) (XP 002153691).

Rounsley et al., Database EMBL, Accession No. B24116 (Oct. 13, 1997) (XP 002153687).

Rounsley et al., Database EMBL, Accession No. B29398 (Oct. 13, 1997) (XP 002153689).

Rounsley et al., Database TREMBL, Accession No. 064684 (Aug. 1, 1998) (XP 002169119).

Scolnik et al., Database EMBL, Accession No. L40577 (Apr. 15, 1995) (XP 002153692).

Shoemaker, Database EMBL, Accession No. AI748688 (Jun. 29, 1999) (XP 002169135).

Shoemaker et al., Database EMBL, Accession No. AI938569 (Aug. 3, 1999) (XP 002169133).

Shoemaker et al., Database EMBL, Accession No. AI988542 (Sep. 7, 1999) (XP 00 2169132).

Shoemaker et al., Database EMBL, Accession No. AW306617 (Jan. 21, 2000) (XP 00 2169134).

Tabata et al., Database EMBL, Accession No. D64001 (Sep. 30, 1995) (XP 002169126).

Tabata et al., Database EMBL, Accession No. D64006 (Sep. 30, 1995) (XP 002169122).

Tabata, Database EMBL, Accession No. D90909 (Oct. 31, 1996) (XP 002169130).

Tabata, Database EMBL, Accession No. D90911 (Oct. 31, 1996) (XP 002169128).

Tabata, Database TREMBL, Accession No. Q55145 (Nov. 1, 1996) (XP 002169127).

Tabata, Database TREMBL, Accession No. Q55500 (Nov. 1, 1996) (XP 002169123).

Walbot et al., Database EMBL, Accession No. AI795655 (Jul. 7, 1999) (XP 002169131).

Zhu et al., "Geranylgeranyl Pyrophosphate Synthase Encoded by the Newly Isolated Gene GGPS6 from *Arabidopsis thaliana* is Localized in Mitochondria," *Plant Molecular Biology*, 35:331–341 (1997).

International Search Report, PCT/US01/12334 (Apr. 2002).

Bevan et al., TREMBL Database Accession No. O65524.

Kaneko et al., EMBL Sequence Database Accession No. D90909.

Chen et al., EMBL Sequence Database Accession No. AI995392. s

Stocker et al., "Identification of the Tocopherol–Cyclase in the Blue–Green Algae *Anabaena variabilis* Kützing (*Cyanobacteria*)" 76:1729–1738 (1993).

Arango et al., "Tocopherol synthesis from homogentisate in *Capsicum anuum* L. (yellow pepper) chromoplast membranes: evidence for tocopherol cyclase", Biochem J. 336:531–533 (1998).

Stocker et al., "The Substrate Specificity of Tocopherol Cyclase", Bioorganic & Medicinal Chemistry 4(7):1129–1134 (1996).

Addlesee et al., "Cloning, sequencing and functional assignment of the chlorophyll biosyntheses gene, chlP, of *Synechocystis*sp. PCC 6803", FEBS Letters 389 (1996) 126–130.

Arigoni et al., "Terpenoid biosynthesis from 1–deoxy–D–xylulose in higher plants by intramolecular skeletal rearrangement", Proc. Natl. Acad. Sci. USA, 94:10600–10605 (1997).

Baker et al., "Sequence and characterization of the gcpE gene of *Escherichia coli*", FEMS Microbiology Letters, 94:175–180 (1992).

Bayley et al., "Engineering 2,4–D resistance into cotton," Theor Appl Genet, 83:645–649 (1992).

Bentley, R., "The Shikimate Pathway—A Metabolic Tree with Many Branches," Critical Reviews™ in Biochemistry and Molecular Biology; vol. 25, Issue 5, 307–384 (1990).

Bevan, M., "Binary *Agrobacterium*vectors for plant transformation", Nucleic Acids Research, 12:8711–8721 (1984).

Beyer et al., "Phytoene–forming activities in wild–type and transformed rice endosperm," IRRN 21:2–3, p 44–45 (Aug.–Dec. 1996).

Bork et al., "Go hunting in sequence databases but watch out for the traps", TIG 12, 10:425–427 (Oct. 1996).

Bouvier et al., "Dedicated Roles of Plastid Transketolases during the Early Onset of Isoprenoid Biogenesis in Pepper Fruits", Plant Physiol., 117:1423–1431 (1998).

Bramley et al., "Biochemical characterization of transgenic tomato plants in which carotenoid synthesis has been inhibited through the expression of antisense RNA to pTOM5," The Plant Journal, 2(3), 343–349 (1992).

Breitenbach et al., "Expression in *Escherichia coli* and properties of the carotene ketolase from *Haematococcus pluvialis,*" FEMS Microbiology Letters 140, 241–246 (1996).

Broun et al., "Catalytic Plasticity of Fatty Acid Modification Enzymes Underlying Chemical Diversity of Plant Lipids," Science, 282:1315–1317 (1998).

Buckner et al., "The y1 Gene of Maize Codes for Phytoene Synthase," Genetics 143:479–488 (May 1996).

Burkhardt et al., "Genetic engineering of provitamin A biosynthesis in rice endosperm," Experientia, 818–821.

Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis" The Plant Journal, 11(5), 1071–1078 (1997).

Cahoon et al., "Production of Fatty Acid Components of Meadowfoam Oil in Somatic Soybean Embryos," Plant Physiology, 124:243–251 (2000).

Chaudhuri et al., "The purification of shikimate dehydrogenase from *Escherichia coli,*" Biochem. J., 226:217–223 (1985).

Cheng et al., "Highly Divergent Methyltransferases Catalyze a Conserved Reaction in Tocopherol and Plastoquinone Synthesis in Cyanobacteria and Photosynthetic Eukaryotes", The Plant Cell, 15:2343–2356 (2003).

Collakova et al., "Isolation and Functional Analysis of Homogentisate Phytyltransferase from *Synechocystis*sp. PCC 6803 and Arabidopsis", Plant Physiology, 127:1113–1124 (2001).

Collakova et al., "Homogentlsate Phytyltransferase Activity is Limiting for Tocopherol Biosynthesis in *Arabidopsis*", Plant Physiology, 131:632–642 (Feb. 2003).

Collakova et al., "Isolation and Characterization of Tocopherol Prenyl Transferase From Synechocystis and Arabidopsis", Poster Abstract see REN–01–026.

Cook et al., "Nuclear Mutations affecting plastoquinone accumulation in maize", Photosynthesis Research, 31:99–111 (1992).

Cunillera et al., "Characterization of dehydrodolichyl diphosphate synthase of *Arabidopsis thaliana*, a key enzyme in dolichol biosynthesis", FEBS Letters, 477:170–174 (2000).

d'Amato et al., "Subcellular localization of chorismate–mutase isoenzymes in protoplasts from mesophyll and suspension–cultured cells of *Nicotiana silvestris*," Planta, 162:104–108 (1984).

Doerks et al., "Protein annotation: detective work for function prediction", TIG, 14:248–250 (1998).

d'Harlingue et al., "Plaslid Enzymes of Terpenoid Biosynthesis, Purification and Characterization of γ Tocopherol Methyltransferase from Capsicum Chromoplasts," The Journal of Biological Chemistry, vol. 260, No. 28, pp. 15200–15203, Dec. 5, 1985.

De Luca, Vincenzo, "Molecular characterization of secondary metabolic pathways", AgBiotech News and Information, 5(6):225N–229N (1993).

Duncan et al., "The overexpression and complete amino acid sequence of *Escherichia coli* 3–dehydroquinase", Biochem. J., 238:475–483 (1986).

Duvold et al., "Incorporation of 2–C–Methyl–D–erythritol, a Putative Isoprenoid Precursor in the Mevalonate–Independent Pathway, into Ubiquinone and Menaquinone of *Escherichia coli*", Tetrahedron Letters, 38(35):6181–6184 (1997).

Elliott, Thomas, "A Method for Constructing Single–Copy Iac Fusions in *Salmonella typhimurium* and Its Application to the hemA–prfA Operon", Journal of Bacteriology, 174:245–253 (1992).

Eisenreich et al., "The deoxyxylulose phosphate pathway of terpenoid biosynthesis in plants and microorganisms", Chemistry & Biology, 5(9):R221–R233 (1998).

Ericson et al., "Analysis of the promoter region of napin genes from *Brassica napus* demonstrates binding of nuclear protein in vitro to a conserved sequence motif", Eur. J. Biochem., 197:741–746 (1991).

Estévez et al., "1–Deoxy–D–xylulose–5–phosphate Synthase, a Limiting Enzyme for Plastidic Isoprenoid Biosynthesis in Plants", The Journal of Biological Chemistry, 276(25):22901–22909 (2001).

Fellermeier et al., "Cell–free conversion of 1–deoxy–D–xylulose 5–phosphate and 2–C–methyl–D–erythritol 4–phosphate into β–carotene in higher plants and its inhibition by fosmidomycin", Tetrahedron Letters, 40:2743–2746 (1999).

Fiedler et al., "The formation of homogentisate in the biosynthesis of tocopherol and plastoquinone in spinach chloroplasts", Planta, 155:511–515 (1982).

Fourgoux–Nicol et al., "Isolation of rapeseed genes expressed early and specifically during development of the male gametophyte", Plant Molecular Biology, 40:857–872 (1999).

Fraser et al., "Enzyme confirmation of reactions involved in routes to astaxanthin formation, elucidated using a direct substrate in vitro assay", Eur. J. Biochem., 252:229–236 (1998).

Fraser et al., "In Vitro Characterization of Astaxanthin Biosynthetic Enzymes", The Journal of Biological Chemistry, 272(10) 6128–6135 (1997).

Fray et al., "Constitutive expression of a fruit phytoene synthase gene in transgenic tomatoes causes dwarfism by redirecting metabolites from the gibberellin pathway", The Plant Journal, 8(5):693–701 (1995).

Fray et al., "Identification and genetic analysis of normal and mutant phytoene synthase genes of tomato by sequencing, complementation and co–suppression", Plant Molecular Biology, 22:589–602 (1993).

Fuqua et al., "Characterization of melA: a gene encoding melanin biosynthesis from the marine bacterium *Shewanella colwelliana*", Gene, 109:131–136 (1991).

Furuya et al., "Production of Tocopherols by Cell Culture of Safflower", Phytochemistry, 26(10):2741–2747 (1987).

Garcia et al., "Subcellular localization and purification of a p–hydroxyphenylpyruvate dioxygenase from cultured carrot cells and characterization of the corresponding cDNA", Biochem. J., 325:761–769 (1997).

Goers et al., "Separation and characterization of two chorismate–mutase isoenzymes from *Nicotiana silvestris*", Planta, 162:109–116 (1984).

Grassse et al., "Loss of $\alpha$–tocopherol in tobacco plants with decreased geranylgeranyl reductase activity does not modify photosynthesis in optimal growth conditions but increases sensitivity to high–light stress", Planta, 213:620–628 (2001).

Harker et al., "Biosynthesis of ketocarotenoids in transgenic cyanobacteria expressing the algal gene for $\beta$–C–4–oxygenase, crtO", FEBS Letters, 404:129–134 (1997).

Harker et al., "Expression of prokaryotic 1–deoxy–D–xylulose–5–phosphatases in *Escherichia coli* increases carotenoid and ubiquinone biosynthesis", FEBS Letters, 448:115–119 (1999).

Hecht et al., "Studies of the nonmevalonate pathway to terpenes: The role of the GcpE (IspG) protein", PNAS, 98(26):14837–14842 (2001).

Herrmann, K.M., "The Shikimate Pathway as an Entry to Aromatic Secondary Metabolism", Plan Physiol., 107:7–12 (1995).

Herz et al., "Biosynthesis of terpenoids: YgbB protein converts 4–diphosphocytidyl–2C–methyl–D–erythritol 2–phosphate to 2C–methyl–D–erythritol 2,4–cyclodiphosphate", Proc. Natl. Acad. Sci. USA, 97(6):2486–2490 (2000).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343–352 (1995).

Kaneko et al., "Complete Genomic Sequence of the Filamentous Nitrogen–fixing Cyanobacterium *Anabaena* sp. Strain PCC 7120", DNA Research, 8(5):205–213 (2001).

Keegstra, K., "Transport and Routing of Proteins into Chloroplasts", Cell, 56(2):247–253 (1989).

Keller et al., "Metabolic compartmentation of plastid prenylipid biosynthesis Evidence for the involvement of a multifunctional geranylgeranyl reductase", Eur. J. Biochem., 251:413–417 (1998).

Kishore et al., "Amino Acid Biosynthesis inhibitors as Herbicides", Ann. Rev. Biochem., 57:627–663 (1988).

Koziel et al., "Optimizing expression of transgenes with an emphasis on post–transcriptional events", Plant Molecular Biology, 32:393–405 (1996).

Kumagai et al., "Cytoplasmic inhibition of carotenoid biosynthesis with virus–derived RNA", Proc. Natl. Acad. Sci. USA, 92:1679–1683 (1995).

Lange et al., "A Family of transketolases that directs isoprenoid biosynthesis via a mevalonate–independent pathway", Proc. Natl. Acad. Sci. USA, 95:2100–2104 (1998).

Lange et al., "Isoprenoid Biosyntheis via a Mevalonate–Independent Pathway in Plants: Cloning and Heterologous Expression of 1–Deoxy–D–xylulose–5–phosphate Reductoisomerase from Peppermint", Archives of Biochemistry and Biophysics, 365(1):170–174 (1999).

Li et al., "Identification of a maize endosperm–specific cDNA encoding lamesyl pyrophosphate synthetase", Gene, 171:193–196 (1996).

Linthorst et al., "Constitutive Expression of Pathogenesis–Related Proteins PR–1,GRP, and PR–S in Tobacco Has No Effect on Virus Infection", The Plant Cell, 1:285–291 (1989).

Lois et al., "Cloning and characterization of a gene from *Escherichia coli* encoding a transketolase–like enzyme that catalyzes the synthesis of D–1–deoxyxylulose 5–phosphate, a common precursor for isoprenoid, thiamin, and pyridoxol biosynthesis", Proc. Natl. Acad. Sci. USA, 95(5):2105–2110 (1998).

Lotan et al., "Cloning and expression in *Escherichia coli* of the gene encoding $\beta$–C–4–oxygenase, that converts $\beta$–carotene to the ketocarotenoid canthaxanthin in *Haematococcus pluvialis*", FEBS Letters, 364:125–128 (1995).

Mahmoud et al., "Metabolic engineering of essential oil yield and composition in mint by altering expression of deoxyxylulose phosphate reductoisomerase and menthofuran synthase", PNAS, 98(15):8915–8920 (2001).

Mandel et al., "CLA1, a novel gene required for chloroplast development, is highly conserved in evolution", The Plant Journal, 9(5):649–658 (1996).

Marshall et al., "Biosynthesis of Tocopherols: A Re–Examination of the Biosynthesis and Metabolism of 2–Methyl–6–Phytyl–1,4–Benzoquinol", Phytochemistry, 24(8):1705–1711 (1985).

Misawa et al., "Expression of an Erwinia phytoene desalurase gene not only confers multiple resistance to herbicides interfering with carotenoid biosynthesis but also alters xanthophyll metabolism in transgenic plants", The Plant Journal, 6(4):481–489 (1994).

Misawa et al., "Elucidation of the *Erwinia uredovora* Carotenoid Biosynthetic Pathway by Functional Analysis of Gene Products Expressed in *Escherichia coli*", Journal of Bacteriology, 172(12):6704–6712 (1990).

Misawa et al., "Functional expression of the *Erwinia uredovora* carotenoid biosynthesis gene crtI in transgenic plants showing an increase of $\beta$–carotene biosynthesis activity and resistance to the bleaching herbicide norflurazon", The Plant Journal, 4(5):833–840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575–6584 (1995).

Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401–414 (1997).

Nawrath et al., "Targeting of the polyhydroxybutyrate biosynthetic pathway to the plastids of *Arabidopsis thaliana* results in high levels of polymer accumulation", Proc. Natl. Acad. Sci. USA, 91:12760–12764 (1994).

Norris et al., "Complementation of the Arabidopsis pds1 Mutation with the Gene Encoding ρ–Hydroxyphenylpyruvate Dioxygenase", Plant Physiol., 117:1317–1323 (1998).

Oh et al., "Molecular Cloning, Expression, and Functional Analysis of a cis–Prenyltransferase from *Arabidopsis thaliana*", The Journal of Biological Chemistry, 275(24):18482–18488 (2000).

Okada et al., "Five Geranylgeranyl Diphosphate Synthases Expressed in Different Organs Are Localized into Three Subcellular Compartments in Arabidopsis", Plant Physiology, 122:1045–1056 (2000).

Oommen et al., "The Elicitor–Inducible Alfalfa Isoflavone Reductase Promoter Confers Different Patterns of Developmental Expression in Homologous and Heterologous Transgenic Plants", The Plant Cell, 6:1789–1803 (1994).

Peisker et al., "Phytol and the Breakdown of Chlorophyll in Senescent Leaves", J. Plant Physiol., 135:428–432 (1989).

Pompliano et al., "Probing Lethal Metabolic Perturbations in Plants with Chemical Inhibition of Dehydroquinate Synthase", J. Am. Chem. Soc., 111:1866–1871 (1989).

Querol et al., "Functional analysis of the *Arabidopsis thaliana* GCPE protein involved in plastid isoprenoid biosynthesis", FEBS Letters, 514:343–346 (2002).

Rippert et al., "Molecular and biochemical characterization of an *Arabidopsis thaliana* arogenate dehydrogenase with two highly similar and active protein domains", Plant Mol. Biol., 48:361–368 (2002).

Rippert et al., "Engineering Plant Shikimate Pathway for Production of Tocotrienol and Improving Herbicide Resistance", Plant Physiology, 134:92–100 (2004).

Rodriguez–Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079–1089 (2002).

Rodriguez–Concepción et al., "1–Deoxy–D–xylulose 5–phosphate reductoisomerase and plastid isoprenoid biosynthesis during tomato fruit ripening", The Plant Journal, 27(3):213–222 (2001).

Rohdich et al., "Cytidine 5'–triphosphate–dependent biosynthesis of isoprenoids: YgbP protein of *Escherichia coli* catalyzes the formation of 4–diphosphocytidyl–2–C–methylerythritol", Proc. Natl. Acad. Sci. USA, 96(21):11758–11763 (1999).

Rohmer et al., "Glyceraldehyde 3–Phosphate and Pyruvate as Precursors of Isoprenic Units in an Alternative Non–mevalonate Pathway for Terpenoid Biosynthesis", J. Am. Chem. Soc., 118:2564–2566 (1996).

Rohmer et al., "Isoprenoid biosynthesis in bacteria: a novel pathway for the early steps leading to isopentenyl diphosphate", Biochem. J., 295:517–524 (1993).

Rohmer, M., "A Mevalonate–independent Route to Isopentenyl Diphosphate", Comprehensive Natural Products Chemistry, 2:45–67 (1999).

Rohmer, M., "Isoprenoid biosynthesis via the mevalonate–independent route, a novel target for antibacterial drugs?", Progress in Drug Research, 50:136–154 (1998).

Römer et al., "Expression of the Genes Encoding the Early Carotenoid Biosynthetic Enzymes in *Capsicum Annuum*", Biochemical and Biophysical Research Communications, 196(3):1414–1421 (1993).

Ruzafa et al., "The protein encoded by the *Shewanella colwelliana* melA gene is a p–hydroxyphenylpyruvate dioxygenase", FEMS Microbiology Letters, 124:179–184 (1994).

Saint–Guily et al., "Complementary DNA Sequence of an Adenylate Translocator from *Arabidopsis thaliana*", Plant Physiol., 100(2):1069–1071 (1992).

Sandmann et al., "New functional assignment of the carotenogenic genes crtB and crtE with constructs of these genes from Erwinia species", FEMS Microbiology Letters, 90:253–258 (1992).

Sato et al., "Structural Analysis of *Arabidopsis thaliana* Chromosome 5. X. Sequence Features of the Regions of 3,076,755 bp Covered by Sixty P1 and TAC Clones", DNA Research, 7(1):31–63 (2000).

Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41–54 (1998).

Savidge et al., "Isolation and Characterization of Homogentisate Phytyltransferase Genes from Synechocystis sp. PCC 6803 and Arabidopsis", Plant Physiology, 129:321–332 (2002).

Schwender et al., "Cloning and heterologous expression of a cDNA encoding 1–deoxy–D–xylulose–5–phosphate reductoisomerase of *Arabidopsis thaliana*", FEBS Letters, 455:140–144 (1999).

Scolnik et al., "Nucleotide Sequence of an Arabidopsis cDNA for Geranylgeranyl Pyrophosphate Synthase", Plant Physiol., 104(4):1469–1470 (1994).

Shewmaker et al., "Seed–specific overexpression of phytoene synthase: increase in carotenoids and other metabolic effects", The Plant Journal, 20(4):401–412 (1999).

Shigeoka et al., "Isolation and properties of γ–tocopherol methyltransferase in *Euglena gracilis*", Biochimica et Biophysica Acta, 1128:220–226 (1992).

Shintani et al., "Elevating the Vitamin E Content of Plants Through Metabolic Engineering", SCIENCE, 282:2098–2100 (1998).

Singh et al., "Chorismate Mutase Isoenzymes from *Sorghum bicolor*. Purification and Properties", Archives of Biochemistry and Biophysics, 243(2):374–384 (1985).

Smith, F.W. et al., "The cloning of two Arabidopsis genes belonging to a phosphate transporter family", Plant Journal, 11(1):83–92 (1997).

Smith, C.J.S. et al., "Antisense RNA inhibition of polygalacturonase gene expression in transgenic tomatoes", Nature, 334:724–726 (1998).

Smith, T.F. et al., "The challenges of genome sequence annotation or the devil is in the details", Nature Biotechnology, 15:1222–1223 (1997).

Soll et al., "Hydrogenation of Geranylgeraniol", Plant Physiol., 71:849–854 (1983).

Soll et al., "Tocopherol and Plastoquinone Synthesis in Spinach Chloroplasts Subfractions", Archives of Biochemistry and Biophysics, 204(2):544–550 (1980).

Soll et al., "2–Methyl–6–Phytylquinol and 2,3–Dimethyl–5–Phytylquinol as Precursors of Tocopherol Synthesis in Spinach Chloroplasts", Phytochemistry, 19:215–218 (1980).

Sprenger et al., "Identification of a thiamin–dependent synthase in *Escherichia coli* required for the formation of the 1–deoxy–D–xylulose 5–phosphate precursor to isoprenoids, thiamin, and pyridoxol", Proc. Natl. Acad. Sci. USA, 94:12857–12862 (1997).

Spurgeon et al., "Biosynthesis of Isoprenoid Compounds", 1:1–45 (1981).

Stam et al., "The Silence of Genes in Transgenic Plants", Annals of Botany, 79:3–12 (1997).

Stocker et al., "The Substrate Specificity of Tocopherol Cyclase", Bioorganic & Medicinal Chemistry, 4(7):1129–1134 (1996).

Sun et al., "Cloning and Functional Analysis of the β–Carotene Hydroxylase of *Arabidopsis thaliana*", The Journal of Biological Chemistry, 271(40):24349–24352 (1996).

Suzich et al., "3–Deoxy–D–arabino–Heptulosonate 7–Phosphate Synthase from Carrot Root (*Daucus carota*) Is a Hysteretic Enzyme", Plant Physiol., 79:765–770 (1985).

Svab et al., "High–frequency plastid transformation in tobacco by selection for a chimeric aadA gene", Proc. Natl. Acad. Sci. USA, 90:913–917 (1993).

Svab et al., "Stable transformation of plastids in higher plants", Proc. Natl. Acad. Sci. USA, 87:8526–8530 (1990).

Takahashi et al., "A 1–deoxy–D–xylulose 5–phosphate reductoisomerase catalyzing the formation of 2–C–methyl–D–erythritol 4–phosphate in an alternative nonmevalonate pathway for terpenoid biosynthesis", Proc. Natl. Acad. Sci. USA, 95:9879–9884 (1998).

Takatsuji, H., "Zinc–finger transcription factors in plants", CMLS Cell. Mol. Life Sci., Birkhauser Verlag Basel CH, 54(6):582–596 (1998).

Tjaden et al., "Altered plastidic ATP/ADP–transporter activity influences potato (*Solanum tubersomum* L.) tuber morphology, yield and composition of tuber starch", The Plant Journal, 16(5):531–540 (1998).

Town et al., "Whole genome shotgun sequencing of Brassica oleracea, BOGKS71TF BOGK Brassica oleracea genomic clone BOGKS71, DNA sequence", Database EMBL Accession No. BH534089 (Dec. 2001).

Town et al, "Whole genome shotgun sequencing of Brassica oleracea, BOGAU46TR BOGA Brassica oleracea genomic clone BOGAU46, DNA sequence", Database EMBL Accession No. BH248880 (Nov. 2001).

Verwoert et al., "Developmental specific expression andd organelle targeting of the *Escherichia coli* fabD gene, encoding malonyl coenzyme A–acyl carrier protein transacylase in transgenic rape and tobacco seeds", Plant Molecular Biology, 26:189–202 (1994).

Xia et al., "A monofunctional prephenate dehydrogenase created by cleavage of the 5' 109 bp of the tyrA gene from *Erwinia herbicola*", Journal of General Micorbiology, 138(7):1309–1316 (1992).

Xia et al., "The pheA 1 tyrA 1 aroF Region from *Erwinia herbicola*: An Emerging Comparative Basis for Analysis of Gene Organization and Regulation in Enteric Bacteria", Database GENBANK on STN, GenBank ACC. No. (GBN): M74133, J. Mol. Evol., 36(2):107–120 Abstract (1993).

Yamamoto, E., "Purification and Metal Requirements of 3–Dehydroquinate Synthase from *Phaseolus mungo* Seedings", Phytochemistry, 19:779–781 (1980).

Zaka et al., "Changes in Carotenoids and Tocopherols During Maturation of Cassia Seeds", Pakistan J. Sci. Ind. Res., 30(11):812–814 (1987).

Zeidler et al., "Inhibition of the Non–Mevalonate 1–Deoxy–D–xylulose–5–phosphate Pathway of Plant Isoprenoid Biosynthesis by Fosmidomycin", A Journal of Biosciences, Zeilschrift fuer Naturforschung, Section C, 53(11/12):980–986 (Nov./Dec. 1998).

Kaneko et al., NCBI General Identifier No. 1653572, Accession No. BAA18485 (Jul. 2001).

Kaneko et al., NCBI General Identifier No. 1001725, Accession No. BAA10562 (Feb. 2003).

Alcala et al., Genbank Accession No. AI 897027 (Jul. 1999).

Bevan et al., TREMBL Database Accession No. O65524 (Aug. 1998).

Campos et al., NCBI General Identifier BAA 18485, Database EMBL, Accession No.: AF148852, (2000).

Chen et al., EMBL Sequence Database Accession No. AI995392 (Sep. 1999).

Fedenko et al., Abstract: RU 2005353, Derwent Accession No.: 1994–253787.

Kaneko et al., EMBL Sequence Database Accession No. D90909 (Oct. 1996).

Lange et al., "Mentha x Piperita 1–deoxy–D–xylulose–5–phosphate Reductoisomerase (DXR) mRNA", complete cds, Entrez Report, Accession No. AF116825 (Apr. 1999).

Lin et al., Database EMBL, Accession No. AC003672 (Dec. 1997).

Nakamura et al., Database EMBL, Accession No.: AB009053, Abstract (Dec. 1997) (1998)(2000).

Nakamura et al., Database EMBL, Accession No.: AB005246 (Jul. 1997).

Newman et al., Database EMBL, Accession No.: AA586087, Abstract (Sep. 1997).

Newman et al., DEBEST ID: 1262303, Entrez Report, Accession No.: AA586087 (Sep. 1997).

Ouyang et al., Database EMBL, Accession No. AF381248 (Jan. 2003).

Schwender et al., *Arabidopsis thaliana* mRNA for Partial 1–deoxy–d–xylulose–5–phosphate Reductoisomerase (dxr gene), Entrez Report, Accession No.: AJ24588 (Aug. 1999).

Shintani et al., Database NCBI, Accession No. AF104220 (Jan. 1999).

Wing et al., Database EMBL, Accession No. AQ690643 (Jul. 1999).

Xia et al., Database EMBL, Accession No. M74133 (Jun. 1993).

Bevan et al., Accession T4 8445.

Bowie et al., "Deciphering the Message in Protein Sequences: Tolerance to Amino Acid Substitutions", Science, 247:1306–1310 (1990).

McConnell et al., "Role of Phabulosa and Phavoluta in determining radial patterning in shoots", Nature, 411(6838): 709–713 (2001).

Baker et al., NCBI Accession No. X64451 (Dec. 1993).

* cited by examiner

```
              *        20         *        40         *        60         *        80
ATPT2    : ---------MESLLSSSLVSAAGGFCWKKQNLKLHSLSEIRVLRCDSSKVVAKPKFRNNLVRPDGQQGSLLLYPKHKSRFRVNATAGQ :  80
SLR1736  : -------------------------------------------------------------------------------------- :   -
ATPT3    : MAFFGLSRVSRRLLKSSVSVTPSSSSALLQSQHKSLSNPVTTHYTNPFTKCYPSWNDNYQVWSKGRELHQEKFFGVGWNYRLICGMSSS :  89
SLR0926  : -------------------------------------------------------------------------------------- :   -
ATPT4    : ---------MWRRSVVYRFSSRISVSSSLPNPRLIPWSRELCAVNSFSQP----------------PVSTESTAKLGITGVRSDANRVFATA :  67
SLL1899  : -------------------------------------------------------------------------------------MVTS :   4
ATPT12   : -----MTSILNTVSTIHSSRVTSVDRVGVLSLRNSDSVEFT--------------------RRRSGFSTLIYESPGRRFVVRAAETDT :  63
SLR0056  : -------------------------------------------------------------------------------------MSDT :   4
ATPT8    : -------------------------------------------------------------------------------------MVLA :   4
SLR1518  : -------------------------------------------------------------------------------------MTES :   4

*       100         *       120         *       140         *       160
ATPT2    : PEAFDSNSKQK---------SFRDSLDAFYR---------------------------------FSRPHTVGTVLSILS---VSFLAVEKVS--DISPLFTGILE : 140
SLR1736  : -----------------MATIQAFWR-------------------------------------FSRPHTLGTTLSVWAVY---LLTILGDGN-SVNSPASEDLVFG :  49
ATPT3    : SSVLEGKPKKDDKEKSDGVVVKKASWIDLYLPEEVRGYAKLARLDKPIGTWELAWPCMWS----------IALAADPGS--LPSFKYMALFGC : 170
SLR0926  : --MVAQTPSSP---------PLWFTIIYL------------------------------------LRWHKPAGRILMIPALWA----VCLAAQ--G-LPLPLGTHAL :  56
ATPT4    : TAAATATATTG---EISSRVAALAGEGHHYAR--------------------------------CYWELSKAKLSMLVVATSG----TGYILGTNAAISFPGECYTCAG : 138
SLL1899  : TKIHRQHDSMG---------AVCKSYYQLTKP-------------------------------RIIPLLLTTAASMMI------ASEQR--VDLPKEITLG :  60
ATPT12   : DKVKSQTPDKAP---AGGSSINQLLGITKGAS-------------------------------QETNKWKIRLQLTKPVTNPPLVWGVVCGRAASGNFHWTPEDVAKSILC : 139
SLR0056  : QNT-GQNQAKA---------RQLLGNIKGAAP-------------------------------GESSIWKIRLQLMKPITHIPLIWGVVCGHASSGYIWSVEDFEKAITC :  73
ATPT8    : EVPKLASAAEY---------FFKRGVQGKQF--------------------------------RSTILLLATALNLRVP-----EALIGEST--DIVTSERVRQR :  63
SLR1518  : SPLAPSTAPAT---------RKLWLAAIKP---------------------------------PMYTVAVPITVG-------SAVAYGLTG--QWHGDVFTIFLL :  59

*       180         *       200         *       220         *       240         *       260
ATPT2    : AVWAALMMNIYIVGL--NQLSDVEIDKVNKPYLPLASGEYSVNTGIAVASFSTMSFWLGWIVGSWPLFWALFVSFMLGTAYS-INEPELR : 228
SLR1736  : AWLACLLGNVYIVGL--NQLWDVDIDRINKPNLPLANGDFSIAQGRWFIWIASGLLT-PFQGIGFGLQLILGLG-LWLGLTVG-LIEIGTAY- : 134
ATPT3    : GAIL---RGAGCTINDLLCTKVDRTKLRPIASGLET--VQVGINGVATMVALIGANG--LAFYLTPLSFWLCVA-----SFILEVF : 246
SLR0926  : GTLA---TSGLGCVVNDIWDRDIDPQVERITKQRDLAARALS-VQVGINGVATMVALIGANG---LASKTNMLAAGLASAN--LVLYAF : 132
ATPT4    : TMWI---AASANSENQIEISNDSKMKQTMLRFLPSGRISVPHAUAWATIAAGASGACL-----LATFVNVLSGCIALSG--IVPYML : 215
SLL1899  : GTLA---AASAQTFNCIVQDIIDYEMLIRTRARDIPAGKVQPRHALFALALGVESFLL-EGGLIRGLID-VWAGHTTPTVFYI-ALG--GSLESY : 137
ATPT12   : MMMSGPCUTGYTQTIINDWYDRIDAINEPYRPIDSGAISEPEVITQWVLEGLIEAGLID-VWAQHDFPLMMVLTLG--GAFVAY : 223
SLR0056  : MLISGPLMTGYTQTIINDFDRDIDAINEPYRPIDSGAISVPQVVTQLILWAGHGVAYGLD-VWAALKNTEVAALATAVEHLVTGETM : 157
ATPT8    : GIAE---ITEMIHVASLFHDVLDDADTRGVGSLNVVMGNKMSVIAGDFLLSRACCGAL----LGLMSMS--WRAQDWTVLELIGVAH : 144
SLR1518  : SAIA---IIAWINLSNDVEDSTGIDVRKAHSVVNLTGNRNLVFLISNFFEAGVLAGVLMSMS--WRAQDWTVLELIGVG : 138
```

```
           *         280         *         300         *         320         *         340         *
ATPT2    : WKR-FALVAAMCILARAIIVQIAFYLH-IQTHVFGRPILFTRPEIFATAFMSFESVIAHFKDIPDIEGEKI-FEHRSFSVTLG-QKR       : 313
SLR1736  : LKR-FSLLAALCILTVRGIVNLGLFLF-FRIGLGYPPLITPRNV-TLFILVEIAIAHFKDVPDMEGDRQ-FKHOTELQIS-KQN            : 218
ATPT3    : SKP-LMKRFTFWPQAFLGLTINWGALTG--KT--AKGSIAPSRVLPDYLSGVCWTHVYDTIYAHQDKEDDVK-MGVKSTALRFG-DNT          : 328
SLR0926  : AWP-GAKRVFPVPQLVLSIAWGFAVLS--WS--ATGDLHDATWV--LPAALYFWQIPHFAALAHLCRNDYAA--GGYKMESLFDP---S       : 213
ATPT4    : VYT-PLKQLHPINTWVGAVVGAIPPLFG--WA--ALSCQISYNSML-UPAALYFWQIPHFAALAHLCRNDYAA--GGYKMESLFDP---S       : 294
SLL1899  : VYTHWLKRHTAQNIVIGGAAGSIPPLVG--WA--AVTGDLSWTPWV-TFALIFLWLPPHFWALALMIKDDYAQ-VNMPMEPVIAGEEKT        : 220
ATPT12   : IMS-APPLKLKQNGWVGNFAIGASYISLPWHAGQAEFGTLLEPDVAH-ETLLYSIAGLGIAIVNDFKSVEGDRA-TGLQSEPVAFG-TET       : 308
SLR0056  : IMS-APPLKLKQNGWLGNYAIGASYIALPWAGHAEFGTLNPTLMWA-ETLIYSLAGFGIAVVNDFKSVEGDRQ-TGLKSEPVMFG-IGT       : 242
ATPT8    : EITSSTEQRYSMDYYMQKTYYKTASLMSNSCKAVALTGQIAEYAWLAFEYGRNLGIAFQLIDDILDFTGTSASLCKGSLSDIRH--GV         : 231
SLR1518  : TWQGPFFRLGYLGLGELICLLTFGPLAI-AAAYYSQSQSFSWMLET-PSVFVGISHAILFCSHFHQVEDLA-AEKKSPIVRLG-TKL         : 223
                                                                                    g             g
           *         360         *         380         *         400         *         420         *         440
ATPT2    : VFWTCVTILQMAYAVAILVGATSPFIWSKVISAVGHVIZATTEWARAKSVDLSSKTEHTS---CYMHIWKLFYAEYELPFLK--             : 393
SLR1736  : VFRGTDILLTGCYLAMAIWGWAAMPLNTAFLMWSHLCELAELWWRSRDVHLESKTEHAS---FYQHIWKEFFLEYDYPEALWLPNFS         : 304
ATPT3    : KLWETGFGTASIGFIALSGFSADLGWQYYASDAAASGQLGWQIGTADLSSGADCS------RKEVSNKWFGALIFSGVTEGRSFQ-         : 407
SLR0926  : GEAVGHFFALTIGCEFYLGMDLLMLNPLYWLSDATAN--VGWMIQYIQLSAPTPEP-KLY--GQIEGQNVIIGFVIAGMLEGWL--         : 292
ATPT4    : GKRHAAVALRNCFYMIPLGFHAYDWGLTSSWFCLESTLETLAIAATAFSFYRDRTMHKA----RKMEHASELFLPVEMSGLLEHRVSND      : 379
SLL1899  : VSQHWYYSLLVVPFSLLVYPLHQLGILYLAEAIH---GGQFLVKAWQLKQAPGDRDLA--RGLEKFSHFYLMELCLAMVEDSLPVT          : 303
ATPT12   : AKWHCVGAIDITQLSVAGYLLASGKPYYALALAWALH--IPQEVFQFKYFLKDPVKYDVK--YQASAQPFLVLGHFVTALASQH--          : 387
SLR0056  : AAWHLCVIMIDVFQAGIAGYLIYVHQLYATIWELFH--IPQHITFQDMYFLRNPLENDWK--YQASAQPFLVFGMATGEALGHAGI-        : 324
ATPT8    : ITAPIEFAMEEFPQHREMVDQVEKDPRNVDIALEYIGKSKGLQRARELAMEHANLAAAIGSLPETDNEDWKRSRRAEIDLTHRVITRN       : 320
SLR1518  : GSQVLTLSVVSLYLHIAHGVECHQAPWQTLLHASEPWAVQLIRHVGQYHDQPEQVSNCK---FIAVNLHFFSGMEMAAGYGWAGLG--        : 307

*         460         *         480         *
ATPT2    : -----------------------------------------                                                        :
SLR1736  : NTIF-------------------------------------                                                        : 308
ATPT3    : -----------------------------------------                                                        :
SLR0926  : -----------------------------------------                                                        :
ATPT4    : NQQQLVEEAGLTNSVSGEVKTQRRKKRVAQPPVAYASAAPFPFLPAPSFYSP                                              : 431
SLL1899  : --HQLVAQMGTLLLG--------------------------                                                        : 316
ATPT12   : -----------------------------------------                                                        :
SLR0056  : -----------------------------------------                                                        :
ATPT8    : K----------------------------------------                                                        : 321
SLR1518  : -----------------------------------------                                                        :
```

Figure 22B

Alignment 1

```
Query-          12194 CACACGTTCTCGTCCTTTTCTTCTTCCTCTCTGCATTCTTCACAGAGTTTGTCACCACCA
genomic
ATCEA4C371+         1                                                            C  est
                                                                               :first
             Met
Query-          12134 ACACCAAACACACCAATTTCACATTCTTTTGCATATTTCTTCTTCTTCTTCCATTATGGA
                      |I.|||||||-||||||||||||||||||||||||||||||||||||||||||||||||||
ATCEA4C371+         2 ACCCCAAACATCACAATTTCACATTCTTTTGCATATTTCTTCTTCTTCTTCCATTATGGA Query-          12075 GATACGGAGCTTGATTGTTTCTATGAACCCTAATTTATCTTCCTTTGAGCTCTCTCGCCC
                      ||||||||||||||||||||||||||||||||||||||||||||||||||||||||||||
ATCEA4C371+        62 GATACGGAGCTTGATTGTTTCTATGAACCCTAATTTATCTTCCTTTGAGCTCTCTCGCCC Query-          12015 TGTATCTCCTCTCACTCGCTCACTAGTTCCGTTCCGATCGACTAAACTAGTTCCCCGCTC
                      ||||||||||||||||||||||||||||||||||||||||||||||||||||||||||||
ATCEA4C371+       122 TGTATCTCCTCTCACTCGCTCACTAGTTCCGTTCCGATCGACTAAACTAGTTCCCCGCTC Query-          11955 CATTTCTAGGGTTTCGGCGTCGATCTCCACCCCGAATAGTGAAACTGACAAGATCTCCGT
                      ||||||||||||||||||||||||||||||||||||||||||||||||||||||||||||
ATCEA4C371+       182 CATTTCTAGGGTTTCGGCGTCGATCTCCACCCCGAATAGTGAAACTGACAAGATCTCCGT Query-          11895 TAAACCTGTTTACGTCCCGACGTCTCCCAATCGCGAACTCCGGACTCGTCACAGTGGGTA
                      |||||||||||||||||||||||||||||||||||||||||||||||||||||||||---
ATCEA4C371+       242 TAAACCTGTTTACGTCCCGACGTCTCCCAATCGCGAACTCCGGACTCCTCACAGTGG
                                                                    Synecho seq aligns from
here Query-          11835 AATTGATCCATTCCATTCCATTTCTCTTCTCTTGTTTGTTTTATTAAGCTCCAATTTCAG
ATCEA4C371+       299

~~ 60 bp removed ~~~

Query-          11715 ************************************************************TTTG
ATCEA4C371+       299
PIR:T04448          1

Query-          11655 GTGGCTCACCATTCGACGACTACTTTTGAATTTGAGTTTTTGAAAAATGCAATTTAACAT
ATCEA4C371+       299
PIR:T04448          1                                                           M  Q  F  N  I
                                                                   arab sequence which is incorrect Query-          11595 CAGAGAGTTTTTTTTTTTATGGTTGATAACTTATTGTTTAACTTTTGAAAAATGCAGATA
                                                                                    |||
ATCEA4C371+       299                                                                     ATA
                      ::::::::::::::::::::::::::::::::::::::::::::::::::::::::::::
PIR:T04448          6                                          R  E  F  F  F  L  W  L  I  T  Y  C  L  T  F  E  K  C  R  Y Query-          11535 CCATTTCGATGGAACACCTCGGAAGTTCTTCGAGGGATGGTATTTCAGGGTTTCCATCCC
                      ||||||||||||||||||||||||||||||||||||||||||||||||||||||||||||
ATCEA4C371+       302 CCATTTCGATGGAACACCTCGGAAGTTCTTCGAGGGATGGTATTTCAGGGTTCCATCCC
                      :::::::::::::::::::::::::::::::::::::::::::::::::::::::::::
PIR:T04448         26 H  F  D  G  T  P  R  K  F  F  E  G  W  Y  F        S  I  P
```

Figure 31A

```
Query-          11475 AGAGAAGAGGGAGAGTTTTTGTTTTATGTATTCTGTGGAGAATCCTGCATTTCGGCAGAG
                      ||||||||||||||||||||||||||||||||||||||||||||||||||||||||||||
ATCEA4C371+       362 AGAGAAGAGGGAGAGTTTTTGTTTTATGTATTCTGTGGAGAATCCTGCATTTCGGCAGAG
                      ::::::::::::::::::::::::::::::::::::::::::::::::::::::::::::
PIR:T04448         46    E  K  R  E  S  F  C  F  M  Y  S  V  E  N  P  A  F  R  Q  S Query-          11415 TTTGTCACCATTGGAAGTGGCTCTATATGGACCTAGATTCACTGGTGTTGGAGCTCAGAT
                      ||||||||||||||||||||||||||||||||||||||||||||||||||||||||||||
ATCEA4C371+       422 TTTGTCACCATTGGAAGTGGCTCTATATGGACCTAGATTCACTGGTGTTGGAGCTCAGAT
                      ::::::::::::::::::::::::::::::::::::::::::::::::::::::::::::
PIR:T04448         66   L  S  P  L  E  V  A  L  Y  G  P  R  F  T  G  V  G  A  Q  I Query-          11355 TCTTGGCGCTAATGATAAATATTTATGCCAATACGAACAAGACTCTCACAATTTCTGGGG
                      |||||||||||||||||||||||||||||||||||||||||||||||||||||||-----
ATCEA4C371+       482 TCTTGGCGCTAATGATAAATATTTATGCCAATACGAACAAGACTCTCACAATTTC
                      ::::::::::::::::::::::::::::::::::::::::::::::::::::::::::::
PIR:T04448         86   L  G  A  N  D  K  Y  L  C  Q  Y  E  Q  D  S  H  N  F  W  G
ATCEA4C371+           Exon     11538      11301  Confidence: 100 100

Query-          11295 AGGTAACTCCTTGACCCTTAAAATGCTGTGTCATGACAATAAGAAATCATATCTGAGTCT
ATCEA4C371+       537 ------------------------------------------------------------

PIR:T04448            :.----------------------------------------------------------
PIR:T04448        106  D
                      Exon     11609      11294  Confidence: 100 100

Query-          11235 TTTCTCTACTTCTAGTACTAATGTTCGTTATTGTTGTTAAAGATCTAAGTCTTATCTGAA
PIR:T04448        107 ------------------------------------------------------------

Query-          11175 TTTTGTTACATTTTGGTTCTGGTGCTTTCTCAACATGAATTTGTATATATGACTTTAAAG
PIR:T04448        107 ------------------------------------------------------------

Query-          11115 ATTGCTTACCTAAAGTTTTTACTCATGCATAGATCGACATGAGCTAGTTTTGGGAATAC
PIR:T04448        107 ------------------------------..::::::::::::::::::::::::::::
                                                     R  H  E  L  V  L  G  N  T Query-          11055 TTTTAGTGCTGTGCCAGGCGCAAAGGCTCCAAACAAGGAGGTTCCACCAGAGGTTCTCAC
                      ::::::::::::::::::::::::::::::::::::::::::::::::::::--------
PIR:T04448        116   F  S  A  V  P  G  A  K  A  P  N  K  E  V  P  P  E
PIR:T04448            Exon     11083      11004  Confidence: 96 100

Query-          10995 TCCTCCCTTGTTGGTTACTTTGTTATCTGTTAAATAGTTTTCCAATTGTATCCGGATAGT
PIR:T04448        133 ------------------------------------------------------------

Query-          10935 GTTCTACTTCTCCTTGTAGAAAATCTCAAGTTTTTGTTACTCTTGCTATTCTCTTGGATG
PIR:T04448        133 ------------------------------------------------------------

Query-          10875 TTGATTTGTAAAGCATGTCGTTTTATTGTAGGAATTTAACAGAAGAGTGTCCGAAGGGTT
                      ------------------------------------:::::::::::::::::::::::
PIR:T04448        133                                       E  F  N  R  R  V  S  E  G  F Query-          10815 CCAAGCTACTCCATTTTGGCATCAAGGTCACATTTGCGATGATGGCCGGTAATTATATGA
                      :::::::::::::::::::::::::::::::::::::::::..----------------
PIR:T04448        143   Q  A  T  P  F  W  H  Q  G  H  I  C  D  D  G  R
PIR:T04448            Exon     10844      10768  Confidence: 100 100

Query-          10755 TTCTATGCACAACAAGAATTCACTATATTATAAATATTGGATATTGAGTATTTTTGTTGA
PIR:T04448        159 ------------------------------------------------------------
```

Figure 31B

```
Query-      10635  TGAAATCTGCTCGTTGGGAGTATAGTACTCGTCCCGTTTACGGTTGGGGTGATGTTGGGG
                  ::::::::::::::::::::::::::::::::::::::::::::::::::::::::::::
PIR:T04448    166    K  S  A  R  W  E  Y  S  T  R  P  V  Y  G  W  G  D  V  G  A Query-      10575  CCAAACAGAAGTCAACTGCAGGCTGGCCTGCAGCTTTTCCTGTATTTGAGCCTCATTGGC
                  ::::::::::::::::::::::::::::::::::::::::::::::::::::::::::::
PIR:T04448    186    K  Q  K  S  T  A  G  W  P  A  A  F  P  V  F  E  P  H  W  Q Query-      10515  AGATATGCATGGCAGGAGGCCTTTCCACAGGTGTGAGCTTTGCTTGATTGACTTAAAGTT
                  ::::::::::::::::::::::::::::.-----------------------------
PIR:T04448    206    I  C  M  A  G  G  L  S  T  G
PIR:T04448         Exon     10655     10486  Confidence:  96 100

Query-      10455  AATAAATAGACGGTTAAGTTTACTTGCCTAGTACTAACAGAAAATTAAGAAAGAAACCAC
                  ------------------------------------------------------------
PIR:T04448    216

Query-      10395  CCTCTTTCTATCAGCAGAAACTGCTATTGTAGTTCTTATTTTTTCTCTTGTATTTGCAGG
                  ------------------------------------------------------------
PIR:T04448    216

Query-      10335  GTGGATAGAATGGGGCGGTGAAAGGTTTGAGTTTCGGGATGCACCTTCTTATTCAGAGAA
                  .:::::::::::::::::::::::::::::::::::::::::::::::::::::::::
PIR:T04448    216    W  I  E  W  G  G  E  R  F  E  F  R  D  A  P  S  Y  S  E  K Query-      10275  GAATTGGGGTGGAGGCTTCCCAAGAAAATGGTTTTGGGTAAAACATTTCATCCTTTTGCT
                  :::::::::::::::::::::::::::::::::::-------------------------
PIR:T04448    236    N  W  G  G  G  F  P  R  K  W  F  W
PIR:T04448         Exon     10336     10239  Confidence:  96 100

Query-      10215  ACATTTCTTGTTGCAGACTTTAGTTAGCTAGTGGACCTGTGTATACACCCACATGTAGTA
                  ------------------------------------------------------------
PIR:T04448    248
Query-      10155  TACTTGTTTGATAGCTTTATTTGTCAATGTCTCTTTACAGGTCCAGTGTAATGTCTTTGA
                  -------------------------------------------:::::::::::::::::
PIR:T04448    248                                                V  Q  C  N  V  F  E Query-      10095  AGGGGCAACTGGAGAAGTTGCTTTAACCGCAGGTGGCGGGTTGAGGCAATTGCCTGGATT
                  ::::::::::::::::::::::::::::::::::::::::::::::::::::::::::::
PIR:T04448    255    G  A  T  G  E  V  A  L  T  A  G  G  G  L  R  Q  L  P  G  L Query-      10035  GACTGAGACCTATGAAAATGCTGCACTGGTATGCACTTATAAGATCTTCTTAAGCAATGA
                  :::::::::::::::::::::::::::::::----------------------------
PIR:T04448    275    T  E  T  Y  E  N  A  A  L
PIR:T04448         Exon     10115     10008  Confidence: 100 100

Query-       9975  CAGTGAGTATTAGAAGGCAGATAGTTTACAAAAGCTCTGGGCCCTTGTAAATCTGCAGGT
                  ----------------------------------------------------------::
PIR:T04448    284                                                                V Query-       9915  TTGTGTACACTATGATGGAAAAATGTACGAGTTTGTTCCTTGGAATGGTGTTGTTAGATG
                  ::::::::::::::::::::::::::::::::::::::::::::::::::::::::::::
PIR:T04448    285    C  V  H  Y  D  G  K  M  Y  E  F  V  P  W  N  G  V  V  R  W
GSDB:S:495-   532  ------------------------------------------------------|||||
                                                                          tagatg
```

Figure 31C

```
Query-      9855 GGAAATGTCTCCCTGGGG TTATTGGTATATAACTGCAGAGAACGAAAACCATGTGGTAA
                 ::::::::::::::::::  ::::::::::::::::::::::::::::::::::::::----
PIR:T04448   305  E  M  S  P  W  G   Y  W  Y  I  T  A  E  N  E  N  H  V
                 ||||||-|||||||||||-||||||||||||||||||||||| || |||||||||||----
GSDB:S:495-  526 ggaaat tctccctgggggttattggtatataactgcagagaNcgNaaaccatgtg
PIR:T04448       Exon       9917     9801  Confidence: 100 100
GSDB:S:495-      Exon       9861     9801  Confidence:  93  93

Query-      9796 ATTTGTTTTACTAGTTTCATTCAGTTTTACTTTTGACATCATATCATTCCCTTATGGCTA
                 ------------------------------------------------------------
PIR:T04448   323
                 ------------------------------------------------------------
GSDB:S:495-  471

Query-      9736 GATTCCAACACCCGATGAATGTCTTGTGACAGGTGGAACTAGAGGCAAGAACAAATGAAG
                 ------------------------------------:::::::::::::::::::::::
PIR:T04448   323                                      V  E  L  E  A  R  T  N  E  A
                 ---------------------------------|||||||||||||| ||||||||||||
GSDB:S:495-  471                                      gtggaactagaggcNagaacaaatgaag Query-      9676 CGGGTACACCTCTGCGTGCTCCTACCACAGAAGTTGGGCTAGCTACGGCTTGCAGAGATA
                 ::::::::::::::::::::::::::::::::::::::::::::::::::::::::::::
PIR:T04448   333  G  T  P  L  R  A  P  T  T  E  V  G  L  A  T  A  C  R  D  S
                 ||||||||||||||||||||||||||||||||||||||||||||||||||||||||||||
GSDB:S:495-  443 cgggtacacctctgcgtgctcctaccacagaagttgggctagctacggcttgcagagata Query-      9616 GTTGTTACGGTGAATTGAAGTTGCAGATATGGGAACGGCTATATGATGGAAGTAAAGGCA
                 ::::::::::::::::::::::::::::::::::::::::::::::::::::::::::::
PIR:T04448   353  C  Y  G  E  L  K  L  Q  I  W  E  R  L  Y  D  G  S  K  G  K
                 ||||||||||||||||||||||||||||||||||||||||||||||||||||||||||||
GSDB:S:495-  383 gttgttacggtgaattgaagttgcagatatgggaacggctatatgatggaagtaaaggca Query-      9556 AGGTATGTATGCTAATGTGATCCAATCCCTGTAGTTAAAAGTCTTAACAAATCCTAAGGC
                 ::----------------------------------------:::::::::::::::::
PIR:T04448   373                                           L  K  V  L  T  N  P  K  A
                 ||----------------------------------------------------------
GSDB:S:495-  323 ag
PIR:T04448       Exon       9704     9555  Confidence: 100 100
GSDB:S:495-      Exon       9704     9555  Confidence:  98 100

Query-      9496 AGTGAAAGAAGATTATGAACGTTTGTTATGGTTAACAATGATGCAGGTGATATTAGAGAC
                 ::::::::::::::::::::::::::::::::::::::::::::::::::::::::::::
PIR:T04448   382  V  K  E  D  Y  E  R  L  L  W  L  T  M  M  Q  V  I  L  E  T
                 ------------------------------------------------||||||||||||
GSDB:S:495-  321                                                 gtgatattagagac
```

Figure 31D

```
Query-      9436 AAAGAGCTCAATGGCAGCAGTGGAGATAGGAGGAGGACCGTGGTTTGGGACATGGAAAGG
                 ::::::::::::::::::::::::::::::::::::::::::::::::::::::::::::
PIR:T04448   402  K  S  S  M  A  A  V  E  I  G  G  G  P  W  F  G  T  W  K  G
                 ||||||||||||||| ||||||||||||||||||||||||||||||||||||||||||||
GSDB:S:495-  307 aaagagctcaatggcaNcagtggagataggaggaggaccgtggtttgggacatggaaagg Query-      9376 AGATACGAGCAACACGCCCGAGCTACTAAAACAGGCTCTTCAGGTCCCATTGGATCTTGA
                 ::::::::::::::::::::::::::::::::::::::::::::::::::::::::::::
PIR:T04448   422  D  T  S  N  T  P  E  L  L  K  Q  A  L  Q  V  P  L  D  L  E
                 ||||||||||||||||||||||||||||||||||||||||||||||||||||||||||||
GSDB:S:495-  247 agatacgagcaacacgcccgagctactaaaacaggctcttcaggtcccattggatcttga Query-      9316 AAGCGCCTTAGGTTTGGTCCCTTTCTTCAAGCCACCGGGTCTGTAA███████████████
(stop)
                 :::::::::::::::::::::::::::::::::::::::::::::-----------------
PIR:T04448   442  S  A  L  G  L  V  P  F  F  K  P  P  G  L
                 ||||||||||||||||||||||||||||||||||||||||||||||||||||||||||||
GSDB:S:495-  187 aagcgccttaggtttggtcccttcttcaagccaccgggtctgtaacattgatgagtgtt
PIR:T04448       Exon     9522     9274  Confidence: 100 100

Query-      9256 ████████████████████████████████████████████████████████████
PIR:T04448   456
                 ||||||||||||||||||||||||||||||||||||||||||||||||||||||||||||
GSDB:S:495-  127 ttgtttgttgatagagacccatgtgatgaatgaagccttagtcatgtcattgctagcttc Query-      9196 ACTATTATGTATGTATGATTTTAGTTCGTTCGGTCCTTGTGGTAAATGATACGGGCCAGT
                 ||||||||||||||||||||||||||||||||||||||||||||||||||||||||||||
GSDB:S:495-  67  actattatgtatgtatgattttagttcgttcggtccttgtggtaaatgatacgggccagt Query-      9136 GTAAAGTCTAGTTCAATAAAAGCCTTGAGTCGCATAATTTCAATTTCAAATTGCATC
                 |||||||-----------------------------------------------------
GSDB:S:495-  7   gtaaagt
GSDB:S:495-      Exon     9450     9130  Confidence: 98 100
```

ATCEA4C37145_1 3063693/emb|CAA18584.1| 4.0e-43 (AL022537) putative protein
[Arabidopsis thaliana]

PIR:T04448 sPIR-T04448 shypothetical protein F4D11.30 - Arabidopsis thaliana;
g3063693|emb|CAA18584.1 (AL022537) putative protein [Arabidopsis thaliana]_F4D11.30

GSDB:S:4955486|AI995392|AI995392|701673779 A. thaliana, Columbia Col-0, inflorescence-
1 Arabidopsis thaliana cDNA clone 701673779, mRNA sequence.

Figure 31E

```
slr1737_SYNSP_S74814_   ------------------------------------------M
slr1737_ARATH_T04448_   MEIRSLIVSMNPNLSSFELSRPVSPLTRSLVPFRSTKLVPRSISRVSASI
CFI_ARATH_P41088_       -------------------------------------------------- slr1737_SYNSP_S74814_   KFP--------------------------PHSGYHWQGQS-PFFEGWYVRLL
slr1737_ARATH_T04448_   STPNSETDKISVKPVYVPTSPNRELRTPHSGYHFDGTPRKFFEGWYFRVS
CFI_ARATH_P41088_       -------------------------------------------------- slr1737_SYNSP_S74814_   LPQSGESFAFMYSIENPASDHHYGGGAVQILGPATK----KQENQEDQLV
slr1737_ARATH_T04448_   IPEKRESFCFMYSVENPAFRQSLSPLEVALYGPRFTGVGAQILGANDKYL
CFI_ARATH_P41088_                             MSSSNACASPSPFPA----VTKLHVDSVslr1737_SYNSP_S74814_   WRTFPSVKKFWASPRQFALG-HWGKCRDNRQ-AKPLLSEEFFATVKEGYQ
slr1737_ARATH_T04448_   CQYEQDSHNFWGDRHELVLGNTFSAVPGAKAPNKEVPPEEFNRRVSEGFQ
CFI_ARATH_P41088_       --TFVPSVKSPASSNPLFLG-GAGVRGLDIQ-GK------FVIFTVIGVY slr1737_SYNSP_S74814_   IHQNQHQGQIIHGDR--------HCRWQFTVEPEVTWGSPNRFPRATAGW
slr1737_ARATH_T04448_   ATPFWHQGHICDDGRTDYAETVKSARWEYSTRPVYGWGDVGAKQKSTAGW
CFI_ARATH_P41088_       LEGNAVPSLSV-------------KWKGKTTEELTESIPFFREIVTGAF slr1737_SYNSP_S74814_   LSFLPLFDPGWQILLAQGRAHGWLKWQREQYEFDHALVYAEKNWGHSFPS
slr1737_ARATH_T04448_   PAAFPVFEPHWQICMAGGLSTGWIEWGGERFEFRDAPSYSEKNWGGGFPR
CFI_ARATH_P41088_       EKFIKVT------------M-----------KLPLTGQQYSEKVTENC slr1737_SYNSP_S74814_   RWFWLQANYFPDHPG-LSVTAAGGERIVLGRPE---EVALIGLHHQGNFY
slr1737_ARATH_T04448_   KWFWVQCNVFEGATGEVALTAGGGLRQLPGLTETYENAALVCVHYDGKMY
CFI_ARATH_P41088_       VAIWKQLGLYTDCEA-KAV-----EKFLEIFKE---ET----------- slr1737_SYNSP_S74814_   EFGPGHGTVTWQVAPWGRWQLKASNDRYWVKLSGKTDKKGSLVHTP-TAQ
slr1737_ARATH_T04448_   EFVPWNGVVRWEMSPWGYWYITAENENHVVELEARTNEAGTPLRAPTTEV
CFI_ARATH_P41088_       -FPPG-SSILFALSPTGSLTVAFSKDDS-IPETGIAVIENKLLAEA-VLE slr1737_SYNSP_S74814_   GLQLNCRDTTRGYLYLQLGSVGHG-----LIVQGETDTAGLEVGG-----
slr1737_ARATH_T04448_   GLATACRDSCYGELKLQIWERLYDGSKGKVILETKSSMAAVEIGGGPWFG
CFI_ARATH_P41088_       --SIIGKNGVSPGTRLSVAERLSQ-----LMMKNKDEKEVSDHSL----- slr1737_SYNSP_S74814_   ----DWGLTEENLSKKT------------VPF------
slr1737_ARATH_T04448_   TWKGDTSNTPELLKQALQVPLDLESALGLVPFFKPPGL
CFI_ARATH_P41088_       ----EEKLAKEN--------------------------
```

NUCLEIC ACID SEQUENCES TO PROTEINS INVOLVED IN TOCOPHEROL SYNTHESIS

INCORPORATION OF SEQUENCE LISTING

A paper copy of the Sequence Listing and a computer readable form of the sequence listing on diskette, containing the file named SeqList.txt, which is 126,173 bytes in size (measured in MS-DOS), and which was created on Aug. 2, 2001, are herein incorporated by reference.

TECHNICAL FIELD

The present invention is directed to nucleic acid and amino acid sequences and constructs, and methods related thereto.

BACKGROUND

Isoprenoids are ubiquitous compounds found in all living organisms. Plants synthesize a diverse array of greater than 22,000 isoprenoids (Connolly and Hill (1992) *Dictionary of Terpenoids*, Chapman and Hall, New York, N.Y.). In plants, isoprenoids play essential roles in particular cell functions such as production of sterols, contributing to eukaryotic membrane architecture, acyclic polyprenoids found in the side chain of ubiquinone and plastoquinone, growth regulators like abscisic acid, gibberellins, brassinosteroids or the photosynthetic pigments chlorophylls and carotenoids. Although the physiological role of other plant isoprenoids is less evident, like that of the vast array of secondary metabolites, some are known to play key roles mediating the adaptative responses to different environmental challenges. In spite of the remarkable diversity of structure and function, all isoprenoids originate from a single metabolic precursor, isopentenyl diphosphate (IPP) (Wright, (1961) *Annu. Rev. Biochem.* 20:525–548; and Spurgeon and Porter, (1981) in *Biosynthesis of Isoprenoids Compounds.*, Porter and Spurgeon eds (John Wiley, New York) Vol. 1, pp 1–46).

A number of unique and interconnected biochemical pathways derived from the isoprenoid pathway leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool.

Tocopherols and tocotrienols (unsaturated tocopherol derivatives) are well known antioxidants, and play an important role in protecting cells from free radical damage, and in the prevention of many diseases, including cardiac disease, cancer, cataracts, retinopathy, Alzheimer's disease, and neurodegeneration, and have been shown to have beneficial effects on symptoms of arthritis, and in anti-aging. Vitamin E is used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products.

The demand for natural tocopherols as supplements has been steadily growing at a rate of 10–20% for the past three years. At present, the demand exceeds the supply for natural tocopherols, which are known to be more biopotent than racemic mixtures of synthetically produced tocopherols. Naturally occurring tocopherols are all d-stereomers, whereas synthetic α-tocopherol is a mixture of eight d,l-α-tocopherol isomers, only one of which (12.5%) is identical to the natural d-α-tocopherol. Natural d-α-tocopherol has the highest vitamin E activity (1.49 IU/mg) when compared to other natural tocopherols or tocotrienols. The synthetic α-tocopherol has a vitamin E activity of 1.1 IU/mg. In 1995, the worldwide market for raw refined As tocopherols was $1020 million; synthetic materials comprised 85–88% of the market, the remaining 12–15% being natural materials. The best sources of natural tocopherols and tocotrienols are vegetable oils and grain products. Currently, most of the natural Vitamin E is produced from γ-tocopherol derived from soy oil processing, which is subsequently converted to α-tocopherol by chemical modification (α-tocopherol exhibits the greatest biological activity).

Methods of enhancing the levels of tocopherols and tocotrienols in plants, especially levels of the more desirable compounds that can be used directly, without chemical modification, would be useful to the art as such molecules exhibit better functionality and bioavailability.

In addition, methods for the increased production of other isoprenoid derived compounds in a host plant cell is desirable. Furthermore, methods for the production of particular isoprenoid compounds in a host plant cell is also needed.

SUMMARY OF THE INVENTION

The present invention is directed to sequences to proteins involved in tocopherol synthesis. The polynucleotides and polypeptides of the present invention include those derived from prokaryotic and eukaryotic sources.

Thus, one aspect of the present invention relates to prenyltransferase, and in particular to isolated polynucleotide sequences encoding prenyltransferase proteins and polypeptides related thereto. In particular, isolated nucleic acid sequences encoding prenyltransferase proteins from bacterial and plant sources are provided.

In another aspect, the present invention provides isolated polynucleotide sequences encoding tocopherol cyclase, and polypeptides related thereto. In particular, isolated nucleic acid sequences encoding tocopherol cyclase proteins from bacterial and plant sources are provided.

Another aspect of the present invention relates to oligonucleotides which include partial or complete prenyltransferase or tocopherol cyclase encoding sequences.

It is also an aspect of the present invention to provide recombinant DNA constructs which can be used for transcription or transcription and translation (expression) of prenyltransferase or tocopherol cyclase. In particular, constructs are provided which are capable of transcription or transcription and translation in host-cells.

In another aspect of the present invention, methods are provided for production of prenyltransferase or tocopherol cyclase in a host cell or progeny thereof. In particular, host cells are transformed or transfected with a DNA construct which can be used for transcription or transcription and translation of prenyltransferase or tocopherol cyclase. The recombinant cells which contain prenyltransferase or tocopherol cyclase are also part of the present invention.

In a further aspect, the present invention relates to methods of using polynucleotide and polypeptide sequences to modify the tocopherol content of host cells, particularly in host plant cells. Plant cells having such a modified tocopherol content are also contemplated herein. Methods and cells in which both prenyltransferase and tocopherol cyclase are expressed in a host cell are also part of the present invention.

The modified plants, seeds and oils obtained by the expression of the prenyltransferase or tocopherol cyclase are also considered part of the invention.

BRIEF DESCRIPTION OF THE DRAWINGS

FIG. 1 provides an amino acid sequence alignment between ATPT2 (SEQ ID NO: 2), ATPT3 (SEQ ID NO: 4), ATPT4 (SEQ ID NO: 6), ATPT8 (SEQ ID NO: 12), and ATPT12 (SEQ ID NO: 17) performed using ClustalW.

FIG. 21 provides an amino acid sequence alignment using ClustalW between the *Synechocystis* prenyltransferase sequences, slr1736 (SEQ ID NO: 37), slr0926 (SEQ ID NO: 32), sll1899 (SEQ ID NO: 33), slr0056 (SEQ ID NO: 34), and slr1518 (SEQ ID NO: 35).

FIG. 22 provides a n amino acid sequence of the ATPT2 (SEQ ID NO: 2), ATPT3 (SEQ ID NO: 4), ATPT4 (SEQ ID NO: 6), ATPT8 (SEQ ID NO: 12), and ATPT12 (SEQ ID NO: 17) protein sequences from *Arabidopsis* and the slr1736 (SEQ ID NO: 37), slr0926 (SEQ ID NO: 32), sll1899 (SEQ ID NO: 33), slr0056 (SEQ ID NO: 34), and the slr1518 (SEQ ID NO: 35) amino acid sequences from *Synechocystis*.

FIG. 31 is a sequence alignment of the *Arabidopsis* homologue (SEQ ID NO: 113) with the sequence of the public database (SEQ ID NO: 112).

FIG. 35 is a sequence alignment of slr1737 (SEQ ID NO: 39), slr1737 *Arabidopsis* homologue (SEQ ID NO: 110) and the *Arabidopsis* chalcone isomerase (SEQ ID NO: 111).

DETAILED DESCRIPTION OF THE INVENTION

Figure 2:
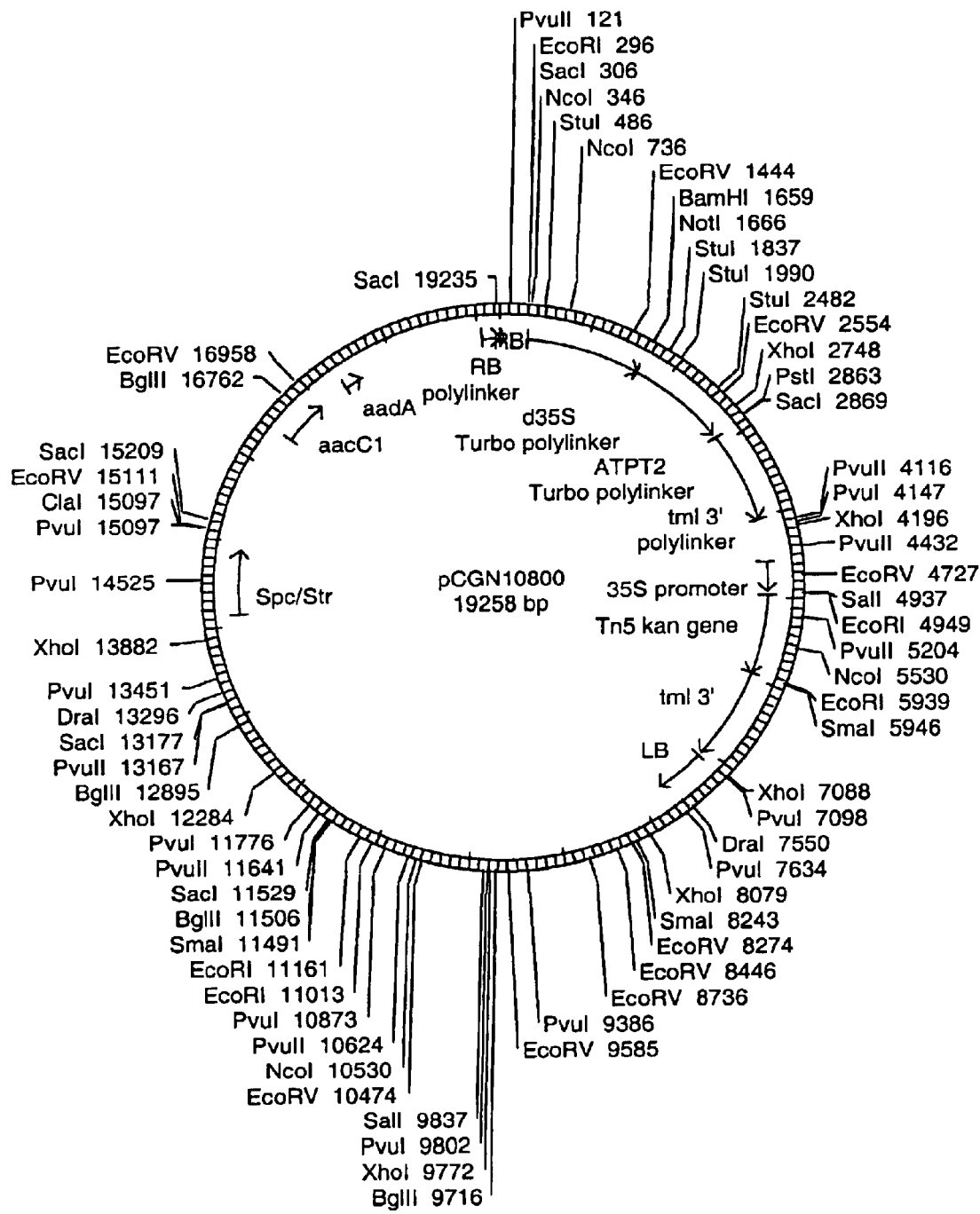
FIG. 2 provides a schematic picture of the expression construct pCGN10800.

The present invention provides, inter alia, compositions and methods for altering (for example, increasing and decreasing) the tocopherol levels and/or modulating their ratios in host cells. In particular, the present invention provides polynucleotides, polypeptides, and methods of use thereof for the modulation of tocopherol content in host plant cells.

The biosynthesis of α-tocopherol in higher plants involves condensation of homogentisic acid and phytylpyrophosphate to form 2-methyl-6 phytylbenzoquinol that can, by cyclization and subsequent methylations (Fiedler et al., 1982, *Planta*, 155: 511–515, Soll et al., 1980, *Arch Biochem. Biophys*. 204: 544–550, Marshall et al., 1985 *Phylochem.*, 24: 1705–1711, all of which are herein incorporated by reference in their entirety), form various tocopherols.

The *Arabidopsis* pds2 mutant identified and characterized by Norris et al. (1995), is deficient in tocopherol and plastiquinone-9 accumulation. Further genetic and biochemical analysis suggested that the protein encoded by PDS2 may be responsible for the prenylation of homogentisic acid. The PDS2 locus identified by Norris et al. (1 995) has been hypothesized to possibly encode the tocopherol phytyl-prenyltransferase, as the pds2 mutant fails to accumulate tocopherols.

Norris et al. (1995) determined that in *Arabidopsis* pds2 lies at the top of chromosome 3, approximately 7 centimorgans above long hypocotyl2, based on the genetic map. ATPT2 is located on chromosome 2 between 36 and 41 centimorgans, lying on BAC F 19F24, indicating that ATPT2 does not correspond to PDS2. Thus, it is an aspect of the present invention to provide novel polynucleotides and polypeptides involved in the prenylation of homogentisic acid.

This reaction may be a rate limiting step in tocopherol biosynthesis, and this gene has yet to be isolated.

U.S. Pat. No. 5,432,069 describes the partial purification and characterization of tocopherol cyclase from *Chlorella protoihecoides, Dunaliella salina* and wheat. The cyclase described as being glycine rich, water soluble and with a predicted MW of 48–50 kDa. However, only limited peptide fragment sequences were available.

In one aspect, the present invention provides polynucleotide and polypeptide sequences involved in the prenylation of straight chain and aromatic compounds. Straight chain prenyltransferases as used herein comprises sequences which encode proteins involved in the prenylation of straight chain compounds, including, but not limited to, geranyl geranyl pyrophosphate and farnesyl pyrophosphate. Aromatic prenyltransferases, as used herein, comprises sequences which encode proteins involved in the prenylation of aromatic compounds, including, but not limited to, menaquinone, ubiquinone, chlorophyll, and homogentisic acid. The prenyltransferase of the present invention preferably prenylates homogentisic acid.

In another aspect, the invention provides polynucleotide and polypeptide sequences to tocopherol cyclization enzymes. The 2,3-dimethyl-5-phytylplastoguinol cyclase (tocopherol cyclase is responsible for the cyclization of 2,3-dimethyl-5-phytylplastoquinol to tocopherol.

Isolated Polynucleotides, Proteins, and Polypeptides

A first aspect of the present invention relates to isolated prenyltransferase polynucleotides. Another aspect of the present invention relates to isolated tocopherol cyclase polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

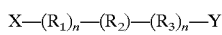

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably those of SEQ ID NOs: 1, 3, 5, 7, 8, 10, 11, 13–16, 18, 23, 29, 36, and 38. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the prenyltransferase or tocopherol cyclase EST sequences. The oligonucleotides are used as primers in polymerase chain reaction (PCR) techniques to obtain 5' and 3' terminal sequence of prenyltransferase or tocopherol cyclase genes. Alternatively, where oligonucleotides of low degeneracy can be prepared from particular prenyltransferase or tocopherol cyclase peptides, such probes may be used directly to screen gene libraries for prenyltransferase or tocopherol cyclase gene sequences. In particular, screening of cDNA libraries in phage vectors is useful in such methods due to lower levels of background hybridization.

Typically, a prenyltransferase or tocopherol cyclase sequence obtainable from the use of nucleic acid probes will show 60–70% sequence identity between the target prenyltransferase or tocopherol cyclase sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an prenyltransferase or tocopherol cyclase enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related prenyltransferase or tocopherol cyclase genes. Shorter probes are often particularly useful for polymerase chain reactions (PCR), especially when highly conserved sequences can be identified. (See, Gould, et al., *PNAS USA* (1989) 86:1934–1938.).

Another aspect of the present invention relates to prenyltransferase or tocopherol cyclase polypeptides. Such polypeptides include isolated polypeptides set forth in the Sequence Listing, as well as polypeptides and fragments thereof, particularly those polypeptides which exhibit prenyltransferase or tocopherol cyclase activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Bioloy*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York.(1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403410 (1990)). The well known Smith Waterman algorithm can also be used to determine identity.

Parameters for polypeptide sequence comparison typically include the following:

Algorithm: Needleman and Wunsch, *J. Mol. Biol.* 48:443–453 (1970) Comparison matrix: BLOSSUM62 from Hentikoff and Hentikoff, *Proc. Nalt. Acad. Sci USA* 89:10915–10919(1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

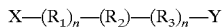

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably those encoded by the sequences provided in SEQ ID NOs: 2, 4, 6, 9, 12, 17, 19–22, 24–28, 30, 32–35, 37, and 39. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein .

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Plant Constructs and Methods of Use

Of particular interest is the use of the nucleotide sequences in recombinant DNA constructs to direct the transcription or transcription and translation (expression) of the prenyltransferase or tocopherol cyclase sequences of the present invention in a host plant cell. The expression constructs generally comprise a promoter functional in a host plant cell operably linked to a nucleic acid sequence encoding a prenyltransferase or tocopherol cyclase of the present invention and a transcriptional termination region functional in a host plant cell.

A first nucleic acid sequence is "operably linked" or "operably associated" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

Those skilled in the art will recognize that there are a number of promoters which are functional in plant cells, and have been described in the literature. Chloroplast and plastid specific promoters, chloroplast or plastid functional promoters, and chloroplast or plastid in operable promoters are also envisioned.

One set of plant functional promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) Nature 313:810–812; Rogers, U.S. Pat. No. 5,378, 619). In addition, it may also be preferred to bring about expression of the prenyltransferase or tocopherol cyclase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., Seed Sci. Res. 1:209:219 (1991)), phaseolin, zein, soybean trypsin inhibitor, ACP, stearoyl-ACP desaturase, soybean α' subunit of β-conglycinin (soy 7s, (Chen et al., Proc. Nalt. Acad. Sci., 83:8560–8564 (1986))) and oleosin.

It may be advantageous to direct the localization of proteins conferring prenyltransferase or tocopherol cyclase to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478481.

Depending upon the intended use, the constructs may contain the nucleic acid sequence which encodes the entire prenyltransferase or tocopherol cyclase protein, or a portion thereof. For example, where antisense inhibition of a given prenyltransferase or tocopherol cyclase protein is desired, the entire prenyltransferase or tocopherol cyclase sequence is not required. Furthermore, where prenyltransferase or tocopherol cyclase sequences used in constructs are intended for use as probes, it may be advantageous to prepare constructs containing only a particular portion of a prenyltransferase or tocopherol cyclase encoding sequence, for example a sequence which is discovered to encode a highly conserved prenyltransferase or tocopherol cyclase region.

The skilled artisan will recognize that there are various methods for the inhibition of expression of endogenous sequences in a host cell. Such methods include, but are not limited to, antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the prenyltransferase or tocopherol cyclase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the prenyltransferase or tocopherol cyclase sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

The prenyltransferase or tocopherol cyclase constructs of the present invention can be used in transformation methods with additional constructs providing for the expression of other nucleic acid sequences encoding proteins involved in the production of tocopherols, or tocopherol precursors such as homogentisic acid and/or phytylpyrophosphate. Nucleic acid sequences encoding proteins involved in the production of homogentisic acid are known in the art, and include but not are limited to, 4-hydroxyphenylpyruvate dioxygenase (HPPD, EC 1.13.11.27) described for example, by Garcia, et al. ((1999) *Plant Physiol.* 119(4)1507–1516), mono or bifunctional tyrA (described for example by Xia, et al. (1992) *J. Gen Microbiol.* 138:1309–1316, and Hudson, et al. (1984) *J. Mol. Biol.* 180:1023–1051), Oxygenase, 4-hydroxyphenylpyruvate di-(9CI), 4-Hydroxyphenylpyruvate dioxygenase; p-Hydroxyphenylpyruvate dioxygenase; p-Hydroxyphenylpyruvate hydroxylase; p-Hydroxyphenylpyruvate oxidase; p-Hydroxyphenylpyruvic acid hydroxylase; p-Hydroxyphenylpyruvic hydroxylase; p-Hydroxyphenylpyruvic oxidase), 4-hydroxyphenylacetate, NAD(P)H:oxygen oxidoreductase (1-hydroxylating); 4-hydroxyphenylacetate 1-monooxygenase, and the like. In addition, constructs for the expression of nucleic acid sequences encoding proteins involved in the production of phytylpyrophosphate can also be employed with the prenyltransferase or tocopherol cyclase constructs of the present invention. Nucleic acid sequences encoding proteins involved in the production of phytylpyrophosphate are known in the art, and include, but are not limited to geranylgeranylpyrophosphate synthase (GGPPS), geranylgeranylpyrophosphate reductase (GGH), 1-deoxyxylulose-5-phosphate synthase, 1-deoxy-D-xylolose-5-phosphate reductoisomerase, 4-diphosphocytidyl-2-C-methylerythritol synthase, isopentyl pyrophosphate isomerase.

The prenyltransferase or tocopherol cyclase sequences of the present invention find use in the preparation of transformation constructs having a second expression cassette for the expression of additional sequences involved in tocopherol biosynthesis. Additional tocopherol biosynthesis sequences of interest in the present invention include, but are not limited to gamma-tocpherol methyltransferase (Shintani, et al. (1998) *Science* 282(5396):2098–2100), tocopherol cyclase, and tocopherol methyltransferase.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a prenyltransferase or tocopherol cyclase nucleic acid sequence.

Plant expression or transcription constructs having a prenyltransferase or tocopherol cyclase as the DNA sequence of interest for increased or decreased expression thereof may be employed with a wide variety of plant life, particularly, plant life involved in the production of vegetable oils for edible and industrial uses. Particularly preferred plants for use in the methods of the present invention include, but are not limited to: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Most especially preferred are temperate oilseed crops. Temperate oilseed crops of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of prenyltransferase or tocopherol cyclase constructs in plants to produce plants or plant parts, including, but not limited to leaves, stems, roots, reproductive, and seed, with a modified content of tocopherols in plant parts having transformed plant cells.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as prenyltransferase or tocopherol cyclase enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for prenyltransferase or tocopherol cyclase activity. Such expression systems are known in the art and are readily available through commercial sources.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of prenyltransferase or tocopherol cyclase can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as *Synechocystis, Shewanella*, yeast, *Pseudomonas, Rhodobacteria*, etc., that lack specific biochemical reactions, or that have been mutated. The sequences of the DNA coding regions can be optimized by gene resynthesis, based on codon usage, for maximum expression in particular hosts.

For the alteration of tocopherol production in a host cell, a second expression construct can be used in accordance with the present invention. For example, the prenyltransferase or tocopherol cyclase expression construct can be introduced into a host cell in conjunction with a second expression construct having a nucleotide sequence for a protein involved in tocopherol biosynthesis.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region (s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride, et al. (*Plant Mol. Biol.* (1 990) 14:269–276), wherein the pRiHRI (Jouanin, et al., *Mol. Gen. Genet.* (1985) 201:370–374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the prenyltransferase or tocopherol cyclase expression construct, or alternatively, transformed plants, one expressing the prenyltransferase or tocopherol cyclase construct and one expressing the second construct, can be crossed to bring the constructs together in the same plant.

Transgenic plants of the present invention may be produced from tissue culture, and subsequent generations grown from seed. Alternatively, transgenic plants may be grown using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus,with apomictic reproduction, heterozygous transgenic plants can maintain their genetic fidelity throughout repeated life cycles. Methods for the production of apomictic plants are known in the art. See, U.S. Pat. No. 5,811,636, which is herein incorporated by reference in its entirety.

The nucleic acid sequences of the present invention can be used in constructs to provide for the expression of the sequence in a variety of host cells, both prokaryotic eukaryotic. Host cells of the present invention preferably include monocotyledenous and dicotyledenous plant cells.

In general, the skilled artisan is familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Maliga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

Methods for the expression of sequences in insect host cells are known in the art. Baculovirus expression vectors are recombinant insect viruses in which the coding sequence for a chosen foreign gene has been inserted behind a baculovirus promoter in place of the viral gene, e.g., polyhedrin (Smith and Summers, U.S. Pat. No. , 4,745,051, the entirety of which is incorporated herein by reference). Baculovirus expression vectors are known in the art, and are described for example in Doerfler, *Curr. Top. Microbiol. Immunol.* 131:51–68 (1968); Luckow and Summers, *Bio/Technology* 6:47–55 (1988a); Miller, *Annual Review of Microbiol.* 42:177–199 (1988); Summers, *Curr. Comm. Molecular Biology*, Cold Spring Harbor Press, Cold Spring Harbor, N.Y. (1988); Summers and Smith, *A Manual of Methods for Baculovirus Vectors and Insect Cell Culture Procedures*, Texas Ag. Exper. Station Bulletin No. 1555 (1988), the entireties of which is herein incorporated by reference)

Methods for the expression of a nucleic acid sequence of interest in a fungal host cell are known in the art. The fungal host cell may, for example, be a yeast cell or a filamentous fungal cell. Methods for the expression of DNA sequences of interest in yeast cells are generally described in "Guide to yeast genetics and molecular biology", Guthrie and Fink, eds. Methods in enzymology, Academic Press, Inc. Vol 194 (1991) and Gene expression technology", Goeddel ed, Methods in Enzymology, Academic Press, Inc., Vol 185 (1991).

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include, but are not limited to, viral promoters such as that from Simian Virus 40 (SV40) (Fiers et al., *Nature* 273:113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells are well known in the art, and may include viral replicons, or sequences which insure integration of the appropriate sequences encoding epitopes into the host genome. Plasmid vectors that greatly facilitate the construction of recombinant viruses have been described (see, for example, Mackett et al, *J Virol.* 49:857 (1984); Chakrabarti et al, *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety).

The invention also includes plants and plant parts, such as seed, oil and meal derived from seed, and feed and food products processed from plants, which are enriched in tocopherols. Of particular interest is seed oil obtained from transgenic plants where the tocopherol level has been increased as compared to seed oil of a non-transgenic plant.

The harvested plant material may be subjected to additional processing to further enrich the tocopherol content. The skilled artisan will recognize that there are many such processes or methods for refining, bleaching and degumming oil. U.S. Pat. No. 5,932,261, issued Aug. 3, 1999, discloses on such process, for the production of a natural carotene rich refined and deodorised oil by subjecting the oil to a pressure of less than 0.060 mbar and to a temperature of less than 200.degree. C. Oil distilled by this process has reduced free fatty acids, yielding a refined, deodorised oil where Vitamin E contained in the feed oil is substantially retained in the processed oil. The teachings of this patent are incorporated herein by reference.

The invention now being generally described, it will be more readily understood by reference to the following examples which are included for purposes of illustration only and are not intended to limit the present invention.

EXAMPLES

Example 1

Identification of Prenyltransferase or Tocopherol Cyclase Sequences

PSI-BLAST (Altschul, et al. (1997) *Nuc Acid Res* 25:3389–3402) profiles were generated for both the straight chain and aromatic classes of prenyltransferases. To generate the straight chain profile, a prenyl-transferase from *Porphyra purpurea* (Genbank accession 1709766) was used as a query against the NCBI non-redundant protein database. The *E. coli* enzyme involved in the formation of ubiquinone, ubiA (genbank accession 1790473) was used as a starting sequence to generate the aromatic prenyltransferase profile. These profiles were used to search public and proprietary DNA and protein data bases. In *Arabidopsis* six putative prenyltransferases of the straight-chain class were identified, ATPT1, (SEQ ID NO:9), ATPT7 (SEQ ID NO:10), ATPT8 (SEQ ID NO:11), ATPT9 (SEQ ID NO:13), ATPT10 (SEQ ID NO:14), and ATPT11 (SEQ ID NO:15), and six were identified of the aromatic class, ATPT2 (SEQ ID NO: 1), ATPT3 (SEQ ID NO:3), ATPT4 (SEQ ID NO:5), ATPT5 (SEQ ID NO:7), ATPT6 (SEQ ID NO:8), and ATPT12 (SEQ ID NO:16). Additional prenyltransferase sequences from other plants related to the aromatic class of prenyltransferases, such as soy (SEQ ID NOs: 19–23, the deduced amino acid sequence of SEQ ID NO:23 is provided in SEQ ID NO:24) and maize (SEQ ID NOs:25–29, and 31) are also identified. The deduced amino acid sequence of ZMPT5 (SEQ ID NO:29) is provided in SEQ ID NO:30.

Searches are performed on a Silicon Graphics Unix computer using additional Bioaccellerator hardware and GenWeb software supplied by Compugen Ltd. This software and hardware enables the use of the Smith-Waterman algorithm in searching DNA and protein databases using profiles as queries. The program used to query protein databases is profilesearch. This is a search where the query is not a single sequence but a profile based on a multiple alignment of amino acid or nucleic acid sequences. The profile is used to query a sequence data set, i.e., a sequence database. The profile contains all the pertinent information for scoring each position in a sequence, in effect replacing the "scoring matrix" used for the standard query searches. The program used to query nucleotide databases with a protein profile is tprofilesearch. Tprofilesearch searches nucleic acid databases using an amino acid profile query. As the search is running, sequences in the database are translated to amino acid sequences in six reading frames. The output file for tprofilesearch is identical to the output file for profilesearch except for an additional column that indicates the frame in which the best alignment occurred.

The Smith-Waterman algorithm, (Smith and Waterman (1981) supra), is used to search for similarities between one sequence from the query and a group of sequences contained in the database. E score values as well as other sequence information, such as conserved peptide sequences are used to identify related sequences.

To obtain the entire coding region corresponding to the *Arabidopsis* prenyltransferase sequences, synthetic oligonucleotide primers are designed to amplify the 5' and 3' ends of partial cDNA clones containing prenyltransferase sequences. Primers are designed according to the respective *Arabidopsis* prenyltransferase sequences and used in Rapid Amplification of cDNA Ends (RACE) reactions (Frohman et al. (1988) *Proc. Natl. Acad. Sci. USA* 85:8998–9002) using the Marathon cDNA amplification kit (Clontech Laboratories Inc, Palo Alto, Calif.).

Figure 1:
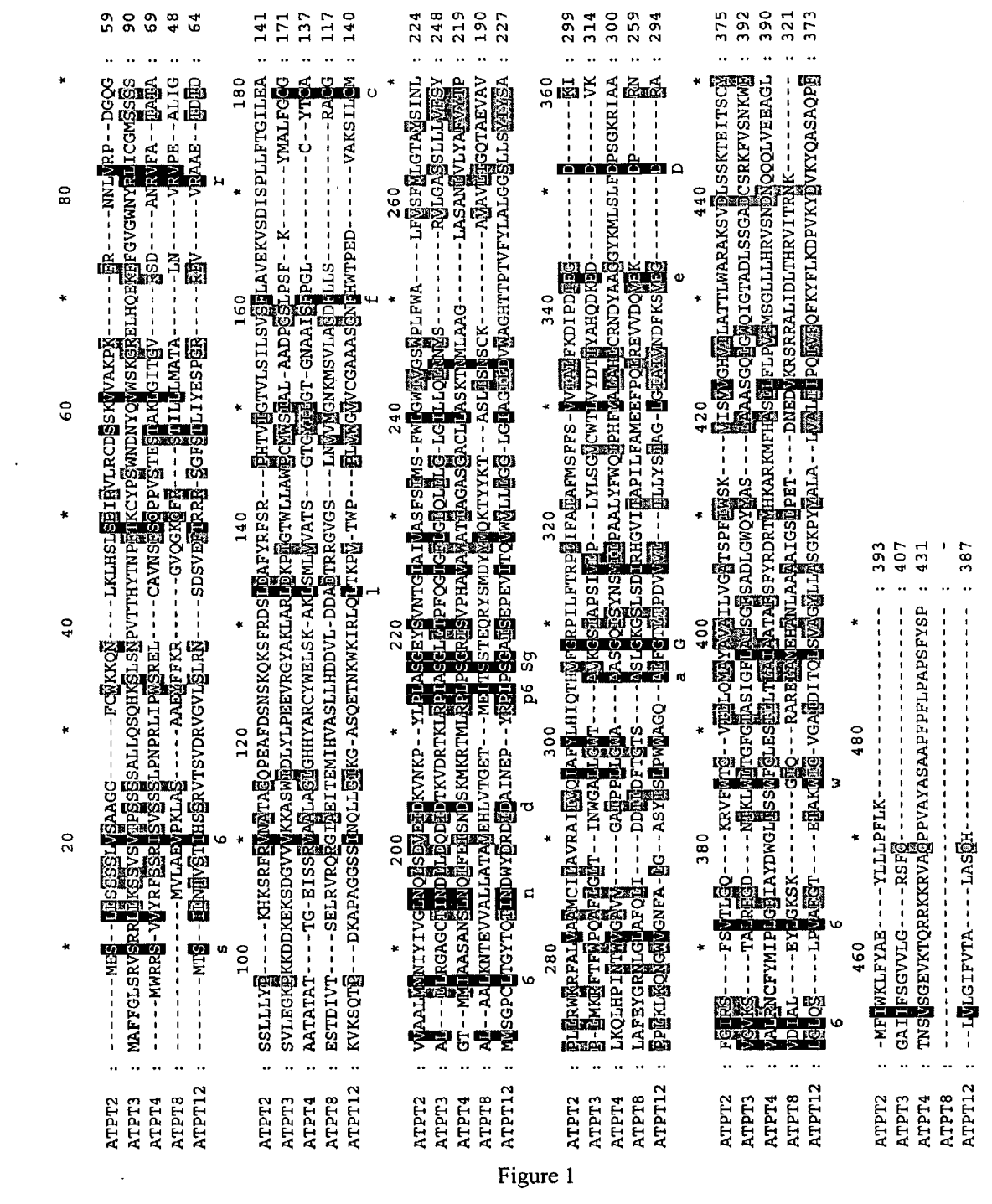

Amino acid sequence alignments between ATPT2 (SEQ ID NO:2), ATPT3 (SEQ ID NO:4), ATPT4 (SEQ ID NO:6), ATPT8 (SEQ ID NO:12), and ATPT12 (SEQ ID NO:17) are performed using ClustalW (FIG. 1), and the percent identity and similarities are provided in Table 1 below.

TABLE 1

|  |  | ATP2 | ATPT3 | ATPT4 | ATPT5 | ATPT12 |
|---|---|---|---|---|---|---|
| ATPT2 | % Identity |  | 12 | 13 | 11 | 15 |
|  | % similar |  | 25 | 25 | 22 | 32 |
|  | % Gap |  | 17 | 20 | 20 | 9 |
| ATPT3 | % Identity |  |  | 12 | 6 | 22 |
|  | % similar |  |  | 29 | 16 | 38 |
|  | % Gap |  |  | 20 | 24 | 14 |
| ATPT4 | % Identity |  |  |  | 9 | 14 |
|  | % similar |  |  |  | 18 | 29 |
|  | % Gap |  |  |  | 26 | 19 |

TABLE 1-continued

|  |  | ATP2 | ATPT3 | ATPT4 | ATPT5 | ATPT12 |
|---|---|---|---|---|---|---|
| ATPT8 | % Identity |  |  |  |  | 7 |
|  | % similar |  |  |  |  | 19 |
|  | % Gap |  |  |  |  | 20 |
| ATPT12 | % Identity |  |  |  |  |  |
|  | % similar |  |  |  |  |  |
|  | % Gap |  |  |  |  |  |

Example 2

Preparation of Prenyl Transferase Expression Constructs

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO:40) was ligated into the cloning vector pBC SK+ (Stratagene) after digestion with the restriction endonuclease BssHII to construct vector pCGN7765. Plamids pCGN3223 and pCGN7765 were digested with Not! and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAA GCTTCCTGCAGG-3' (SEQ ID NO:41) and 5'-TCGACCTGCAGGAAGCTTGCGGCCGCGGATCC-3' (SEQ ID NO:42) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTT GCGGCCGCGGATCC-3' (SEQ ID NO:43) and 5'-TCGAGGATCCGCGGCCGCAAGCTTCCTGCAGG-3' (SEQ ID NO:44) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow a fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCTT CCTGCAGGAGCT-3' (SEQ ID NO:45) and 5'-CCTGCAGGAAGCTTGCGGCCGCGGATCC-3' (SEQ ID NO:46) into SalI/SacI-digested pCGN7787. A fragment containing the d35S promoter, polylinker and tml 3' region was removed from pCGN8620 by complete digestion with Asp718I and partial digestion with NotI. The fragment was blunt-ended by filling in the 5' overhangs with Kienow fragment then ligated into pCGN5139 that had been digested with Asp718I and HindIII and blunt-ended by filling in the 5' overhangs with Kienow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTT GCGGCCGCGGATCCAGCT-3' (SEQ ID NO:47) and 5'-GGATCCGCGGCCGCAAGCTTCCTGCAGG-3' (SEQ ID NO:48) into SalI/SacI-digested pCGN7787. A fragment containing the d35S promoter, polylinker and tml 3' region was removed from pCGN862 I by complete digestion with Asp718I and partial digestion with NotI. The fragment was blunt-ended by filling in the 5' overhangs with Kienow fragment then ligated into pCGN5139 that had been digested with Asp718I and HindIII and blunt-ended by filling in the 5' overhangs with Kienow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The plasmid construct pCGN8640 is a modification of pCGN8624 described above. A 938 bp PstI fragment isolated from transposon Tn7 which encodes bacterial spectinomycin and streptomycin resistance (Fling et al. (1985), Nucleic Acids Research 13(19):7095–7106), a determinant for E. coli and Agrobacterium selection, was blunt ended with Pfu polymerase. The blunt ended fragment was ligated into pCGN8624 that had been digested with SpeI and blunt ended with Pfu polymerase. The region containing the PstI fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp AvrII-SnaBI fragment from pCGN8623 or pCGN8622, described above. The resulting plasmids were pCGN8641 and pCGN8643, respectively.

The plasmid pCGN8644 was constructed by ligating oligonucleotides 5'-GATCACCTGCAGGAAG CTTGCGGCCGCGGATCCAATGCA-3' (SEQ ID NO:49) and 5'-TTGGATCCGCGGCCGCAAGCTTCCTGCAGGT-3' (SEQ ID NO:50) into BamHI-PstI digested pCGN8640.

Synthetic oligonulceotides were designed for use in Polymerase Chain Reactions (PCR) to amplify the coding sequences of ATPT2, ATPT3, ATPT4, ATPT8, and ATPT12 for the preparation of expression constructs and are provided in Table 2 below.

TABLE 2

| Name | Restriction Site | Sequence | SEQ ID NO: |
|---|---|---|---|
| ATPT2 5' | NotI | GGATCCGCGGCCGCACAATGGAGTC TCTGCTCTCTAGTTCT | 51 |
| ATPT2 3' | SseI | GGATCCTGCAGGTCACTTCAAAAAA GGTAACAGCAAGT | 52 |
| ATPT3 5' | NotI | GGATCCGCGGCCGCACAATGGCGTT TTTTGGGCTCTCCCGTGTTT | 53 |
| ATPT3 3' | SseI | GGATCCTGCAGGTTATTGAAAACTT CTTCCAAGTACAACT | 54 |
| ATPT4 5' | NotI | GGATCCGCGGCCGCACAATGTGGCG AAGATCTGTTGTT | 55 |
| ATPT4 3' | SseI | GGATCCTGCAGGTCATGGAGAGTAG AAGGAAGGAGCT | 56 |
| ATPT8 5' | NotI | GGATCCGCGGCCGCACAATGGTACT TGCCGAGGTTCCAAAGCTTGCCTCT | 57 |
| ATPT8 3' | SseI | GGATCCTGCAGGTCACTTGTTTCTG GTGATGACTCTAT | 58 |
| ATPT12 5' | NotI | GGATCCGCGGCCGCACAATGACTTC GATTCTCAACACT | 59 |
| ATPT12 3' | SseI | GGATCCTGCAGGTCAGTGTTGCGAT GCTAATGCCGT | 60 |

The coding sequences of ATPT2, ATPT3, ATPT4, ATPT8, and ATPT12 were all amplified using the respective PCR primers shown in Table 2 above and cloned into the TopoTA vector (Invitrogen). Constructs containing the respective prenyltransferase sequences were digested with NotI and Sse83871 and cloned into the turbobinary vectors described above.

The sequence encoding ATPT2 prenyltransferase (SEQ ID NO: 1) was cloned in the sense orientation into pCGN8640 to produce the plant transformation construct pCGN10800 (FIG. 2). The ATPT2 sequence is under control of the 35S promoter.

Figure 3:
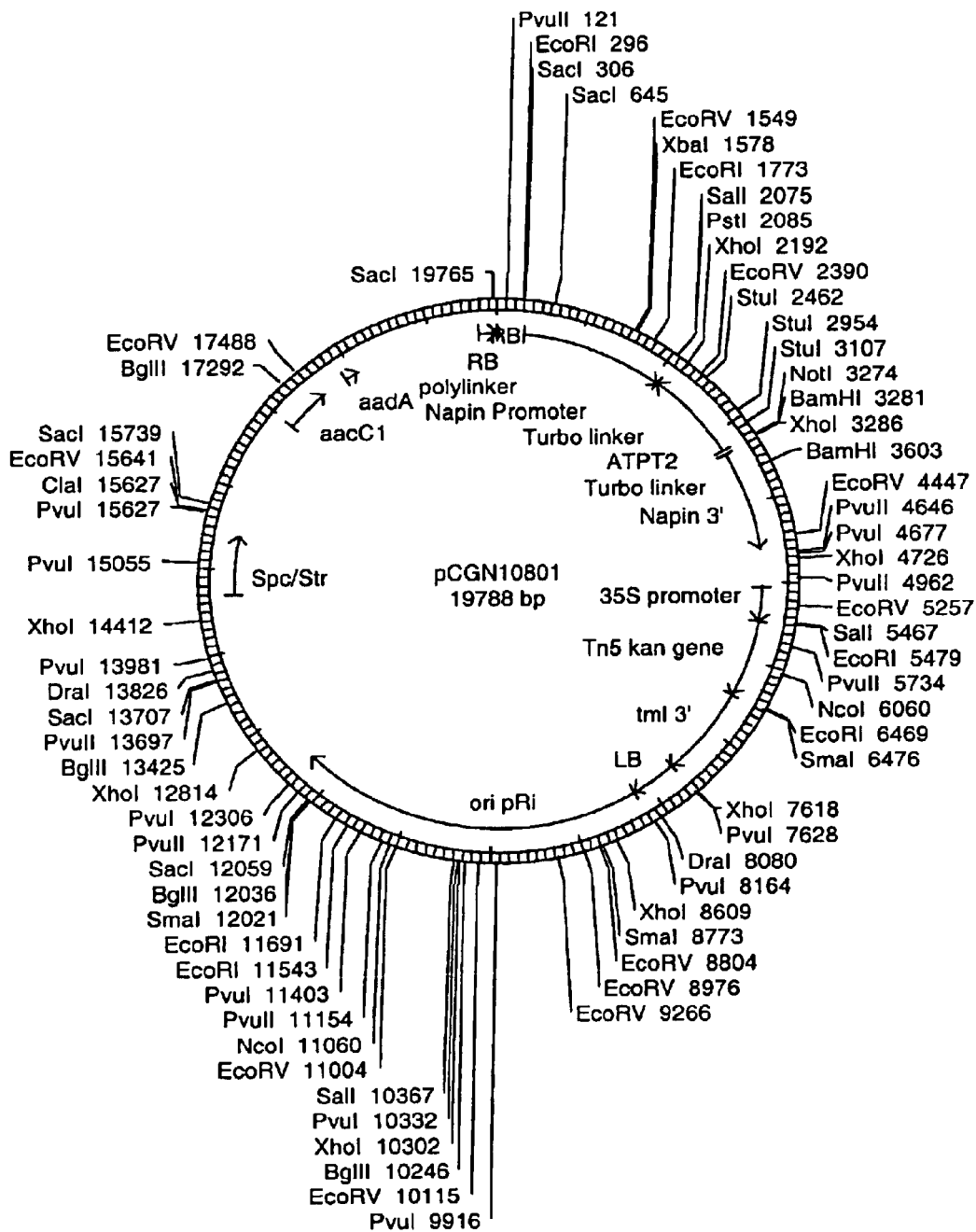
FIG. 3 provides a schematic picture of the expression construct pCGN10801.

The ATPT2 sequence (SEQ ID NO: 1) was also cloned in the antisense orientation into the construct pCGN8641 to create pCGN10801 (FIG. 3). This construct provides for the antisense expression of the ATPT2 sequence from the napin promoter.

The ATPT2 coding sequence (SEQ ID NO: 1) was also cloned in the sense orientation into the vector pCGN9643 to create the plant transformation construct pCGN10822.

Figure 4:
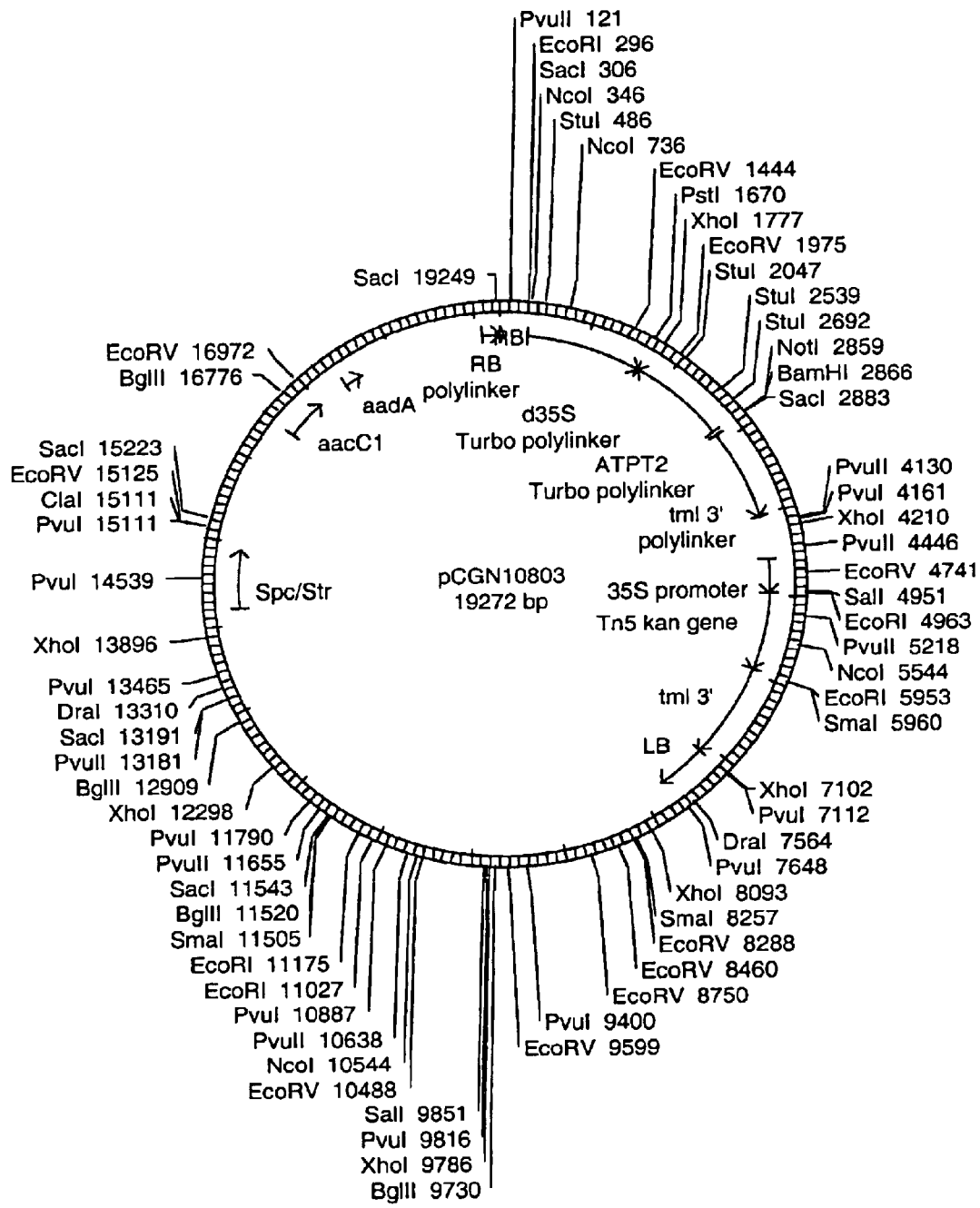
FIG. 4 provides a schematic picture of the expression construct pCGN10803.

The ATPT2 coding sequence (SEQ ID NO: 1) was also cloned in the antisense orientation into the vector pCGN8644 to create the plant transformation construct pCGN10803 (FIG. 4).

Figure 5:
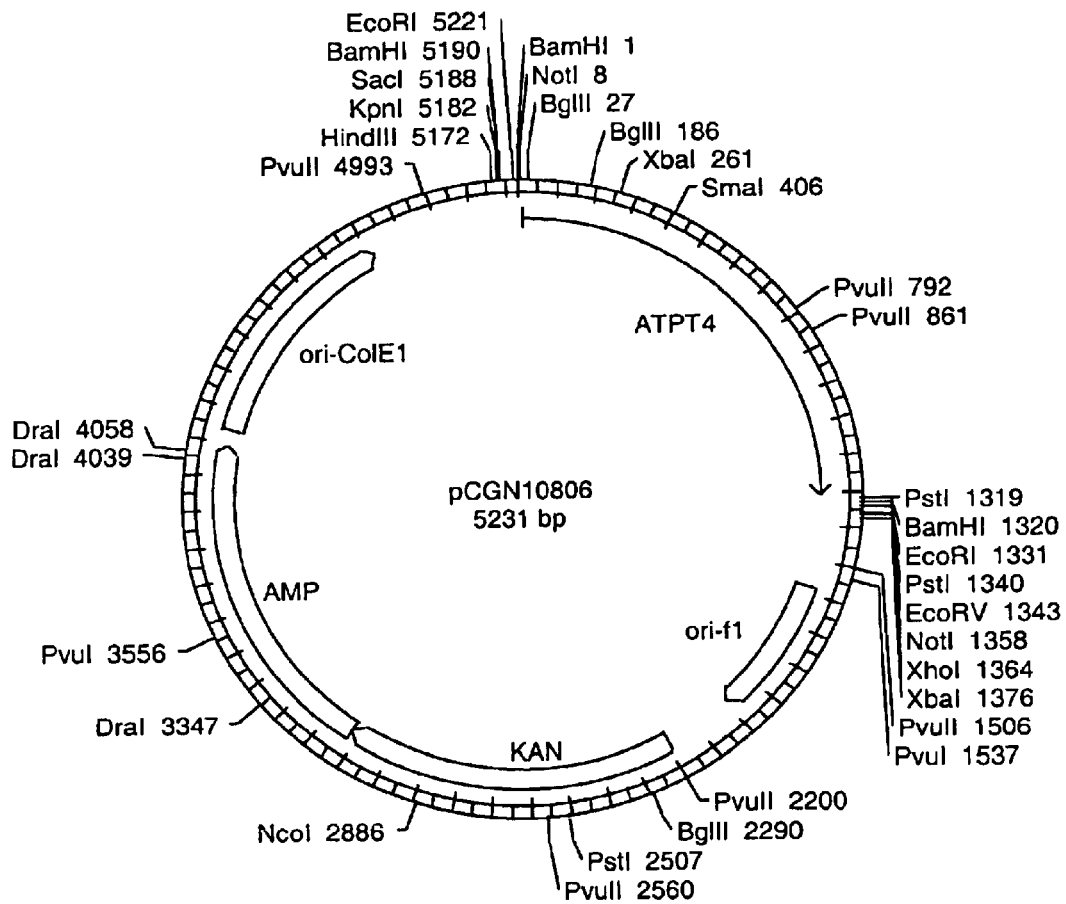
FIG. 5 provides a schematic picture of the construct pCGN10806.
Figure 6:
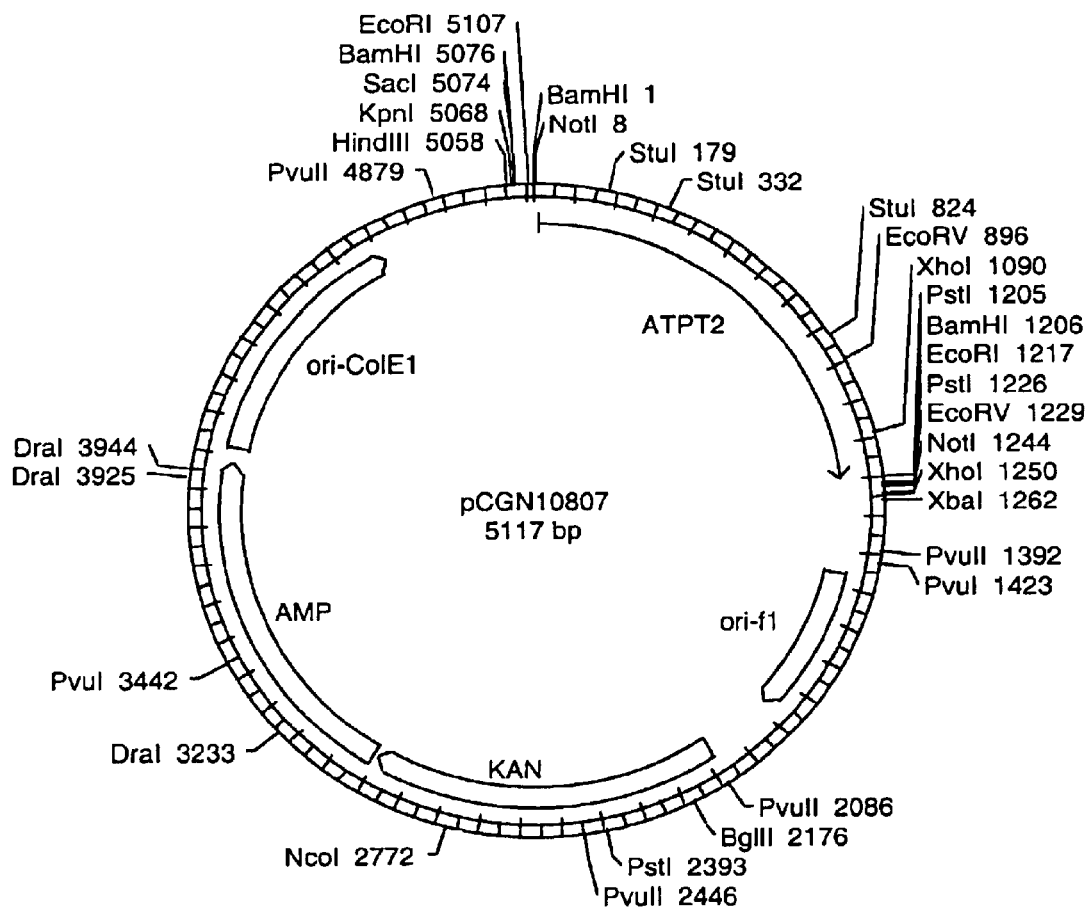
FIG. 6 provides a schematic picture of the construct pCGN10807.
Figure 7:
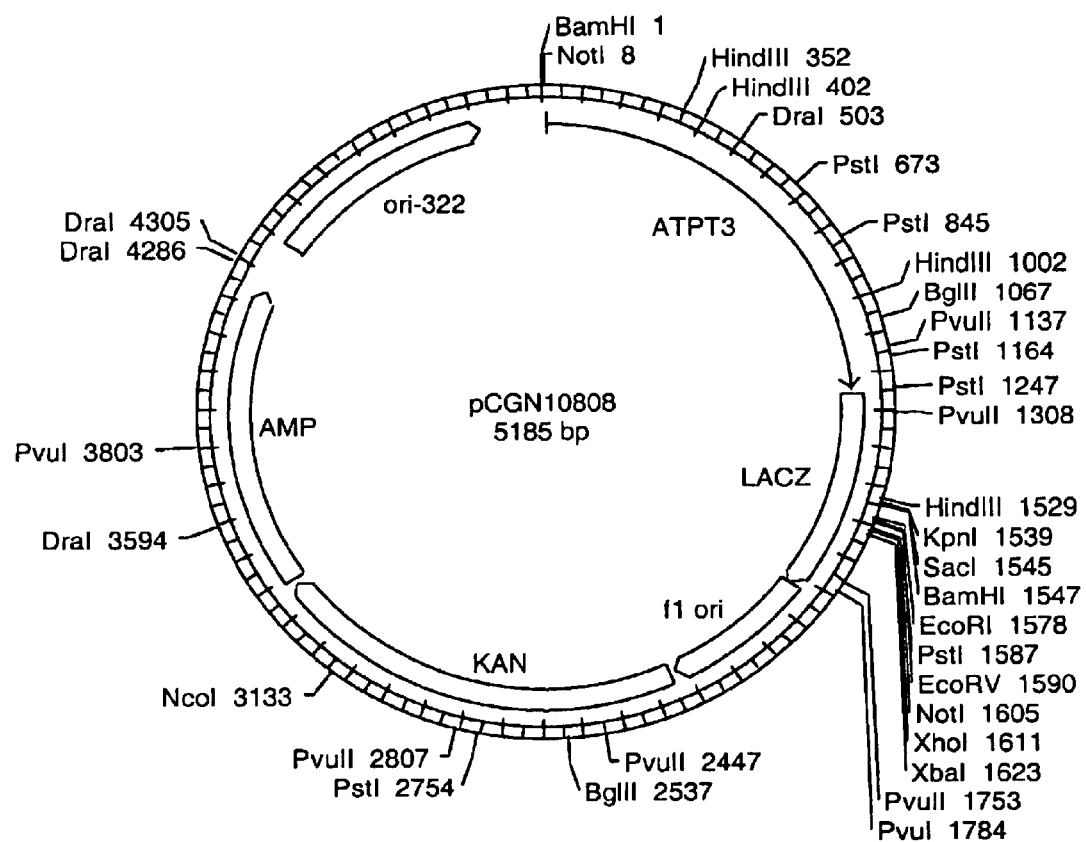
FIG. 7 provides a schematic picture of the construct pCGN10808.
Figure 8:
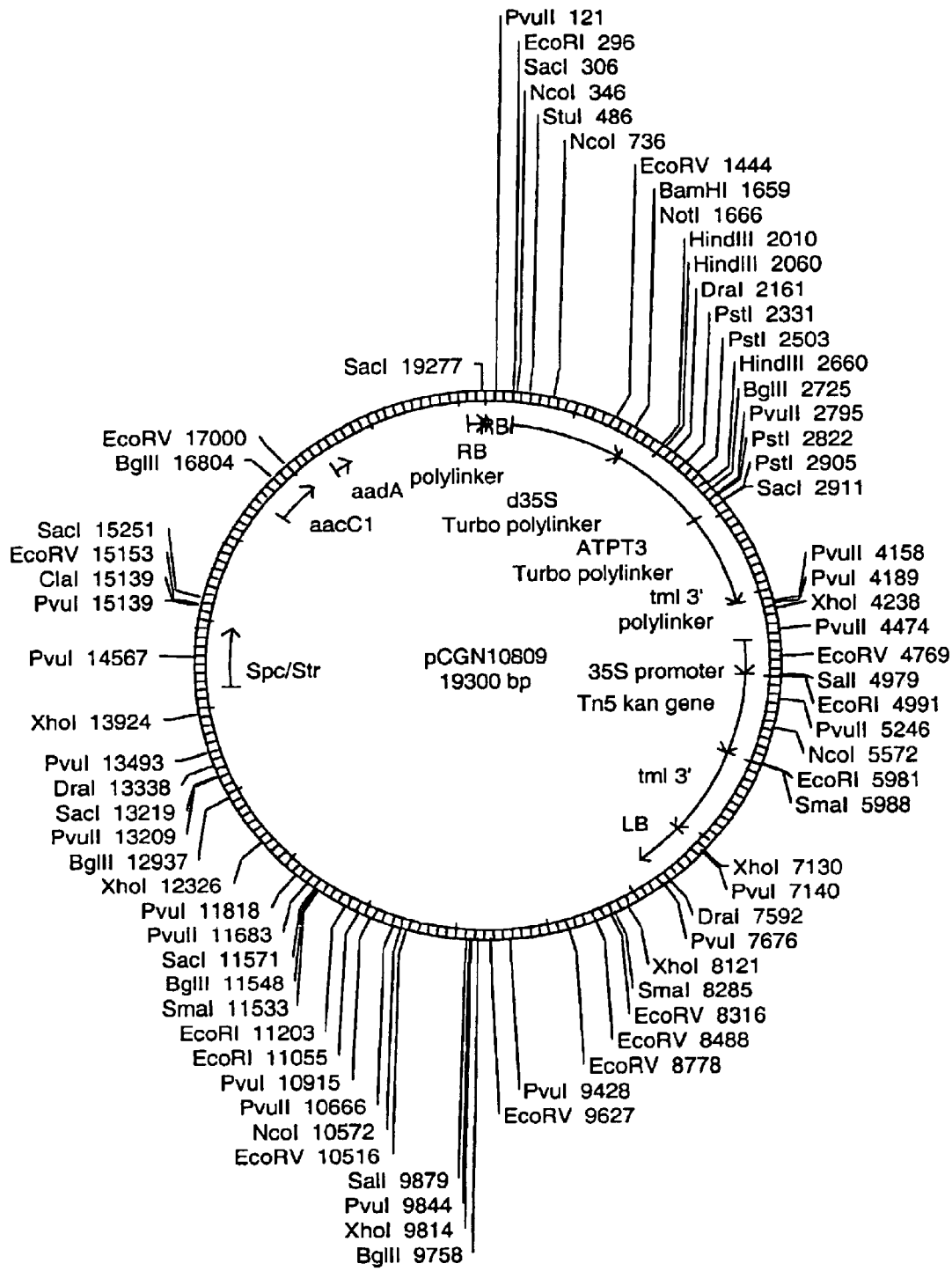
FIG. 8 provides a schematic picture of the expression construct pCGN10809.
Figure 9:
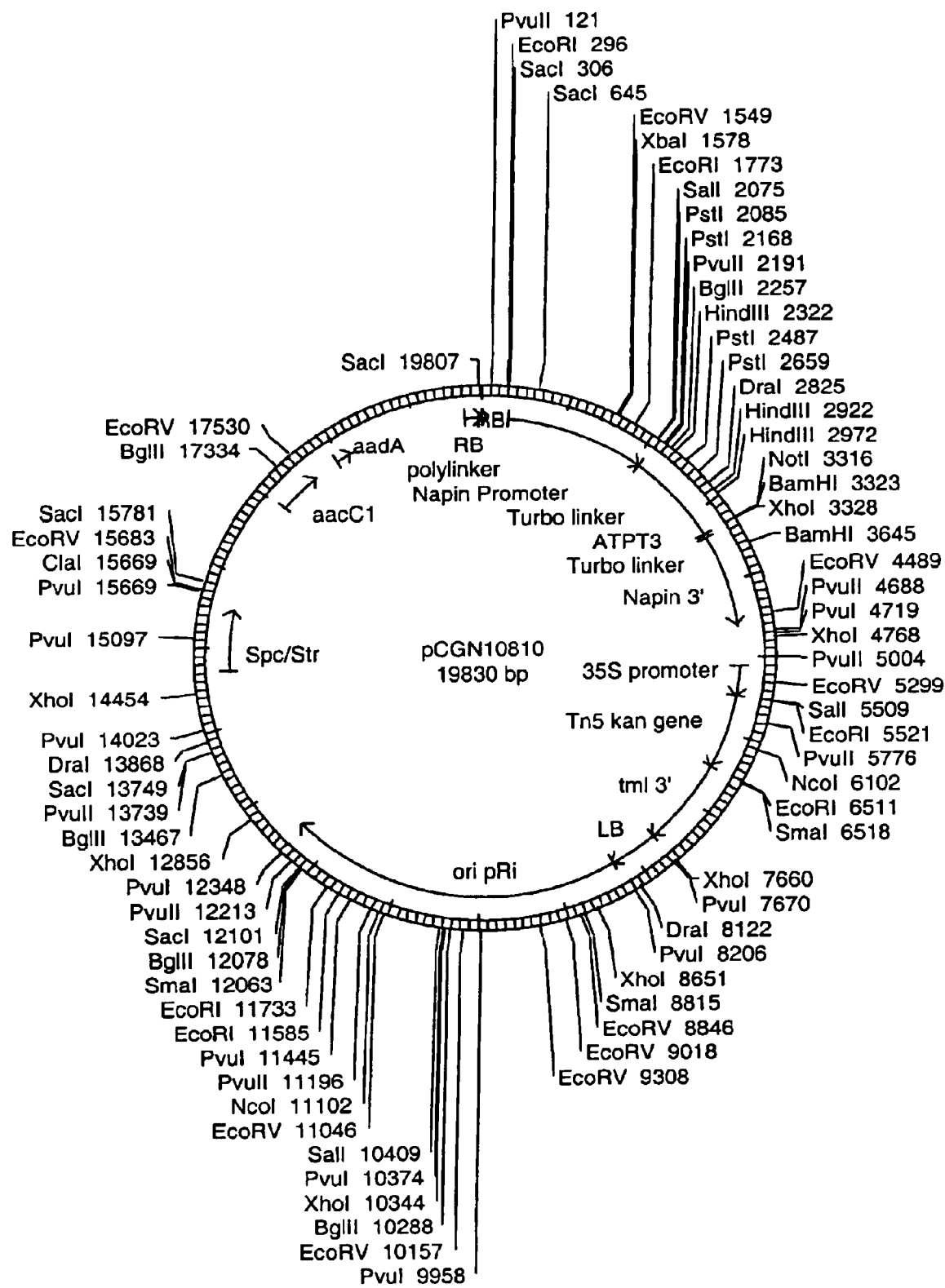
FIG. 9 provides a schematic picture of the expression construct pCGN10810.
Figure 10:
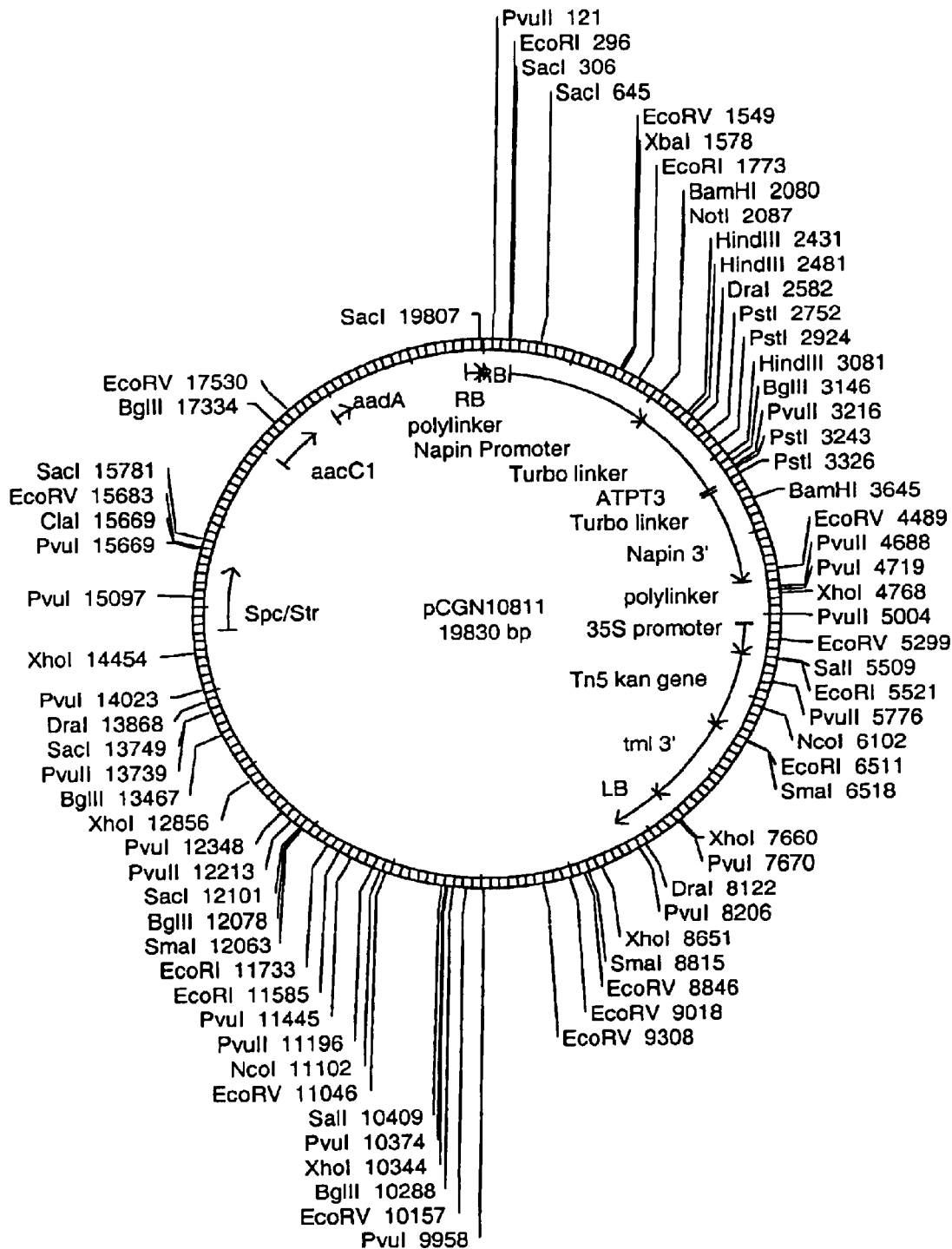
FIG. 10 provides a schematic picture of the expression construct pCGN10811.
Figure 11:
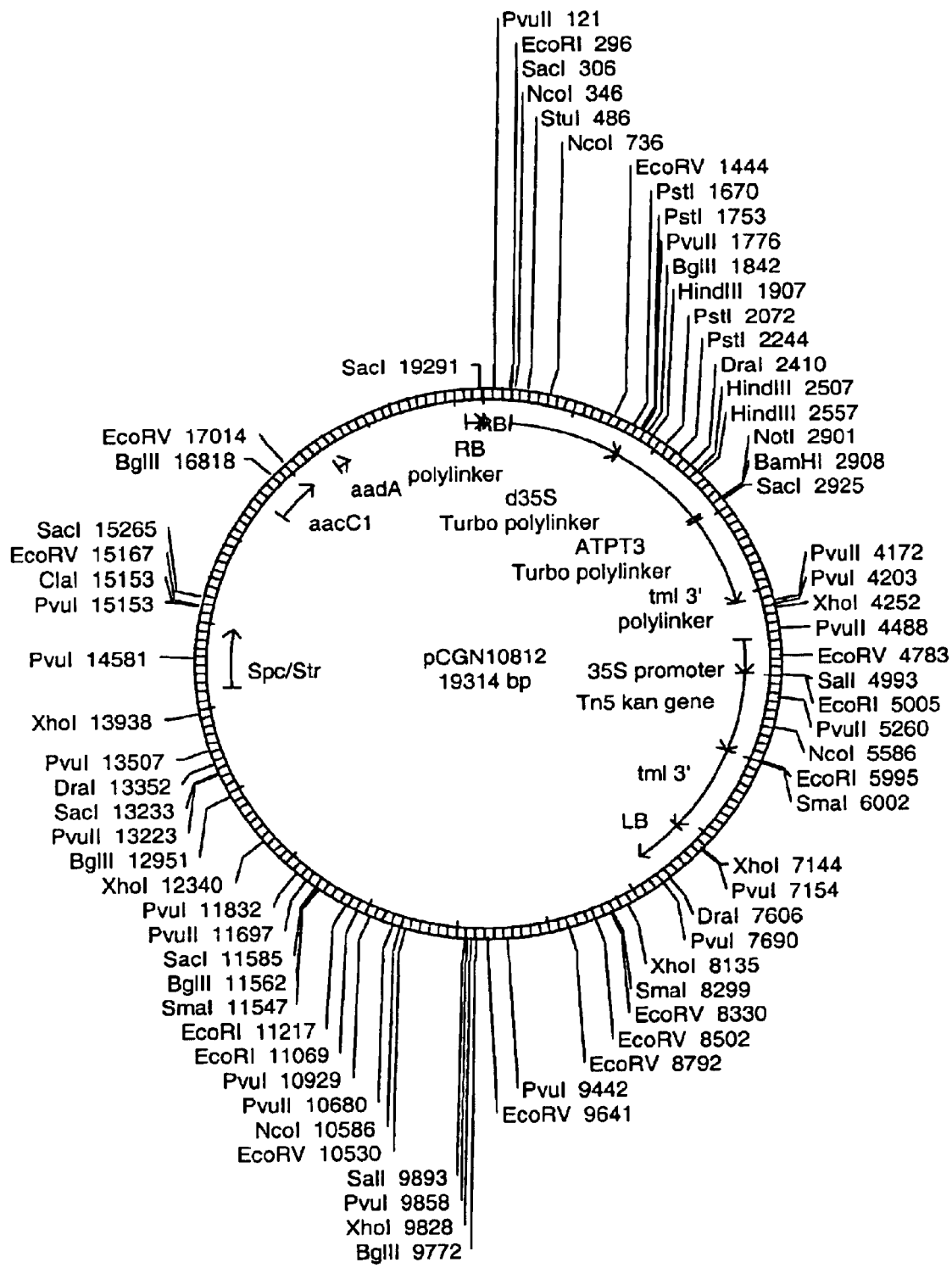
FIG. 11 provides a schematic picture of the expression construct pCGN10812.
Figure 12:
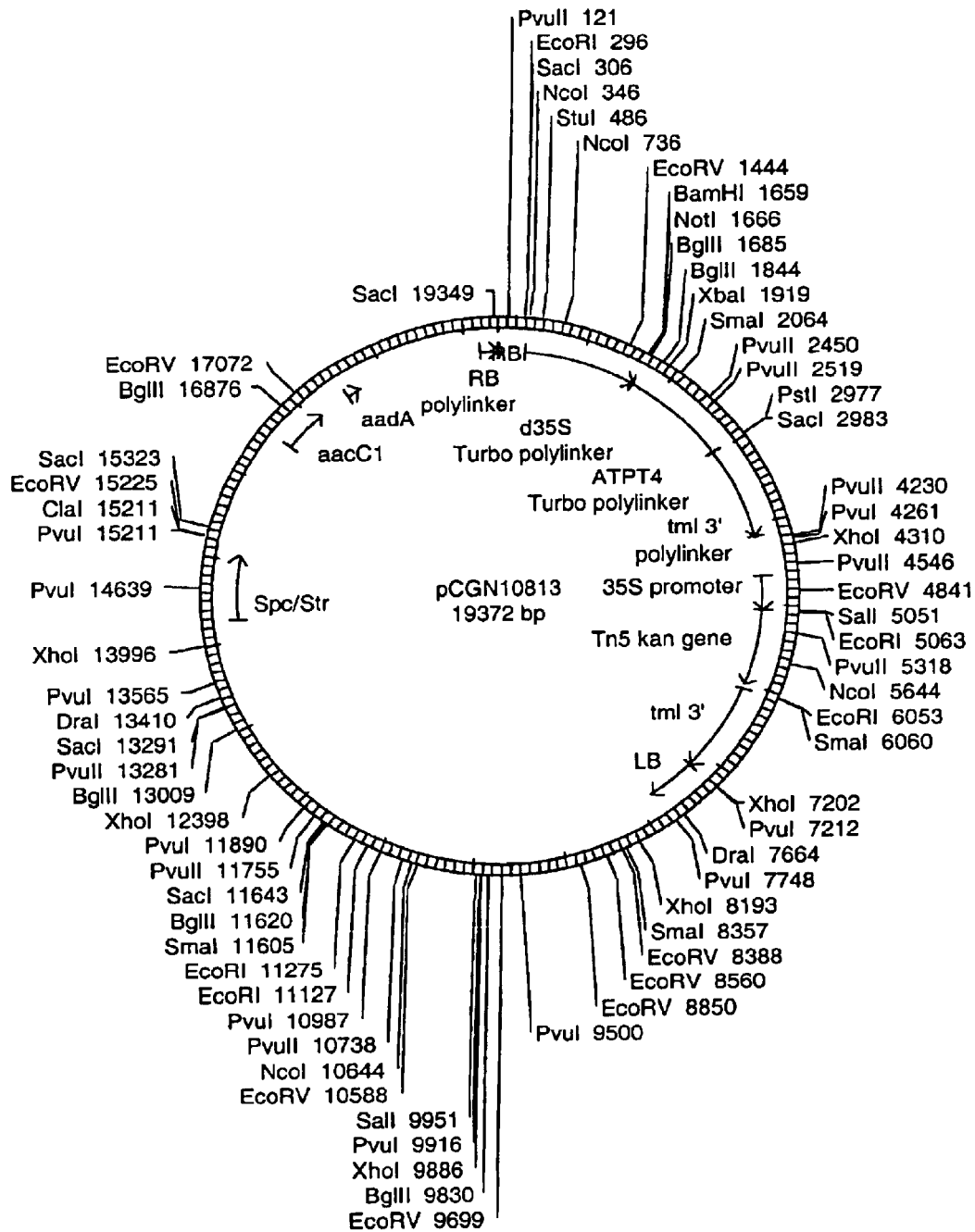
FIG. 12 provides a schematic picture of the expression construct pCGN10813.
Figure 13:
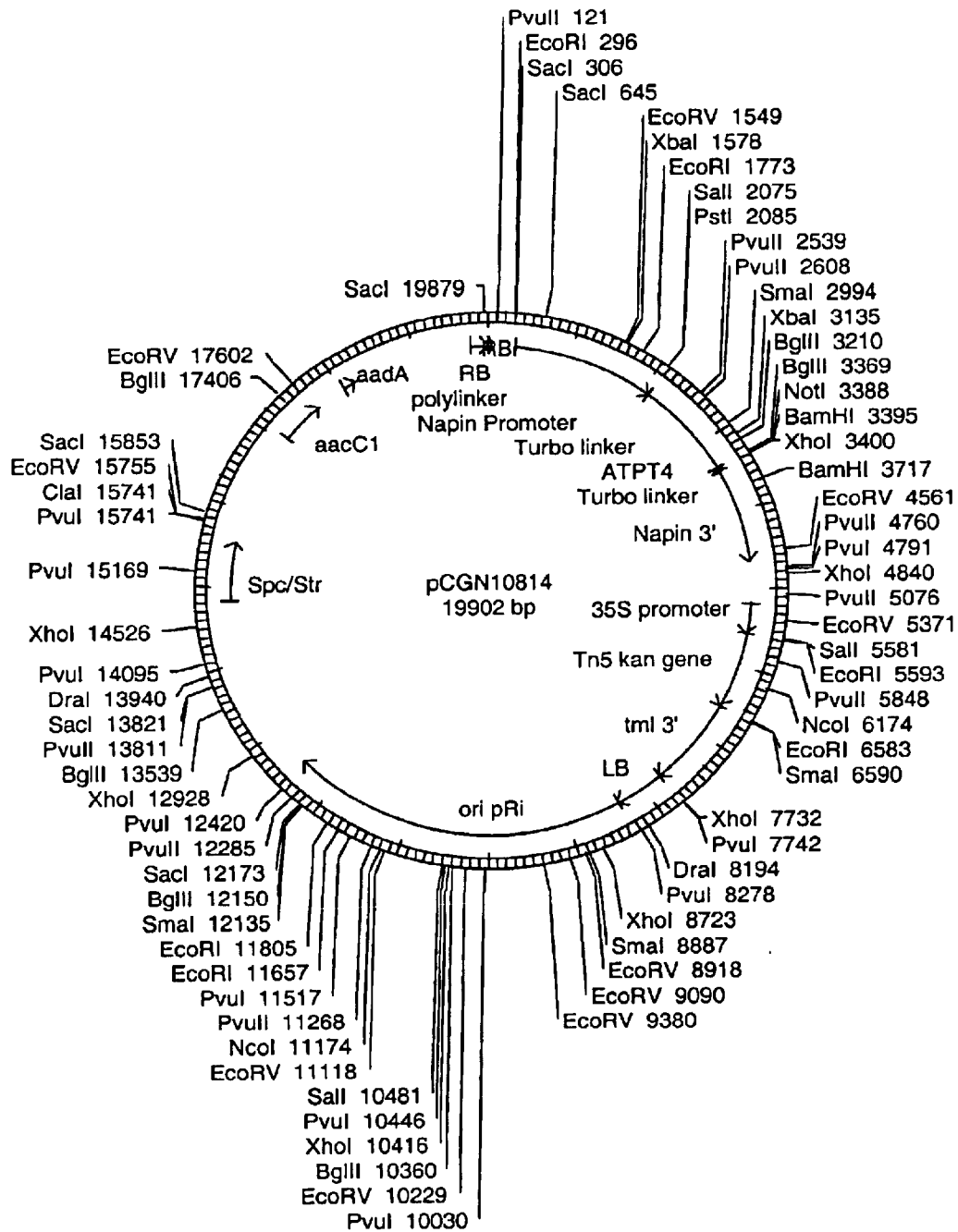
FIG. 13 provides a schematic picture of the expression construct pCGN10814.
Figure 14:
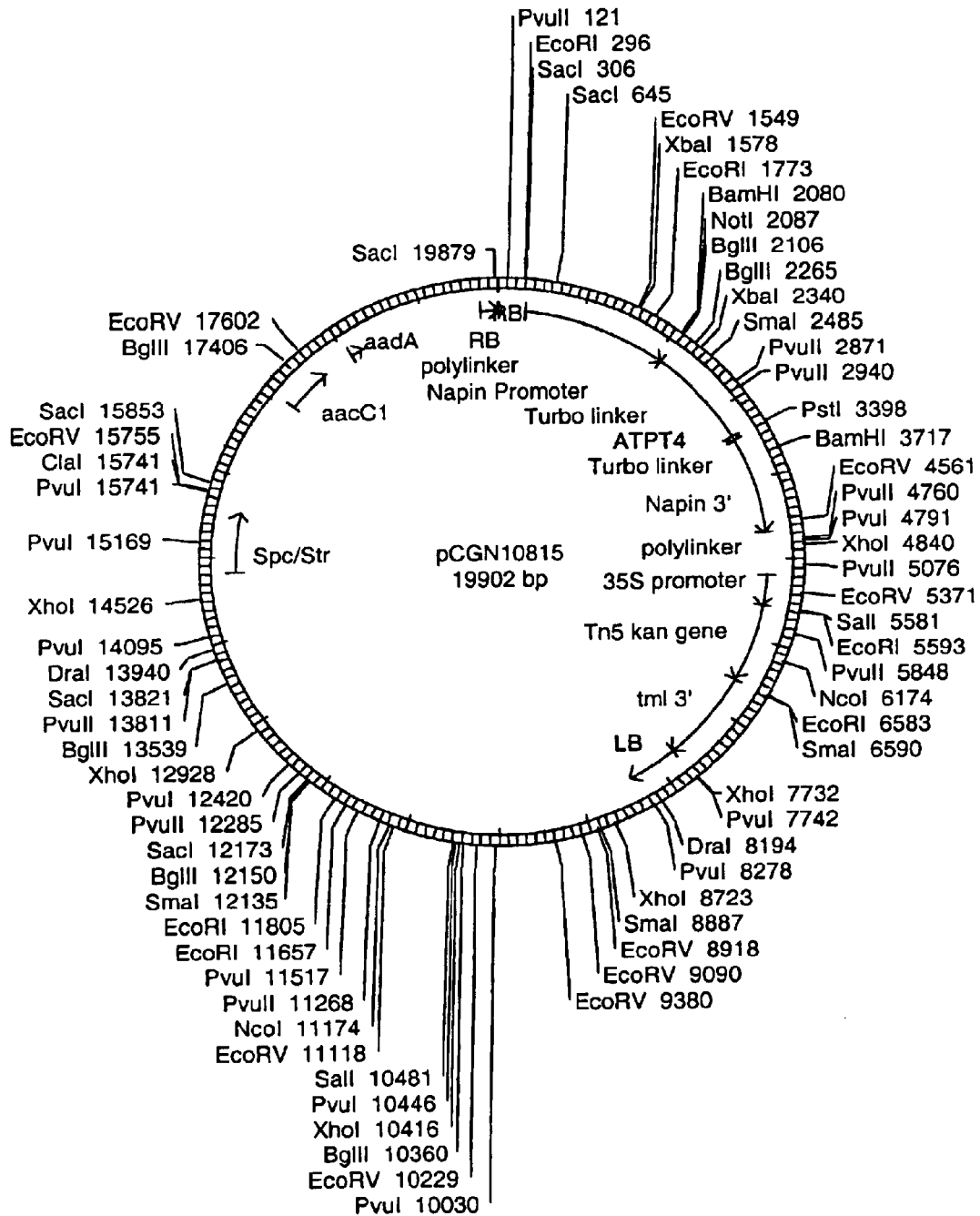
FIG. 14 provides a schematic picture of the expression construct pCGN10815.
Figure 15:
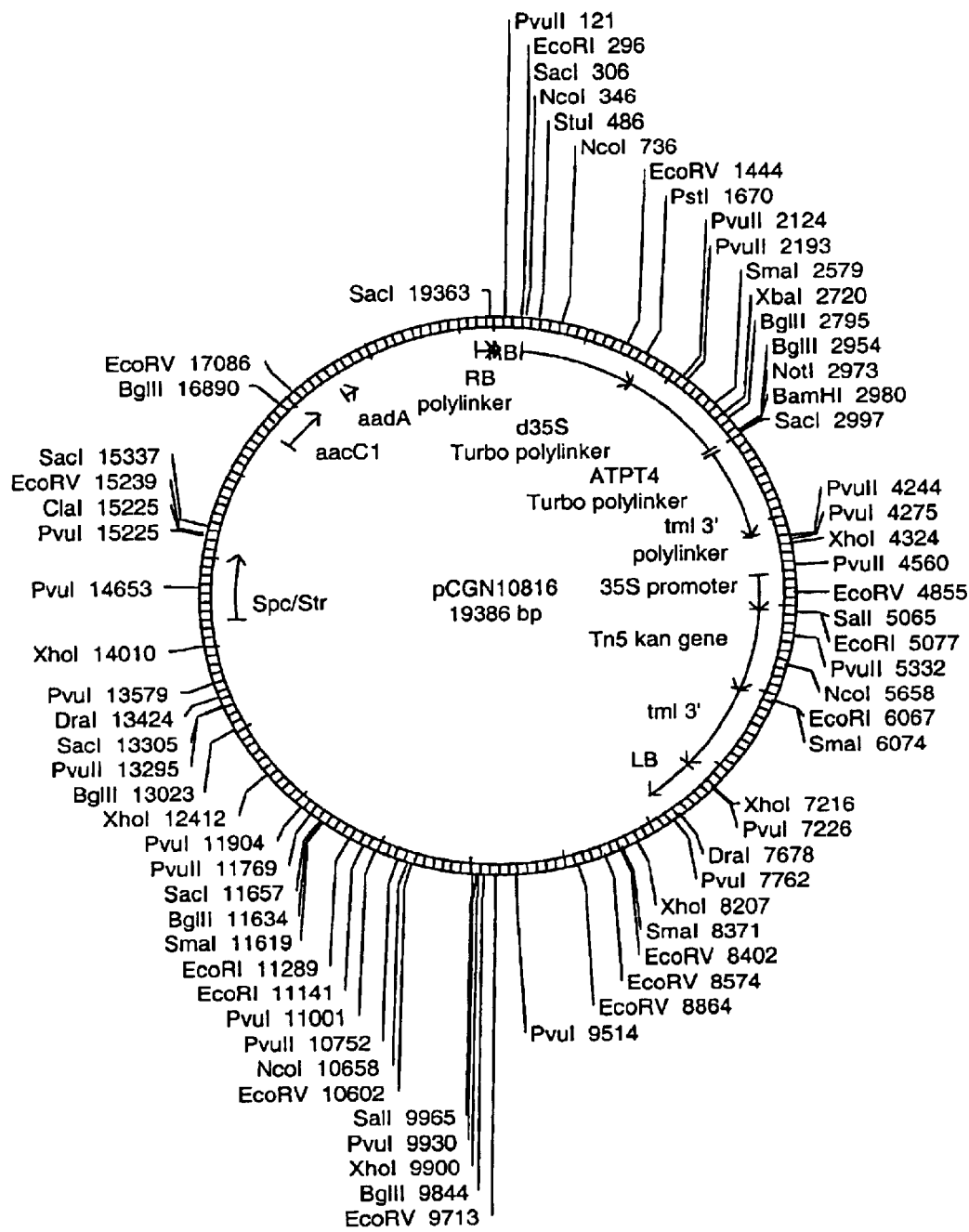
FIG. 15 provides a schematic picture of the expression construct pCGN10816.
Figure 16:
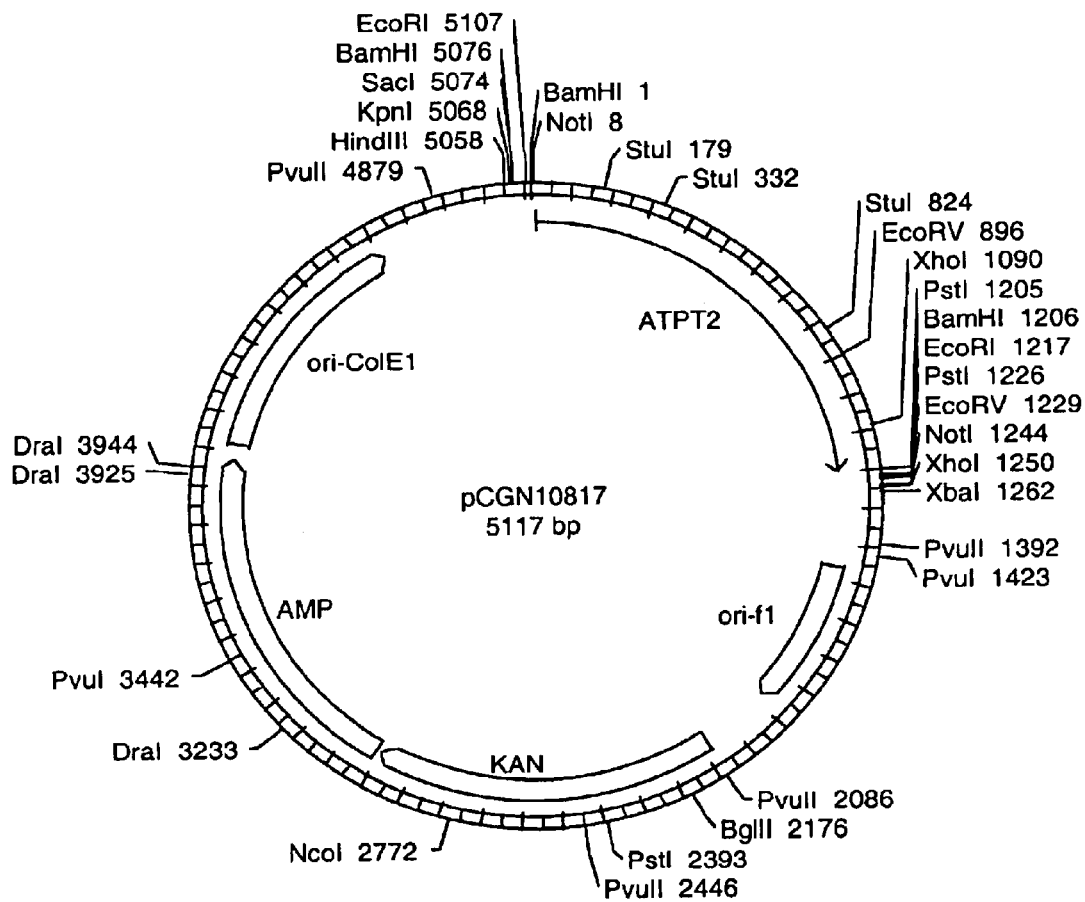
FIG. 16 provides a schematic picture of the expression construct pCGN10817.
Figure 17:
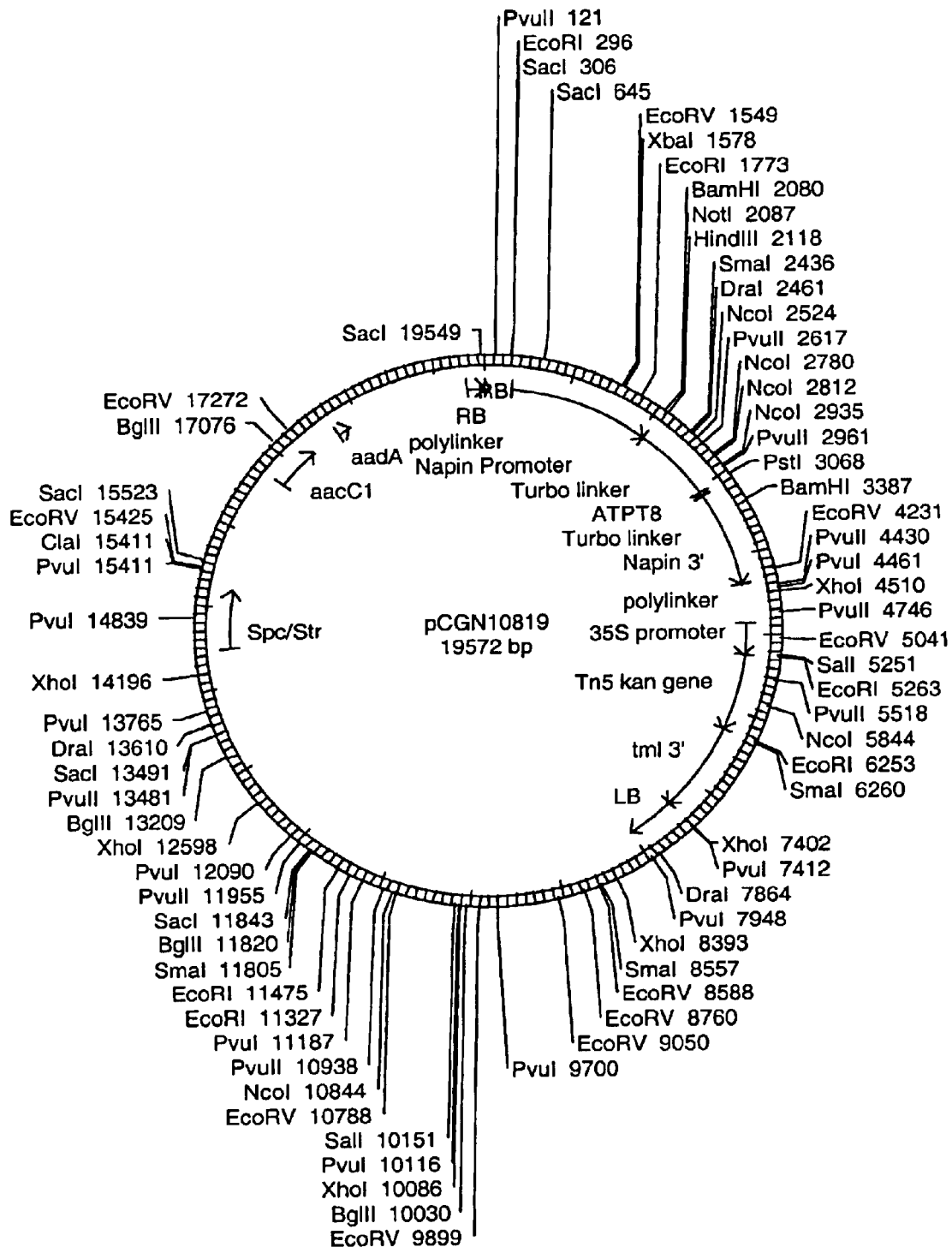
FIG. 17 provides a schematic picture of the expression construct pCGN10819.
Figure 18:
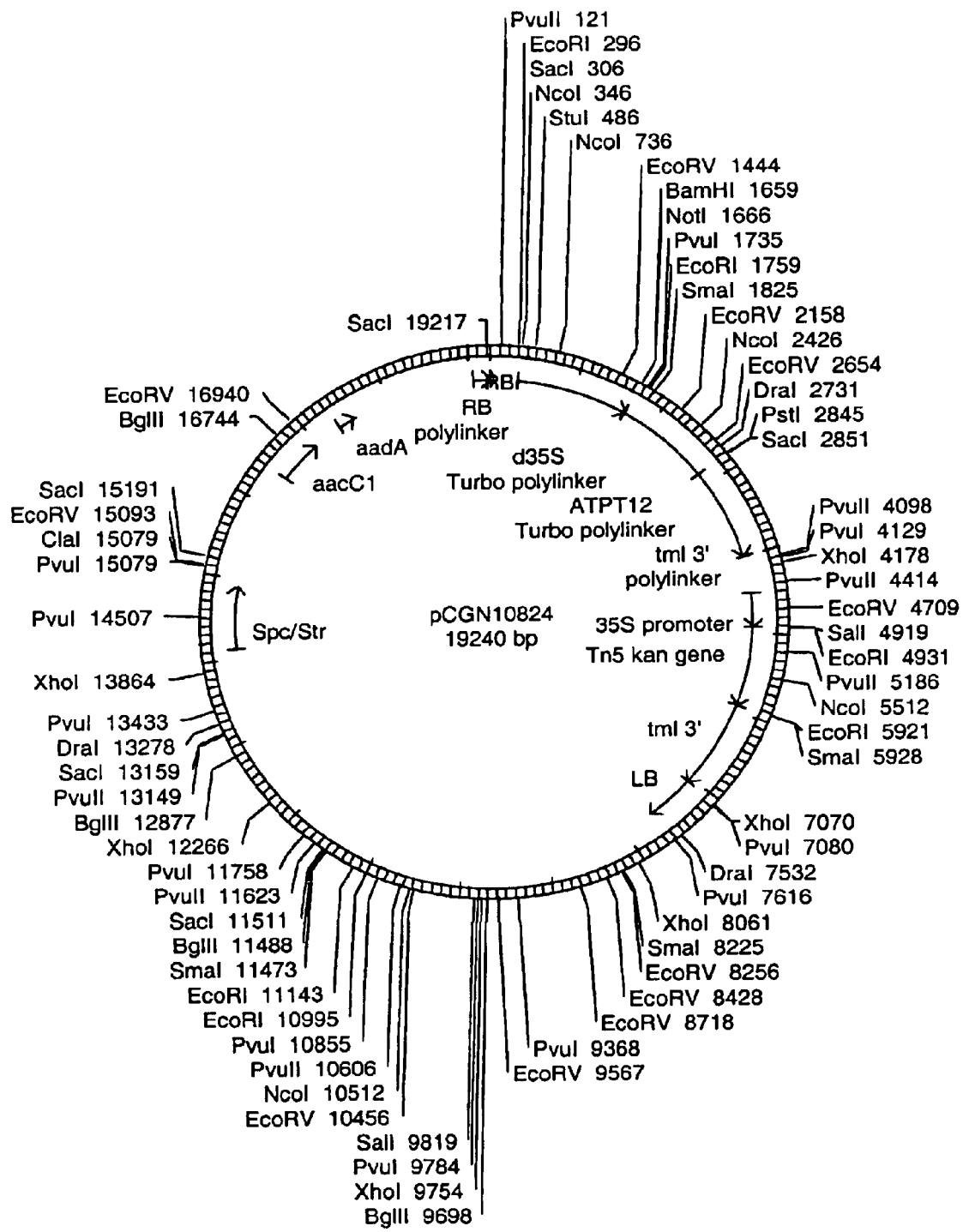
FIG. 18 provides a schematic picture of the expression construct pCGN10824.
Figure 19:
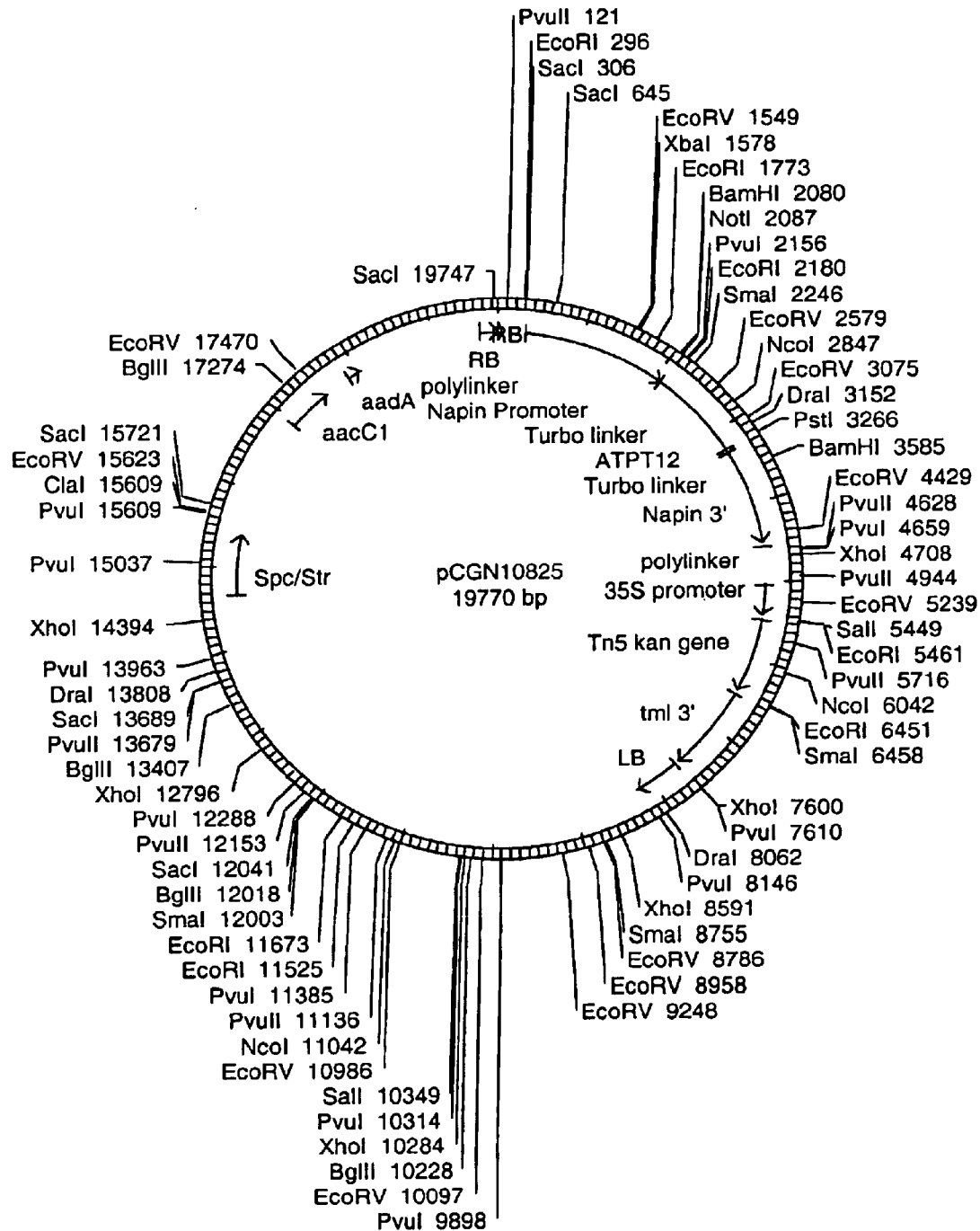
FIG. 19 provides a schematic picture of the expression construct pCGN10825.
Figure 20:
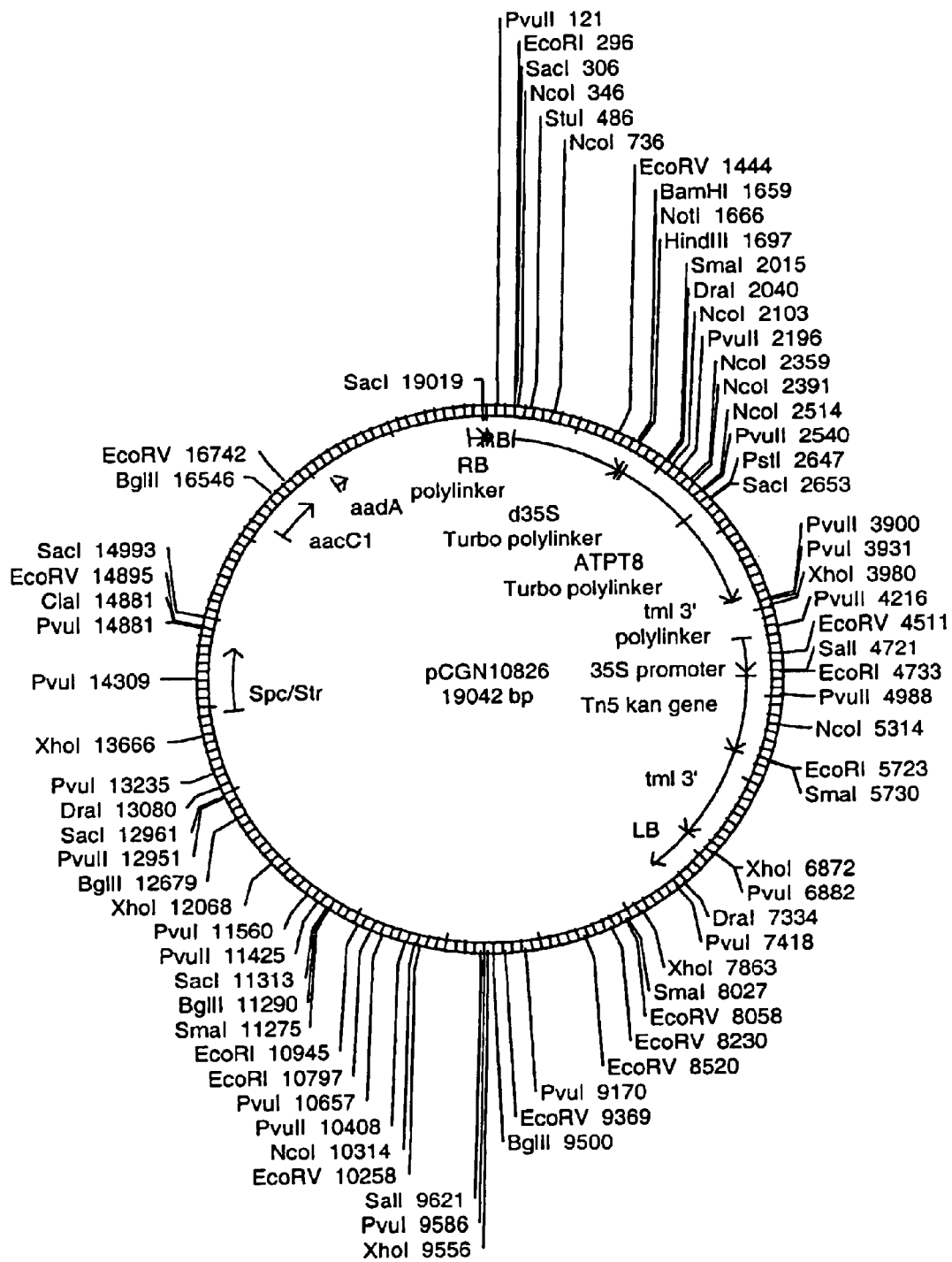
FIG. 20 provides a schematic picture of the expression construct pCGN10826.

The ATPT4 coding sequence (SEQ ID NO: 5) was cloned into the vector pCGN864 to create the plant transformation construct pCGN10806 (FIG. 5). The ATPT2 coding sequence (SEQ ID NO: 1) was cloned into the vector TopoTA™ vector from Invitrogen, to create the plant transformation construct pCGN10807 (FIG. 6). The ATPT3 (SEQ ID NO: 3) coding sequence was cloned into the TopoTA vector to create the plant transformation construct pCGN10808 (FIG. 7). The ATPT3 (SEQ ID NO: 3) coding sequence was cloned in the sense orientation into the vector pCGN8640 to create the plant transformation construct pCGN10809 (FIG. 8). The ATPT3 (SEQ ID NO: 3) coding sequence was cloned in the antisense orientation into the vector pCGN8641 to create the plant transformation construct pCGN10810 (FIG. 9). The ATPT3 (SEQ ID NO: 3) coding sequence was cloned into the vector pCGN8643 to create the plant transformation construct pCGN10811 (FIG. 10). The ATPT3 (SEQ ID NO: 3) coding sequence was cloned into the vector pCGN8644 to create the plant transformation construct pCGN10812 (FIG. 11). The ATPT4 (SEQ ID NO: 5) coding sequence was cloned into the vector pCGN8640 to create the plant transformation construct pCGN10813 (FIG. 12). The ATPT4 (SEQ ID NO: 5) coding sequence was cloned into the vector pCGN8641 to create the plant transformation construct pCGN10814 (FIG. 13). The ATPT4 (SEQ ID NO: 5) coding sequence was cloned into the vector pCGN8643 to create the plant transformation construct pCGN10815 (FIG. 14). The ATPT4 (SEQ ID NO: 5) coding sequence was cloned in the antisense orientation into the vector pCGN8644 to create the plant transformation construct pCGN10816 (FIG. 15). The ATPT8 (SEQ ID NO: 11) coding sequence was cloned in the sense orientation into the vector pCGN8643 to create the plant transformation construct pCGN10819 (FIG. 17). The ATPT12 (SEQ ID NO: 16) coding sequence was cloned into the vector pCGN8640 to create the plant transformation construct pCGN10824 (FIG. 18). The ATPT12 (SEQ D NO: 16) coding sequence was cloned into the vector pCGN8643 to create the plant transformation construct pCGN10825 (FIG. 19). The ATPT8 (SEQ ED NO: 11) coding sequence was cloned into the vector pCGN8640 to create the plant transformation construct pCGN10826 (FIG. 20).

Example 3

Plant Transformation with Prenyl Transferase Constructs

Transgenic *Brassica* plants are obtained by *Agrobacterium*-mediated transformation as described by Radke et al. (*Theor. Appl. Genet.* (1988) 75:685–694; *Plant Cell Reports* (1992) 11:499–505). Transgenic *Arabidopsis thaliano* plants may be obtained by *Agrobacterium*-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C.R.Acad.Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain nuclear transformed plants.

Example 4

Identification of Additional Prenyltransferases

Additional BLAST searches were performed using the ATPT2 sequence (SEQ ID NO: 1), a sequence in the class of aromatic prenyltransferases. ESTs, and in some cases, full-length coding regions, were identified in proprietary DNA libraries.

Soy full-length homologs to ATPT2 were identified by a combination of BLAST (using ATPT2 protein sequence) and 5' RACE. Two homologs resulted (SEQ ID NO:95 and SEQ ID NO:96). Translated amino acid sequences are provided by SEQ ID NO:97 and SEQ ID NO:98.

A rice est ATPT2 homolog is shown in SEQ ID NO:99 (obtained from BLAST using the wheat ATPT2 homolog).

Other homolog sequences were obtained using ATPT2 and PSI-BLAST, including est sequences from wheat (SEQ ID NO:100), leek (SEQ ID NOs:101 and 102), canola (SEQ ID NO:103), corn (SEQ ID NOs:104, 105 and 106), cotton (SEQ ID NO:107) and tomato (SEQ ID NO: 108).

A PSI-Blast profile generated using the *E. coli* ubiA (genbank accession 1790473) sequence was used to analyze the *Synechocystis* genome. This analysis identified 5 open reading frames (ORFs) in the *Synechocystis* genome that were potentially prenyltransferases; slr0926 (annotated as ubiA (4-hydroxybenzoate-octaprenyltransferase, SEQ ID NO:32)), sll1899 (annotated as ctaB (cytocrome c oxidase folding protein, SEQ ID NO:33)), slr0056 (annotated as g4 (chlorophyll synthase 33 kd subunit, SEQ ID NO:34)), slr1518 (annotated as menA (menaquinone biosynthesis protein, SEQ ID NO:35)), and slr1736 (annotated as a hypothetical protein of unknown function (SEQ ID NO: 37)).

4A. *Synechocystis* Knock-outs

To determine the functionality of these ORFs and their involvement, if any, in the biosynthesis of tocopherols, knockouts constructs were made to disrupt the ORF identified in *Synechocystis*.

Synthetic oligos were designed to amplify regions from the 5' (5'-TAATGTGTACATTGTCGGCCTC (1 7365') (SEQ ID NO:61) and 5'-GCAATGTAACATCAGA GATTTTGAGACACAACGTGGCTTTCCA- CAATTCCCCGCACC GTC (1736kanpr1)) (SEQ ID NO:62) and 3'(5'- AGGCTAATAAGCACAAATGGGA (17363') (SEQ ID NO:63) and 5'-GGTATGAGTCAGCAACACCTTCTT CACGAGGCAGACCTCAGC GGAATTGGTTTAGGT- TATCCC (1736kanpr2)) (SEQ ID NO:64) ends of the sir 736 ORF. The 1736kanpr1 and 1736kanpr2 oligos contained 20 bp of homology to the slr1736 ORF with an additional 40 bp of sequence homology to the ends of the kanamycin resistance cassette. Separate PCR steps were completed with these oligos and the products were gel purified and combined with the kanamycin resistance gene from puc4K (Pharmacia) that had been digested with HincII and gel purified away from the vector backbone. The combined fragments were allowed to assemble without oligos under the following conditions: 94° C. for 1 min, 55° C. for 1 min, 72° C. for 1 min plus 5 seconds per cycle for 40 cycles using pfu polymerase in 100 ul reaction volume (Zhao, H and Arnold (1997) *Nucleic Acids Res*. 25(6):1307–1308). One microliter or five microliters of this assembly reaction was then amplified using 5' and 3' oligos nested within the ends of the ORF fragment, so that the resulting product contained 100–200 bp of the 5' end of the *Synechocystis* gene to be knocked out, the kanamycin resistance cassette, and 100–200 bp of the 3' end of the gene to be knocked out. This PCR product was then cloned into the vector pGemT easy (Promega) to create the construct pMON21681 and used for *Synechocystis* transformation.

Primers were also synthesized for the preparation of *Synechocystis* knockout constructs for the other sequences using the same method as described above, with the following primers. The ubiA 5' sequence was amplified using the primers 5'-GGATCCATGGTTGCCCAAACCCCATC (SEQ ID NO:65) and 5'-GCAATGTAA CATCA- GAGATTTTGAGACACAACGTGGCTTT GGGTAAG- CAACAATGACCGGC (SEQ ID NO:66). The 3' region was amplified using the synthetic oligonucleotide primers 5'-GAATTCTCAAAGCCAGCCCAGTAAC (SEQ ID NO:67) and 5'-GGTATGAGTCAGCAACACCTTC TTCACGAGGCAGACCTCAGCGGGTGC- GAAAAGGGTTTTCCC (SEQ ID NO:68). The amplification products were combined with the kanamycin resistance gene from puc4K (Pharmacia) that had been digested with HincII and gel purified away from the vector backbone. The annealed fragment was amplified using 5' and 3' oligos nested within the ends of the OPF fragment (5'- CCAGTGGTTfAGGCTGTGTGGTC (SEQ ID NO:69) and 5'-CTGAGTTGGATGTATTGGATC (SEQ ID NO:70)), so that the resulting product contained 100–200 bp of the 5' end of the *Synechocystis* gene to be knocked out, the kanamycin resistance cassette, and 100–200 bp of the 3' end of the gene to be knocked out. This PCR product was then cloned into the vector pGemT easy (Promega) to create the construct pMON21682 and used for *Synechocystis* transformation.

Primers were also synthesized for the preparation of *Synechocystis* knockout constructs for the other sequences using the same method as described above, with the following primers. The sll1899 5' sequence was amplified using the primers 5'-GGATCCATGGTTACTTCG ACAAAAATCC (SEQ ID NO:71) and 5'-GCAATGTAACATCAGAGATTTTGAGACACAACG TGGCTTTGCTAGGCAACCGCTTAGTAC (SEQ ID NO:72). The 3' region was amplified using the synthetic oligonucleotide primers 5'-GAATTCTTAA CCCAACAG- TAAAGTTCCC (SEQ ID NO:73) and 5'-GGTATGAGTCAGCAACACCTTCTTCACGAGGCA GACCTCAGCGCCGGCATTGTCTTTTACATG (SEQ ID NO:74). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GGAACCCTTGCAGCCGCTTC (SEQ ID NO:75) and 5'-GTATGCCCAACTGGTGCAGAGG (SEQ ID NO:76)), so that the resulting product contained 100–200 bp of the 5' end of the *Synechocystis* gene to be knocked out, the kanamycin resistance cassette, and 100–200 bp of the 3' end of the gene to be knocked out. This PCR product was then cloned into the vector pGemT easy (Promega) to create the construct pMON21679 and used for *Synechocystis* transformation.

Primers were also synthesized for the preparation of *Synechocystis* knockout constructs for the other sequences using the same method as described above, with the following primers. The slr0056 5' sequence was amplified using the primers 5'-GGATCCATGTCTGACACACAAAATACCG (SEQ ID NO:77) and 5'-GCAATGTAACATCA GAGATTTTGAGACACAACGTGGCTTT CGC- CAATACCAGCCACCAACAG (SEQ ID NO:78). The 3' region was amplified using the synthetic oligonucleotide primers 5'-GAATTCTCAAATCCCCGCATGGCCTAG (SEQ ID NO:79) and 5'-GGTATGA GTCAGCAACACCT- TCTTCACGAGGCAGACCTCAGCGGCCTAC GGCT- TGGACGTGTGGG (SEQ ID NO:80). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-CACTTGGATTCCCCTGATCTG (SEQ ID NO:81) and 5'-GCAATACCCGCTTGGAAAACG (SEQ ID NO:82)), so that the resulting product contained 100–200 bp of the 5' end of the *Synechocystis* gene to be knocked out, the kanamycin resistance cassette, and 100–200 bp of the 3' end of the gene to be knocked out. This PCR product was then cloned into the vector pGemT easy (Promega) to create the construct pMON21677 and used for *Synechocystis* transformation.

Primers were also synthesized for the preparation of *Synechocystis* knockout constructs for the other sequences using the same method as described above, with the following primers. The slr1518 5' sequence was amplified using the primers 5'-GGATCCATGACCGAATCTTCGCCCCTAGC (SEQ ID NO:83) and 5'-GCAAT GTAACATCAGAGAT-TGAGACACAACGTGGCTTTCAATCCTAG-GTAGCCGAGGCG (SEQ ID NO:84). The 3' region was amplified using the synthetic oligonucleotide primers 5'-GAATTCTTAGCCCAGGCCAGCCCAGCC (SEQ ID NO:85) and 5'-GGTATGAGTCAGCAACACCTTCTT CACGAGGCAGACCTCAGCGGGGAATTGA TTTGTT-TAATTACC (SEQ ID NO:86). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GCGATCGCCATTATCGCTTGG (SEQ ID NO:87) and 5'-GCAGACTGGCAATTATCAGTAACG (SEQ ID NO:88)), so that the resulting product contained 100–200 bp of the 5' end of the *Synechocystis* gene to be knocked out, the kanamycin resistance cassette, and 100–200 bp of the 3' end of the gene to be knocked out. This PCR product was then cloned into the vector pGemT easy (Promega) to create the construct pMON2 1680 and used for *Synechocystis* transformation.

4B. Transformation of *Synechocystis*

Cells of *Synechocystis* 6803 were grown to a density of approximately $2\times10^8$ cells per ml and harvested by centrifugation. The cell pellet was re-suspended in fresh BG-11 medium (ATCC Medium 616) at a density of $1\times10^9$ cells per ml and used immediately for transformation. One-hundred microliters of these cells were mixed with 5 ul of mini prep DNA and incubated with light at 30 C for 4 hours. This mixture was then plated onto nylon filters resting on BG-11 agar supplemented with TES pH8 and allowed to grow for 12–18 hours. The filters were then transferred to BG-11 agar+TES+5 ug/ml kanamycin and allowed to grow until colonies appeared within 7–10 days (Packer and Glazer, 1988). Colonies were then picked into BG-11 liquid media containing 5 ug/ml kanamycin and allowed to grow for 5 days. These cells were then transferred to Bg-11 media containing 10 ug/ml kanamycin and allowed to grow for 5 days and then transferred to Bg-11+kanamycin at 25 ug/ml and allowed to grow for 5 days. Cells were then harvested for PCR analysis to determine the presence of a disrupted ORF and also for HPLC analysis to determine if the disruption had any effect on tocopherol levels.

PCR analysis of the *Synechocystis* isolates for slr1736 and sll1899 showed complete segregation of the mutant genome, meaning no copies of the wild type genome could be detected in these strains. This suggests that function of the native gene is not essential for cell function. HPLC analysis of these same isolates showed that the sll1899 strain had no detectable reduction in tocopherol levels. However, the strain carrying the knockout for slr1736 produced no detectable levels of tocopherol.

Figure 21:
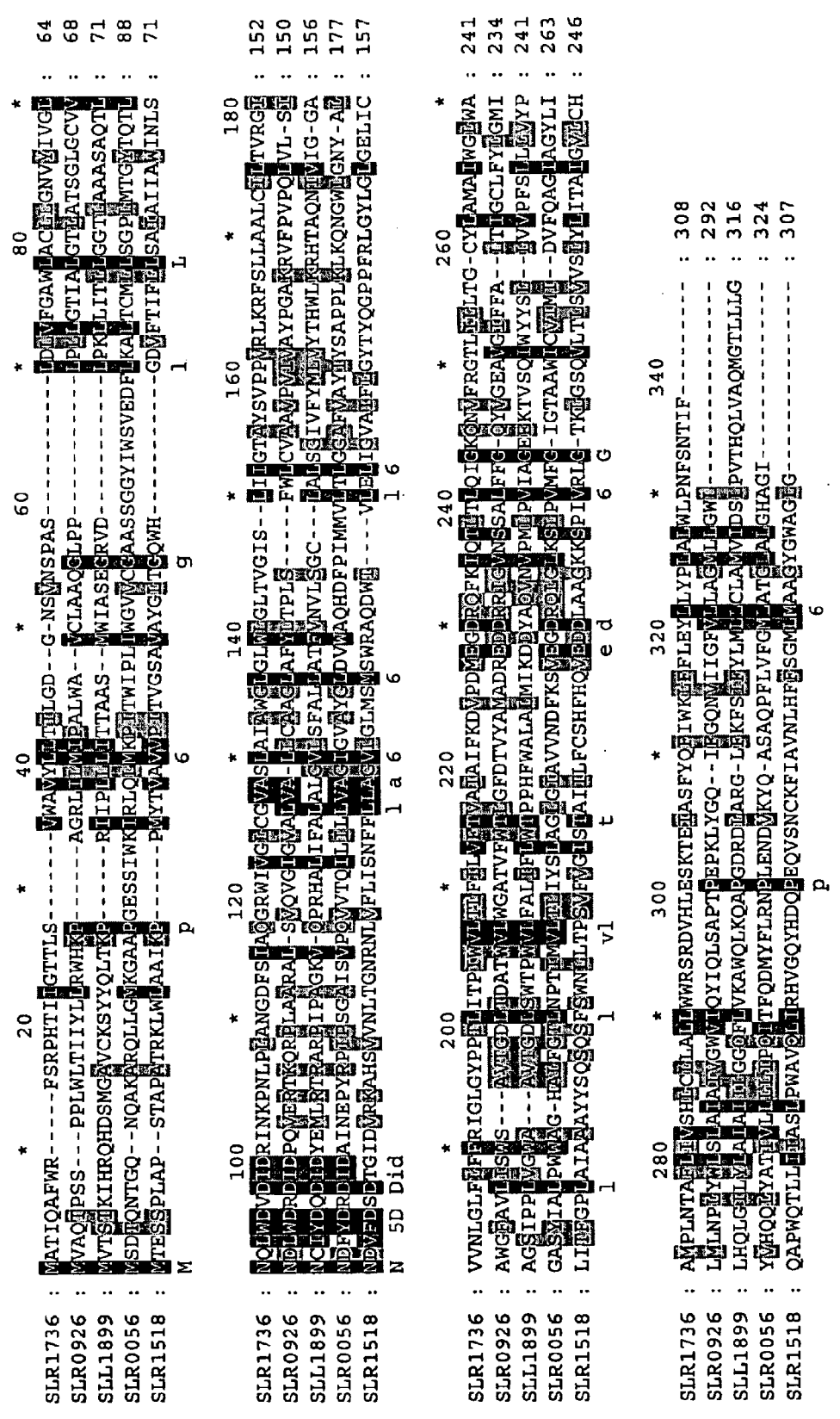

The amino acid sequences for the *Synechocystis* knockouts, slr1736 (SEQ ID NO: 37), slr0926 (SEQ ID NO: 32), sll1899 (SEQ ID NO: 33), s0056 (SEQ ID NO: 34), and slr1518 (SEQ ID NO: 35), are compared using ClustalW, and are provided in Table 3 below. Provided are the percent identities, percent similarity, and the percent gap. The alignment of the sequences is provided in FIG. 21.

TABLE 3

|  |  | Slr1736 | slr0926 | sll1899 | slr0056 | slr1518 |
|---|---|---|---|---|---|---|
| slr1736 | % identity |  | 14 | 12 | 18 | 11 |
|  | % similar |  | 29 | 30 | 34 | 26 |
|  | % gap |  | 8 | 7 | 10 | 5 |
| slr0926 | % identity |  |  | 20 | 19 | 14 |
|  | % similar |  |  | 39 | 32 | 28 |
|  | % gap |  |  | 7 | 9 | 4 |
| sll1899 | % identity |  |  |  | 17 | 13 |
|  | % similar |  |  |  | 29 | 29 |
|  | % gap |  |  |  | 12 | 9 |
| slr0056 | % identity |  |  |  |  | 15 |
|  | % similar |  |  |  |  | 31 |
|  | % gap |  |  |  |  | 8 |
| slr1518 | % identity |  |  |  |  |  |
|  | % similar |  |  |  |  |  |
|  | % gap |  |  |  |  |  |

Amino acid sequence comparisons are performed using various *Arabidopsis* prenyltransferase sequences, ATPT2 (SEQ ID NO: 2), ATPT3 (SEQ ID NO: 4), ATPT4 (SEQ ID NO: 6), ATPT8 (SEQ ID NO: 12), and ATPT12 (SEQ ID NO: 17), and the *Synechocystis* sequences, slr1736 (SEQ ID NO: 37), slr0926 (SEQ ID NO: 32), sll1899 (SEQ ID NO: 33), slr0056 (SEQ ID NO: 34), and slr1518 (SEQ ID NO: 35). The comparisons are presented in Table 4 below. Provided are the percent identities, percent similarity, and the percent gap. The alignment of the sequences is provided in FIG. 22.

TABLE 4

|  | ATPT2 | slr1736 | ATPT3 | slr0926 | ATPT4 | sil1899 | ATPT12 | slr0056 | ATPT8 | slr1518 |
|---|---|---|---|---|---|---|---|---|---|---|
| ATPT2 |  | 29 | 9 | 9 | 8 | 8 | 12 | 9 | 7 | 9 |
|  |  | 46 | 23 | 21 | 20 | 20 | 28 | 23 | 21 | 20 |
|  |  | 27 | 13 | 28 | 23 | 29 | 11 | 24 | 25 | 24 |
| slr1736 |  |  | 9 | 13 | 8 | 12 | 13 | 15 | 8 | 10 |
|  |  |  | 19 | 28 | 19 | 28 | 26 | 33 | 21 | 26 |
|  |  |  | 34 | 12 | 34 | 15 | 26 | 10 | 12 | 10 |
| ATPT3 |  |  |  | 23 | 11 | 14 | 13 | 10 | 5 | 11 |
|  |  |  |  | 36 | 26 | 26 | 26 | 21 | 14 | 22 |
|  |  |  |  | 29 | 21 | 31 | 16 | 30 | 30 | 30 |
|  |  |  |  |  | 12 | 20 | 17 | 20 | 11 | 14 |

TABLE 4-continued

| | ATPT2 | slr1736 | ATPT3 | slr0926 | ATPT4 | sil1899 | ATPT12 | slr0056 | ATPT8 | slr1518 |
|---|---|---|---|---|---|---|---|---|---|---|
| slr0926 | | | | | 24 | 37 | 28 | 33 | 24 | 29 |
| | | | | | 33 | 12 | 25 | 10 | 11 | 9 |
| | | | | | | 18 | 11 | 8 | 6 | 7 |
| ATPT4 | | | | | | 33 | 23 | 18 | 16 | 19 |
| | | | | | | 28 | 19 | 32 | 32 | 33 |
| | | | | | | | 13 | 17 | 10 | 12 |
| sil1899 | | | | | | | 24 | 30 | 23 | 26 |
| | | | | | | | 27 | 13 | 10 | 11 |
| | | | | | | | | 52 | 8 | 11 |
| ATPT12 | | | | | | | | 66 | 19 | 26 |
| | | | | | | | | 18 | 25 | 23 |
| | | | | | | | | | 9 | 13 |
| slr0056 | | | | | | | | | 23 | 32 |
| | | | | | | | | | 10 | 8 |
| | | | | | | | | | | 7 |
| ATPT8 | | | | | | | | | | 23 |
| | | | | | | | | | | 7 |
| slr1518 | | | | | | | | | | |

4C. Phytyl Prenyltransferase Enzyme Assays

[$^3$H] Homogentisic acid in 0.1% $H_3PO_4$ (specific radioactivity 40 Ci/mmol). Phytyl pyrophosphate was synthesized as described by Joo, et al. (1973) Can J. Biochem. 51:1527. 2-methyl-6-phytylquinol and 2,3-dimethyl-5-phytylquinol were synthesized as described by Soll, et al. (1980) Phytochemistry 19:215. Homogentisic acid, α, β, δ, and γ-tocopherol, and tocol, were purchased commercially.

The wild-type strain of Synechocystis sp. PCC 6803 was grown in BG11 medium with bubbling air at 30° C. under 50 $\mu$E.m$^{-2}$.s$^{-1}$ fluorescent light, and 70% relative humidity. The growth medium of slr736 knock-out (potential PPT) strain of this organism was supplemented with 25 $\mu$g mL$^{-1}$ kanamycin. Cells were collected from 0.25 to 1 liter culture by centrifugation at 5000 g for 10 min and stored at −80° C.

Total membranes were isolated according to Zak's procedures with some modifications (Zak, et al. (1999) Eur J. Biochem 261:31 1). Cells were broken on a French press. Before the French press treatment, the cells were incubated for 1 hour with lysozyme (0.5%, w/v) at 30° C. in a medium containing 7 mM EDTA, 5 mM NaCl and 10 mM Hepes-NaOH, pH 7.4. The spheroplasts were collected by centrifugation at 5000 g for 10 min and resuspended at 0.1–0.5 mg chlorophyll mL$^{-1}$ in 20 mM potassium phosphate buffer, pH 7.8. Proper amount of protease inhibitor cocktail and DNAase I from Boehringer Mannheim were added to the solution. French press treatments were performed two to three times at 100 MPa. After breakage, the cell suspension was centrifuged for 10 min at 5000 g to pellet unbroken cells, and this was followed by centrifugation at 100 000 g for 1 hour to collect total membranes. The final pellet was resuspended in a buffer containing 50 mM Tris-HCL and 4 mM $MgCl_2$.

Chloroplast pellets were isolated from 250 g of spinach leaves obtained from local markets. Devined leaf sections were cut into grinding buffer (2 1/250 g leaves) containing 2 mM EDTA, 1 mM $MgCl_2$, 1 mM $MnCl_2$, 0.33 M sorbitol, 0.1% ascorbic acid, and 50 mM Hepes at pH 7.5. The leaves were homogenized for 3 sec three times in a 1-L blendor, and filtered through 4 layers of mirocloth. The supernatant was then centrifuged at 5000 g for 6 min. The chloroplast pellets were resuspended in small amount of grinding buffer (Douce, et al Methods in Chloroplast Molecular Biology, 239 (1982)

Chloroplasts in pellets can be broken in three ways. Chloroplast pellets were first aliquoted in 1 mg of chlorophyll per tube, centrifuged at 6000 rpm for 2 min in microcentrifuge, and grinding buffer was removed. Two hundred microliters of Triton X-100 buffer (0.1% Triton X-100, 50 mM Tris-HCl pH 7.6 and 4 mM $MgCl_2$) or swelling buffer (10 mM Tris pH 7.6 and 4 mM $MgCl_2$) was added to each tube and incubated for ½ hour at 4° C. Then the broken chloroplast pellets were used for the assay immediately. In addition, broken chloroplasts can also be obtained by freezing in liquid nitrogen and stored at −80° C. for ½ hour, then used for the assay.

In some cases chloroplast pellets were further purified with 400%/80% percoll gradient to obtain intact chloroplasts. The intact chloroplasts were broken with swelling buffer, then either used for assay or further purified for envelope membranes with 20.5%/31.8% sucrose density gradient (Sol, et al (1980) supra). The membrane fractions were centrifuged at 100 000 g for 40 min and resuspended in 50 mM Tris-HCl pH 7.6, 4 MM $MgCl_2$.

Various amounts of [$^3$H]HGA, 40 to 60 $\mu$M unlabelled HGA with specific activity in the range of 0.16 to 4 Ci/mmole were mixed with a proper amount of 1 M Tris-NaOH pH 10 to adjust pH to 7.6. HGA was reduced for 4 min with a trace amount of solid $NaBH_4$. In addition to HGA, standard incubation mixture (final vol 1 mL) contained 50 mM Tris-HCl, pH 7.6, 3–5 mM $MgCl_2$, and 100 $\mu$M phytyl pyrophosphate. The reaction was initiated by addition of Synechocystis total membranes, spinach chloroplast pellets, spinach broken chloroplasts, or spinach envelope membranes. The enzyme reaction was carried out for 2 hour at 23° C. or 30° C. in the dark or light. The reaction is stopped by freezing with liquid nitrogen, and stored at −80° C. or directly by extraction.

A constant amount of tocol was added to each assay mixture and reaction products were extracted with a 2 mL mixture of chloroform/methanol (1:2, v/v) to give a monophasic solution. NaCl solution (2 mL; 0.9%) was added with vigorous shaking. This extraction procedure was repeated three times. The organic layer containing the prenylquinones was filtered through a 20 m$\mu$ filter, evaporated under $N_2$, and then resuspended in 100 $\mu$L of ethanol.

The samples were mainly analyzed by Normal-Phase HPLC method (Isocratic 90% Hexane and 10% Methyl-t-butyl ether), and use a Zorbax silica column, 4.6×250 mm. The samples were also analyzed by Reversed-Phase HPLC method (Isocratic 0.1% $H_3PO_4$ in MeOH), and use a Vydac 201HS54 C18 column; 4.6×250 mm coupled with an Alltech C18 guard column. The amount of products were calculated based on the substrate specific radioactivity, and adjusted according to the % recovery based on the amount of internal standard.

The amount of chlorophyll was determined as described in Amon (1949) *Plant Physiol.* 24:1. Amount of protein was determined by the Bradford method using gamma globulin as a standard (Bradford, (1976) *Anal. Biochem.* 72:248)

Figure 23:
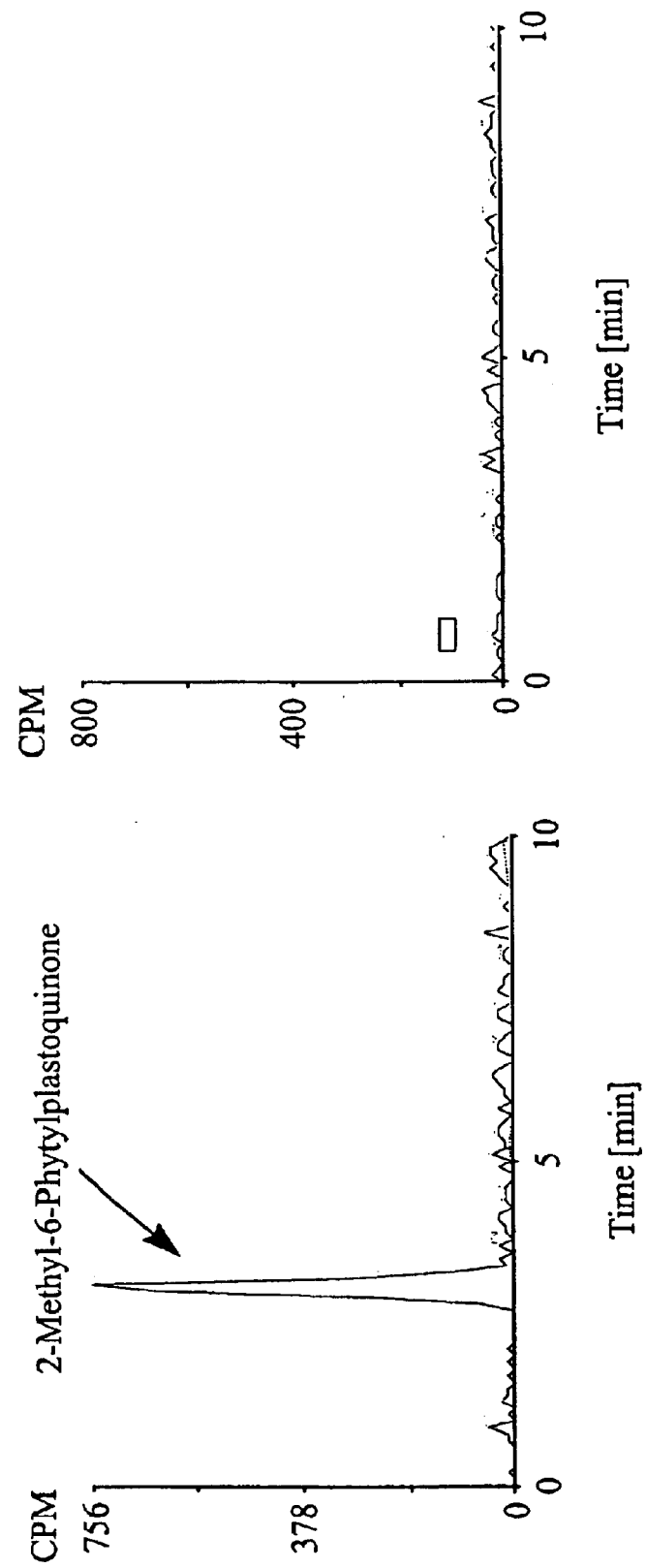
FIG. 23 provides the results of the enzymatic assay from preparations of wild type *Synechocystis* strain 6803, and *Synechocystis* slr1736 knockout.

Results of the assay demonstrate that 2-Methyl-6-Phytylplastoquinone is not produced in the *Synechocystis* slr1736 knockout preparations. The results of the phytyl prenyltransferase enzyme activity assay for the slr1736 knock out are presented in FIG. 23.

4D. Complementation of the slr1736 Knockout with ATPT2

In order to determine whether ATPT2 could complement the knockout of slr1736 in *Synechocystis* 6803, a plasmid was constructed to express the ATPT2 sequence from the TAC promoter. A vector, plasmid psl1211, was obtained from the lab of Dr. Himadri Pakrasi of Washington University, and is based on the plasmid RSF1010 which is a broad host range plasmid (Ng W.-O., Zentella R., Wang, Y., Taylor J-S. A., Pakrasi, H. B. 2000. phrA, the major photoreactivating factor in the cyanobacterium *Synechocystis* sp. strain PCC 6803 codes for a cyclobutane pyrimidine dimer specific DNA photolyase. *Arch. Microbiol.* (in press)). The ATPT2 gene was isolated from the vector pCGN10817 by PCR using the following primers. ATPT2nco.pr 5'-CCATGGATTCGAGTAAAGTTGTCGC (SEQ ID NO:89); ATPT2ri.pr-5'-GAATTCACTTCAAAAAAGGTAACAG (SEQ ID NO:90). These primers will remove approximately 112 BP from the 5' end of the ATPT2 sequence, which is thought to be the chloroplast transit peptide. These primers will also add an NcoI site at the 5' end and an EcoRI site at the 3' end which can be used for sub-cloning into subsequent vectors. The PCR product from using these primers and pCGN10817 was ligated into pGEM T easy and the resulting vector pMON21689 was confirmed by sequencing using the m13forward and ml3reverse primers. The NcoI/EcoRI fragment from pMON21689 was then ligated with the EagI/EcoRI and EagI/NcoI fragments from psl1211 resulting in pMON21690. The plasmid pMON21690 was introduced into the slr1736 *Synechocystis* 6803 KO strain via conjugation. Cells of sl906 (a helper strain) and DH10B cells containing pMON21690 were grown to log phase (O.D. 600=0.4) and 1 ml was harvested by centrifugation. The cell pellets were washed twice with a sterile BG-11 solution and resuspended in 200 ul of BG-11. The following was mixed in a sterile eppendorf tube: 50 ul SL906, 50 ul DH10B cells containing pMON21690, and 100 ul of a fresh culture of the slr1736 *Synechocystis* 6803 KO strain (O.D. 730=0.2–0.4). The cell mixture was immediately transferred to a nitrocellulose filter resting on BG-11 and incubated for 24 hours at 30 C and 2500 LUX(50 ue) of light. The filter was then transferred to BG-11 supplemented with 10 ug/ml Gentamycin and incubated as above for 5 days. When colonies appeared, they were picked and grown up in liquid BG-11+ Gentamycin 10 ug/ml. (Elhai, J. and Wolk, P. 1988. Conjugal transfer of DNA to Cyanobacteria. *Methods in Enzymology* 167, 747–54) The liquid cultures were then assayed for tocopherols by harvesting 1 ml of culture by centrifugation, extracting with ethanol/pyrogallol, and HPLC separation. The slr1736 *Synechocystis* 6803 KO strain, did not contain any detectable tocopherols, while the slr1736 *Synechocystis* 6803 KO strain transformed with pmon21690 contained detectable alpha tocopherol. A *Synechocystis* 6803 strain transformed with psl1211 (vector control) produced alpha tocopherol as well.

4E: Additional Evidence of Prenyltransferase Activity

To test the hypothesis that slr1736 or ATPT2 are sufficient as single genes to obtain phytyl prenyltransferase activity, both genes were expressed in SF9 cells and in yeast. When either slr1736 or ATPT2 were expressed in insect cells (Table 5) or in yeast, phytyl prenyltransferase activity was detectable in membrane preparations, whereas membrane preparations of the yeast vector control, or membrane preparations of insect cells did not exhibit phytyl prenyltransferase activity.

TABLE 5

Phytyl prenyltransferase activity

| Enzyme source | Enzyme activity [pmol/mg x h] |
|---|---|
| slr1736 expressed in SF9 cells | 20 |
| ATPT2 expressed in SF9 cells | 6 |
| SF9 cell control | <0.05 |
| Synechocystis 6803 | 0.25 |
| Spinach chloroplasts | 0.20 |

Example 5

Transgenic Plant Analysis

5A. *Arabidopsis*

*Arabidopsis* plants transformed with constructs for the sense or antisense expression of the ATPT proteins were analyzed by High Pressure Liquid Chromatography (HPLC) for altered levels of total tocopherols, as well as altered levels of specific tocopherols (alpha, beta, gamma, and delta tocopherol).

Extracts of leaves and seeds were prepared for HPLC as follows. For seed extracts, 10 mg of seed was added to 1 g of microbeads (Biospec) in a sterile microfuge tube to which 500 ul 1% pyrogallol (Sigma Chem)/ethanol was added. The mixture was shaken for 3 minutes in a mini Beadbeater (Biospec) on "fast" speed. The extract was filtered through a 0.2 μm filter into an autosampler tube. The filtered extracts were then used in HPLC analysis described below.

Leaf extracts were prepared by mixing 30–50 mg of leaf tissue with 1 g microbeads and freezing in liquid nitrogen until extraction. For extraction, 500 ul 1% pyrogallol in ethanol was added to the leaf/bead mixture and shaken for 1 minute on a Beadbeater (Biospec) on "fast" speed. The resulting mixture was centrifuged for 4 minutes at 14,000 rpm and filtered as described above prior to HPLC analysis.

HPLC was performed on a Zorbax silica HPLC column (4.6 mm×250 mm) with a fluorescent detection, an excitation at 290 nm, an emission at 336 nm, and bandpass and slits. Solvent A was hexane and solvent B was methyl-t-butyl ether. The injection volume was 20 ul, the flow rate was 1.5 ml/min, the run time was 12 min (40° C.) using the gradient (Table 6):

TABLE 6

| Time | Solvent A | Solvent B |
|---|---|---|
| 0 min. | 90% | 10% |
| 10 min. | 90% | 10% |
| 11 min. | 25% | 75% |
| 12 min. | 90% | 10% |

Tocopherol standards in 1% pyrogallov ethanol were also run for comparison (alpha tocopherol, gamma tocopherol, beta tocopherol, delta tocopherol, and tocopherol (tocol) (all from Matreya).

Standard curves for alpha, beta, delta, and gamma tocopherol were calculated using Chemstation software. The absolute amount of component x is: Absolute amount of x=Response$_x$×RF$_x$ x dilution factor where Response$_x$ is the area of peak x, RF$_x$ is the response factor for component x (Amount$_x$/Response$_x$) and the dilution factor is 500 ul. The ng/mg tissue is found by: total ng component/mg plant tissue.

Figure 24:
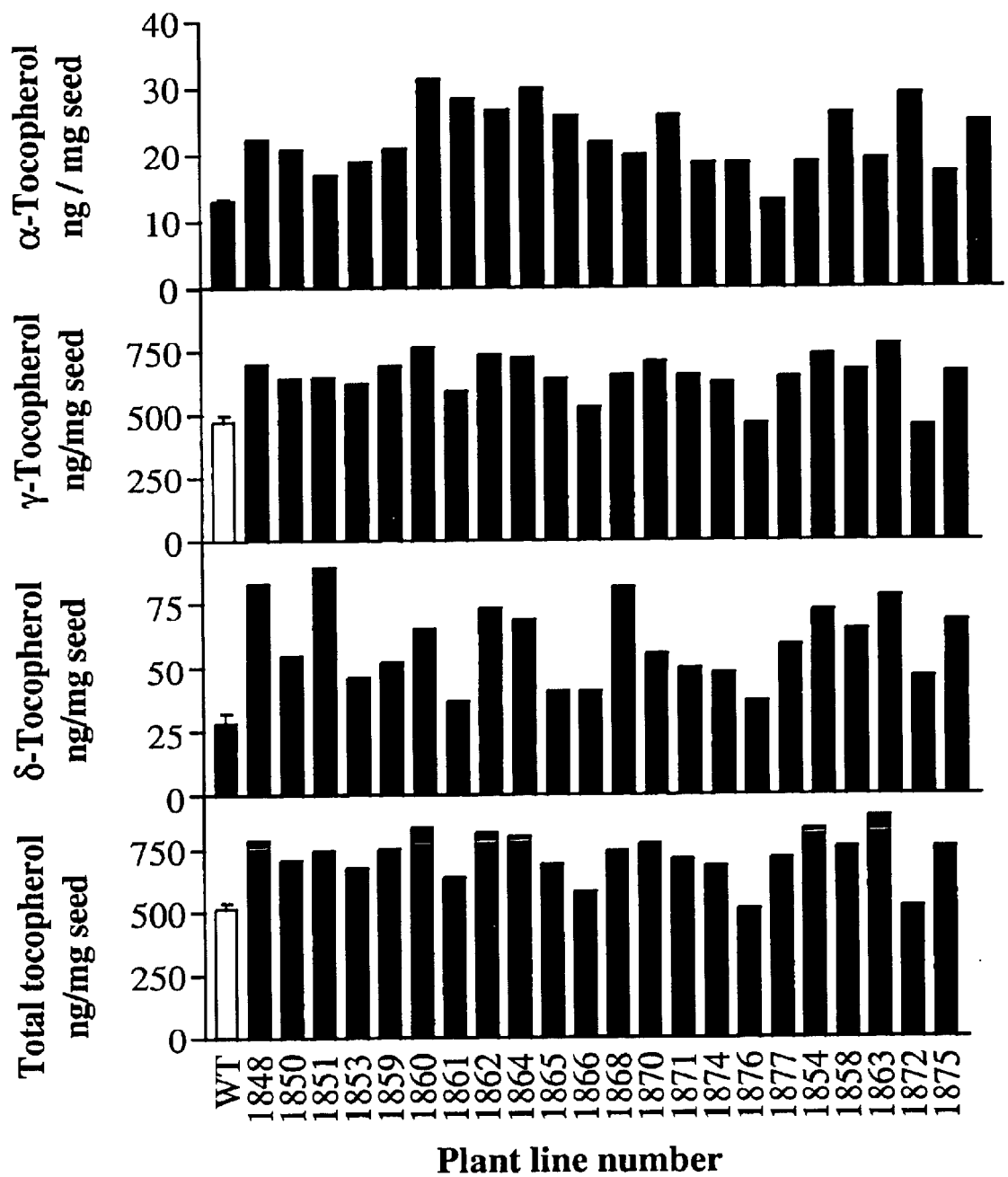
FIG. 24 provides bar graphs of HPLC data obtained from seed extracts of transgenic *Arabidopsis* containing pCGN10822, which provides of the expression of the ATPT2 sequence, in the sense orientation, from the napin promoter. Provided are graphs for alpha, gamma, and delta tocopherols, as well as total tocopherol for 22 transformed lines, as well as a nontransformed (wildtype) control.

Results of the HPLC analysis of seed extracts of transgenic *Arabidopsis* lines containing pMON10822 for the expression of ATPT2 from the napin promoter are provided in FIG. 24.

Figure 25:
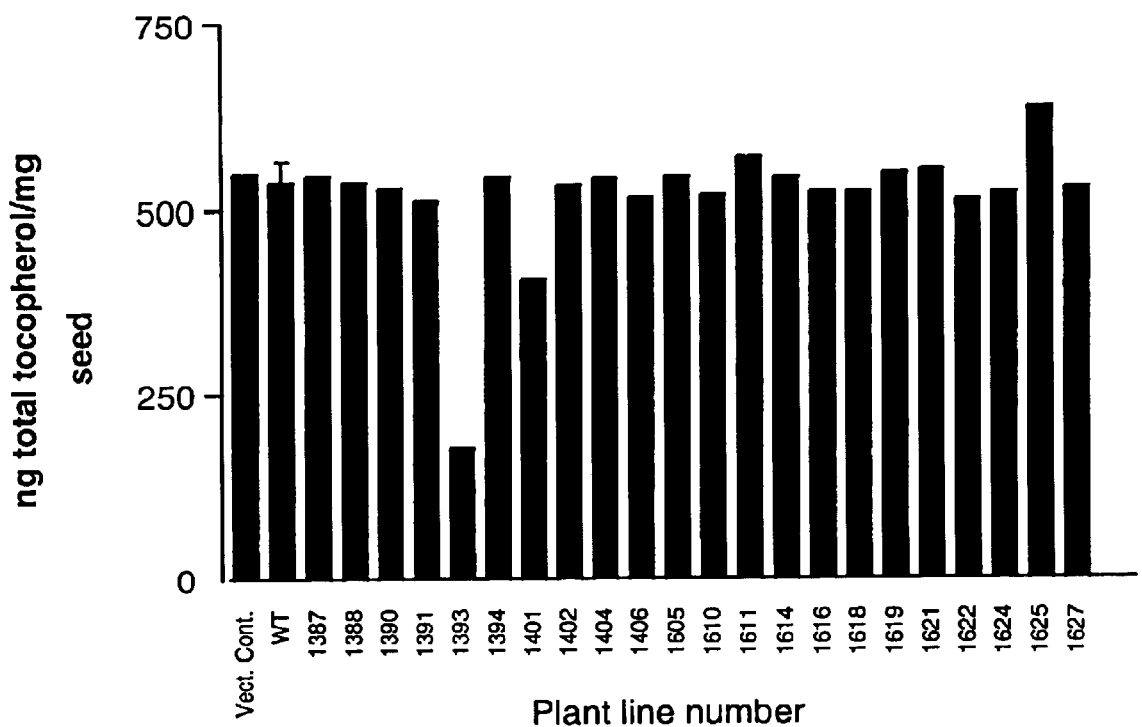
FIG. 25 provides a bar graph of HPLC analysis of seed extracts from *Arabidopsis* plants transformed with pCGN10803 (35S-ATPT2, in the antisense orientation), pCGN10822 (line 1625, napin ATPT2 in the sense orientation), pCGN10809 (line 1627, 35S-ATPT3 in the sense orientation), a nontransformed (wt) control, and an empty vector transformed control.
Figure 26:
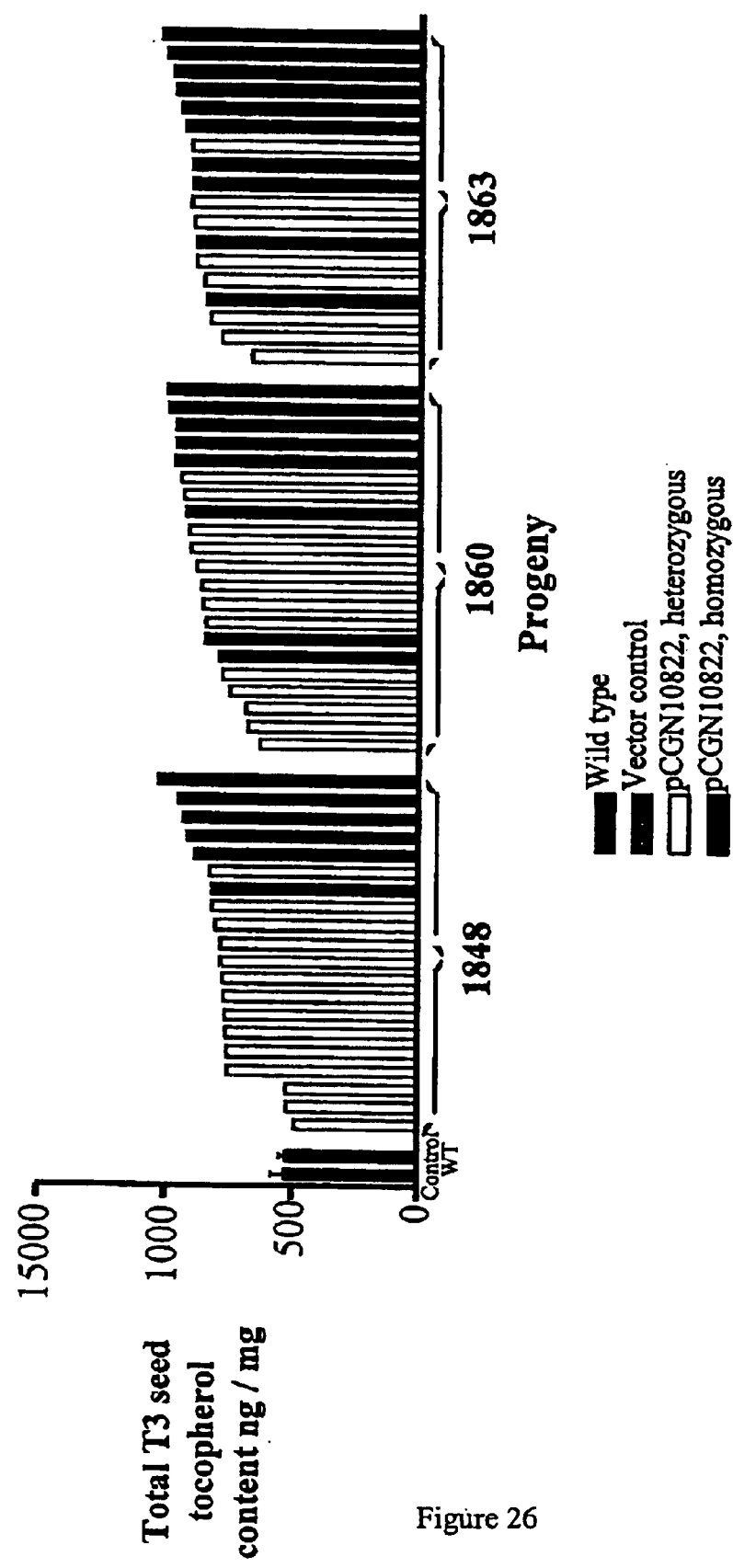
FIG. 26 shows total tocopherol levels measured in T# *Arabidopsis* seed of line.

HPLC analysis results of segregating T2 *Arabidopsis* seed tissue expressing the ATPT2 sequence from the napin promoter (pCGN10822) demonstrates an increased level of tocopherols in the seed. Total tocopherol levels are increased as much as 50% over the total tocopherol levels of non-transformed (wild-type) *Arabidopsis* plants (FIG. 25). Homozygous progeny from the top 3 lines (T3 seed) have up to a two-fold (100%) increase in total tocopherol levels over control *Arabidopsis* seed (FIG. 26.)

Furthermore, increases of particular tocopherols are also increased in transgenic *Arabidopsis* plants expressing the ATPT2 nucleic acid sequence from the napin promoter. Levels of delta tocopherol in these lines are increased greater than 3 fold over the delta tocopherol levels obtained from the seeds of wild type *Arabidopsis* lines. Levels of gamma tocopherol in transgenic *Arabidopsis* lines expressing the ATPT2 nucleic acid sequence are increased as much as about 60% over the levels obtained in the seeds of non-transgenic control lines. Furthermore, levels of alpha tocopherol are increased as much as 3 fold over those obtained from non-transgenic control lines.

Figure 27:
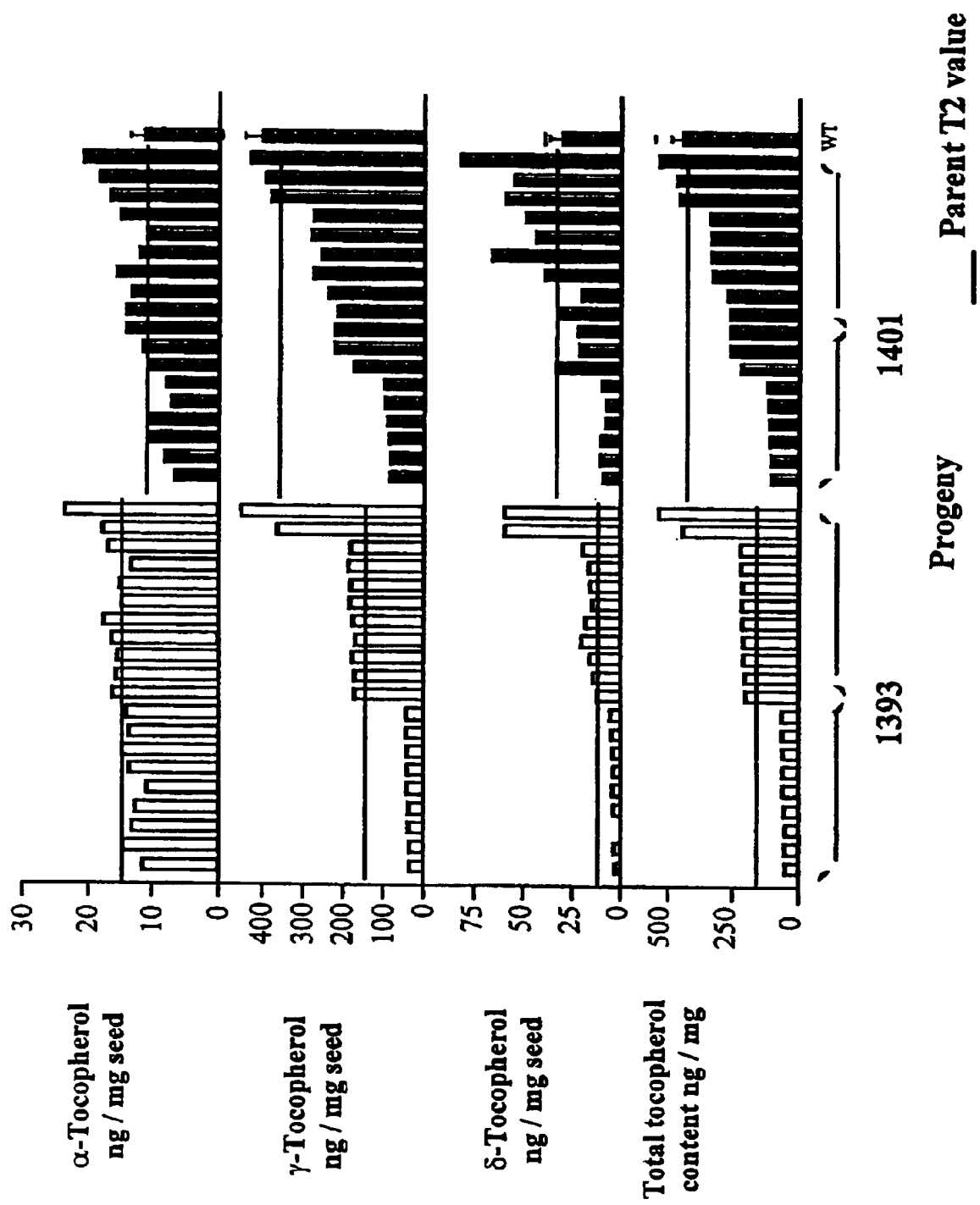
FIG. 27 shows total tocopherol levels measured in T# *Arabidopsis* seed of line.

Results of the HPLC analysis of seed extracts of transgenic *Arabidopsis* lines containing pCGN10803 for the expression of ATPT2 from the enhanced 35S promoter (antisense orientation) are provided in FIG. 25. Two lines were identified that have reduced total tocopherols, up to a ten-fold decrease observed in T3 seed compared to control *Arabidopsis* (FIG. 27.)

5B. Canola

*Brassica napus*, variety SP30021, was transformed with pCGN10822 (napin-ATPT2-napin 3', sense orientation) using *Agrobacterium lumefaciens*-mediated transformation. Flowers of the R0 plants were tagged upon pollination and developing seed was collected at 35 and 45 days after pollination (DAP).

Figure 28:
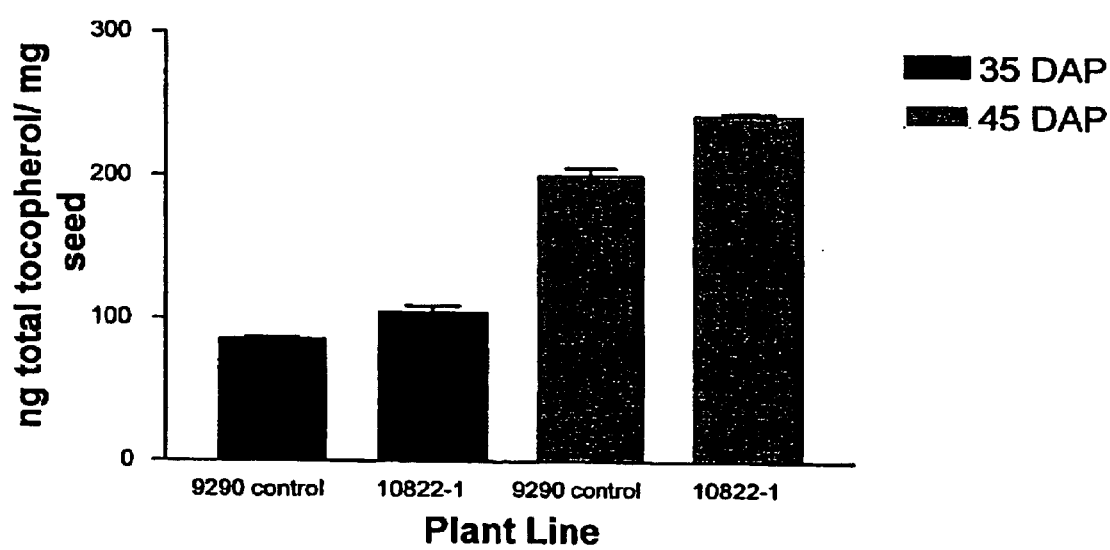
FIG. 28 shows total tocopherol levels measured in developing canola seed of line.

Developing seed was assayed for tocopherol levels, as described above for *Arabidopsis*. Line 10822-1 shows a 20% increase of total tocopherols, compared to the wild-type control, at 45 DAP. FIG. 28 shows total tocopherol levels measured in developing canola seed.

Example 6

Sequences to Tocopherol Cyclase

6A. Preparation of the slr1737 Knockout

The *Synechocystis* sp. 6803 slr1737 knockout was constructed by the following method. The GPS™-1 Genome Priming System (New England Biolabs) was used to insert, by a Tn7 Transposase system, a Kanamycin resistance cassette into slr1737. A plasmid from a *Synechocystis* genomic library clone containing 652 base pairs of the targeted orf (*Synechocystis* genome base pairs 1324051–1324703; the predicted orf base pairs 1323672–1324763, as annotated by Cyanobase) was used as target DNA. The reaction was performed according to the manufacturers protocol. The reaction mixture was then transformed into *E. coli* DH10B electrocompetant cells and plated. Colonies from this transformation were then screened for transposon insertions into the target sequence by amplifying with M13 Forward and Reverse Universal primers, yielding a product of 652 base pairs plus ~1700 base pairs, the size of the transposon kanamycin cassette, for a total fragment size of ~2300 base pairs. After this determination, it was then necessary to determine the approximate location of the insertion within the targeted orf, as 100 base pairs of orf sequence was estimated as necessary for efficient homologous recombination in *Synechocystis*. This was accomplished through amplification reactions using either of the primers to the ends of the transposon, Primer S (5' end) or N (3' end), in combination with either a M13 Forward or Reverse primer. That is, four different primer combinations were used to map each potential knockout construct: Primer S-M13 Forward, Primer S-M13 Reverse, Primer N-M13 Forward, Primer N-M13 Reverse. The construct used to transform *Synechocystis* and knockout slr1737 was determined to consist of a approximately 150 base pairs of slr1737 sequence on the 5' side of the transposon insertion and approximately 500 base pairs on the 3' side, with the transcription of the orf and kanamycin cassette in the same direction. The nucleic acid sequence of slr1737 is provided in SEQ ID NO:38 the deduced amino acid sequence is provided in SEQ ID NO:39.

Cells of *Synechocystis* 6803 were grown to a density of ~2×10$^8$ cells per ml and harvested by centrifigation. The cell pellet was re-suspended in fresh BG-11 medium at a density of 1×10$^9$ cells per ml and used immediately for transformation. 100 ul of these cells were mixed with 5 ul of mini prep DNA and incubated with light at 30 C for 4 hours. This mixture was then plated onto nylon filters resting on BG-11 agar supplemented with TES ph8 and allowed to grow for 12–18 hours. The filters were then transferred to BG-11 agar+TES+5 ug/ml kanamycin and allowed to grow until colonies appeared within 7–10 days (Packer and Glazer, 1988). Colonies were then picked into BG-11 liquid media containing 5 ug/ml kanamycin and allowed to grow for 5 days. These cells were then transferred to Bg-11 media containing 10 ug/ml kanamycin and allowed to grow for 5 days and then transferred to Bg-11+kanamycin at 25 ug/ml and allowed to grow for 5 days. Cells were then harvested for PCR analysis to determine the presence of a disrupted ORF and also for HPLC analysis to determine if the disruption had any effect on tocopherol levels.

PCR analysis of the *Synechocystis* isolates, using primers to the ends of the slr1737 orf, showed complete segregation of the mutant genome, meaning no copies of the wild type genome could be detected in these strains. This suggests that function of the native gene is not essential for cell function. HPLC analysis of the strain carrying the knockout for slr1737 produced no detectable levels of tocopherol.

6B. The Relation of slr1737 and slr1736

Figure 29:
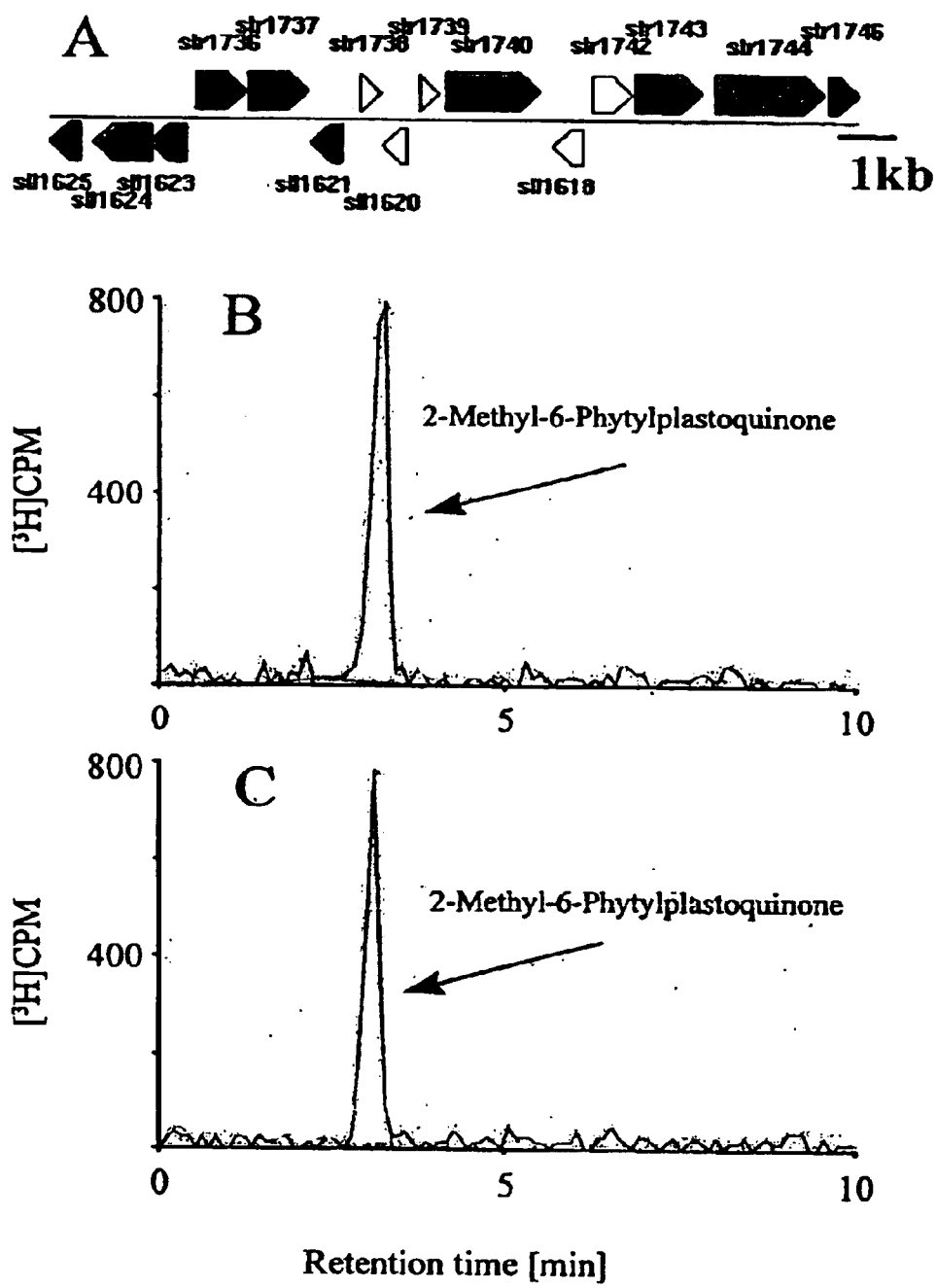
FIG. 29 shows results of phytyl prenyltransferase activity assay using *Synechocystis* wild type and slr1737 knockout mutant membrane preparations.
Figure 30A:
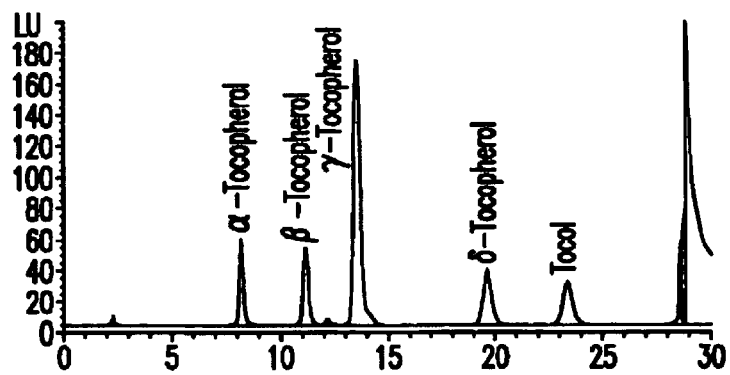
FIG. 30 is the chromatograph from an HPLC analysis of *Synechocystis* extracts.
Figure 30B:
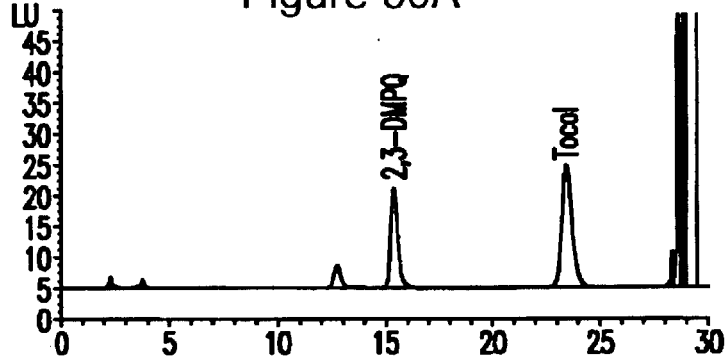
Figure 30C:
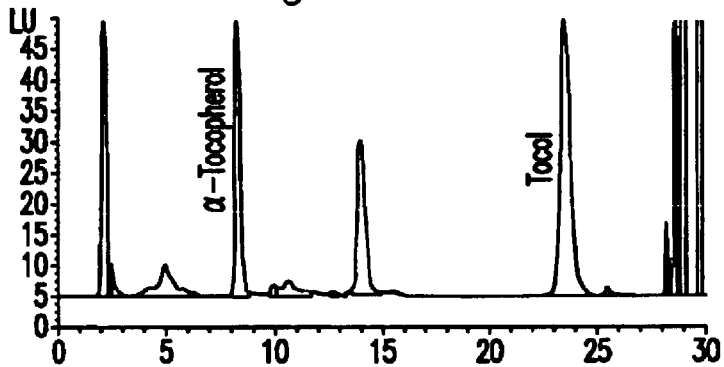
Figure 30D:
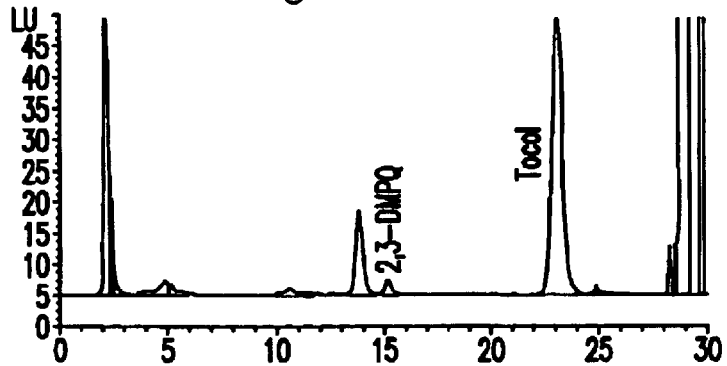

The slr1737 gene occurs in *Synechocystis* downstream and in the same orientation as slr1736, the phytyl prenyltransferase. In bacteria this proximity often indicates an operon structure and therefore an expression pattern that is linked in all genes belonging to this operon. Occasionally such operons contain several genes that are required to constitute one enzyme. To confirm that slr1737 is not required for phytyl prenyltransferase activity, phytyl prenyltransferase was measured in extracts from the *Synechocystis* slr1737 knockout mutant. FIG. 29 shows that extracts from the *Synechocystis* slr1737 knockout mutant still contain phytyl prenyltransferase activity. The molecular organization of genes in *Synechocystis* 6803 is shown in A. FIGS. B and C show HPLC traces (normal phase HPLC) of reaction products obtained with membrane preparations from *Synechocystis* wild type and slr1737 membrane preparations, respectively.

The fact that slr1737 is not required for the PPT activity provides additional data that ATPT2 and slr1736 encode phytyl prenyltransferases.

6C *Synechocystis* Knockouts

*Synechocystis* 6803 wild type and *Synechocystis* slr1737 knockout mutant were grown photoautotrophically. Cells from a 20 ml culture of the late logarithmic growth phase were harvested and extracted with ethanol. Extracts were separated by isocratic normal-phase HPLC using a Hexane/Methyl-t-butyl ether (95/5) and a Zorbax silica column, 4.6×250 mm. Tocopherols and tocopherol intermediates were detected by fluorescence (excitement 290 nm, emission 336 nm) (FIG. 30).

Extracts of *Synechocystis* 6803 contained a clear signal of alpha-tocopherol. 2,3-Dimethyl-5-phytylplastoquinol was below the limit of detection in extracts from the *Synechocystis* wild type (C). In contrast, extracts from the *Synechocystis* slr1737 knockout mutant did not contain alpha-tocopherol, but contained 2,3-dimethyl-5-phytylplastoquinol (D), indicating that the interruption of slr1737 has resulted in a block of the 2,3-dimethyl-5-phytylplastoquinol cyclase reaction.

Chromatograms of standard compounds alpha, beta, gamma, delta-tocopherol and 2,3-dimethyl-5-phytylplastoquinol are shown in A and B. Chromatograms of extracts form *Synechocystis* wild type and the *Synechocystis* slr1737 knockout mutant are shown in C and D, respectively. Abbreviations: 2,3-DMPQ, 2,3-dimethyl-5-phytylplastoquinol.

6D. Incubation with Lysozyme Treated *Synechocystis*

*Synechocystis* 6803 wild type and slr1737 knockout mutant cells from the late logarithmic growth phase (approximately 1 g wet cells per experiment in a total volume of 3 ml) were treated with Lysozyme and subsequently incubated with S-adenosylmethionine, and phytylpyrophosphate, plus radiolabelled homogentisic acid. After 17 h incubation in the dark at room temperature the samples were extracted with 6 ml chloroform/methanol (½ v/v). Phase separation was obtained by the addition of 6 ml 0.9% NaCl solution. This procedure was repeated three times. Under these conditions 2,3dimethyl-5-phytylplastoquinol is oxidized to form 2,3-dimethyl-5-phytylplastoquinone.

The extracts were analyzed by normal phase and reverse phase HPLC. Using extracts from wild type *Synechocystis* cells radiolabelled gamma-tocopherol and traces of radiolabelled 2,3-dimethyl-5-phytylplastoquinone were detected. When extracts from the slr1737 knockout mutant were analyzed, only radiolabelled 2,3-dimethyl-5-phytylplastoquinone was detectable. The amount of 2,3-dimethyl-5-phytylplastoquinone was significantly increased compared to wild type extracts. Heat treated samples of the wild type and the slr1737 knockout mutant did not produce radiolabelled 2,3-dimethyl-5-phytylplastoquinone, nor radiolabelled tocopherols. These results further support the role of the slr1737 expression product in the cyclization of 2,3-dimethyl-5-phytylplastoquinol.

6E. *Arabidopsis* Homologue to slr1737

An *Arabidopsis* homologue to slr1737 was identified from a BLASTALL search using *Synechocystis* sp 6803 gene slr1737 as the query, in both public and proprietary databases. SEQ ID NO: 109 and SEQ ID NO: 110 are the DNA and translated amino acid sequences, respectively, of the *Arabidopsis* homologue to slr1737. The start if found at the ATG at base 56 in SEQ ID NO:109.

The sequences obtained for the homologue from the proprietary database differs from the public database (F4D11.30, BAC AL022537), in having a start site 471 base pairs upstream of the start identified in the public sequence. A comparison of the public (SEQ ID NO: 112) and proprietary (SEQ ID NO: 113) sequences is provided in FIG. 31. The correct start correlates within the public database sequence at 12080, while the public sequence start is given as being at 11609.

Attempts to amplify a slr1737 homologue were unsuccessful using primers designed from the public database, while amplification of the gene was accomplished with primers obtained from SEQ ID NO: 109.

Analysis of the protein sequence to identify transit peptide sequence predicted two potential cleavage sites, one between amino acids 48 and 49, and the other between amino acids 98 and 99.

6F. slr1737 Protein Information

Figure 32:
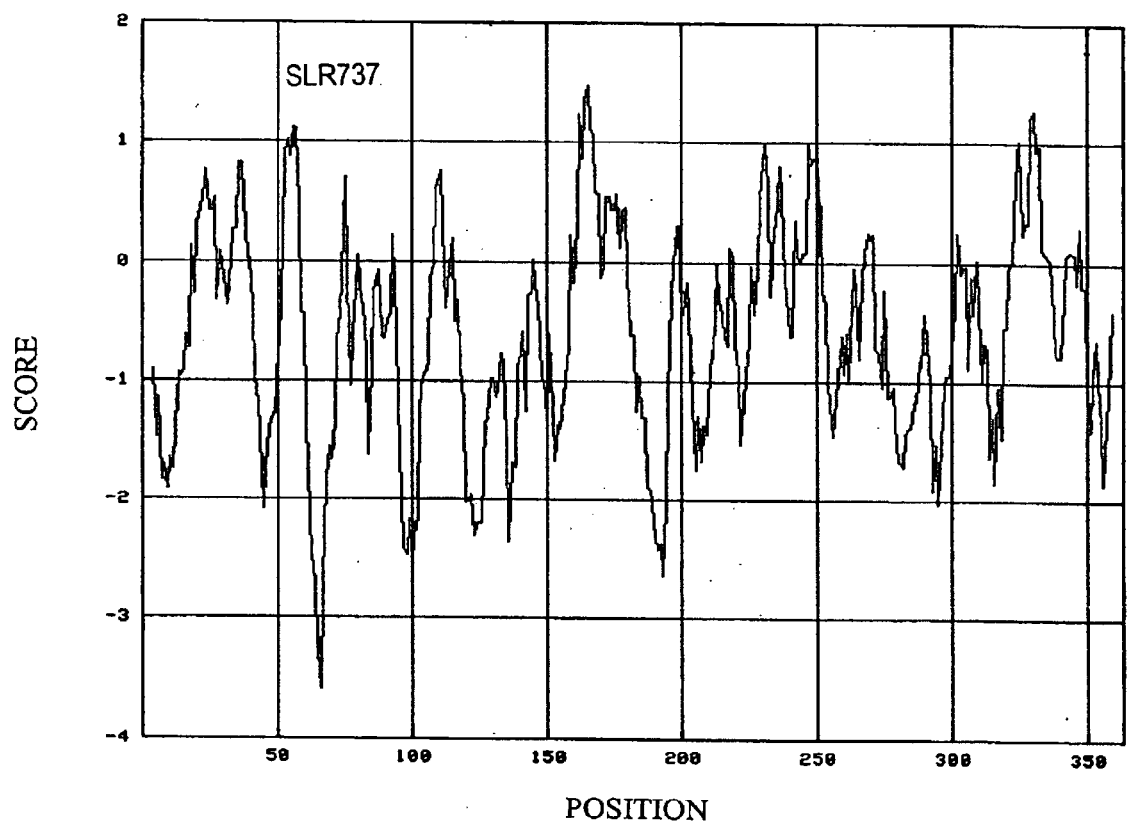
FIG. 32 shows the results of hydropathic analysis of slr1737

The slr1737 orf comprises 363 amino acid residues and has a predicted MW of 41 kDa (SEQ ID NO: 39). Hydropathic analysis indicates the protein is hydrophillic (FIG. 32).

Figure 33:
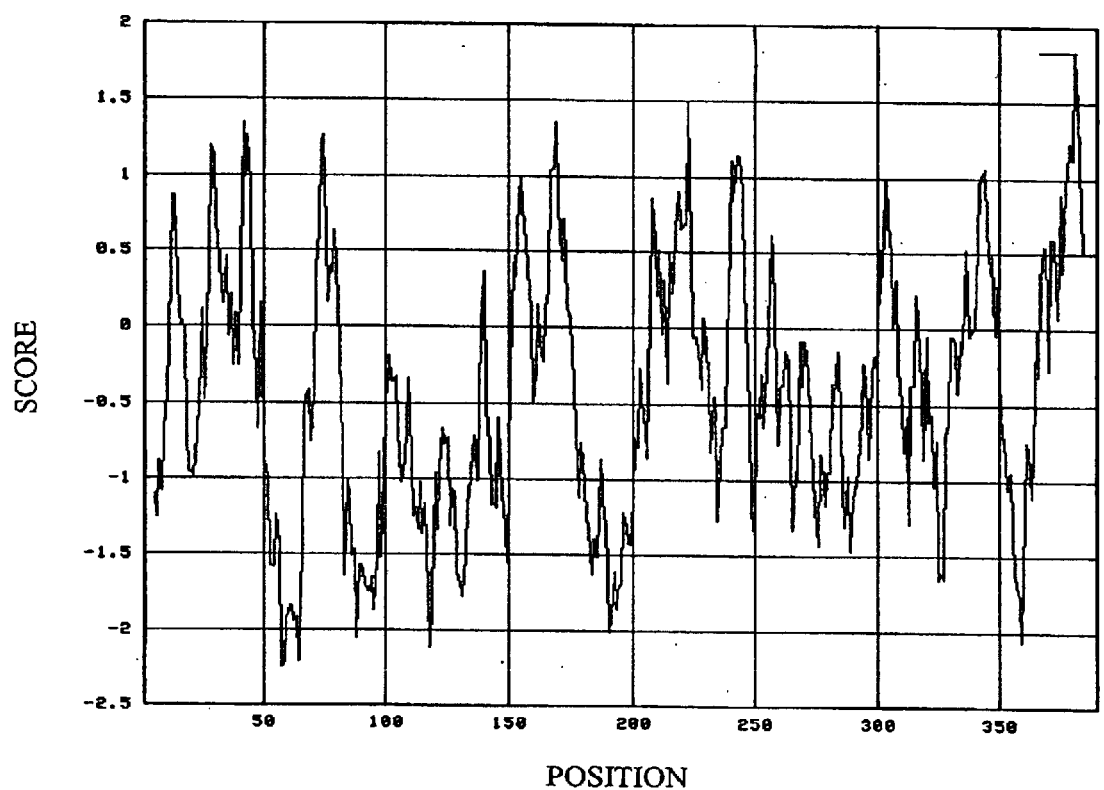
FIG. 33 shows the results of hydropathic analysis of the *Arabidopsis* homologue of slr1737.

The *Arabidopsis* homologue to slr1737 (SEQ ID NO: 110) comprises 488 amino acid residues, has a predicted MW of 55 kDa, and has a putative transit peptide sequence comprising the first 98 amino acids. The predicted MW of the mature form of the *Arabidopsis* homologue is 44 kDa. The hydropathic plot for the *Arabidopsis* homologue also reveals that it is hydrophillic (FIG. 33). Further blast analysis of the *Arabidopsis* homologue reveals limited sequence identity (25% sequence identity) with the beta-subunit of respiratory nitrate reductase. Based on the sequence identity to nitrate reductase, it suggests the slr1737 ORF is an enzyme that likely involves general acid catalysis mechanism.

Figure 34:
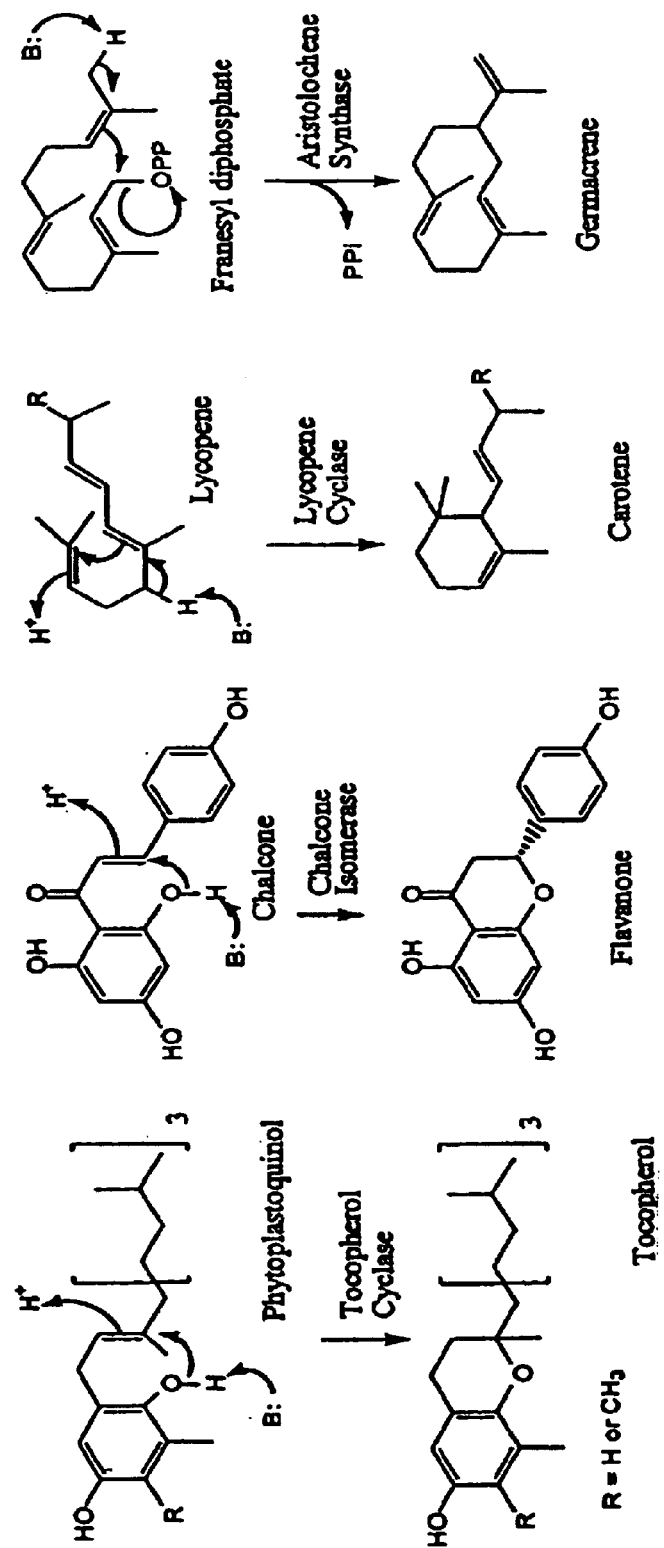
FIG. 34 shows the catalytic mechanism of various cyclase enzymes

Investigation of known enzymes involved in tocopherol metabolism indicated that the best candidate corresponding to the general acid mechanism is the tocopherol cyclase. There are many known examples of cyclases including, tocopherol cyclase, chalcone isomerase, lycopene cyclase, and aristolochene synthase. By further examination of the microscopic catalytic mechanism of phytoplastoquinol cyclization, as an example, chalcone isomerase has a catalytic mechanism most similar to tocopherol cyclase. (FIG. 34).

Multiple sequence alignment was performed between slr1737 (SEQ ID NO: 39), slr1737 *Arabidopsis* homologue (SEQ ID NO: 110) and the *Arabidopsis* chalcone isomerase (SEQ ID NO: 111) (Genbank:P41088) (FIG. 35). Sixty-five percent of the conserved residues among the three enzymes are strictly conserved within the known chalcone isomerases. The crystal structure of alfalfa chalcone isomerase has been solved (Jez, Joseph M., Bowman, Marianne E., Dixon, Richard A., and Noel, Joseph P. (2000) "Structure and mechanism of the evolutionarily unique plant enzyme chalcone isomerase". *Nature Structural Biology* 7: 786–791.) It has been demonstrated that tyrosine (Y) 106 of the alfalfa chalcone isomerase serves as the general acid during cyclization reaction (Genbank: P28012). The equivalent residue in slr1737 (SEQ ID NO: 39), and the slr1737 *Arabidopsis* homologue (SEQ ID NO: 110) is lysine (K), which is an excellent catalytic residue as general acid.

The information available from partial purification of tocopherol cyclase from *Chlorella protothecoides* (U.S. Pat. No. 5,432,069), i.e., described as being glycine rich, water soluble and with a predicted MW of 48–50 kDa, is consistent with the protein informatics information obtained for the slr1737 and the *Arabidopsis* slr1737 homologue.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid molecule encoding a tocopherol cyclase, wherein the isolated nucleic acid molecule is operably linked to a heterologous promoter functional in a plant and wherein said nucleic acid molecule encodes an amino acid sequence of SEQ ID NO: 39.

2. The isolated nucleic acid molecule of claim 1, wherein said tocopherol cyclase is encoded by a nucleotide sequence of SEQ ID NO: 38.

3. An isolated nucleic acid molecule comprising a nucleic acid sequence which is at least 95% identical over its entire length to the nucleic acid sequence of SEQ ID NO: 38, wherein the isolated nucleic acid molecule is operably linked to a heterologous promoter functional in a plant.

4. The isolated nucleic acid molecule of claim 3, wherein said nucleic acid molecule encodes a polypeptide comprising the amino acid sequence of SEQ ID NO: 39.

5. An isolated nucleic acid molecule which encodes a polypeptide comprising an amino acid sequence which is at least 90% identical over its entire length to the amino acid sequence of SEQ ID NO: 39, wherein the isolated nucleic acid molecule is operably linked to a heterologous promoter functional in a plant.

* * * * *

SEQUENCE LISTING

```
<160> NUMBER OF SEQ ID NOS: 114

<210> SEQ ID NO 1
<211> LENGTH: 1182
<212> TYPE: DNA
<213> ORGANISM: Arabidopsis sp.

<400> SEQUENCE: 1
atggagtctc tgctctctag ttcttctctt gtttccgctg ctggtgggtt ttgttggaag      60
aagcagaatc taaagctcca ctctttatca gaaatccgag ttctgcgttg tgattcgagt     120
aaagttgtcg caaaaccgaa gtttaggaac aatcttgtta ggcctgatgg tcaaggatct     180
tcattgttgt tgtatccaaa acataagtcg agatttcggt taatgccac tgcgggtcag      240 cctgaggctt tcgactcgaa tagcaaacag aagtctttta gagactcgtt agatgcgttt     300
tacaggtttt ctaggcctca tacagttatt ggcacagtgc ttagcatttt atctgtatct     360
ttcttagcag tagagaaggt ttctgatata tctcctttac ttttcactgg catcttggag     420
gctgttgttg cagctctcat gatgaacatt tacatagttg ggctaaatca gttgtctgat     480
gttgaaatag ataaggttaa caagccctat cttccattgg catcaggaga atattctgtt     540
aacaccggca ttgcaatagt agcttccttc tccatcatga gtttctggct tgggtggatt     600
gttggttcat ggccattgtt ctgggctctt tttgtgagtt tcatgctcgg tactgcatac     660
tctatcaatt tgccactttt acggtggaaa agatttgcat tggttgcagc aatgtgtatc     720
ctcgctgtcc gagctattat tgttcaaatc gcctttatc tacatattca gacacatgtg      780
tttggaagac caatcttgtt cactaggcct cttattttcg ccactgcgtt tatgagcttt     840
ttctctgtcg ttattgcatt gtttaaggat atacctgata tcgaagggga taagatattc     900
ggaatccgat cattctctgt aactctgggt cagaaacggg tgttttggac atgtgttaca     960
ctacttcaaa tggcttacgc tgttgcaatt ctagttggag ccacatctcc attcatatgg    1020
agcaaagtca tctcggttgt gggtcatgtt atactcgcaa caactttgtg ggctcgagct    1080
aagtccgttg atctgagtag caaaaccgaa ataacttcat gttatatgtt catatggaag    1140 ctctttttatg cagagtactt gctgttacct tttttgaagt ga                     1182

<210> SEQ ID NO 2
<211> LENGTH: 393
<212> TYPE: PRT
<213> ORGANISM: Arabidopsis sp.

<400> SEQUENCE: 2

Met Glu Ser Leu Leu Ser Ser Ser Ser Leu Val Ser Ala Ala Gly Gly
 1               5                  10                  15

Phe Cys Trp Lys Lys Gln Asn Leu Lys Leu His Ser Leu Ser Glu Ile
                20                  25                  30

Arg Val Leu Arg Cys Asp Ser Ser Lys Val Val Ala Lys Pro Lys Phe
            35                  40                  45
```

```
Arg Asn Asn Leu Val Arg Pro Asp Gly Gln Gly Ser Ser Leu Leu Leu
 50                  55                  60

Tyr Pro Lys His Lys Ser Arg Phe Arg Val Asn Ala Thr Ala Gly Gln
 65                  70                  75                  80

Pro Glu Ala Phe Asp Ser Asn Ser Lys Gln Lys Ser Phe Arg Asp Ser
                 85                  90                  95

Leu Asp Ala Phe Tyr Arg Phe Ser Arg Pro His Thr Val Ile Gly Thr
                100                 105                 110

Val Leu Ser Ile Leu Ser Val Ser Phe Leu Ala Val Glu Lys Val Ser
                115                 120                 125

Asp Ile Ser Pro Leu Leu Phe Thr Gly Ile Leu Glu Ala Val Val Ala
130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
                180                 185                 190

Met Ser Phe Trp Leu Gly Trp Ile Val Gly Ser Trp Pro Leu Phe Trp
                195                 200                 205

Ala Leu Phe Val Ser Phe Met Leu Gly Thr Ala Tyr Ser Ile Asn Leu
210                 215                 220

Pro Leu Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
                260                 265                 270

Phe Ala Thr Ala Phe Met Ser Phe Phe Ser Val Ile Ala Leu Phe
                275                 280                 285

Lys Asp Ile Pro Asp Ile Glu Gly Asp Lys Ile Phe Gly Ile Arg Ser
290                 295                 300

Phe Ser Val Thr Leu Gly Gln Lys Arg Val Phe Trp Thr Cys Val Thr
305                 310                 315                 320

Leu Leu Gln Met Ala Tyr Ala Val Ala Ile Leu Val Gly Ala Thr Ser
                325                 330                 335

Pro Phe Ile Trp Ser Lys Val Ile Ser Val Val Gly His Val Ile Leu
                340                 345                 350

Ala Thr Thr Leu Trp Ala Arg Ala Lys Ser Val Asp Leu Ser Ser Lys
                355                 360                 365

Thr Glu Ile Thr Ser Cys Tyr Met Phe Ile Trp Lys Leu Phe Tyr Ala
                370                 375                 380

Glu Tyr Leu Leu Leu Pro Phe Leu Lys
385                 390

<210> SEQ ID NO 3
<211> LENGTH: 1224
<212> TYPE: DNA
<213> ORGANISM: Arabidopsis sp.

<400> SEQUENCE: 3
atggcgtttt ttgggctctc ccgtgtttca agacggttgt tgaaatcttc cgtctccgta      60
actccatctt cttcctctgc tcttttgcaa tcacaacata aatccttgtc caatcctgtg     120
actacccatt acacaaatcc tttcactaag tgttatcctt catggaatga taattaccaa     180
```

-continued

```
gtatggagta aaggaagaga attgcatcag gagaagtttt ttggtgttgg ttggaattac      240
agattaattt gtggaatgtc gtcgtcttct tcggttttgg agggaaagcc gaagaaagat      300
gataaggaga agagtgatgg tgttgttgtt aagaaagctt cttggataga tttgtattta      360
ccagaagaag ttagaggtta tgctaagctt gctcgattgg ataaacccat tggaacttgg      420
ttgcttgcgt ggccttgtat gtggtcgatt gcgttggctg ctgatcctgg aagccttcca      480
agttttaaat atatggcttt atttggttgc ggagcattac ttcttagagg tgctggttgt      540
actataaatg atctgcttga tcaggacata gatacaaagg ttgatcgtac aaaactaaga      600
cctatcgcca gtggtctttt gacaccattt caagggattg gatttctcgg gctgcagttg      660
cttttaggct tagggattct tctccaactt aacaattaca gccgtgtttt agggg cttca      720 tctttgttac ttgtcttttc ctacccactt atgaagaggt ttacattttg gcctcaagcc      780
tttttaggtt tgaccataaa ctggggagca ttgttaggat ggactgcagt taaaggaagc      840
atagcaccat ctattgtact ccctctctat ctctccggag tctgctggac ccttgtttat      900
gatactattt atgcacatca ggacaaagaa gatgatgtaa agttggtgt taagtcaaca      960 gcccttagat tcggtgataa tacaaagctt tggttaactg gatttggcac agcatccata     1020
ggttttcttg cactttctgg attcagtgca gatctcgggt ggcaatatta cgcatcactg     1080
gccgctgcat caggacagtt aggatggcaa atagggacac tgacttatc atctggtgct      1140 gactgcagta gaaaatttgt gtcgaacaag tggtttggtg ctattatatt tagtggagtt     1200
gtacttggaa gaagttttca ataa                                           1224
```

<210> SEQ ID NO 4
<211> LENGTH: 407
<212> TYPE: PRT
<213> ORGANISM: Arabidopsis sp.

<400> SEQUENCE: 4

```
Met Ala Phe Phe Gly Leu Ser Arg Val Ser Arg Arg Leu Leu Lys Ser
 1               5                  10                  15

Ser Val Ser Val Thr Pro Ser Ser Ser Ala Leu Leu Gln Ser Gln
            20                  25                  30

His Lys Ser Leu Ser Asn Pro Val Thr Thr His Tyr Thr Asn Pro Phe
        35                  40                  45

Thr Lys Cys Tyr Pro Ser Trp Asn Asp Asn Tyr Gln Val Trp Ser Lys
    50                  55                  60

Gly Arg Glu Leu His Gln Glu Lys Phe Phe Gly Val Gly Trp Asn Tyr
65                  70                  75                  80

Arg Leu Ile Cys Gly Met Ser Ser Ser Ser Val Leu Glu Gly Lys
                85                  90                  95

Pro Lys Lys Asp Asp Lys Glu Lys Ser Asp Gly Val Val Lys Lys
            100                 105                 110

Ala Ser Trp Ile Asp Leu Tyr Leu Pro Glu Glu Val Arg Gly Tyr Ala
        115                 120                 125

Lys Leu Ala Arg Leu Asp Lys Pro Ile Gly Thr Trp Leu Leu Ala Trp
    130                 135                 140

Pro Cys Met Trp Ser Ile Ala Leu Ala Ala Asp Pro Gly Ser Leu Pro
145                 150                 155                 160

Ser Phe Lys Tyr Met Ala Leu Phe Gly Cys Gly Ala Leu Leu Leu Arg
                165                 170                 175

Gly Ala Gly Cys Thr Ile Asn Asp Leu Leu Asp Gln Asp Ile Asp Thr
```

```
                    180                 185                 190
Lys Val Asp Arg Thr Lys Leu Arg Pro Ile Ala Ser Gly Leu Leu Thr
                195                 200                 205
Pro Phe Gln Gly Ile Gly Phe Leu Gly Leu Gln Leu Leu Leu Gly Leu
            210                 215                 220
Gly Ile Leu Leu Gln Leu Asn Asn Tyr Ser Arg Val Leu Gly Ala Ser
225                 230                 235                 240
Ser Leu Leu Leu Val Phe Ser Tyr Pro Leu Met Lys Arg Phe Thr Phe
                245                 250                 255
Trp Pro Gln Ala Phe Leu Gly Leu Thr Ile Asn Trp Gly Ala Leu Leu
            260                 265                 270
Gly Trp Thr Ala Val Lys Gly Ser Ile Ala Pro Ser Ile Val Leu Pro
            275                 280                 285
Leu Tyr Leu Ser Gly Val Cys Trp Thr Leu Val Tyr Asp Thr Ile Tyr
        290                 295                 300
Ala His Gln Asp Lys Glu Asp Val Lys Gly Val Lys Ser Thr
305                 310                 315                 320
Ala Leu Arg Phe Gly Asp Asn Thr Lys Leu Trp Leu Thr Gly Phe Gly
                325                 330                 335
Thr Ala Ser Ile Gly Phe Leu Ala Leu Ser Gly Phe Ser Ala Asp Leu
            340                 345                 350
Gly Trp Gln Tyr Tyr Ala Ser Leu Ala Ala Ala Ser Gly Gln Leu Gly
        355                 360                 365
Trp Gln Ile Gly Thr Ala Asp Leu Ser Ser Gly Ala Asp Cys Ser Arg
        370                 375                 380
Lys Phe Val Ser Asn Lys Trp Phe Gly Ala Ile Ile Phe Ser Gly Val
385                 390                 395                 400
Val Leu Gly Arg Ser Phe Gln
                405

<210> SEQ ID NO 5
<211> LENGTH: 1296
<212> TYPE: DNA
<213> ORGANISM: Arabidopsis sp.

<400> SEQUENCE: 5
atgtggcgaa gatctgttgt ttctcgttta tcttcaagaa tctctgtttc ttcttcgtta        60
ccaaacccta gactgattcc ttggtcccgc gaattatgtg ccgttaatag cttctcccag       120
cctccggtct cgacggaatc aactgctaag ttagggatca ctggtgttag atctgatgcc       180
aatcgagttt ttgccactgc tactgccgcc gctacagcta cagctaccac cggtgagatt       240
tcgtctagag ttgcggcttt ggctggatta gggcatcact acgctcgttg ttattgggag       300
ctttctaaag ctaaacttag tatgcttgtg gttgcaactt ctggaactgg gtatattctg       360
ggtacgggaa atgctgcaat tagcttcccg gggctttgtt acacatgtgc aggaaccatg       420
atgattgctg catctgctaa ttccttgaat cagattttg agataagcaa tgattctaag       480
atgaaaagaa cgatgctaag gccattgcct caggacgta ttagtgttcc acacgctgtt        540
gcatgggcta ctattgctgg tgcttctggt gcttgtttgt tggccagcaa gactaatatg       600
ttggctgctg gacttgcatc tgccaatctt gtacttatg cgtttgttta tactccgttg        660
aagcaacttc accctatcaa tacatgggtt ggcgctgttg ttggtgctat cccacccttg       720
cttgggtggg cggcagcgtc tggtcagatt tcatacaatt cgatgattct tccagctgct       780
ctttactttt ggcagatacc tcattttatg gcccttgcac atctctgccg caatgattat       840
```

-continued

```
gcagctggag gttacaagat gttgtcactc tttgatccgt cagggaagag aatagcagca    900
gtggctctaa ggaactgctt ttacatgatc cctctcggtt tcatcgccta tgactggggg    960
ttaacctcaa gttggttttg cctcgaatca acacttctca cactagcaat cgctgcaaca   1020 gcatttcat tctaccgaga ccggaccatg cataaagcaa ggaaaatgtt ccatgccagt    1080
cttctcttcc ttcctgtttt catgtctggt cttcttctac accgtgtctc taatgataat   1140
cagcaacaac tcgtagaaga agccggatta acaaattctg tatctggtga agtcaaaact   1200
cagaggcgaa agaaacgtgt ggctcaacct ccggtggctt atgcctctgc tgcaccgttt   1260
cctttcctcc cagctccttc cttctactct ccatga                             1296
```

<210> SEQ ID NO 6
<211> LENGTH: 431
<212> TYPE: PRT
<213> ORGANISM: Arabidopsis sp.

<400> SEQUENCE: 6

```
Met Trp Arg Arg Ser Val Val Tyr Arg Phe Ser Ser Arg Ile Ser Val
 1               5                  10                  15

Ser Ser Ser Leu Pro Asn Pro Arg Leu Ile Pro Trp Ser Arg Glu Leu
            20                  25                  30

Cys Ala Val Asn Ser Phe Ser Gln Pro Pro Val Ser Thr Glu Ser Thr
        35                  40                  45

Ala Lys Leu Gly Ile Thr Gly Val Arg Ser Asp Ala Asn Arg Val Phe
    50                  55                  60

Ala Thr Ala Thr Ala Ala Ala Thr Ala Thr Thr Gly Glu Ile
65                  70                  75                  80

Ser Ser Arg Val Ala Ala Leu Ala Gly Leu Gly His His Tyr Ala Arg
                85                  90                  95

Cys Tyr Trp Glu Leu Ser Lys Ala Lys Leu Ser Met Leu Val Val Ala
            100                 105                 110

Thr Ser Gly Thr Gly Tyr Ile Leu Gly Thr Gly Asn Ala Ala Ile Ser
        115                 120                 125

Phe Pro Gly Leu Cys Tyr Thr Cys Ala Gly Thr Met Met Ile Ala Ala
    130                 135                 140

Ser Ala Asn Ser Leu Asn Gln Ile Phe Glu Ile Ser Asn Asp Ser Lys
145                 150                 155                 160

Met Lys Arg Thr Met Leu Arg Pro Leu Pro Ser Gly Arg Ile Ser Val
                165                 170                 175

Pro His Ala Val Ala Trp Ala Thr Ile Ala Gly Ala Ser Gly Ala Cys
            180                 185                 190

Leu Leu Ala Ser Lys Thr Asn Met Leu Ala Ala Gly Leu Ala Ser Ala
        195                 200                 205

Asn Leu Val Leu Tyr Ala Phe Val Tyr Thr Pro Leu Lys Gln Leu His
    210                 215                 220

Pro Ile Asn Thr Trp Val Gly Ala Val Gly Ala Ile Pro Pro Leu
225                 230                 235                 240

Leu Gly Trp Ala Ala Ala Ser Gly Gln Ile Ser Tyr Asn Ser Met Ile
                245                 250                 255

Leu Pro Ala Ala Leu Tyr Phe Trp Gln Ile Pro His Phe Met Ala Leu
            260                 265                 270

Ala His Leu Cys Arg Asn Asp Tyr Ala Ala Gly Gly Tyr Lys Met Leu
        275                 280                 285
```

```
Ser Leu Phe Asp Pro Ser Gly Lys Arg Ile Ala Ala Val Ala Leu Arg
    290                 295                 300

Asn Cys Phe Tyr Met Ile Pro Leu Gly Phe Ile Ala Tyr Asp Trp Gly
305                 310                 315                 320

Leu Thr Ser Ser Trp Phe Cys Leu Glu Ser Thr Leu Leu Thr Leu Ala
                325                 330                 335

Ile Ala Ala Thr Ala Phe Ser Phe Tyr Arg Asp Arg Thr Met His Lys
                340                 345                 350

Ala Arg Lys Met Phe His Ala Ser Leu Leu Phe Leu Pro Val Phe Met
            355                 360                 365

Ser Gly Leu Leu Leu His Arg Val Ser Asn Asp Asn Gln Gln Gln Leu
    370                 375                 380

Val Glu Glu Ala Gly Leu Thr Asn Ser Val Ser Gly Glu Val Lys Thr
385                 390                 395                 400

Gln Arg Arg Lys Lys Arg Val Ala Gln Pro Pro Val Ala Tyr Ala Ser
                405                 410                 415

Ala Ala Pro Phe Pro Phe Leu Pro Ala Pro Ser Phe Tyr Ser Pro
            420                 425                 430
```

<210> SEQ ID NO 7
<211> LENGTH: 479
<212> TYPE: DNA
<213> ORGANISM: Arabidopsis sp.

<400> SEQUENCE: 7

```
ggaaactccc ggagcacctg tttgcaggta ccgctaacct taatcgataa tttatttctc    60
ttgtcaggaa ttatgtaagt ctggtggaag gctcgcatac catttttgca ttgcctttcg   120
ctatgatcgg gtttactttg ggtgtgatga accaggcgt ggcttatgg tatggcgaaa     180
acccattttt atccaatgct gcattccctc ccgatgattc gttctttcat tcctatacag   240
gtatcatgct gataaaactg ttactggtac tggtttgtat ggtatcagca agaagcgcgg   300
cgatggcgtt taaccggtat ctcgacaggc attttgacgc gaagaacccg cgtactgcca   360
tccgtgaaat acctgcgggc gtcatatctg ccaacagtgc gctggtgttt acgataggct   420
gctgcgtggt attctgggtg gcctgttatt tcattaacac gatctgtttt tacctggcg    479
```

<210> SEQ ID NO 8
<211> LENGTH: 551
<212> TYPE: DNA
<213> ORGANISM: Arabidopsis sp.
<220> FEATURE:
<221> NAME/KEY: misc_feature
<222> LOCATION: (1)...(551)
<223> OTHER INFORMATION: n = A,T,C or G

<400> SEQUENCE: 8

```
ttgtggctta caccttaatg agcatacgcc agnccattac ggctcgttaa tcggcgccat    60
ngccggngct gntgcaccgg tagtgggcta ctgcgccgtg accaatcagc ttgatctagc   120
ggctcttatt ctgttttttaa ttttactgtt ctggcaaatg ccgcattttt acgcgatttc   180
catttttcagg ctaaaagact tttcagcggc ctgtattccg gtgctgccca tcattaaaga   240
cctgcgctat accaaaatca gcatgctggt ttacgtgggc ttatttacac tggctgctat   300
catgccggcc ctcttagggt atgccggttg gatttatggg atagcggcct taattttagg   360
cttgtattgg ctttatattg ccatacaagg attcaagacc gccgatgatc aaaaatggtc   420
tcgtaagatg tttggatctt cgattttaat cattaccctc ttgtcggtaa tgatgcttgt   480
```

```
ttaaacttac tgcctcctga agtttatata tcgataattt cagcttaagg aggcttagtg    540
gttaattcaa t                                                         551
```

<210> SEQ ID NO 9
<211> LENGTH: 297
<212> TYPE: PRT
<213> ORGANISM: Arabidopsis sp.

<400> SEQUENCE: 9

```
Met Val Leu Ala Glu Val Pro Lys Leu Ala Ser Ala Glu Tyr Phe
  1               5                  10                  15

Phe Lys Arg Gly Val Gln Gly Lys Gln Phe Arg Ser Thr Ile Leu Leu
                 20                  25                  30

Leu Met Ala Thr Ala Leu Asn Val Arg Val Pro Glu Ala Leu Ile Gly
             35                  40                  45

Glu Ser Thr Asp Ile Val Thr Ser Glu Leu Arg Val Arg Gln Arg Gly
 50                  55                  60

Ile Ala Glu Ile Thr Glu Met Ile His Val Ala Ser Leu Leu His Asp
 65                  70                  75                  80

Asp Val Leu Asp Asp Ala Asp Thr Arg Arg Gly Val Gly Ser Leu Asn
                 85                  90                  95

Val Val Met Gly Asn Lys Val Val Ala Leu Ala Thr Ala Val Glu
                100                 105                 110

His Leu Val Thr Gly Glu Thr Met Glu Ile Thr Ser Ser Thr Glu Gln
            115                 120                 125

Arg Tyr Ser Met Asp Tyr Tyr Met Gln Lys Thr Tyr Tyr Lys Thr Ala
    130                 135                 140

Ser Leu Ile Ser Asn Ser Cys Lys Ala Val Ala Val Leu Thr Gly Gln
145                 150                 155                 160

Thr Ala Glu Val Ala Val Leu Ala Phe Glu Tyr Gly Arg Asn Leu Gly
                165                 170                 175

Leu Ala Phe Gln Leu Ile Asp Asp Ile Leu Asp Phe Thr Gly Thr Ser
            180                 185                 190

Ala Ser Leu Gly Lys Gly Ser Leu Ser Asp Ile Arg His Gly Val Ile
        195                 200                 205

Thr Ala Pro Ile Leu Phe Ala Met Glu Glu Phe Pro Gln Leu Arg Glu
    210                 215                 220

Val Val Asp Gln Val Glu Lys Asp Pro Arg Asn Val Asp Ile Ala Leu
225                 230                 235                 240

Glu Tyr Leu Gly Lys Ser Lys Gly Ile Gln Arg Ala Arg Glu Leu Ala
                245                 250                 255

Met Glu His Ala Asn Leu Ala Ala Ala Ile Gly Ser Leu Pro Glu
            260                 265                 270

Thr Asp Asn Glu Asp Val Lys Arg Ser Arg Arg Ala Leu Ile Asp Leu
    275                 280                 285

Thr His Arg Val Ile Thr Arg Asn Lys
    290                 295
```

<210> SEQ ID NO 10
<211> LENGTH: 561
<212> TYPE: DNA
<213> ORGANISM: Arabidopsis sp.

<400> SEQUENCE: 10

```
aagcgcatcc gtcctcttct acgattgccg ccagccgcat gtatggctgc ataaccgacc    60
```

-continued

| | |
|---|---|
| gcccctatcc gctcgcggcc gcggtcgaat tcattcacac cgcgacgctg ctgcatgacg | 120 |
| acgtcgtcga tgaaagcgat ttgcgccgcg gccgcgaaag cgcgcataag gttttcggca | 180 |
| atcaggcgag cgtgctcgtc ggcgatttcc ttttctcccg cgccttccag ctgatggtgg | 240 |
| aagacggctc gctcgacgcg ctgcgcattc tctcggatgc ctccgccgtg atcgcgcagg | 300 |
| gcgaagtgat gcagctcggc accgcgcgca atcttgaaac caatatgagc cagtatctcg | 360 |
| atgtgatcag cgcgaagacc gccgcgctct ttgccgccgc ctgcgaaatc ggcccggtga | 420 |
| tggcgaacgc gaaggcggaa gatgctgccg cgatgtgcga atacggcatg aatctcggta | 480 |
| tcgccttcca gatcatcgac gaccttctcg attacggcac cggcggccac gccgagcttg | 540 |
| gcaagaacac gggcgacgat t | 561 |

<210> SEQ ID NO 11
<211> LENGTH: 966
<212> TYPE: DNA
<213> ORGANISM: Arabidopsis sp.

<400> SEQUENCE: 11

| | |
|---|---|
| atggtacttg ccgaggttcc aaagcttgcc tctgctgctg agtacttctt caaaagggt | 60 |
| gtgcaaggaa aacagtttcg ttcaactatt ttgctgctga tggcgacagc tctgaatgta | 120 |
| cgcgttccag aagcattgat tggggaatca acagatatag tcacatcaga attacgcgta | 180 |
| aggcaacggg gtattgctga aatcactgaa atgatacacg tcgcaagtct actgcacgat | 240 |
| gatgtcttgg atgatgccga tacaaggcgt ggtgttggtt ccttaaatgt tgtaatgggt | 300 |
| aacaagatgt cggtattagc aggagacttc ttgctctccc gggcttgtgg ggctctcgct | 360 |
| gctttaaaga acacagaggt tgtagcatta cttgcaactg ctgtagaaca tcttgttacc | 420 |
| ggtgaaacca tggaaataac tagttcaacc gagcagcgtt atagtatgga ctactacatg | 480 |
| cagaagacat attataagac agcatcgcta atctctaaca gctgcaaagc tgttgccgtt | 540 |
| ctcactggac aaacagcaga agttgccgtg ttagcttttg agtatgggag gaatctgggt | 600 |
| ttagcattcc aattaataga cgacattctt gatttcacgg gcacatctgc ctctctcgga | 660 |
| aagggatcgt tgtcagatat tcgccatgga gtcataacag ccccaatcct ctttgccatg | 720 |
| gaagagtttc ctcaactacg cgaagttgtt gatcaagttg aaaaagatcc taggaatgtt | 780 |
| gacattgctt tagagtatct tgggaagagc aagggaatac agagggcaag agaattagcc | 840 |
| atggaacatg cgaatctagc agcagctgca atcgggtctc tacctgaaac agacaatgaa | 900 |
| gatgtcaaaa gatcgaggcg ggcacttatt gacttgaccc atagagtcat caccagaaac | 960 |
| aagtga | 966 |

<210> SEQ ID NO 12
<211> LENGTH: 321
<212> TYPE: PRT
<213> ORGANISM: Arabidopsis sp.

<400> SEQUENCE: 12

Met Val Leu Ala Glu Val Pro Lys Leu Ala Ser Ala Ala Glu Tyr Phe
1               5                   10                  15

Phe Lys Arg Gly Val Gln Gly Lys Gln Phe Arg Ser Thr Ile Leu Leu
            20                  25                  30

Leu Met Ala Thr Ala Leu Asn Val Arg Val Pro Glu Ala Leu Ile Gly
        35                  40                  45

Glu Ser Thr Asp Ile Val Thr Ser Glu Leu Arg Val Arg Gln Arg Gly
    50                  55                  60

```
Ile Ala Glu Ile Thr Glu Met Ile His Val Ala Ser Leu Leu His Asp
 65                  70                  75                  80

Asp Val Leu Asp Asp Ala Asp Thr Arg Arg Gly Val Gly Ser Leu Asn
                 85                  90                  95

Val Val Met Gly Asn Lys Met Ser Val Leu Ala Gly Asp Phe Leu Leu
            100                 105                 110

Ser Arg Ala Cys Gly Ala Leu Ala Ala Leu Lys Asn Thr Glu Val Val
        115                 120                 125

Ala Leu Leu Ala Thr Ala Val Glu His Leu Val Thr Gly Glu Thr Met
    130                 135                 140

Glu Ile Thr Ser Ser Thr Glu Gln Arg Tyr Ser Met Asp Tyr Tyr Met
145                 150                 155                 160

Gln Lys Thr Tyr Tyr Lys Thr Ala Ser Leu Ile Ser Asn Ser Cys Lys
                165                 170                 175

Ala Val Ala Val Leu Thr Gly Gln Thr Ala Glu Val Ala Val Leu Ala
            180                 185                 190

Phe Glu Tyr Gly Arg Asn Leu Gly Leu Ala Phe Gln Leu Ile Asp Asp
        195                 200                 205

Ile Leu Asp Phe Thr Gly Thr Ser Ala Ser Leu Gly Lys Gly Ser Leu
    210                 215                 220

Ser Asp Ile Arg His Gly Val Ile Thr Ala Pro Ile Leu Phe Ala Met
225                 230                 235                 240

Glu Glu Phe Pro Gln Leu Arg Glu Val Val Asp Gln Val Glu Lys Asp
                245                 250                 255

Pro Arg Asn Val Asp Ile Ala Leu Glu Tyr Leu Gly Lys Ser Lys Gly
            260                 265                 270

Ile Gln Arg Ala Arg Glu Leu Ala Met Glu His Ala Asn Leu Ala Ala
        275                 280                 285

Ala Ala Ile Gly Ser Leu Pro Glu Thr Asp Asn Glu Asp Val Lys Arg
    290                 295                 300

Ser Arg Arg Ala Leu Ile Asp Leu Thr His Arg Val Ile Thr Arg Asn
305                 310                 315                 320

Lys

<210> SEQ ID NO 13
<211> LENGTH: 621
<212> TYPE: DNA
<213> ORGANISM: Arabidopsis sp.

<400> SEQUENCE: 13
gctttctcct tgctaattc ttgagctttc ttgatcccac cgcgatttct aactatttca      60
atcgcttctt caagcgatcc aggctcacaa aactcagact caatgatctc tcttagcctt    120
ggctcattct ctagcgcgaa gatcactggc gccgttatgt tacctttggc taagtcatta    180
gctgcaggct tacctaactg ctctgtggac tgagtgaagt ccagaatgtc atcaactact    240
tgaaaagata aaccgagatt cttcccgaac tgatacattt gctctgcgac cttgctttcg    300
actttactga aaattgctgc tcctttggtg cttgcagcta ctaatgaagc tgtcttgtag    360
taactcttta gcatgtagtc atcaagcttg acatcacaat cgaataaact cgatgcttgc    420
tttatctcac cgcttgcaaa atctttgatc acctgcaaaa agataaatca agattcagac    480
caaatgttct ttgtattgag tagcttcatc taatctcaga aaggaatatt acctgactta    540
tgagcttaat gacttcaagg ttttcgagat ttgtaagtac catgatgctt gagcaacatg    600
```

| aaatccccag ctaatacagc t | 621 |

<210> SEQ ID NO 14
<211> LENGTH: 741
<212> TYPE: DNA
<213> ORGANISM: Arabidopsis sp.

<400> SEQUENCE: 14

| ggtgagtttt gttaatagtt atgagattca tctattttg tcataaaatt gtttggtttg | 60 |
| gtttaaactc tgtgtataat tgcaggaaag gaaacagttc atgagctttt cggcacaaga | 120 |
| gtagcggtgc tagctggaga tttcatgttt gctcaagcgt catggtactt agcaaatctc | 180 |
| gagaatcttg aagttattaa gctcatcagt caggtactta gttactctta cattgttttt | 240 |
| ctatgaggtt gagctatgaa tctcatttcg ttgaataatg ctgtgcctca aactttttt | 300 |
| catgttttca ggtgatcaaa gactttgcaa gcggagagat aaagcaggcg tccagcttat | 360 |
| ttgactgcga caccaagctc gacgagtact tactcaaaag tttctacaag acagcctctt | 420 |
| tagtggctgc gagcaccaaa ggagctgcca ttttcagcag agttgagcct gatgtgacag | 480 |
| aacaaatgta cgagtttggg aagaatctcg gtctctcttt ccagatagtt gatgatattt | 540 |
| tggatttcac tcagtcgaca gagcagctcg ggaagccagc agggagtgat ttggctaaag | 600 |
| gtaacttaac agcacctgtg attttcgctc tggagaggga gccaaggcta agagagatca | 660 |
| ttgagtcaaa gttctgtgag gcgggttctc tggaagaagc gattgaagcg gtgacaaaag | 720 |
| gtgggggat aagagagca c | 741 |

<210> SEQ ID NO 15
<211> LENGTH: 1087
<212> TYPE: DNA
<213> ORGANISM: Arabidopsis sp.

<400> SEQUENCE: 15

| cctcttcagc caatccagag gaagaagaga caacttttta tctttcgtca agagtctccg | 60 |
| aaaacgcacg gttttatgct ctctcttctg ccctcacctc acaagacgca gggcacatga | 120 |
| ttcaaccaga gggaaaaagc aacgataaca actctgcttt tgatttcaag ctgtatatga | 180 |
| tccgcaaagc cgagtctgta aatgcggctc tcgacgtttc cgtaccgctt ctgaaacccc | 240 |
| ttacgatcca agaagcggtc aggtactctt tgctagccgg cggaaaacgt gtgaggcctc | 300 |
| tgctctgcat tgccgcttgt gagcttgtgg ggggcgacga ggctactgcc atgtcagccg | 360 |
| cttgcgcggt cgagatgatc cacacaagct ctctcattca tgacgatctt ccgtgcatgg | 420 |
| acaatgccga cctccgtaga ggcaagccca ccaatcacaa ggtatgttgt ttaattatat | 480 |
| gaaggctcag agataatgct gaactagtgt tgaaccaatt tttgctcaaa caaggtatat | 540 |
| ggagaagaca tggcggtttt ggcaggtgat gcactccttg cattggcgtt tgagcacatg | 600 |
| acggttgtgt cgagtgggtt ggtcgctccc gagaagatga ttcgcgccgt ggttgagctg | 660 |
| gccagggcca tagggactac agggctagtt gctggacaaa tgatagacct agccagcgaa | 720 |
| agactgaatc cagacaaggt tggattggag catctagagt tcatccatct ccacaaaacg | 780 |
| gcggcattgt tggaggcagc ggcagtttta ggggttataa tgggaggtgg aacagaggaa | 840 |
| gaaatcgaaa agcttagaaa gtatgctagg tgtattggac tactgtttca ggttgttgat | 900 |
| gacattctcg acgtaacaaa atctactgag gaattgggta agacagccgg aaaagacgta | 960 |
| atggccggaa agctgacgta tccaaggctg ataggtttgg agggatccag ggaagttgca | 1020 |
| gagcacctga ggagagaagc agaggaaaag cttaaagggt ttgatccaag tcaggcggcg | 1080 |

-continued

```
cctctgg                                                              1087

<210> SEQ ID NO 16
<211> LENGTH: 1164
<212> TYPE: DNA
<213> ORGANISM: Arabidopsis sp.

<400> SEQUENCE: 16
atgacttcga ttctcaacac tgtctccacc atccactctt ccagagttac ctccgtcgat     60
cgagtcggag tcctctctct tcggaattcg gattccgttg agttcactcg ccggcgttct    120
ggtttctcga cgttgatcta cgaatcaccc gggcggagat ttgttgtgcg tgcggcggag    180
actgatactg ataaagttaa atctcagaca cctgacaagg caccagccgg tggttcaagc    240
attaaccagc ttctcggtat caaaggagca tctcaagaaa ctaataaatg gaagattcgt    300
cttcagctta caaaaccagt cacttggcct ccactggttt ggggagtcgt ctgtggtgct    360
gctgcttcag ggaactttca ttggacccca gaggatgttg ctaagtcgat tctttgcatg    420
atgatgtctg gtccttgtct tactggctat acacagacaa tcaacgactg gtatgataga    480
gatatcgacg caattaatga gccatatcgt ccaattccat ctggagcaat atcagagcca    540
gaggttatta cacaagtctg ggtgctatta ttgggaggtc ttggtattgc tggaatatta    600
gatgtgtggg cagggcatac cactcccact gtcttctatc ttgctttggg aggatcattg    660
ctatcttata tatactctgc tccacctctt aagctaaaac aaaatggatg ggttggaaat    720
tttgcacttg gagcaagcta tattagtttg ccatggtggg ctggccaagc attgtttggc    780
actcttacgc cagatgttgt tgttctaaca ctcttgtaca gcatagctgg gttaggaata    840
gccattgtta acgacttcaa aagtgttgaa ggagatagag cattaggact tcagtctctc    900
ccagtagctt ttggcaccga aactgcaaaa tggatatgcg ttggtgctat agacattact    960
cagctttctg ttgccggata tctattagca tctgggaaac cttattatgc gttggcgttg   1020
gttgctttga tcattcctca gattgtgttc cagtttaaat actttctcaa ggaccctgtc   1080
aaatacgacg tcaagtacca ggcaagcgcg cagccattct tggtgctcgg aatatttgta   1140
acggcattag catcgcaaca ctga                                          1164

<210> SEQ ID NO 17
<211> LENGTH: 387
<212> TYPE: PRT
<213> ORGANISM: Arabidopsis sp.

<400> SEQUENCE: 17

Met Thr Ser Ile Leu Asn Thr Val Ser Thr Ile His Ser Ser Arg Val
  1               5                  10                  15

Thr Ser Val Asp Arg Val Gly Val Leu Ser Leu Arg Asn Ser Asp Ser
                 20                  25                  30

Val Glu Phe Thr Arg Arg Arg Ser Gly Phe Ser Thr Leu Ile Tyr Glu
             35                  40                  45

Ser Pro Gly Arg Arg Phe Val Val Arg Ala Ala Glu Thr Asp Thr Asp
 50                  55                  60

Lys Val Lys Ser Gln Thr Pro Asp Lys Ala Pro Ala Gly Gly Ser Ser
 65                  70                  75                  80

Ile Asn Gln Leu Leu Gly Ile Lys Gly Ala Ser Gln Glu Thr Asn Lys
                 85                  90                  95

Trp Lys Ile Arg Leu Gln Leu Thr Lys Pro Val Thr Trp Pro Pro Leu
            100                 105                 110
```

```
Val Trp Gly Val Val Cys Gly Ala Ala Ala Ser Gly Asn Phe His Trp
            115                 120                 125
Thr Pro Glu Asp Val Ala Lys Ser Ile Leu Cys Met Met Met Ser Gly
        130                 135                 140
Pro Cys Leu Thr Gly Tyr Thr Gln Thr Ile Asn Asp Trp Tyr Asp Arg
145                 150                 155                 160
Asp Ile Asp Ala Ile Asn Glu Pro Tyr Arg Pro Ile Pro Ser Gly Ala
                165                 170                 175
Ile Ser Glu Pro Glu Val Ile Thr Gln Val Trp Val Leu Leu Leu Gly
            180                 185                 190
Gly Leu Gly Ile Ala Gly Ile Leu Asp Val Trp Ala Gly His Thr Thr
        195                 200                 205
Pro Thr Val Phe Tyr Leu Ala Leu Gly Gly Ser Leu Leu Ser Tyr Ile
    210                 215                 220
Tyr Ser Ala Pro Pro Leu Lys Leu Lys Gln Asn Gly Trp Val Gly Asn
225                 230                 235                 240
Phe Ala Leu Gly Ala Ser Tyr Ile Ser Leu Pro Trp Trp Ala Gly Gln
                245                 250                 255
Ala Leu Phe Gly Thr Leu Thr Pro Asp Val Val Leu Thr Leu Leu
            260                 265                 270
Tyr Ser Ile Ala Gly Leu Gly Ile Ala Ile Val Asn Asp Phe Lys Ser
        275                 280                 285
Val Glu Gly Asp Arg Ala Leu Gly Leu Gln Ser Leu Pro Val Ala Phe
    290                 295                 300
Gly Thr Glu Thr Ala Lys Trp Ile Cys Val Gly Ala Ile Asp Ile Thr
305                 310                 315                 320
Gln Leu Ser Val Ala Gly Tyr Leu Leu Ala Ser Gly Lys Pro Tyr Tyr
                325                 330                 335
Ala Leu Ala Leu Val Ala Leu Ile Ile Pro Gln Ile Val Phe Gln Phe
            340                 345                 350
Lys Tyr Phe Leu Lys Asp Pro Val Lys Tyr Asp Val Lys Tyr Gln Ala
        355                 360                 365
Ser Ala Gln Pro Phe Leu Val Leu Gly Ile Phe Val Thr Ala Leu Ala
    370                 375                 380
Ser Gln His
385

<210> SEQ ID NO 18
<211> LENGTH: 981
<212> TYPE: DNA
<213> ORGANISM: Arabidopsis sp.

<400> SEQUENCE: 18
atgttgttta gtggttcagc gatcccatta agcagcttct gctctcttcc ggagaaaccc      60
cacactcttc ctatgaaact ctctcccgct gcaatccgat cttcatcctc atctgccccg     120
gggtcgttga acttcgatct gaggacgtat tggacgactc tgatcaccga gatcaaccag     180
aagctggatg aggccatacc ggtcaagcac cctgcgggga ctacgaggc tatgagatac      240
tctgtactcg cacaaggcgc caagcgtgcc cctcctgtga tgtgtgtggc ggcctgcgag     300
ctcttcggtg gcgatcgcct cgccgctttc cccaccgcct gtgccctaga aatggtgcac     360
gcggcttcgt tgatacacga cgacctcccc tgtatggacg acgatcctgt gcgcagagga     420
aagccatcta accacactgt ctacggctct ggcatggcca ttctcgccgg tgacgccctc     480
```

```
ttcccactcg ccttccagca cattgtctcc cacacgcctc ctgaccttgt tccccgagcc    540
accatcctca gactcatcac tgagattgcc cgcactgtcg gctccactgg tatggctgca    600
ggccagtacg tcgaccttga aggaggtccc tttcctcttt cctttgttca ggagaagaaa    660 tcggagcca tgggtgaatg ctctgccgtg tgcggtggcc tattgggcgg tgccactgag    720
gatgagctcc agagtctccg aaggtacggg agagccgtcg ggatgctgta tcaggtggtc    780
gatgacatca ccgaggacaa gaagaagagc tatgatggtg gagcagagaa gggaatgatg    840
gaaatggcgg aagagctcaa ggagaaggcg aagaaggagc ttcaagtgtt tgacaacaag    900 tatgaggag gagacacact tgttcctctc tacaccttcg ttgactacgc tgctcatcga    960
cattttcttc ttccctctg a                                              981

<210> SEQ ID NO 19
<211> LENGTH: 245
<212> TYPE: DNA
<213> ORGANISM: Glycine sp.

<400> SEQUENCE: 19
gcaacatctg ggactgggtt tgtcttgggg agtggtagtg ctgttgatct ttcggcactt     60
tcttgcactt gcttgggtac catgatggtt gctgcatctg ctaactcttt gaatcaggtg    120
tttgagatca ataatgatgc taaaatgaag agaacaagtc gcaggccact accctcagga    180
cgcatcacaa tacctcatgc agttggctgg gcatcctctg ttggattagc tggtacggct    240
ctact                                                               245

<210> SEQ ID NO 20
<211> LENGTH: 253
<212> TYPE: DNA
<213> ORGANISM: Glycine sp.

<400> SEQUENCE: 20
attggctttc caagatcatt gggttttctt gttgcattca tgaccttcta ctccttgggt     60
ttggcattgt ccaaggatat acctgacgtt gaaggagata agagcacgg cattgattct    120 tttgcagtac gtctaggtca gaaacgggca ttttggattt gcgtttcctt ttttgaaatg    180
gctttcggag ttggtatcct ggccggagca tcatgctcac acttttggac taaaattttc    240
acgggtatgg gaa                                                      253

<210> SEQ ID NO 21
<211> LENGTH: 275
<212> TYPE: DNA
<213> ORGANISM: Glycine sp.

<400> SEQUENCE: 21
tgatcttcta ctctctgggt atggcattgt ccaaggatat atctgacgtt aaaggagata     60
aagcatacgg catcgatact ttagcgatac gtttgggtca aaaatgggta ttttggattt    120
gcattatcct ttttgaaatg cttttggag ttgccctctt ggcaggagca acatcttctt    180 accttttggat taaaattgtc acgggtctgg gacatgctat tcttgcttca attctcttgt    240
accaagccaa atctatatac ttgagcaaca aagtt                               275

<210> SEQ ID NO 22
<211> LENGTH: 299
<212> TYPE: DNA
<213> ORGANISM: Glycine sp.
<220> FEATURE:
<221> NAME/KEY: misc_feature
```

-continued

<222> LOCATION: (1)...(299)
<223> OTHER INFORMATION: n = A,T,C or G

<400> SEQUENCE: 22

```
ccanaatang tncatcttng aaagacaatt ggcctcttca acacacaagt ctgcatgtga    60
agaagaggcc aattgtcttt ccaagatcac ttatngtggc tattgtaatc atgaacttct   120
tctttgtggg tatggcattg gcaaaggata tacctanctg ttgaaggaga taaaatatat   180
ggcattgata cttttgcaat acgtataggt caaaaacaag tattttggat ttgtattttc   240
ctttttgaaa ggctttcgga gtttccctag tggcaggagc aacatcttct agccttggt    299
```

<210> SEQ ID NO 23
<211> LENGTH: 767
<212> TYPE: DNA
<213> ORGANISM: Glycine sp.

<400> SEQUENCE: 23

```
gtggaggctg tggttgctgc cctgtttatg aatatttata ttgttggttt gaatcaattg    60
tctgatgttg aaatagacaa gataaacaag ccgtatcttc cattagcatc tggggaatat   120
tcctttgaaa ctggtgtcac tattgttgca tcttttttcaa ttctgagttt ttggcttggc   180
tgggttgtag gttcatggcc attatttttgg gccctttttg taagctttgt gctaggaact   240
gcttattcaa tcaatgtgcc tctgttgaga tggaagaggt ttgcagtgct gcagcgatg    300
tgcattctag ctgttcgggc agtaatagtt caacttgcat ttttccttca catgcagact   360
catgtgtaca agaggccacc tgtcttttca agaccattga ttttttgctac tgcattcatg   420
agcttcttct ctgtagttat agcactgttt aaggatatac ctgacattga aggagataaa   480
gtatttggca tccaatcttt ttcagtgtgt ttaggtcaga agccggtgtt ctggacttgt   540
gttaccttc ttgaaatagc ttatggagtc gccctcctgg tgggagctgc atctccttgt   600
cttttggagca aaattttcac gggtctggga cacgctgtgc tggcttcaat tctctggttt   660
catgccaaat ctgtagattt gaaaagcaaa gcttcgataa catccttcta tatgtttatt   720
tggaagctat tttatgcaga atacttactc attccttttg ttagatg               767
```

<210> SEQ ID NO 24
<211> LENGTH: 255
<212> TYPE: PRT
<213> ORGANISM: Glycine sp.

<400> SEQUENCE: 24

```
Val Glu Ala Val Val Ala Ala Leu Phe Met Asn Ile Tyr Ile Val Gly
 1               5                  10                  15

Leu Asn Gln Leu Ser Asp Val Glu Ile Asp Lys Ile Asn Lys Pro Tyr
            20                  25                  30

Leu Pro Leu Ala Ser Gly Glu Tyr Ser Phe Glu Thr Gly Val Thr Ile
        35                  40                  45

Val Ala Ser Phe Ser Ile Leu Ser Phe Trp Leu Gly Trp Val Val Gly
    50                  55                  60

Ser Trp Pro Leu Phe Trp Ala Leu Phe Val Ser Phe Val Leu Gly Thr
65                  70                  75                  80

Ala Tyr Ser Ile Asn Val Pro Leu Leu Arg Trp Lys Arg Phe Ala Val
                85                  90                  95

Leu Ala Ala Met Cys Ile Leu Ala Val Arg Ala Val Ile Val Gln Leu
            100                 105                 110

Ala Phe Phe Leu His Met Gln Thr His Val Tyr Lys Arg Pro Pro Val
```

```
                115                 120                 125
Phe Ser Arg Pro Leu Ile Phe Ala Thr Ala Phe Met Ser Phe Ser
    130                 135                 140

Val Val Ile Ala Leu Phe Lys Asp Ile Pro Asp Ile Glu Gly Asp Lys
145                 150                 155                 160

Val Phe Gly Ile Gln Ser Phe Ser Val Cys Leu Gly Gln Lys Pro Val
                165                 170                 175

Phe Trp Thr Cys Val Thr Leu Leu Glu Ile Ala Tyr Gly Val Ala Leu
            180                 185                 190

Leu Val Gly Ala Ala Ser Pro Cys Leu Trp Ser Lys Ile Phe Thr Gly
        195                 200                 205

Leu Gly His Ala Val Leu Ala Ser Ile Leu Trp Phe His Ala Lys Ser
    210                 215                 220

Val Asp Leu Lys Ser Lys Ala Ser Ile Thr Ser Phe Tyr Met Phe Ile
225                 230                 235                 240

Trp Lys Leu Phe Tyr Ala Glu Tyr Leu Leu Ile Pro Phe Val Arg
                245                 250                 255

<210> SEQ ID NO 25
<211> LENGTH: 360
<212> TYPE: DNA
<213> ORGANISM: Zea sp.
<220> FEATURE:
<221> NAME/KEY: misc_feature
<222> LOCATION: (1)...(360)
<223> OTHER INFORMATION: n = A,T,C or G

<400> SEQUENCE: 25
ggcgtcttca cttgttctgg tcttctcgta tccctgatg  aagaggttca cattttggcc    60
tcaggcttat cttggcctga cattcaactg gggagcttta ctagggtggg ctgctattaa   120
ggaaagcata gaccctgcaa atcatccttc cattgtatac agctggtatt tgttggacgc   180
tggtgtatga tactatatat gcgcatcagg tgtttcgcta tccctacttt catattaatc   240
cttgatgaag tggccatttc atgttgtcgc ggtggtctta tcttgcata  tctccatgca   300 tctcaggaca aagangatga cctgaaagta ggagtccaag tccacagctt aagatttggg   360

<210> SEQ ID NO 26
<211> LENGTH: 299
<212> TYPE: DNA
<213> ORGANISM: Zea sp.
<220> FEATURE:
<221> NAME/KEY: misc_feature
<222> LOCATION: (1)...(299)
<223> OTHER INFORMATION: n = A,T,C or G

<400> SEQUENCE: 26
gatggttgca gcatctgcaa atacccctcaa ccaggtgttt gngataaaaa atgatgctaa    60
aatgaaaagg acaatgcgtg cccctgcca  tctggtcgca ttagtcctgc acatgctgcg   120
atgtgggcta caagtgttgg agttgcagga acagctttgt tggcctggaa ggctaatggc   180
ttggcagctg gcttgcagc  ttctaatctt gttctgtatg catttgtgta tacgccgttg   240
aagcaaatac accctgttaa tacatgggtt ggggcagtcg ttggtgccat cccaccact    299

<210> SEQ ID NO 27
<211> LENGTH: 255
<212> TYPE: DNA
<213> ORGANISM: Zea sp.
<220> FEATURE:
<221> NAME/KEY: misc_feature
```

```
<222> LOCATION: (1)...(255)
<223> OTHER INFORMATION: n = A,T,C or G

<400> SEQUENCE: 27
anacttgcat atctccatgc ntctcaggac aaagangatg acctgaaagt aggtgtcaag    60
tccacagcat taagatttgg agatttgacc nnatactgna tcagtggctt tggcgcggca   120
tgcttcggca gcttagcact cagtggttac aatgctgacc ttggttggtg tttagtgtga   180
tgcttgagcg aagaatggta tngttttttac ttgatattga ctccagacct gaaatcatgt   240
tggacagggt ggccc                                                    255

<210> SEQ ID NO 28
<211> LENGTH: 257
<212> TYPE: DNA
<213> ORGANISM: Zea sp.

<400> SEQUENCE: 28
attgaagggg ataggactct ggggcttcag tcacttcctg ttgcttttgg gatggaaact    60
gcaaaatgga tttgtgttgg agcaattgat atcactcaat tatctgttgc aggttaccta   120
ttgagcaccg gtaagctgta ttatgccctg gtgttgcttg ggctaacaat tcctcaggtg   180
ttctttcagt tccagtactt cctgaaggac cctgtgaagt atgatgtcaa atatcaggca   240
agcgcacaac cattctt                                                  257

<210> SEQ ID NO 29
<211> LENGTH: 368
<212> TYPE: DNA
<213> ORGANISM: Zea sp.

<400> SEQUENCE: 29
atccagttgc aaataataat ggcgttcttc tctgttgtaa tagcactatt caaggatata    60
cctgacatcg aaggggaccg catattcggg atccgatcct tcagcgtccg gttagggcaa   120
aagaaggtct tttggatctg cgttggcttg cttgagatgg cctacagcgt tgcgatactg   180
atgggagcta cctcttcctg tttgtggagc aaaacagcaa ccatcgctgg ccattccata   240
cttgccgcga tcctatggag ctgcgcgcga tcggtggact tgacgagcaa agccgcaata   300
acgtccttct acatgttcat ctggaagctg ttctacgcgg agtacctgct catccctctg   360
gtgcggtg                                                            368

<210> SEQ ID NO 30
<211> LENGTH: 122
<212> TYPE: PRT
<213> ORGANISM: Zea sp.

<400> SEQUENCE: 30

Ile Gln Leu Gln Ile Ile Met Ala Phe Phe Ser Val Val Ile Ala Leu
  1               5                  10                  15

Phe Lys Asp Ile Pro Asp Ile Glu Gly Asp Arg Ile Phe Gly Ile Arg
             20                  25                  30

Ser Phe Ser Val Arg Leu Gly Gln Lys Lys Val Phe Trp Ile Cys Val
         35                  40                  45

Gly Leu Leu Glu Met Ala Tyr Ser Val Ala Ile Leu Met Gly Ala Thr
     50                  55                  60

Ser Ser Cys Leu Trp Ser Lys Thr Ala Thr Ile Ala Gly His Ser Ile
 65                  70                  75                  80

Leu Ala Ala Ile Leu Trp Ser Cys Ala Arg Ser Val Asp Leu Thr Ser
```

85                  90                  95
Lys Ala Ala Ile Thr Ser Phe Tyr Met Phe Ile Trp Lys Leu Phe Tyr
                100                 105                 110
Ala Glu Tyr Leu Leu Ile Pro Leu Val Arg
            115                 120

<210> SEQ ID NO 31
<211> LENGTH: 278
<212> TYPE: DNA
<213> ORGANISM: Zea sp.

<400> SEQUENCE: 31
tattcagcac cacctctcaa gctcaagcag aatggatgga ttgggaactt cgctctgggt      60
gcgagttaca tcagcttgcc ctggtgggct ggccaggcgt tatttggaac tcttacacca     120
gatatcattg tcttgactac tttgtacagc atagctgggc tagggattgc tattgtaaat     180
gatttcaaga gtattgaagg ggataggact ctggggcttc agtcacttcc tgttgctttt     240
gggatggaaa ctgcaaaatg gatttgtgtt ggagcaat                             278

<210> SEQ ID NO 32
<211> LENGTH: 292
<212> TYPE: PRT
<213> ORGANISM: Synechocystis sp.

<400> SEQUENCE: 32

Met Val Ala Gln Thr Pro Ser Ser Pro Pro Leu Trp Leu Thr Ile Ile
 1               5                  10                  15

Tyr Leu Leu Arg Trp His Lys Pro Ala Gly Arg Leu Ile Leu Met Ile
                20                  25                  30

Pro Ala Leu Trp Ala Val Cys Leu Ala Ala Gln Gly Leu Pro Pro Leu
            35                  40                  45

Pro Leu Leu Gly Thr Ile Ala Leu Gly Thr Leu Ala Thr Ser Gly Leu
        50                  55                  60

Gly Cys Val Val Asn Asp Leu Trp Asp Arg Asp Ile Asp Pro Gln Val
65                  70                  75                  80

Glu Arg Thr Lys Gln Arg Pro Leu Ala Ala Arg Ala Leu Ser Val Gln
                85                  90                  95

Val Gly Ile Gly Val Ala Leu Val Ala Leu Leu Cys Ala Ala Gly Leu
                100                 105                 110

Ala Phe Tyr Leu Thr Pro Leu Ser Phe Trp Leu Cys Val Ala Ala Val
            115                 120                 125

Pro Val Ile Val Ala Tyr Pro Gly Ala Lys Arg Val Phe Pro Val Pro
        130                 135                 140

Gln Leu Val Leu Ser Ile Ala Trp Gly Phe Ala Val Leu Ile Ser Trp
145                 150                 155                 160

Ser Ala Val Thr Gly Asp Leu Thr Asp Ala Thr Trp Val Leu Trp Gly
                165                 170                 175

Ala Thr Val Phe Trp Thr Leu Gly Phe Asp Thr Val Tyr Ala Met Ala
            180                 185                 190

Asp Arg Glu Asp Asp Arg Arg Ile Gly Val Asn Ser Ser Ala Leu Phe
        195                 200                 205

Phe Gly Gln Tyr Val Gly Glu Ala Val Gly Ile Phe Phe Ala Leu Thr
    210                 215                 220

Ile Gly Cys Leu Phe Tyr Leu Gly Met Ile Leu Met Leu Asn Pro Leu
225                 230                 235                 240

```
Tyr Trp Leu Ser Leu Ala Ile Ala Ile Val Gly Trp Val Ile Gln Tyr
                245                 250                 255

Ile Gln Leu Ser Ala Pro Thr Pro Glu Pro Lys Leu Tyr Gly Gln Ile
                260                 265                 270

Phe Gly Gln Asn Val Ile Ile Gly Phe Val Leu Leu Ala Gly Met Leu
                275                 280                 285

Leu Gly Trp Leu
        290

<210> SEQ ID NO 33
<211> LENGTH: 316
<212> TYPE: PRT
<213> ORGANISM: Synechocystis sp.

<400> SEQUENCE: 33

Met Val Thr Ser Thr Lys Ile His Arg Gln His Asp Ser Met Gly Ala
  1               5                  10                  15

Val Cys Lys Ser Tyr Tyr Gln Leu Thr Lys Pro Arg Ile Ile Pro Leu
                 20                  25                  30

Leu Leu Ile Thr Thr Ala Ala Ser Met Trp Ile Ala Ser Glu Gly Arg
             35                  40                  45

Val Asp Leu Pro Lys Leu Leu Ile Thr Leu Leu Gly Gly Thr Leu Ala
 50                  55                  60

Ala Ala Ser Ala Gln Thr Leu Asn Cys Ile Tyr Asp Gln Asp Ile Asp
 65                  70                  75                  80

Tyr Glu Met Leu Arg Thr Arg Ala Arg Pro Ile Pro Ala Gly Lys Val
                 85                  90                  95

Gln Pro Arg His Ala Leu Ile Phe Ala Leu Ala Leu Gly Val Leu Ser
                100                 105                 110

Phe Ala Leu Leu Ala Thr Phe Val Asn Val Leu Ser Gly Cys Leu Ala
            115                 120                 125

Leu Ser Gly Ile Val Phe Tyr Met Leu Val Tyr Thr His Trp Leu Lys
130                 135                 140

Arg His Thr Ala Gln Asn Ile Val Ile Gly Gly Ala Ala Gly Ser Ile
145                 150                 155                 160

Pro Pro Leu Val Gly Trp Ala Ala Val Thr Gly Asp Leu Ser Trp Thr
                165                 170                 175

Pro Trp Val Leu Phe Ala Leu Ile Phe Leu Trp Thr Pro Pro His Phe
                180                 185                 190

Trp Ala Leu Ala Leu Met Ile Lys Asp Asp Tyr Ala Gln Val Asn Val
            195                 200                 205

Pro Met Leu Pro Val Ile Ala Gly Glu Glu Lys Thr Val Ser Gln Ile
210                 215                 220

Trp Tyr Tyr Ser Leu Leu Val Val Pro Phe Ser Leu Leu Val Tyr
225                 230                 235                 240

Pro Leu His Gln Leu Gly Ile Leu Tyr Leu Ala Ile Ala Ile Ile Leu
                245                 250                 255

Gly Gly Gln Phe Leu Val Lys Ala Trp Gln Leu Lys Gln Ala Pro Gly
                260                 265                 270

Asp Arg Asp Leu Ala Arg Gly Leu Phe Lys Phe Ser Ile Phe Tyr Leu
                275                 280                 285

Met Leu Leu Cys Leu Ala Met Val Ile Asp Ser Leu Pro Val Thr His
            290                 295                 300

Gln Leu Val Ala Gln Met Gly Thr Leu Leu Leu Gly
305                 310                 315
```

<210> SEQ ID NO 34
<211> LENGTH: 324
<212> TYPE: PRT
<213> ORGANISM: Synechocystis sp.

<400> SEQUENCE: 34

Met Ser Asp Thr Gln Asn Thr Gly Gln Asn Gln Ala Lys Ala Arg Gln
1               5                   10                  15

Leu Leu Gly Met Lys Gly Ala Ala Pro Gly Glu Ser Ser Ile Trp Lys
            20                  25                  30

Ile Arg Leu Gln Leu Met Lys Pro Ile Thr Trp Ile Pro Leu Ile Trp
        35                  40                  45

Gly Val Val Cys Gly Ala Ala Ser Ser Gly Gly Tyr Ile Trp Ser Val
    50                  55                  60

Glu Asp Phe Leu Lys Ala Leu Thr Cys Met Leu Leu Ser Gly Pro Leu
65                  70                  75                  80

Met Thr Gly Tyr Thr Gln Thr Leu Asn Asp Phe Tyr Asp Arg Asp Ile
            85                  90                  95

Asp Ala Ile Asn Glu Pro Tyr Arg Pro Ile Pro Ser Gly Ala Ile Ser
            100                 105                 110

Val Pro Gln Val Val Thr Gln Ile Leu Ile Leu Leu Val Ala Gly Ile
        115                 120                 125

Gly Val Ala Tyr Gly Leu Asp Val Trp Ala Gln His Asp Phe Pro Ile
    130                 135                 140

Met Met Val Leu Thr Leu Gly Gly Ala Phe Val Ala Tyr Ile Tyr Ser
145                 150                 155                 160

Ala Pro Pro Leu Lys Leu Lys Gln Asn Gly Trp Leu Gly Asn Tyr Ala
                165                 170                 175

Leu Gly Ala Ser Tyr Ile Ala Leu Pro Trp Trp Ala Gly His Ala Leu
            180                 185                 190

Phe Gly Thr Leu Asn Pro Thr Ile Met Val Leu Thr Leu Ile Tyr Ser
        195                 200                 205

Leu Ala Gly Leu Gly Ile Ala Val Val Asn Asp Phe Lys Ser Val Glu
    210                 215                 220

Gly Asp Arg Gln Leu Gly Leu Lys Ser Leu Pro Val Met Phe Gly Ile
225                 230                 235                 240

Gly Thr Ala Ala Trp Ile Cys Val Ile Met Ile Asp Val Phe Gln Ala
                245                 250                 255

Gly Ile Ala Gly Tyr Leu Ile Tyr Val His Gln Gln Leu Tyr Ala Thr
            260                 265                 270

Ile Val Leu Leu Leu Leu Ile Pro Gln Ile Thr Phe Gln Asp Met Tyr
        275                 280                 285

Phe Leu Arg Asn Pro Leu Glu Asn Asp Val Lys Tyr Gln Ala Ser Ala
    290                 295                 300

Gln Pro Phe Leu Val Phe Gly Met Leu Ala Thr Gly Leu Ala Leu Gly
305                 310                 315                 320

His Ala Gly Ile

<210> SEQ ID NO 35
<211> LENGTH: 307
<212> TYPE: PRT
<213> ORGANISM: Synechocystis sp.

<400> SEQUENCE: 35

| Met | Thr | Glu | Ser | Ser | Pro | Leu | Ala | Pro | Ser | Thr | Ala | Pro | Ala | Thr | Arg |
| 1 | | | | 5 | | | | | 10 | | | | | 15 | |

| Lys | Leu | Trp | Leu | Ala | Ala | Ile | Lys | Pro | Pro | Met | Tyr | Thr | Val | Ala | Val |
| | | | 20 | | | | | 25 | | | | | 30 | | |

| Val | Pro | Ile | Thr | Val | Gly | Ser | Ala | Val | Ala | Tyr | Gly | Leu | Thr | Gly | Gln |
| | | | 35 | | | | 40 | | | | | 45 | | | |

| Trp | His | Gly | Asp | Val | Phe | Thr | Ile | Phe | Leu | Leu | Ser | Ala | Ile | Ala | Ile |
| | 50 | | | | | 55 | | | | | 60 | | | | |

| Ile | Ala | Trp | Ile | Asn | Leu | Ser | Asn | Asp | Val | Phe | Asp | Ser | Asp | Thr | Gly |
| 65 | | | | | 70 | | | | | 75 | | | | | 80 |

| Ile | Asp | Val | Arg | Lys | Ala | His | Ser | Val | Val | Asn | Leu | Thr | Gly | Asn | Arg |
| | | | | 85 | | | | | 90 | | | | | 95 | |

| Asn | Leu | Val | Phe | Leu | Ile | Ser | Asn | Phe | Phe | Leu | Leu | Ala | Gly | Val | Leu |
| | | | | 100 | | | | | 105 | | | | | 110 | |

| Gly | Leu | Met | Ser | Met | Ser | Trp | Arg | Ala | Gln | Asp | Trp | Thr | Val | Leu | Glu |
| | | | 115 | | | | | 120 | | | | | 125 | | |

| Leu | Ile | Gly | Val | Ala | Ile | Phe | Leu | Gly | Tyr | Thr | Tyr | Gln | Gly | Pro | Pro |
| | | 130 | | | | | 135 | | | | | 140 | | | |

| Phe | Arg | Leu | Gly | Tyr | Leu | Gly | Leu | Gly | Glu | Leu | Ile | Cys | Leu | Ile | Thr |
| 145 | | | | | 150 | | | | | 155 | | | | | 160 |

| Phe | Gly | Pro | Leu | Ala | Ile | Ala | Ala | Ala | Tyr | Tyr | Ser | Gln | Ser | Gln | Ser |
| | | | | 165 | | | | | 170 | | | | | 175 | |

| Phe | Ser | Trp | Asn | Leu | Leu | Thr | Pro | Ser | Val | Phe | Val | Gly | Ile | Ser | Thr |
| | | | | 180 | | | | | 185 | | | | | 190 | |

| Ala | Ile | Ile | Leu | Phe | Cys | Ser | His | Phe | His | Gln | Val | Glu | Asp | Asp | Leu |
| | | 195 | | | | | 200 | | | | | 205 | | | |

| Ala | Ala | Gly | Lys | Lys | Ser | Pro | Ile | Val | Arg | Leu | Gly | Thr | Lys | Leu | Gly |
| | 210 | | | | | 215 | | | | | 220 | | | | |

| Ser | Gln | Val | Leu | Thr | Leu | Ser | Val | Val | Ser | Leu | Tyr | Leu | Ile | Thr | Ala |
| 225 | | | | | 230 | | | | | 235 | | | | | 240 |

| Ile | Gly | Val | Leu | Cys | His | Gln | Ala | Pro | Trp | Gln | Thr | Leu | Leu | Ile | Ile |
| | | | | 245 | | | | | 250 | | | | | 255 | |

| Ala | Ser | Leu | Pro | Trp | Ala | Val | Gln | Leu | Ile | Arg | His | Val | Gly | Gln | Tyr |
| | | | | 260 | | | | | 265 | | | | | 270 | |

| His | Asp | Gln | Pro | Glu | Gln | Val | Ser | Asn | Cys | Lys | Phe | Ile | Ala | Val | Asn |
| | | | 275 | | | | | 280 | | | | | 285 | | |

| Leu | His | Phe | Phe | Ser | Gly | Met | Leu | Met | Ala | Ala | Gly | Tyr | Gly | Trp | Ala |
| | | 290 | | | | | 295 | | | | | 300 | | | |

| Gly | Leu | Gly |
| 305 | | |

<210> SEQ ID NO 36
<211> LENGTH: 927
<212> TYPE: DNA
<213> ORGANISM: Synechocystis sp.

<400> SEQUENCE: 36

```
atggcaacta tccaagcttt ttggcgcttc tcccgccccc ataccatcat tggtacaact    60
ctgagcgtct gggctgtgta tctgttaact attctcgggg atggaaactc agttaactcc   120
cctgcttccc tggatttagt gttcggcgct tggctggcct gcctgttggg taatgtgtac   180
attgtcggcc tcaaccaatt gtgggatgtg acattgacc gcatcaataa gccgaatttg   240
cccctagcta acgagatttt ttctatcgcc caggccgtt ggattgtggg actttgtggc   300
gttgcttcct ggcgatcgc ctggggatta gggctatggc tggggctaac ggtgggcatt   360
```

-continued

```
agtttgatta ttggcacggc ctattcggtg ccgccagtga ggttaaagcg ctttccctg    420 ctggcggccc tgtgtattct gacggtgcgg ggaattgtgg ttaacttggg cttatttta    480 tttttagaa ttggtttagg ttatccccc actttaataa ccccatctg ggttttgact     540 ttatttatct tagttttcac cgtggcgatc gccattttta aagatgtgcc agatatggaa   600
ggcgatcggc aatttaagat tcaaacttta actttgcaaa tcggcaaaca aaacgttttt   660
cggggaacct taattttact cactggttgt tatttagcca tggcaatctg ggcttatgg    720 gcggctatgc ctttaaatac tgctttcttg attgtttccc atttgtgctt attagcctta   780
ctctggtggc ggagtcgaga tgtacactta gaaagcaaaa ccgaaattgc tagttttat    840 cagtttattt ggaagctatt tttcttagag tacttgctgt atcccttggc tctgtggtta   900
cctaattttt ctaatactat tttttag                                       927
```

<210> SEQ ID NO 37
<211> LENGTH: 308
<212> TYPE: PRT
<213> ORGANISM: Synechocystis sp.

<400> SEQUENCE: 37

```
Met Ala Thr Ile Gln Ala Phe Trp Arg Phe Ser Arg Pro His Thr Ile
  1               5                  10                  15

Ile Gly Thr Thr Leu Ser Val Trp Ala Val Tyr Leu Leu Thr Ile Leu
             20                  25                  30

Gly Asp Gly Asn Ser Val Asn Ser Pro Ala Ser Leu Asp Leu Val Phe
         35                  40                  45

Gly Ala Trp Leu Ala Cys Leu Leu Gly Asn Val Tyr Ile Val Gly Leu
     50                  55                  60

Asn Gln Leu Trp Asp Val Asp Ile Asp Arg Ile Asn Lys Pro Asn Leu
 65                  70                  75                  80

Pro Leu Ala Asn Gly Asp Phe Ser Ile Ala Gln Gly Arg Trp Ile Val
                 85                  90                  95

Gly Leu Cys Gly Val Ala Ser Leu Ala Ile Ala Trp Gly Leu Gly Leu
            100                 105                 110

Trp Leu Gly Leu Thr Val Gly Ile Ser Leu Ile Ile Gly Thr Ala Tyr
        115                 120                 125

Ser Val Pro Pro Val Arg Leu Lys Arg Phe Ser Leu Leu Ala Ala Leu
    130                 135                 140

Cys Ile Leu Thr Val Arg Gly Ile Val Val Asn Leu Gly Leu Phe Leu
145                 150                 155                 160

Phe Phe Arg Ile Gly Leu Gly Tyr Pro Pro Thr Leu Ile Thr Pro Ile
                165                 170                 175

Trp Val Leu Thr Leu Phe Ile Leu Val Phe Thr Val Ala Ile Ala Ile
            180                 185                 190

Phe Lys Asp Val Pro Asp Met Glu Gly Asp Arg Gln Phe Lys Ile Gln
        195                 200                 205

Thr Leu Thr Leu Gln Ile Gly Lys Gln Asn Val Phe Arg Gly Thr Leu
    210                 215                 220

Ile Leu Leu Thr Gly Cys Tyr Leu Ala Met Ala Ile Trp Gly Leu Trp
225                 230                 235                 240

Ala Ala Met Pro Leu Asn Thr Ala Phe Leu Ile Val Ser His Leu Cys
                245                 250                 255

Leu Leu Ala Leu Leu Trp Trp Arg Ser Arg Asp Val His Leu Glu Ser
            260                 265                 270
```

-continued

```
Lys Thr Glu Ile Ala Ser Phe Tyr Gln Phe Ile Trp Lys Leu Phe Phe
        275                 280                 285

Leu Glu Tyr Leu Leu Tyr Pro Leu Ala Leu Trp Leu Pro Asn Phe Ser
    290                 295                 300

Asn Thr Ile Phe
305

<210> SEQ ID NO 38
<211> LENGTH: 1092
<212> TYPE: DNA
<213> ORGANISM: Synechocystis sp.

<400> SEQUENCE: 38
atgaaatttc cgccccacag tggttaccat tggcaaggtc aatcaccttt ctttgaaggt      60
tggtacgtgc gcctgctttt gccccaatcc ggggaaagtt ttgcttttat gtactccatc     120
gaaaatcctg ctagcgatca tcattacggc ggcggtgctg tgcaaatttt agggccggct     180
acgaaaaaac aagaaaatca ggaagaccaa cttgtttggc ggacatttcc ctcggtaaaa     240
aaattttggg ccagtcctcg ccagtttgcc ctagggcatt ggggaaaatg tagggataac     300
aggcaggcga accccctact ctccgaagaa tttttttgcca cggtcaagga aggttatcaa    360
atccatcaaa atcagcacca aggacaaatc attcatggcg atcgccattg tcgttggcag     420
ttcaccgtag aaccggaagt aacttggggg agtcctaacc gatttcctcg ggctacagcg     480
ggttggcttt ccttttttacc cttgtttgat cccggttggc aaattctttt agcccaaggt    540
agagcgcacg gctggctgaa atggcagagg gaacagtatg aatttgacca cgccctagtt     600
tatgccgaaa aaaattgggg tcactccttt ccctcccgct ggttttggct ccaagcaaat     660
tattttcctg accatccagg actgagcgtc actgccgctg gcggggaacg gattgttctt     720
ggtcgccccg aagaggtagc tttaattggc ttacatcacc aaggtaattt ttacgaattt     780
ggcccgggcc atggcacagt cacttggcaa gtagctccct ggggccgttg gcaattaaaa     840
gccagcaatg ataggtattg ggtcaagttg tccggaaaaa cagataaaaa aggcagttta    900
gtccacactc ccaccgccca gggcttacaa ctcaactgcc gagataccac tagggctat    960 ttgtatttgc aattgggatc tgtgggtcac ggcctgatag tgcaagggga aacggacacc    1020
gcggggctag aagttggagg tgattggggt ttaacagagg aaaatttgag caaaaaaaca   1080
gtgccattct ga                                                        1092

<210> SEQ ID NO 39
<211> LENGTH: 363
<212> TYPE: PRT
<213> ORGANISM: Synechocystis sp.

<400> SEQUENCE: 39

Met Lys Phe Pro Pro His Ser Gly Tyr His Trp Gln Gly Gln Ser Pro
1               5                   10                  15

Phe Phe Glu Gly Trp Tyr Val Arg Leu Leu Leu Pro Gln Ser Gly Glu
            20                  25                  30

Ser Phe Ala Phe Met Tyr Ser Ile Glu Asn Pro Ala Ser Asp His His
        35                  40                  45

Tyr Gly Gly Gly Ala Val Gln Ile Leu Gly Pro Ala Thr Lys Lys Gln
    50                  55                  60

Glu Asn Gln Glu Asp Gln Leu Val Trp Arg Thr Phe Pro Ser Val Lys
65                  70                  75                  80
```

```
Lys Phe Trp Ala Ser Pro Arg Gln Phe Ala Leu Gly His Trp Gly Lys
                85                  90                  95

Cys Arg Asp Asn Arg Gln Ala Lys Pro Leu Leu Ser Glu Glu Phe Phe
                100                 105                 110

Ala Thr Val Lys Glu Gly Tyr Gln Ile His Gln Asn Gln His Gln Gly
                115                 120                 125

Gln Ile Ile His Gly Asp Arg His Cys Arg Trp Gln Phe Thr Val Glu
            130                 135                 140

Pro Glu Val Thr Trp Gly Ser Pro Asn Arg Phe Pro Arg Ala Thr Ala
145                 150                 155                 160

Gly Trp Leu Ser Phe Leu Pro Leu Phe Asp Pro Gly Trp Gln Ile Leu
                165                 170                 175

Leu Ala Gln Gly Arg Ala His Gly Trp Leu Lys Trp Gln Arg Glu Gln
                180                 185                 190

Tyr Glu Phe Asp His Ala Leu Val Tyr Ala Glu Lys Asn Trp Gly His
                195                 200                 205

Ser Phe Pro Ser Arg Trp Phe Trp Leu Gln Ala Asn Tyr Phe Pro Asp
            210                 215                 220

His Pro Gly Leu Ser Val Thr Ala Ala Gly Glu Arg Ile Val Leu
225                 230                 235                 240

Gly Arg Pro Glu Glu Val Ala Leu Ile Gly Leu His His Gln Gly Asn
                245                 250                 255

Phe Tyr Glu Phe Gly Pro Gly His Gly Thr Val Thr Trp Gln Val Ala
                260                 265                 270

Pro Trp Gly Arg Trp Gln Leu Lys Ala Ser Asn Asp Arg Tyr Trp Val
            275                 280                 285

Lys Leu Ser Gly Lys Thr Asp Lys Lys Gly Ser Leu Val His Thr Pro
290                 295                 300

Thr Ala Gln Gly Leu Gln Leu Asn Cys Arg Asp Thr Thr Arg Gly Tyr
305                 310                 315                 320

Leu Tyr Leu Gln Leu Gly Ser Val Gly His Gly Leu Ile Val Gln Gly
                325                 330                 335

Glu Thr Asp Thr Ala Gly Leu Glu Val Gly Gly Asp Trp Gly Leu Thr
                340                 345                 350

Glu Glu Asn Leu Ser Lys Lys Thr Val Pro Phe
                355                 360

<210> SEQ ID NO 40
<211> LENGTH: 56
<212> TYPE: DNA
<213> ORGANISM: Artificial Sequence
<220> FEATURE:
<223> OTHER INFORMATION: oligonucleotide adapter

<400> SEQUENCE: 40
cgcgatttaa atggcgcgcc ctgcaggcgg ccgcctgcag ggcgcgccat ttaaat        56

<210> SEQ ID NO 41
<211> LENGTH: 32
<212> TYPE: DNA
<213> ORGANISM: Artificial Sequence
<220> FEATURE:
<223> OTHER INFORMATION: oligonucleotide

<400> SEQUENCE: 41
tcgaggatcc gcggccgcaa gcttcctgca gg                                  32
```

<210> SEQ ID NO 42
<211> LENGTH: 32
<212> TYPE: DNA
<213> ORGANISM: Artificial Sequence
<220> FEATURE:
<223> OTHER INFORMATION: oligonucleotide

<400> SEQUENCE: 42
tcgacctgca ggaagcttgc ggccgcggat cc                          32

<210> SEQ ID NO 43
<211> LENGTH: 32
<212> TYPE: DNA
<213> ORGANISM: Artificial Sequence
<220> FEATURE:
<223> OTHER INFORMATION: oligonucleotide

<400> SEQUENCE: 43
tcgacctgca ggaagcttgc ggccgcggat cc                          32

<210> SEQ ID NO 44
<211> LENGTH: 32
<212> TYPE: DNA
<213> ORGANISM: Artificial Sequence
<220> FEATURE:
<223> OTHER INFORMATION: oligonucleotide

<400> SEQUENCE: 44
tcgaggatcc gcggccgcaa gcttcctgca gg                          32

<210> SEQ ID NO 45
<211> LENGTH: 36
<212> TYPE: DNA
<213> ORGANISM: Artificial Sequence
<220> FEATURE:
<223> OTHER INFORMATION: oligonucleotide

<400> SEQUENCE: 45
tcgaggatcc gcggccgcaa gcttcctgca ggagct                      36

<210> SEQ ID NO 46
<211> LENGTH: 28
<212> TYPE: DNA
<213> ORGANISM: Artificial Sequence
<220> FEATURE:
<223> OTHER INFORMATION: oligonucleotide

<400> SEQUENCE: 46
cctgcaggaa gcttgcggcc gcggatcc                               28

<210> SEQ ID NO 47
<211> LENGTH: 36
<212> TYPE: DNA
<213> ORGANISM: Artificial Sequence
<220> FEATURE:
<223> OTHER INFORMATION: oligonucleotide

<400> SEQUENCE: 47
tcgacctgca ggaagcttgc ggccgcggat ccagct                      36

<210> SEQ ID NO 48
<211> LENGTH: 28
<212> TYPE: DNA
<213> ORGANISM: Artificial Sequence
<220> FEATURE:
<223> OTHER INFORMATION: oligonucleotide

```
<400> SEQUENCE: 48
ggatccgcgg ccgcaagctt cctgcagg                                          28

<210> SEQ ID NO 49
<211> LENGTH: 39
<212> TYPE: DNA
<213> ORGANISM: Artificial Sequence
<220> FEATURE:
<223> OTHER INFORMATION: oligonucleotide

<400> SEQUENCE: 49
gatcacctgc aggaagcttg cggccgcgga tccaatgca                              39

<210> SEQ ID NO 50
<211> LENGTH: 31
<212> TYPE: DNA
<213> ORGANISM: Artificial Sequence
<220> FEATURE:
<223> OTHER INFORMATION: oligonucleotide

<400> SEQUENCE: 50
ttggatccgc ggccgcaagc ttcctgcagg t                                      31

<210> SEQ ID NO 51
<211> LENGTH: 41
<212> TYPE: DNA
<213> ORGANISM: Artificial Sequence
<220> FEATURE:
<223> OTHER INFORMATION: Synthetic Oligonucleotides

<400> SEQUENCE: 51
ggatccgcgg ccgcacaatg gagtctctgc tctctagttc t                           41

<210> SEQ ID NO 52
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 52
ggatcctgca ggtcacttca aaaaggtaa cagcaagt                                38

<210> SEQ ID NO 53
<211> LENGTH: 45
<212> TYPE: DNA
<213> ORGANISM: Artificial Sequence
<220> FEATURE:
<223> OTHER INFORMATION: Synthetic Oligonucleotides

<400> SEQUENCE: 53
ggatccgcgg ccgcacaatg gcgttttttg ggctctcccg tgttt                       45

<210> SEQ ID NO 54
<211> LENGTH: 40
<212> TYPE: DNA
<213> ORGANISM: Artificial Sequence
<220> FEATURE:
<223> OTHER INFORMATION: Synthetic Oligonucleotides

<400> SEQUENCE: 54
ggatcctgca ggttattgaa aacttcttcc aagtacaact                             40

<210> SEQ ID NO 55
<211> LENGTH: 38
```

-continued

```
<212> TYPE: DNA
<213> ORGANISM: Artificial Sequence
<220> FEATURE:
<223> OTHER INFORMATION: Synthetic Oligonucleotides

<400> SEQUENCE: 55
ggatccgcgg ccgcacaatg tggcgaagat ctgttgtt                          38

<210> SEQ ID NO 56
<211> LENGTH: 37
<212> TYPE: DNA
<213> ORGANISM: Artificial Sequence
<220> FEATURE:
<223> OTHER INFORMATION: Synthetic Oligonucleotides

<400> SEQUENCE: 56
ggatcctgca ggtcatggag agtagaagga aggagct                           37

<210> SEQ ID NO 57
<211> LENGTH: 50
<212> TYPE: DNA
<213> ORGANISM: Artificial Sequence
<220> FEATURE:
<223> OTHER INFORMATION: Synthetic Oligonucleotides

<400> SEQUENCE: 57
ggatccgcgg ccgcacaatg gtacttgccg aggttccaaa gcttgcctct             50

<210> SEQ ID NO 58
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 58
ggatcctgca ggtcacttgt ttctggtgat gactctat                          38

<210> SEQ ID NO 59
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 59
ggatccgcgg ccgcacaatg acttcgattc tcaacact                          38

<210> SEQ ID NO 60
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 60
ggatcctgca ggtcagtgtt gcgatgctaa tgccgt                            36

<210> SEQ ID NO 61
<211> LENGTH: 22
<212> TYPE: DNA
<213> ORGANISM: Artificial Sequence
<220> FEATURE:
<223> OTHER INFORMATION: Region of slr1736 open reading frame

<400> SEQUENCE: 61
```

```
taatgtgtac attgtcggcc tc                                              22

<210> SEQ ID NO 62
<211> LENGTH: 60
<212> TYPE: DNA
<213> ORGANISM: Artificial Sequence
<220> FEATURE:
<223> OTHER INFORMATION: Region of slr1736 open reading frame

<400> SEQUENCE: 62
gcaatgtaac atcagagatt ttgagacaca acgtggcttt ccacaattcc ccgcaccgtc    60

<210> SEQ ID NO 63
<211> LENGTH: 22
<212> TYPE: DNA
<213> ORGANISM: Artificial Sequence
<220> FEATURE:
<223> OTHER INFORMATION: Region of slr1736 open reading frame

<400> SEQUENCE: 63
aggctaataa gcacaaatgg ga                                              22

<210> SEQ ID NO 64
<211> LENGTH: 63
<212> TYPE: DNA
<213> ORGANISM: Artificial Sequence
<220> FEATURE:
<223> OTHER INFORMATION: Region of slr1736 open reading frame

<400> SEQUENCE: 64
ggtatgagtc agcaacacct tcttcacgag gcagacctca gcggaattgg tttaggttat    60
ccc                                                                   63

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65
ggatccatgg ttgcccaaac cccatc                                          26

<210> SEQ ID NO 66
<211> LENGTH: 61
<212> TYPE: DNA
<213> ORGANISM: Artificial Sequence
<220> FEATURE:
<223> OTHER INFORMATION: Primer

<400> SEQUENCE: 66
gcaatgtaac atcagagatt ttgagacaca acgtggcttt gggtaagcaa caatgaccgg    60
c                                                                     61

<210> SEQ ID NO 67
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 67
gaattctcaa agccagccca gtaac                                           25
```

<210> SEQ ID NO 68
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 68
ggtatgagtc agcaacacct tcttcacgag gcagacctca gcgggtgcga aaagggtttt    60
ccc                                                                  63

<210> SEQ ID NO 69
<211> LENGTH: 23
<212> TYPE: DNA
<213> ORGANISM: Artificial Sequence
<220> FEATURE:
<223> OTHER INFORMATION: End of open reading frame fragment

<400> SEQUENCE: 69
ccagtggttt aggctgtgtg gtc                                            23

<210> SEQ ID NO 70
<211> LENGTH: 21
<212> TYPE: DNA
<213> ORGANISM: Artificial Sequence
<220> FEATURE:
<223> OTHER INFORMATION: End of open reading frame fragment

<400> SEQUENCE: 70
ctgagttgga tgtattggat c                                              21

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
ggatccatgg ttacttcgac aaaaatcc                                       28

<210> SEQ ID NO 72
<211> LENGTH: 60
<212> TYPE: DNA
<213> ORGANISM: Artificial Sequence
<220> FEATURE:
<223> OTHER INFORMATION: Primer

<400> SEQUENCE: 72
gcaatgtaac atcagagatt ttgagacaca acgtggcttt gctaggcaac cgcttagtac    60

<210> SEQ ID NO 73
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 73
gaattcttaa cccaacagta aagttccc                                       28

<210> SEQ ID NO 74
<211> LENGTH: 63
<212> TYPE: DNA
<213> ORGANISM: Artificial Sequence
<220> FEATURE:

```
<223> OTHER INFORMATION: Oligonucleotide primer

<400> SEQUENCE: 74
ggtatgagtc agcaacacct tcttcacgag gcagacctca gcgccggcat tgtcttttac        60
atg                                                                      63

<210> SEQ ID NO 75
<211> LENGTH: 20
<212> TYPE: DNA
<213> ORGANISM: Artificial Sequence
<220> FEATURE:
<223> OTHER INFORMATION: Open reading frame fragment

<400> SEQUENCE: 75
ggaacccttg cagccgcttc                                                    20

<210> SEQ ID NO 76
<211> LENGTH: 22
<212> TYPE: DNA
<213> ORGANISM: Artificial Sequence
<220> FEATURE:
<223> OTHER INFORMATION: Open reading frame fragment

<400> SEQUENCE: 76
gtatgcccaa ctggtgcaga gg                                                 22

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
ggatccatgt ctgacacaca aaataccg                                           28

<210> SEQ ID NO 78
<211> LENGTH: 62
<212> TYPE: DNA
<213> ORGANISM: Artificial Sequence
<220> FEATURE:
<223> OTHER INFORMATION: Primer

<400> SEQUENCE: 78
gcaatgtaac atcagagatt ttgagacaca acgtggcttt cgccaatacc agccaccaac        60
ag                                                                       62

<210> SEQ ID NO 79
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 79
gaattctcaa atccccgcat ggcctag                                            27

<210> SEQ ID NO 80
<211> LENGTH: 65
<212> TYPE: DNA
<213> ORGANISM: Artificial Sequence
<220> FEATURE:
<223> OTHER INFORMATION: Synthetic oligonucleotide primer

<400> SEQUENCE: 80
```

```
ggtatgagtc agcaacacct tcttcacgag gcagacctca gcggcctacg gcttggacgt    60
gtggg                                                                65
```

<210> SEQ ID NO 81
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 81

```
cacttggatt cccctgatct g                                              21
```

<210> SEQ ID NO 82
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 82

```
gcaatacccg cttggaaaac g                                              21
```

<210> SEQ ID NO 83
<211> LENGTH: 29
<212> TYPE: DNA
<213> ORGANISM: Artificial Sequence
<220> FEATURE:
<223> OTHER INFORMATION: Primer

<400> SEQUENCE: 83

```
ggatccatga ccgaatcttc gccccctagc                                     29
```

<210> SEQ ID NO 84
<211> LENGTH: 61
<212> TYPE: DNA
<213> ORGANISM: Artificial Sequence
<220> FEATURE:
<223> OTHER INFORMATION: Primer

<400> SEQUENCE: 84

```
gcaatgtaac atcagagatt ttgagacaca acgtggcttt caatcctagg tagccgaggc    60
g                                                                    61
```

<210> SEQ ID NO 85
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 85

```
gaattcttag cccaggccag cccagcc                                        27
```

<210> SEQ ID NO 86
<211> LENGTH: 66
<212> TYPE: DNA
<213> ORGANISM: Artificial Sequence
<220> FEATURE:
<223> OTHER INFORMATION: Synthetic oligonucleotide primer

<400> SEQUENCE: 86

```
ggtatgagtc agcaacacct tcttcacgag gcagacctca gcggggaatt gatttgttta    60
```

| attacc | 66 |

<210> SEQ ID NO 87
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 87

| gcgatcgcca ttatcgcttg g | 21 |

<210> SEQ ID NO 88
<211> LENGTH: 24
<212> TYPE: DNA
<213> ORGANISM: Artificial Sequence
<220> FEATURE:
<223> OTHER INFORMATION: Open reading frame fragment

<400> SEQUENCE: 88

| gcagactggc aattatcagt aacg | 24 |

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89

| ccatggattc gagtaaagtt gtcgc | 25 |

<210> SEQ ID NO 90
<211> LENGTH: 25
<212> TYPE: DNA
<213> ORGANISM: Artificial Sequence
<220> FEATURE:
<223> OTHER INFORMATION: Primer

<400> SEQUENCE: 90

| gaattcactt caaaaaaggt aacag | 25 |

<210> SEQ ID NO 91
<211> LENGTH: 4550
<212> TYPE: DNA
<213> ORGANISM: Arabidopsis sp.

<400> SEQUENCE: 91

| attttacacc aatttgatca cttaactaaa ttaattaaat tagatgatta tcccaccata | 60 |
| tttttgagca ttaaaccata aaaccatagt tataagtaac tgttttaatc gaatatgact | 120 |
| cgattaagat taggaaaaat ttataaccgg taattaagaa aacattaacc gtagtaaccg | 180 |
| taaatgccga ttcctcccct tgtctaaaga cagaaaacat atattttatt ttgccccata | 240 |
| tgtttcactc tatttaattt caggcacaat acttttggtt ggtaacaaaa ctaaaaagga | 300 |
| caacacgtga tacttttcct cgtccgtcag tcagattttt tttaaactag aaacaagtgg | 360 |
| caaatctaca ccacattttt tgcttaatct attaacttgt aagttttaaa ttcctaaaaa | 420 |
| agtctaacta attcttctaa tataagtaca ttccctaaat ttcccaaaaa gtcaaattaa | 480 |
| taattttcaa aatctaatct aaatatctaa taattcaaaa tcattaaaaa gacacgcaac | 540 |
| aatgacacca attaatcatc ctcgacccac acaattctac agttctcatg ctaaaccata | 600 |
| ttttttgctc tctgttcctt caaaatcatt tctttctctt ctttgattcc caaagatcac | 660 |

-continued

| | |
|---|---|
| ttctttgtct ttgattttg atttttttc tctctggcgt gaaggaagaa gctttatttc | 720 |
| atggagtctc tgctctctag ttcttctctt gtttccgctg gtaaatctcg tccttttctg | 780 |
| gtttcaggtt ttatttgttg tttaggtttc gttttgtga ttcagaacca tacaaaaagt | 840 |
| ttgaactttt ctgaatataa aataaggaaa aagtttcgat ttttataatg aattgtttac | 900 |
| tagatcgaag taggtgacaa aggttattgt gtggagaagc ataatttctg ggcttgactt | 960 |
| tgaattttgt ttctcatgca tgcaacttat caatcagctg gtgggttttg ttggaagaag | 1020 |
| cagaatctaa agctccactc tttatcaggt tcgttagggt tttatgggtt tttgaaatta | 1080 |
| aatactcaat catcttagtc tcattattct attggttgaa tcacattttc taatttggaa | 1140 |
| tttatgagac aatgtatgtt ggacttagtt gaagttcttc tctttggtta tagttgaagt | 1200 |
| gttactgatg ttgtttagct ctttacacca atatatacac ccaattttgc agaaatccga | 1260 |
| gttctgcgtt gtgattcgag taaagttgtc gcaaaaccga agtttaggaa caatcttgtt | 1320 |
| aggcctgatg gtcaaggatc ttcattgttg ttgtatccaa aacataagtc gagatttcgg | 1380 |
| gttaatgcca ctgcgggtca gcctgaggct ttcgactcga atagcaaaca gaagtctttt | 1440 |
| agagactcgt tagatgcgtt ttacaggttt tctaggcctc atacagttat tggcacagtt | 1500 |
| aagtttctct ttaaaaatgt aactctttta aaacgcaatc tttcagggtt ttcaaggaga | 1560 |
| taacattagc tctgtgattg gatttgcagg tgcttagcat tttatctgta tctttcttag | 1620 |
| cagtagagaa ggtttctgat atatctcctt tactttttcac tggcatcttg gaggtaatga | 1680 |
| atatataaca cataatgacc gatgaagaag atacattttt ttcgtctctc tgtttaaaca | 1740 |
| attgggtttt gttttcaggc tgttgttgca gctctcatga tgaacattta catagttggg | 1800 |
| ctaaatcagt tgtctgatgt tgaaatagat aaggtaacat gcaaattttc ttcatatgag | 1860 |
| ttcgagagac tgatgagatt aatagcagct agtgcctaga tcatctctat gtgggttttt | 1920 |
| gcaggttaac aagccctatc ttccattggc atcaggagaa tattctgtta acaccggcat | 1980 |
| tgcaatagta gcttccttct ccatcatggt atggtgccat tttcacaaaa tttcaacttt | 2040 |
| tagaattcta taagttactg aaatagtttg ttataaatcg ttatagagtt tctggcttgg | 2100 |
| gtggattgtt ggttcatggc cattgttctg ggctcttttt gtgagtttca tgctcggtac | 2160 |
| tgcatactct atcaatgtaa gtaagtttct caatactaga atttggctca atcaaaatc | 2220 |
| tgcagtttct agttttaggt taatgaggtt ttaataactt acttctacta caaacagttg | 2280 |
| ccacttttac ggtggaaaag atttgcattg gttgcagcaa tgtgtatcct cgctgtccga | 2340 |
| gctattattg ttcaaatcgc cttttatcta catattcagg tactaaacca ttttccttat | 2400 |
| gttttgtagt tgtttttcatc aaaatcactt ttatattact aaagctgtga aactttgttg | 2460 |
| cagacacatg tgtttggaag accaatcttg ttcactaggc ctcttatttt cgccactgcg | 2520 |
| tttatgagct ttttctctgt cgttattgca ttgtttaagg taaacaaaga tggaaaaaga | 2580 |
| ttaaatctat gtatacttaa agtaaagcat tctactgtta ttgatgagaa gttttctttt | 2640 |
| ttggttggat gcaggatata cctgatatcg aagggataa gatattcgga atccgatcat | 2700 |
| tctctgtaac tctgggtcag aaacgggtac gatatctaaa ctaaagaaat tgttttgact | 2760 |
| caagtgttgg attaagatta cagaagaaag aaaactgttt ttgtttcttg caaaattcag | 2820 |
| gtgttttgga catgtgttac actacttcaa atggcttacg ctgttgcaat tctagttgga | 2880 |
| gccacatctc cattcatatg gagcaaagtc atctcggtaa caatctttct ttacccatcg | 2940 |
| aaaactcgct aattcatcgt ttgagtggta ctggtttcat tttgttccgt tctgttgatt | 3000 |

```
ttttttcagg ttgtgggtca tgttatactc gcaacaactt tgtgggctcg agctaagtcc      3060
gttgatctga gtagcaaaac cgaaataact tcatgttata tgttcatatg gaaggttaga      3120
ttcgtttata aatagagtct ttactgcctt tttatgcgct ccaatttgga attaaaatag      3180
cctttcagtt tcatcgaatc accattatac tgataaattc tcatttctgc atcagctctt      3240
ttatgcagag tacttgctgt taccttttt gaagtgactg acattagaag agaagaagat       3300
ggagataaaa gaataagtca tcactatgct tctgttttta ttacaagttc atgaaattag      3360
gtagtgaact agtgaattag agttttattc tgaaacatgg cagactgcaa aaatatgtca      3420
aagatatgaa tttctgttgg gtaaagaagt ctctgcttgg gcaaaatctt aaggttcggt      3480
gtgttgatat aatgctaagc gaagaaatcg attctatgta gaaatttccg aaactatgtg      3540
taaacatgtc agaacatctc cattctatat cttcttctgc aagaaagctc tgtttttatc      3600
acctaaactc tttatctctg tgtagttaag atatgtatat gtacgtgact acatttttt       3660 gttgatgtaa tttgcagaac gtatggattt ttgttagaaa gcatgagttc gaaagtatat      3720
gtttatatat atggataatt cagacctaac gtcgaagctc acaagcataa attcactact      3780
atagtttgct ctgtaataga tagttccatt gatgtcttga aactgtacgt aactgcctgg      3840
gcgttttgtg gttgatactg actactgagt gttctttgtg agtgttgtaa gtatacaaga      3900
agaagaatat aggctcacgg gaacgactgt ggtggaagat gaaatggaga tcatcacgta      3960
gcggctttgc caaagaccga gtcacgatcg agtctatgaa gtctttacag ctgctgatta      4020
tgattgacca ttgcttagag acgcattgga atcttactag ggacttgcct gggagttt ct    4080 tcaagtacgt gtcagatcat acgatgtagg agatttcacg gctttgatgt gtttgtttgg     4140
agtcacaatg cttaatgggc ttattggccc aataatagct agctctttg ctttagccgt      4200 ttcgtttgtc ccctggtggt gagtattatt agggtatggt gtgaccaaag tcaccagacc      4260
tagagtgaat ctagtagagt cctagaccat ggtccatggc ttttatttgt aatttgaaaa      4320
atgaacaatt ctttttgtaa ggaaaacttt tatatagtag acgtttacta tatagaaact      4380
agttgaacta acttcgtgca attgcataat aatggtgtga aatagagggt gcaaaactca      4440
ataaacattt cgacgtacca agagttcgaa acaataagca aaatagattt ttttgcttca     4500
gactaatttg tacaatgaat ggttaataaa ccattgaagc ttttattaat                4550
```

<210> SEQ ID NO 92
<211> LENGTH: 4450
<212> TYPE: DNA
<213> ORGANISM: Arabidopsis sp.

<400> SEQUENCE: 92

```
tttaggttac aaaatcaatg atattgcgta tgtcaactat aaaagccaaa agtaaagcct        60
cttgtttgac cagaaggtca tgatcattgt atacatacag ccaaactacc tcctggaaga      120
aaagacatgg atcccaaaca acaacaatag cttcttttac aagaaccagt agtaactagt      180
cactaatcta aaagagttaa gtttcagctt ttctggcaat ggctccttga tcatttcaat      240
cctgaaggag acccactttg tagcaagacc atgtcctctg tttcacttac agtgtgtctc      300
aaaagtctac ttcaattctt catatatagg ttcctcacac tacagcttca tcctcattcg      360
ttgacagaga gagagtcttt attgaaaact tcttccaagt acaactccac taaatataat     420
agcaccaaac cacttgttcg acacaaatct gtacagatat aaaaacacta ttaggttttc      480
caaggcaaat cacataattg gattgtgaaa gagtacaaaa gataaaccca aatttt cata    540
```

-continued

```
ctttctactg cagtcagcac cagatgataa gtcagctgtc cctatttgcc atcctaactg      600
tcctgatgca gcggccagtg atgcgtaata ttgccaccct taatcattag agcgagaaac      660
aaaaagaatc aaaagacagt aaatggaatt aggaatcaca aatgagtcct tgtaaagttt      720
attgagtacc gagatctgca ctgaatccag aaagtgcaag aaaacctatg gatgctgtgc      780
caaatccagt taaccaaagc tttgtattat caccgaatct aagggctgtt gacttaacac      840
caacttttac atcatcttct tgtcctggga gacacaatat attagacatt agtccatgga      900
aaaaaaatga tttaacctag aatatctcaa aattacttgc ataaaaactg aacttgagct      960
gaaattttgg gttcgtagct tgtggcatat actatttcat tttcaatggg ccacaaaggt     1020
aactttcttt tctcacttct gttgcaaacg ggaagacttt tatggggcta actcttcact     1080
taaagtatag aaatcagatg gaaaggtgg gagatcaggg taattttctt ctttatgatt      1140
gacaaaagtc gaacatcgaa atggatgcat ttgcatgaga catgaaacaa agctgaaaa      1200 agaaatctgt ggtggtgaag ctagaaaaag aaaacaaagc aagcaatatg cacacattga     1260
gattaactac tttgctactg gtcataatca aatagatttt gaagctaaaa ataaaaagt      1320 gaatatacct gatgtgcata aatagtatca taaacaaggg tccagcagac tccggagaga     1380
tagagaggga gtacaataga tggtgctatg cttcctttaa ctgcagtcca tcctaacaat     1440
gctccccagt ttatggtcaa acctaaaaag gcttgaggct gcaattataa aaacgaatca     1500
atcataagaa aatcagaaaa tatataatgt ctaactttga gaagccagaa tagatttaaa     1560
ttacccaaaa tgtaaacctc ttcataagtg ggtaggaaaa gacaagtaac aaagatgaag     1620
cccctaaaac acggctgcag aatatacata ctgaaatgag ctcaagtaga aaagaatttg     1680
atcacaaaac taaagacaag acctgagaac atatcttcag aatttgggcc aactacataa     1740
gggtgaacca tatgtgtatg tgaatttta acaaacact tgcaaatacg cgactttagg       1800
gcaagtaaaa aatccaaaca aacctgtaat tgttaagttg gagaagaatc cctaagccta     1860
aaagcaactg cagcccgaga atccaatcc cttgaaatgg tgtcaaaaga ccactggcga      1920
taggtcttag ttttgtacga tcaacctgga tataaaagaa atttgtaaga caacataatc     1980
taaaacaaaa caaccataca aaatcttgag ctttacatac aagcaaccca tctttgttta    2040
tggaagaatg aatccagtta catgaatgct gtgtatctac cctaactact aaacacatat    2100
ttcaatcgaa aaacatattc caccttcacc atatctaaca cctgaagtct ttcacttttt     2160
gaacgaagtc atcagaacat gcagataagc tattacccaa aacagagata tgactggaaa    2220
tgttgtcgta aattgatcca acatagaaaa atcaagacca gttccagatg tcaaagcaat     2280
aacactttcc caccatggtt acagaaacca tagttacaca aaacatgttt cctaaaccaa     2340
catactaaag ggatatataa atttgacatc actttatcac cataccataa gatagcttaa     2400
aaacaaactg accttttgtat ctatgtcctg atcaagcaga tcatttatag tacaaccagc    2460
acctctaaga agtaatgctc cgcaaccaaa taaagccata tatttaaaac ttggaaggct     2520
tccaggatca gcagccaacg caatcgacct atacaacaat gatggagatt cagagtatcg    2580
atctatttac atagctctgg aactagatcc atgacgaaac atggaacatc gttataatat    2640
ctaaagactt ccaaacagat tcctgagtaa gaaacccagt ggaactatag tactgtaaca     2700 tatataaat caaagaaaac tcaggtttat agcattatcc aatcctgatt tctgccaatc      2760
cttaaccact ctcccatgct atcaaaaacc tcagctcaag atcatactac ctaattgcct     2820
atgagctctt gggaagatca ttatggattt gataactgaa aaaagtaaca gagaaatagc    2880
agactgcaag aactactcca aacttctcca ctgatatgta tgtagtctaa caataataaa    2940
```

-continued

```
cagacataaa ttcttttatc aagcttcaag agcaagttag tcagaaaaca tcacagccaa    3000
accaaccagg aaaacacata actttatcac ataaaactaa atttaatgta atctgactta    3060
acataaacca tcctttggga cgaaaggaaa ctatataaac atgcagtctt tctttccctc    3120
agctattctt tcggatggat tataatgaat ctcaaaagtg aaatgtcttg attctcagct    3180
acattactca aaggcgaaga taaacttacc acatacaagg ccacgcaagc aaccaagttc    3240
caatgggttt atccaatcga gcaagcttag cataacctct aacttcttct ggtaaataca    3300
aatctatcca agaagcttcc ttaacaacaa caccatcact cttctcccta tcatctttct    3360
tcggctttcc ctccaaaacc gaagaagacg acgacattcc acaaattaat ctgtaattcc    3420
aaccaacacc aaaaaacttc tcctgatgca attctcttcc tttactccat acttggtaat    3480
tatcattcca tgaaggataa cacttagtga aaggatttgt gtaatgggta gtcacaggat    3540
tggacaagga tttatgttgt gattgcaaaa gagcagagga agaagatgga gttacggaga    3600
cggaagattt caacaaccgt cttgaaacac gggagagccc aaaaaacgcc atctttgaga    3660
gaaattgttg cctggaagaa acaaagactt gagatttcaa acgtaagtga attcttacga    3720
acgaaagcta acttctcaag agaatcagat tagtgattcc tcaaaaacaa acaaaactat    3780
ctaatttcag tttcgagtga tgaagcctta agaatctaga acctccatgg cgtttctaat    3840
ctctcagaga taatcgaatt ccttaaacaa tcaaagctta gaaagagaag aacaacaaca    3900
acaacaaaaa aaatcagatt aacaaccgac cagagagcaa cgacgacgcc ggcgagaaag    3960
agcacgtcgt ctcggagcaa gacttcttct ccagtaaccc ggatggatcg ttaatgggcc    4020
tgtagattat tatatttggg ccgaaacaat tgggtcagca aaacttgggg ggataatgaa    4080
gaaacacgta cagtatgcat ttaggctcca aattaattgg ccatataatt cgaatcgat    4140 aaactaatca accccctacct tactatttc tcactgtttt tatttctacc ttagtagttg    4200
aagaaacact tttattttatc ttttcgggac ccaaatttga taggatcggg ccattactca    4260
tgagcgtcag acacatatta gccttatcag attagtgggg taaggttttt ttaattcggt    4320
aagaagcaac aatcaatgtc ggagaaatta aagaatctgc atgggcgtgg cgtgatgata    4380
tgtgcatatg gagtcagttg ccgatcatat ataactattt ataaactaca tataaagact    4440
actaatagat                                                          4450
```

<210> SEQ ID NO 93
<211> LENGTH: 2850
<212> TYPE: DNA
<213> ORGANISM: Arabidopsis sp.

<400> SEQUENCE: 93

```
aattaaaatt tgagcggtct aaaccattag accgtttaga gatccctcca acccaaaata     60
gtcgattttc acgtcttgaa catatattgg gccttaatct gtgtggttag taaagactttt   120 tattggtcaa agaaaaacaa ccatggccca acatgttgat actttttattt aattatacaa   180 gtaccccctga attctctgaa atatatttga ttgacccaga tattaatttt aattatcatt   240
tcctgtaaaa gtgaaggagt caccgtgact cgtcgtaatc tgaaaccaat ctgttcatat    300
gatgaagaag tttctctcgt tctcctccaa cgcgtagaaa attctgacgg cttaacgatg    360
tggcgaagat ctgttgttta tcgtttctct tcaagaatct ctgtttcttc ttcgttacca    420
aaccctagac tgattccttg gtcccgcgaa ttatgtgccg ttaatagctt ctcccagcct    480
ccggtctcga cggaatcaac tgctaagtta gggatcactg gtgttagatc tgatgccaat    540
```

```
cgagtttttg ccactgctac tgccgccgct acagctacag ctaccaccgg tgagatttcg    600
tctagagttg cggctttggc tggattaggg catcactacg ctcgttgtta ttgggagctt    660
tctaaagcta aacttaggta tgtgtttact tttcttttct catgaaaaat ctgaaatttt    720
ccaattgttg gattcttaaa ttctcatttg ttttatggtt gtagtatgct tgtggttgca    780
acttctggaa ctgggtatat tctgggtacg ggaaatgctg caattagctt cccgggcttt    840
tgttacacat gtgcaggaac catgatgatt gctgcatctg ctaattcctt gaatcaggtc    900
attgaaatgt tgagaagttc ataaatttcg aatccttgtt gtgtttatgt agttgatctt    960
gcttgcttat gtttatgtag ttgaaaagtt taaaaatttc taatccttgg tagttgatct   1020
cgcttgtttg ttttttcatt ttctagattt ttgagataag caatgattct aagatgaaaa   1080
gaacgatgct aaggccattg ccttcaggac gtattagtgt tccacacgct gttgcatggg   1140
ctactattgc tggtgcttct ggtgcttgtt tgttggccag caaggtgaat gtttgttttt   1200
ttatatgtga tttctttgtt ttatgaatgg gtgattgaga gattatggat ctaaactttt   1260
gcttccacga caaggttatt gcagactaat atgttggctg ctggacttgc atctgccaat   1320
cttgtacttt atgcgtttgt ttatactccg ttgaagcaac ttcaccctat caatacatgg   1380
gttggcgctg ttgttggtgc tatcccaccc ttgcttgggt aaatttttgt tccttttctt   1440
ctttatttta gcagattctg tttttgttgga tactgctttt aattcaaaat gtagtcatgg   1500
ttcaccaatt ctatgcttat ctattttgtg tgttgtcagg tgggcggcag cgtctggtca   1560
gatttcatac aattcgatga ttcttccagc tgctctttac ttttggcaga tacctcattt   1620
tatggccctt gcacatctct gccgcaatga ttatgcagct ggagggtaag accatatggt   1680
gtcatatgag attagaatgt ctccttccat gtagtgttga tcttgaacta gttcaatttc   1740
gtggaatgat cagagtgtcc tagatagtgt cacagcagtc gacattttag tggctagata   1800
atgagttctt tccgttagag ataaacattc gcgaacattg tttccagctt ccgcgaccca   1860
acttctgatt ttgtttcttg gtaccttgtt ttcagttaca agatgttgtc actctttgat   1920
ccgtcaggga agagaatagc agcagtggct ctaaggaact gcttttacat gatccctctc   1980
ggtttcatcg cctatgactg tgagtcttgt agattcatct ttttttttgta gtttattgac   2040 tgcattgctg tatctgattt ttgctgttcc ttccaatttt tgtgacaggg gggtaaccct   2100
caagttggtt ttgcctcgaa tcaacacttc tcacactagc aatcgctgca acagcatttt   2160
cattctaccg agaccggacc atgcataaag caaggaaaat gttccatgcc agtcttctct   2220
tccttcctgt tttcatgtct ggtcttcttc tacaccgtgt ctctaatgat aatcagcaac   2280
aactcgtaga agaagccgga ttaacaaatt ctgtatctgg tgaagtcaaa actcagaggc   2340
gaaagaaacg tgtggctcaa cctccggtgg cttatgcctc tgctgcaccg tttccttttcc   2400 tcccagctcc ttccttctac tctccatgat aacctttaag caagctattg aattttttgga   2460 aacagaaatt aaaaaaaaaa tctgaaaagt tcttaagttt aatctttggt taataatgaa   2520
gtggagaacg catacaagtt tatgtatttt ttctcatctc cacataattg tatttttttct   2580 ctaagtatgt ttcaaatgat acaaaataca tactttatca attatctgat caaattgatg   2640 aattttttgag ctttgacgtg ttaggtctat ctaataaacg tagtaacgaa tttggttttg   2700
gaaatgaaat ccgataaccg atgatggtgt agagttaaac gattaaaccg ggttggttaa   2760
aggtctcgag tctcgacggc tgcggaaatc ggaaaatcac gattgaggac tttgagctgc   2820
cacgaagatg gcgatgaggt tgaaatcaat                                     2850
```

<210> SEQ ID NO 94
<211> LENGTH: 3660
<212> TYPE: DNA
<213> ORGANISM: Arabidopsis sp.

<400> SEQUENCE: 94

| | | | | | | |
|---|---|---|---|---|---|---|
| tatttgtatt | tttattgtta | aattttatga | tttcacccgg | tatatatcat | cccatattaa | 60 |
| tattagattt | atttttttggg | ctttatttgg | gttttcgatt | taaactgggc | ccattctgct | 120 |
| tcaatgaaac | cctaatgggt | tttgtttggg | ctttggattt | aaaccgggcc | cattctgctt | 180 |
| caatgaaggt | cctttgtcca | acaaaactaa | catccgacac | aactagtatt | gccaagagga | 240 |
| tcgtgccaca | tggcagttat | tgaatcaaag | gccgccaaaa | ctgtaacgta | gacattactt | 300 |
| atctccggta | acgacaaacc | actcgtttcc | cgaaacagca | actcacagac | tcacaccact | 360 |
| ccagtctccg | gcttaactac | caccagagac | gattctctct | tccgtcggtt | ctatgacttc | 420 |
| gattctcaac | actgtctcca | ccatccactc | ttccagagtt | acctccgtcg | atcgagtcgg | 480 |
| agtcctctct | cttcggaatt | cggattccgt | tgagttcact | cgccggcgtt | ctggtttctc | 540 |
| gacgttgatc | tacgaatcac | ccggtagtta | gcattctgtt | ggatagattg | atgaatgttt | 600 |
| tcttcgattt | tttttttact | gatcttgttg | tggatctctc | gtagggcgga | gatttgttgt | 660 |
| gcgtgcggcg | gagactgata | ctgataaagg | tatgattttt | tagttgtttt | tattttctct | 720 |
| ctcttcaaaa | ttctctttc | aaacactgtg | gcgtttgaat | ttccgacggc | agttaaatct | 780 |
| cagacacctg | acaaggcacc | agccggtggt | tcaagcatta | accagcttct | cggtatcaaa | 840 |
| ggagcatctc | aagaaactgt | aattttgttc | atctcctcag | aatcttttaa | attatcatat | 900 |
| ttgtggataa | tgatgtgtta | gtttaggaat | tttcctacta | aagtaatctc | cttttgagga | 960 |
| caagtcttgt | ttttagctta | gaaatgatgt | gaaaatgttg | tttgttagct | aaaaagagtt | 1020 |
| tgttgttata | ttctgtattc | agaataaatg | gaagattcgt | cttcagctta | caaaaccagt | 1080 |
| cacttggcct | ccactggttt | ggggagtcgt | ctgtggtgct | gctgcttcag | gtaatcatac | 1140 |
| gaacctcttt | tggatcatgc | aatactgtac | agaaagtttt | ttcattttcc | ttccaattgt | 1200 |
| ttcttctggc | agggaacttt | cattggaccc | cagaggatgt | tgctaagtcg | attctttgca | 1260 |
| tgatgatgtc | tggtccttgt | cttactggct | atacacaggt | ctggttttac | acaacaaaaa | 1320 |
| gctgacttgt | tcttattcta | gtgcatttgc | ttggtgctac | aataacctag | acttgtcgat | 1380 |
| ttccagacaa | tcaacgactg | gtatgataga | gatatcgacg | caattaatga | gccatatcgt | 1440 |
| ccaattccat | ctggagcaat | atcagagcca | gaggtaactg | agacagaaca | ttgtgagctt | 1500 |
| ttatctcttt | tgtgattctg | atttctcctt | actccttaaa | atgcaggtta | ttacacaagt | 1560 |
| ctgggtgcta | ttattgggag | gtcttggtat | tgctggaata | ttagatgtgt | gggtaagttg | 1620 |
| gcccttctga | cattaactag | tacagttaaa | gggcacatca | gatttgctaa | aatcttccct | 1680 |
| tatcaggcag | ggcataccac | tcccactgtc | ttctatcttg | ctttgggagg | atcattgcta | 1740 |
| tcttatatat | actctgctcc | acctcttaag | gtaagtttta | ttcctaactt | ccactctcta | 1800 |
| gtgataagac | actccatcca | agttttggag | ttttgaatat | cgatatctga | actgatctca | 1860 |
| ttgcagctaa | aacaaaatgg | atgggttgga | aattttgcac | ttggagcaag | ctatattagt | 1920 |
| ttgccatggt | aagatatctc | gtgtatcaat | aatatatggc | gttgttctca | tctcattgat | 1980 |
| ttgtttcttg | ctcacttgac | tgataggtgg | gctggccaag | cattgtttgg | cactcttacg | 2040 |
| ccagatgttg | ttgttctaac | actcttgtac | agcatagctg | gggtactctt | ttggcaaacc | 2100 |
| ttttatgttg | cttttttcgt | tatctgttgt | aatatgctct | gcttcatgt | tgtacctttg | 2160 |

| | |
|---|---|
| tgataatgca gttaggaata gccattgtta acgacttcaa aagtgttgaa ggagatagag | 2220 |
| cattaggact tcagtctctc ccagtagctt ttggcaccga aactgcaaaa tggatatgcg | 2280 |
| ttggtgctat agacattact cagctttctg ttgccggtat gtactatcca ctgtttttgt | 2340 |
| gcagctgtgg cttctatttc ttttccttga tcttatcaac tggatattca ccaatggtaa | 2400 |
| agcacaaatt aatgaagctg aatcaacaaa ggcaaaacat aaaagtacat tctaatgaaa | 2460 |
| tgagctaatg aagaggaggc atctactttt atgtttcatt agtgtgattg atggattttc | 2520 |
| atttcatgct tctaaaacaa gtattttcaa cagtgtcatg aaataacaga acttatatct | 2580 |
| tcatttgtac ttttactagt ggatgagtta cacaatcatt gttatagaac caaatcaaag | 2640 |
| gtagagatca tcattagtat atgtctattt tggttgcagg atatctatta gcatctggga | 2700 |
| aaccttatta tgcgttggcg ttggttgctt tgatcattcc tcagattgtg ttccaggtaa | 2760 |
| agacgttaac agtctcacat tataattaat caaattcttg tcactcgtct gattgctaca | 2820 |
| ctcgcttcta taaactgcag tttaaatact ttctcaagga ccctgtcaaa tacgacgtca | 2880 |
| agtaccaggt aagtcaactt agtacacatg tttgtgttct tttgaaatat ctttgagagg | 2940 |
| tctcttaatc agaagttgct tgaaacactc atcttgatta caggcaagcg cgcagccatt | 3000 |
| cttggtgctc ggaatatttg taacggcatt agcatcgcaa cactgaaaaa ggcgtatttt | 3060 |
| gatggggttt tgtcgaaagc agaggtgttg acacatcaaa tgtgggcaag tgatggcatc | 3120 |
| aactagttta aaagattttg taaaatgtat gtaccgttat tactagaaac aactcctgtt | 3180 |
| gtatcaattg agcaaaacgg ctgagaaatt gtaattgatg ttaccgtatt tgcgctccat | 3240 |
| ttttgcattt cctgctcata tcgaggattg gggtttatgt tagttctgtc acttctctgc | 3300 |
| tttcagaatg ttttttgtttt ctgtagtgga tttaactat tttcatcact ttttgtattg | 3360 |
| attctaaaca tgtatccaca taaaaacagt aatatacaaa aatgatactt cctcaaactt | 3420 |
| tttataatct aaatctaaca actagctagt aacccaacta acttcataca attaatttga | 3480 |
| gaaactacaa agactagact atacatatgt tatttaacaa cttgaaactg tgttattact | 3540 |
| acctgatttt tttctattct acagccattt gatatgctgc aatcttaaca tatcaagtct | 3600 |
| cacgttgttg gacacaacat actatcacaa gtaagacacg aagtaaaacc aaccggcaac | 3660 |

<210> SEQ ID NO 95
<211> LENGTH: 1236
<212> TYPE: DNA
<213> ORGANISM: Glycine sp.

<400> SEQUENCE: 95

| | |
|---|---|
| atggattcac tgcttcttcg atctttccct aatattaata acgcctcttc tctcaccacc | 60 |
| actggtgcaa atttctccag gactaaatct ttcgccaaca tttaccatgc aagttcttat | 120 |
| gtgccaaatg cttcatggca caataggaaa atccaaaaag aatataattt tttgaggttt | 180 |
| cggtggccaa gtttgaacca tcattacaaa ggcattgagg gagcgtgtac atgtaaaaaa | 240 |
| tgtaatataa aatttgttgt gaaagcgacc tctgaaaaat ctcttgagtc tgaacctcaa | 300 |
| gcttttgatc caaaaagcat tttggactct gtcaagaatt ccttggatgc tttctacagg | 360 |
| ttttccaggc ctcacacagt tattggcaca gcattaagca taatttctgt gtctcttctt | 420 |
| gctgttgaga aaatatcaga tatatctcca ttatttttta ctggtgtgtt ggaggctgtg | 480 |
| gttgctgccc tgtttatgaa tatttatatt gttggtttga atcaattgtc tgatgttgaa | 540 |
| atagacaaga taaacaagcc gtatcttcca ttagcatctg gggaatattc ctttgaaact | 600 |
| ggtgtcacta ttgttgcatc ttttttcaatt ctgagttttt ggcttggctg ggttgtaggt | 660 |

-continued

```
tcatggccat tattttgggc ccttttttgta agctttgtgc taggaactgc ttattcaatc    720
aatgtgcctc tgttgagatg aagaggttt gcagtgcttg cagcgatgtg cattctagct    780
gttcgggcag taatagttca acttgcattt tccttcaca tgcagactca tgtgtacaag    840
aggccacctg tctttcaag accattgatt tttgctactg cattcatgag cttcttctct    900
gtagttatag cactgtttaa ggatatacct gacattgaag agataaagt atttggcatc    960 caatcttttt cagtgcgttt aggtcagaag ccggtgttct ggacttgtgt tacccttctt   1020
gaaatagctt atgagtcgc cctcctggtg ggagctgcat ctccttgtct ttggagcaaa    1080
attttcacgg gtctgggaca cgctgtgctg gcttcaattc tctggtttca tgccaaatct   1140
gtagatttga aaagcaaagc ttcgataaca tccttctata tgtttatttg aagctatttt   1200
tatgcagaat acttactcat cctttttgtt agatga                              1236
```

<210> SEQ ID NO 96
<211> LENGTH: 1188
<212> TYPE: DNA
<213> ORGANISM: Glycine sp.

<400> SEQUENCE: 96

```
atggattcga tgcttcttcg atctttttcct aatattaaca acgcttcttc tctcgccacc     60
actggttctt atttgccaaa tgcttcatgg cacaatagga aatccaaaa agaatataat    120 tttttgaggt ttcggtggcc aagtttgaac caccattaca aaagcattga aggagggtgt    180
acatgtaaaa aatgtaatat aaaatttgtt gtgaaagcga cctctgaaaa atcttttgag    240 tctgaaccc aagcttttga tccaaaaagc attttggact ctgtcaagaa ttccttggat    300
gctttctaca ggttttccag acctcacaca gttattggca cagcattaag cataatttct    360
gtgtccctcc ttgctgttga gaaaatatca gatatatctc cattattttt tactggtgtg    420
ttggaggctg tggttgctgc cctgtttatg aatatttata ttgttggttt gaatcaattg    480
tctgatgttg aaatagacaa gataaacaag ccgtatcttc cattagcatc tggggaatat    540
tcctttgaaa ctggtgtcac tattgttgca tcttttttcaa ttctgagttt ttggcttggc    600
tgggttgtag gttcatggcc attattttgg gccctttttg taagctttgt gctaggaact    660
gcttattcaa tcaatgtgcc tctgttgaga tggaagaggt ttgcagtgct tgcagcgatg    720
tgcattctag ctgttcgggc agtaatagtt caacttgcat ttttccttca catccagact    780
catgtataca agaggccacc tgtctttttca agatcattga ttttttgctac tgcattcatg    840 agcttcttct ctgtagttat agcactgttt aaggatatac ctgacattga aggagataaa    900
gtatttggca tccaatcttt ttcagtgcgt ttaggtcaga agccggtatt ctggacttgt    960
gttatccttc ttgaaatagc ttatggagtc gccctcctgg tgggagctgc atctccttgt   1020
ctttggagca aaattgtcac gggtctggga cacgctgttc tggcttcaat tctctggttt   1080
catgccaaat ctgtagattt gaaaagcaaa gcttcgataa catccttcta tatgtttatt   1140
tggaagctat tttatgcaga atacttactc attcctttg ttagatga                1188
```

<210> SEQ ID NO 97
<211> LENGTH: 395
<212> TYPE: PRT
<213> ORGANISM: Glycine sp.

<400> SEQUENCE: 97

```
Met Asp Ser Met Leu Leu Arg Ser Phe Pro Asn Ile Asn Asn Ala Ser
1               5                   10                  15
```

-continued

```
Ser Leu Ala Thr Thr Gly Ser Tyr Leu Pro Asn Ala Ser Trp His Asn
             20                  25                  30
Arg Lys Ile Gln Lys Glu Tyr Asn Phe Leu Arg Phe Arg Trp Pro Ser
         35                  40                  45
Leu Asn His His Tyr Lys Ser Ile Glu Gly Gly Cys Thr Cys Lys Lys
     50                  55                  60
Cys Asn Ile Lys Phe Val Val Lys Ala Thr Ser Glu Lys Ser Phe Glu
 65                  70                  75                  80
Ser Glu Pro Gln Ala Phe Asp Pro Lys Ser Ile Leu Asp Ser Val Lys
             85                  90                  95
Asn Ser Leu Asp Ala Phe Tyr Arg Phe Ser Arg Pro His Thr Val Ile
            100                 105                 110
Gly Thr Ala Leu Ser Ile Ile Ser Val Ser Leu Leu Ala Val Glu Lys
            115                 120                 125
Ile Ser Asp Ile Ser Pro Leu Phe Phe Thr Gly Val Leu Glu Ala Val
        130                 135                 140
Val Ala Ala Leu Phe Met Asn Ile Tyr Ile Val Gly Leu Asn Gln Leu
145                 150                 155                 160
Ser Asp Val Glu Ile Asp Lys Ile Asn Lys Pro Tyr Leu Pro Leu Ala
                165                 170                 175
Ser Gly Glu Tyr Ser Phe Glu Thr Gly Val Thr Ile Val Ala Ser Phe
            180                 185                 190
Ser Ile Leu Ser Phe Trp Leu Gly Trp Val Val Gly Ser Trp Pro Leu
        195                 200                 205
Phe Trp Ala Leu Phe Val Ser Phe Val Leu Gly Thr Ala Tyr Ser Ile
    210                 215                 220
Asn Val Pro Leu Leu Arg Trp Lys Arg Phe Ala Val Leu Ala Ala Met
225                 230                 235                 240
Cys Ile Leu Ala Val Arg Ala Val Ile Val Gln Leu Ala Phe Phe Leu
                245                 250                 255
His Ile Gln Thr His Val Tyr Lys Arg Pro Pro Val Phe Ser Arg Ser
            260                 265                 270
Leu Ile Phe Ala Thr Ala Phe Met Ser Phe Phe Ser Val Val Ile Ala
        275                 280                 285
Leu Phe Lys Asp Ile Pro Asp Ile Glu Gly Asp Lys Val Phe Gly Ile
    290                 295                 300
Gln Ser Phe Ser Val Arg Leu Gly Gln Lys Pro Val Phe Trp Thr Cys
305                 310                 315                 320
Val Ile Leu Leu Glu Ile Ala Tyr Gly Val Ala Leu Leu Val Gly Ala
                325                 330                 335
Ala Ser Pro Cys Leu Trp Ser Lys Ile Val Thr Gly Leu Gly His Ala
            340                 345                 350
Val Leu Ala Ser Ile Leu Trp Phe His Ala Lys Ser Val Asp Leu Lys
        355                 360                 365
Ser Lys Ala Ser Ile Thr Ser Phe Tyr Met Phe Ile Trp Lys Leu Phe
    370                 375                 380
Tyr Ala Glu Tyr Leu Leu Ile Pro Phe Val Arg
385                 390                 395

<210> SEQ ID NO 98
<211> LENGTH: 411
<212> TYPE: PRT
<213> ORGANISM: Glycine sp.
```

<400> SEQUENCE: 98

```
Met Asp Ser Leu Leu Arg Ser Phe Pro Asn Ile Asn Asn Ala Ser
1               5                   10                  15

Ser Leu Thr Thr Thr Gly Ala Asn Phe Ser Arg Thr Lys Ser Phe Ala
            20                  25                  30

Asn Ile Tyr His Ala Ser Ser Tyr Val Pro Asn Ala Ser Trp His Asn
            35                  40                  45

Arg Lys Ile Gln Lys Glu Tyr Asn Phe Leu Arg Phe Arg Trp Pro Ser
        50                  55                  60

Leu Asn His His Tyr Lys Gly Ile Glu Gly Ala Cys Thr Cys Lys Lys
65                  70                  75                  80

Cys Asn Ile Lys Phe Val Val Lys Ala Thr Ser Glu Lys Ser Leu Glu
                85                  90                  95

Ser Glu Pro Gln Ala Phe Asp Pro Lys Ser Ile Leu Asp Ser Val Lys
            100                 105                 110

Asn Ser Leu Asp Ala Phe Tyr Arg Phe Ser Arg Pro His Thr Val Ile
            115                 120                 125

Gly Thr Ala Leu Ser Ile Ile Ser Val Ser Leu Leu Ala Val Glu Lys
        130                 135                 140

Ile Ser Asp Ile Ser Pro Leu Phe Phe Thr Gly Val Leu Glu Ala Val
145                 150                 155                 160

Val Ala Ala Leu Phe Met Asn Ile Tyr Ile Val Gly Leu Asn Gln Leu
                165                 170                 175

Ser Asp Val Glu Ile Asp Lys Ile Asn Lys Pro Tyr Leu Pro Leu Ala
            180                 185                 190

Ser Gly Glu Tyr Ser Phe Glu Thr Gly Val Thr Ile Val Ala Ser Phe
        195                 200                 205

Ser Ile Leu Ser Phe Trp Leu Gly Trp Val Val Gly Ser Trp Pro Leu
210                 215                 220

Phe Trp Ala Leu Phe Val Ser Phe Val Leu Gly Thr Ala Tyr Ser Ile
225                 230                 235                 240

Asn Val Pro Leu Leu Arg Trp Lys Arg Phe Ala Val Leu Ala Ala Met
                245                 250                 255

Cys Ile Leu Ala Val Arg Ala Val Ile Val Gln Leu Ala Phe Phe Leu
            260                 265                 270

His Met Gln Thr His Val Tyr Lys Arg Pro Pro Val Phe Ser Arg Pro
        275                 280                 285

Leu Ile Phe Ala Thr Ala Phe Met Ser Phe Phe Ser Val Val Ile Ala
        290                 295                 300

Leu Phe Lys Asp Ile Pro Asp Ile Glu Gly Asp Lys Val Phe Gly Ile
305                 310                 315                 320

Gln Ser Phe Ser Val Arg Leu Gly Gln Lys Pro Val Phe Trp Thr Cys
                325                 330                 335

Val Thr Leu Leu Glu Ile Ala Tyr Gly Val Ala Leu Val Gly Ala
            340                 345                 350

Ala Ser Pro Cys Leu Trp Ser Lys Ile Phe Thr Gly Leu Gly His Ala
        355                 360                 365

Val Leu Ala Ser Ile Leu Trp Phe His Ala Lys Ser Val Asp Leu Lys
370                 375                 380

Ser Lys Ala Ser Ile Thr Ser Phe Tyr Met Phe Ile Trp Lys Leu Phe
385                 390                 395                 400

Tyr Ala Glu Tyr Leu Leu Ile Pro Phe Val Arg
            405                 410
```

<210> SEQ ID NO 99
<211> LENGTH: 964
<212> TYPE: DNA
<213> ORGANISM: Oryza sp.

<400> SEQUENCE: 99

| | | | | | |
|---|---|---|---|---|---|
| gagcagcact | gggtcttaca | ttccaatgga | gctcgcctgt | tgctttcatt | acatgcttcg | 60 |
| tgactttatt | tgctttggtc | attgctataa | ccaaagatct | cccagatgtt | gaagggggatc | 120 |
| ggaagtatca | aatatcaact | ttggcgacaa | agctcggtgt | cagaaacatt | gcatttcttg | 180 |
| gctctggttt | attgatagca | aattatgttg | ctgctattgc | tgtagctttt | ctcatgcctc | 240 |
| aggctttcag | gcgcactgta | atggtgcctg | tgcatgctgc | ccttgccgtt | ggtataattt | 300 |
| tccagacatg | ggttctggag | caagcaaaat | atactaagga | tgctatttca | cagtactacc | 360 |
| ggttcatttg | gaatctcttc | tatgctgaat | acatcttctt | cccgttgata | tagagaccaa | 420 |
| gcaatctgat | atggtctgca | tgttgagtgc | ggcaaaaact | agaagcccat | atgaacagtg | 480 |
| ggagtagggg | aacgaacatg | ccatccatgg | gaagactctg | ataactctct | ctcgcccggg | 540 |
| ctgtaaaggg | taagcactgt | tgggcatata | tatgaaagga | aggtgataaa | gcagggatgc | 600 |
| taaattgcta | ctgggatcct | caaaggctta | tagtggtcac | cagtggaatg | tgccttaata | 660 |
| atttggttac | ccagcagagc | aagttttgc | aggttattag | gtaatatctt | tgagggaatg | 720 |
| aacttagatt | tcattgtttt | aaggtctggt | cacacaacgg | gtagtagtgc | tggagcggca | 780 |
| aaaaacgacc | ttgttttaca | ctaccaaggg | aggttaactc | tagttttcat | gtgaccactt | 840 |
| accttgagag | ttgagaccat | ggaatcactt | gtcgactcct | cggcttgtat | atttctagtg | 900 |
| tcagcatttg | cattctcctc | cccacttgta | cttgaaaagt | tgaagacaac | ttttttgttt | 960 |
| gtgt | | | | | | 964 |

<210> SEQ ID NO 100
<211> LENGTH: 421
<212> TYPE: DNA
<213> ORGANISM: Triticum sp.

<400> SEQUENCE: 100

| | | | | | |
|---|---|---|---|---|---|
| cgtccgcgga | cgcgtgggtg | cttattcagt | caatctgccg | cactttctat | ggaagagatc | 60 |
| tgctgttgtt | gcagcactct | gcatattagc | agtgcgtgcg | gtgatagttc | aactggcatt | 120 |
| ttttctccac | attcagacat | ttgttttcag | aaggccggca | gacttttcaa | agccattgat | 180 |
| atttgcaact | gccttcatga | cattcttctc | agttgtaata | gcattattca | aggatatacc | 240 |
| cgatattgaa | ggggaccgca | tctttggaat | ccaatctttt | agtggtagac | taggtcaaag | 300 |
| cagggggttc | tggacttgcg | ttggcctact | tgaggttgcc | tacggtgttg | cgatactgag | 360 |
| gggggtaact | tcttccagtt | tgtggagcaa | atctataact | gttgtgggcc | atgcaatcct | 420 |
| c | | | | | | 421 |

<210> SEQ ID NO 101
<211> LENGTH: 705
<212> TYPE: DNA
<213> ORGANISM: Allium porrum

<400> SEQUENCE: 101

| | | | | | |
|---|---|---|---|---|---|
| gtttccccc | ctcgaatttt | tttttttttt | ttttacttca | tttttctgtg | aataaattct | 60 |
| taaaaagac | aaagaaaacc | actggatatc | ctaaattcaa | cataggctat | tgtcattcaa | 120 |

-continued

```
tgataatctt taacacaaca tacaacatga atataattaa ggagaaatga tctgcaattg      180
ttgaaagaac tctccgtttt taagatgaca attaaagcgt tgttaattcc agccatttct      240
gcctccatta tctactcatc ttctcttgcg attcttttcc atgtaggtca taaaccctca      300
tcttacaaaa ggaatgagca agtactcagc atagaagagc ttccacacga acatataaaa      360
agatgtaata gtggttttgg tcattggtcc atgagatcta gcacgattcc aaagtaacga      420
cccaagaatt gcatgaccta tcactgttaa gcatttgctc cataggcatg aggaagtagc      480
tccaacaacc atgacaacag tgtaggccat ctcaaggaga tatatacata tccaaaacac      540
cctctcctgg ccaaggcgca cgctgaaaga atggatgcca aatattttgt ctccgtctat      600
atcaggtata tccttaaata gagcaataac aactgagaag aagctcatga aggcagttgc      660
aaatatcaat ggccttgtga aacttgctgg tcttttgaaa acaaa              705

<210> SEQ ID NO 102
<211> LENGTH: 637
<212> TYPE: DNA
<213> ORGANISM: Allium porrum
<220> FEATURE:
<221> NAME/KEY: misc_feature
<222> LOCATION: (1)...(637)
<223> OTHER INFORMATION: n = A, T, C, or G

<400> SEQUENCE: 102
nattcggcac gagttttgaa gaagttaagc atggactccc tccttaccaa gccagttgta      60
atacctctgc cttctccagt ttgttcacta ccaatcttgc gaggcagttc tgcaccaggg     120
cagtattcat gtagaaacta caatccaata agaattcaaa ggtgcctcgt aaattatgaa     180
catgtgaaac caaggtttac aacatgtagt aggtctcaaa aacttggtca tgtaaaagcc     240
acatccgagc attctttaga atctggatcc gaaggataca ctcctagaag catatgggaa     300
gccgtactag cttcactgaa tgttctatac aaattttcac gacctcacac aataatagga     360
acagcaatgg gcataatgtc agtttctttg cttgttgtcg agagcctatc cgatatttct     420
cctctgtttt ttgtgggatt attagaggct gtggttgctg cattgtttat gaatgtttac     480
attgtaggtc tgaatcaatt atttgacata gaaatagaca aggtcaataa acctgatctt     540
cctcttgcat ctggagaata ctcaccaaga gctggtactg ctattgtcat tgcttcagcc     600
atcatgagct ttggcattgg atggttagtt ggctctt              637

<210> SEQ ID NO 103
<211> LENGTH: 677
<212> TYPE: DNA
<213> ORGANISM: Brassica napus

<400> SEQUENCE: 103 ttttttttt tttttttcaa aaagaccaat cctttagtat gtacatgaac aaagtgattt       60
tgtctccaag ctacaaagaa gaagaagaga ggtatacaaa gaaaactaca aatgttcacc     120
atgaatgcta aagaagggg aataacagat actctgcgta aagagattc catataaacc      180 ggtaatatcc tgctatagct tcctttgtgt agtttgcttt ttctagcacc catgtctgga     240 aaccaagca tgaagccaag atcatatgtg caggaatcat caagctacct ctaaaaacct     300
gaggcatgta gaaagctagt gatatggcag aaatatagtt cactagcaga agtccagaac     360
cgaggaatgc aatgttcctc actccaagct ttgttgctag tgttgatatt tggaacttgc     420
gatctccttc aacatcagga agatcttttg taatagcaat gactagtgca aacagtgtca     480
caaaagacgt gatgaaagcc acaggtgcac tccactgaaa cgaaagtcca agagcagctc     540
```

```
tagtagcatg gtacacacca aaattaagaa gaaaacctcg taccgtggca ataataagaa      600
acgctgcaac tggaaatctc ttcattctaa atggtggaac agaatagatg gtccccagat      660
cggacgcgtg ggtcgac                                                    677

<210> SEQ ID NO 104
<211> LENGTH: 1431
<212> TYPE: DNA
<213> ORGANISM: Zea sp.

<400> SEQUENCE: 104
ccacgcgtcc gcccggccaa gggatggacg cgcttcgcct acggccgtcc ctcctccccg       60
tgcggcccgg cgcggcccgc cgcgagatc attttctacc accatgttgt tccatacaac      120
gaaatggtga aggacgaatt tgcttttcta gccaaaggac ccaaggtcct accttgcatc      180
accatcagaa attcttcgaa tggaaatcct cctattgtag gatatcacat cggtcattaa      240
atacttctgt taatgcttcg gggcaacagc tgcagtctga acctgaaaca catgattcta      300
caaccatctg gagggcaata tcatcttctc tagatgcatt ttacagattt tcccggccac      360
atactgtcat aggaacagca ttaagcatag tctcagtttc ccttctagct gtccagagct      420
tgtctgatat atcacctttg ttcctcactg gtttgctgga ggcagtggta gctgcccttt      480
tcatgaatat ctatattgtt ggactgaacc agttattcga cattgagata gacaaggtta      540
acaagccaac tcttccattg gcatctgggg aatacaccct tgcaactggg gttgcaatag      600
tttcggtctt tgccgctatg agctttggcc ttggatgggc tgttggatca caacctctgt      660
tttgggctct tttcataagc tttgttcttg ggactgcata ttcaatcaat ctgccgtacc      720
ttcgatggaa gagatttgct gttgttgcag cactgtgcat attagcagtt cgtgcagtga      780
ttgttcagct ggccttttttt ctccacattc agacttttgt tttcaggaga ccggcagtgt      840
tttctaggcc attattattt gcaactggat ttatgacgtt cttctctgtt gtaatagcac      900
tattcaagga tacctgac atcgaagggg accgcatatt cgggatccga tccttcagcg      960
tccggttagg gcaaaagaag gtctttttgga tctgcgttgg cttgcttgag atggcctaca    1020
gcgttgcgat actgatggga gctacctctt cctgtttgtg gagcaaaaca gcaaccatcg    1080
ctggccattc catacttgcc gcgatcctat ggagctgcgc gcgatcggtg gacttgacga    1140
gcaaagccgc aataacgtcc ttctacatgt tcatctggaa gctgttctac gcggagtacc    1200
tgctcatccc tctggtgcgg tgagcgcgag gcgaggtggt ggcagacgga tcggcgtcgg    1260
cggggcggca aacaactcca cgggagaact tgagtgccgg aagtaaactc ccgtttgaaa    1320
gttgaagcgt gcaccaccgg caccgggcag agagagacac ggtggctgga tggatacgga    1380
tggcccccccc aataaattcc cccgtgcatg gtaaaaaaaa aaaaaaaaa a              1431

<210> SEQ ID NO 105
<211> LENGTH: 1870
<212> TYPE: DNA
<213> ORGANISM: Zea sp.

<400> SEQUENCE: 105
gccgcgcagc gcgacgagcg ccacctgctt gctgccgcgt gcctgcgtgc gtgtgcgtcc       60
accactgacc ccgcgcccgc ccgccgcccc tgcccctcca ctccacttgc tcactcgtcg      120
cggcccgctt ccccccggc caagggatgg acgcgcttcg cctacggccg tccctcctcc      180
ccgtgcggcc cggcgcggcc cgcccgcgag atcatttttct accaccatgt tgttccatac      240
```

-continued

```
aacgaaatgg tgaaggacga atttgctttt ctagccaaag gacccaaggt cctaccttgc      300
atcaccatca gaaattcttc gaatggaaat cctcctattg taggatatca catcggtcat      360
taaatacttc tgttaatgct tcggggcaac agctgcagtc tgaacctgaa acacatgatt      420
ctacaaccat ctggagggca atatcatctt ctctagatgc attttacaga ttttcccggc      480
cacatactgt cataggaaca gcattaagca tagtctcagt ttcccttcta gctgtccaga      540
gcttgtctga tatatcacct ttgttcctca ctggtttgct ggaggcagtg gtagctgccc      600
ttttcatgaa tatctatatt gttggactga accagttatt cgacattgag atagacaagg      660
ttaacaagcc aactcttcca ttggcatctg gggaatacac ccttgcaact ggggttgcaa      720
tagtttcggt ctttgccgct atgagctttg gccttggatg gctgttgga tcacaacctc       780
tgttttgggc tcttttcata agctttgttc ttgggactgc atattcaatc aatctgccgt      840
accttcgatg gaagagattt gctgttgttg cagcactgtg catattagca gttcgtgcag      900
tgattgttca gctggccttt tttctccaca ttcagacttt tgttttcagg agaccggcag      960
tgttttctag gccattatta tttgcaactg gatttatgac gttcttctct gttgtaatag     1020
cactattcaa ggatatacct gacatcgaag gggaccgcat attcgggatc cgatccttca     1080
gcgtccggtt agggcaaaag aaggtctttt ggatctgcgt tggcttgctt gagatggcct     1140
acagcgttgc gatactgatg ggagctacct cttcctgttt gtggagcaaa acagcaacca     1200
tcgctggcca ttccatactt gccgcgatcc tatggagctg cgcgcgatcg gtggacttga     1260
cgagcaaagc cgcaataacg tccttctaca tgttcatctg gaagctgttc tacgcggagt     1320
acctgctcat ccctctggtg cggtgagcgc gaggcgaggt ggtggcagac ggatcggcgt     1380
cggcggggcg gcaaacaact ccacgggaga acttgagtgc cggaagtaaa ctcccgtttg     1440
aaagttgaag cgtgcaccac cggcaccggg cagagagaga cacggtggct ggatggatac     1500
ggatggcccc cccaataaat tcccccgtgc atggtacccc acgctgcttg atgatatccc     1560
atgtgtccgg gtgaccggac ctgatcgtct ctagagagat tggttgcaca acgtccaaca     1620
tagcccgtag gtattgctac cactgctagt atgatactcc ttcctagtcc ttgccagcac     1680
cagtgaccca aacttggtcg gctgagctca gcgctcagca gctttacgtg catctgcgcc     1740
ttgacttgtg cagtgggcgt cgctagcatg aatgatgtat ggtgcgtcac ggcctgacgg     1800
ttcgtcagtc tgggccgtgt tttgtgtccg aggaagatcg tctgtcagag atctggattg     1860
cctcgctgct                                                            1870
```

<210> SEQ ID NO 106
<211> LENGTH: 642
<212> TYPE: DNA
<213> ORGANISM: Zea sp.

<400> SEQUENCE: 106

```
cggccggact cttctgactt ggcaaccgcc gcgcagcgcg acgagcgcca cctgcttgct       60
gccgcgtgcc tgcgtgcgtg tgcgtccacc actgacccccg cgcccgcccg ccgcccctgc     120
ccctccactc cacttgctca ctcgtcggct cgtcgcggcc cgcttccccc ccggccaagg     180
gatggacgcg cttcgcctac ggccgtccct cctccccgtg cggcccggcg cggcccgccc     240
gcgaggcagt ggtagctgcc cttttcatga atatctatat tgttggactg aaccagttat     300
tcgacattga gatagacaag gttaacaagc caactcttcc attggcatct ggggaataca     360
cccttgcaac tggggttgca atagtttcgg tctttgccgc tatgagcttt ggccttggat     420
ggctgttgg atcacaacct ctgttttggg ctcttttcat aagctttgtt cttgggactg      480
```

```
catattcaat caatctgccg taccttcgat ggaagagatt tgctgttgtt gcagcactgt      540
gcatattagc agttcgtgca gtgattgttc agctggcctt ttttctccac attcagactt      600
ttgttttcag gagaccggca gtgttttcta ggccattatt at                        642
```

<210> SEQ ID NO 107
<211> LENGTH: 362
<212> TYPE: DNA
<213> ORGANISM: Gossypium sp.

<400> SEQUENCE: 107

```
cccacgcgtc cgaacattgt ttgcacttgt tattgccata accaaggatc ttccagatgt       60
agaaggagat cgcaaatttc aaatatcaac attagcaaca aagcttggag ttagaaatat      120
tgcatttctt ggttccggac ttctactggt gaattatgtt gctgctgtgt tggctgcaat      180
atacatgcct caggctttca ggcgtagttt aatgatacct gctcatatct ttttggcggt      240
ctgcttgatt tttcagacat gggtgttgga acaagcaaat tacaaaaagg aagcaatctc      300
ggggttctat cgtttcatat ggaatctctt ctatgcagag tatgcgattt tccccttcgt      360
gt                                                                     362
```

<210> SEQ ID NO 108
<211> LENGTH: 575
<212> TYPE: DNA
<213> ORGANISM: Lycopersicon sp.

<400> SEQUENCE: 108

```
cagatcaatt ccagttcctg ctgagttttc tccactcaaa accagttcac atgcaatagt       60
acgggttttg aaatgtaaag catggaagag accaaaaaag cactattcct cttcaatgaa      120
gttgcagcgg cagtatatca cgcaagagca tgttggagga agtgatctaa gcactattgc      180
tgctgataaa aaacttaaag ggagattttt ggtgcacgca tcatctgaac accctcttga      240
atctcaacct tctaaaagtc cttgggactc agttaatgat gccgtagatg ctttctacag      300
gttctcgcgg ccccatacca taataggaac agcattgagc ataatttcag tttctctcct      360
tgcagttgag aagttctctg attttttctcc attattttc actggggtgt tagaggccat      420
tgttgctgcc ctattcatga acatttacat agttggttta aaccagttgt ctgacatcga      480
aatagacaag gtaaacaagc catatcttcc attggcatca ggggaatact ctgtacaaac      540
tggagtgatt gttgtgtcgt cttttgccat tttga                                 575
```

<210> SEQ ID NO 109
<211> LENGTH: 1663
<212> TYPE: DNA
<213> ORGANISM: Arabidopsis sp.

<400> SEQUENCE: 109

```
aacaccaaac acacaatttc acattctttt gcatatttct tcttcttctt ccattatgga       60
gatacggagc ttgattgttt ctatgaaccc taatttatct cctttgagc tctctcgccc       120 tgtatctcct ctcactcgct cactagttcc gttccgatcg actaaactag ttccccgctc      180
catttctagg gggatcccgt cgatctccac cccgaatagt gaaactgaca agatctccgt      240
taaacctgtt tacgtcccga cgtctcccaa tcgcgaactc cggactcctc acagtggata      300
ccatttcgat ggaacacctc ggaagttctt cgagggatgg tggatccggg tttccatccc      360
agagaagagg gagagttttt gttttatgta ttctgtggag aatcctgcat tcggcagag       420
```

-continued

```
tttgtcacca ttggaagtgg ctctatatgg acctagattc actggtgttg gagctcagat    480
tcttggcgct aatgataaat atttatgcca atacgaacaa gactctcaca atttctgggg    540
agatcgacat gagctagttt tggggaatac ttttagtgct gtgccaggcg caaaggctcc    600
aaacaaggag gttccaccag aggaatttaa cagaagagtg tccgaagggt tccaagctac    660
tccattttgg catcaaggtc acatttgcga tgatggccgt actgactatg cggaaactgt    720
gaaatctgct cgttgggagt atagtactcg tcccgtttac ggttggggtg atgttggggc    780
caaacagaag tcaactgcag gctggcctgc agcttttcct gtatttgagc ctcattggca    840
gatatgcatg gcaggaggcc tttccacagg gtggatagaa tggggcggtg aaaggtttga    900
gtttcgggat gcaccttctt attcagagaa gaattggggt ggaggcttcc aagaaaatg     960
gttttgggtc cagtgtaatg tctttgaagg ggcaactgga gaagttgctt taaccgcagg   1020
tggcgggttg aggcaattgc ctggattgac tgagacctat gaaaatgctg cactggtttg   1080
tgtacactat gatggaaaaa tgtacgagtt tgttccttgg aatggtgttg ttagatggga   1140
aatgtctccc tggggttatt ggtatataac tgcagagaac gaaaaccatg tggtggaact   1200
agaggcaaga acaaatgaag cgggtacacc tctgcgtgct cctaccacag aagttgggct   1260
agctacggct tgcagagata gttgttacgg tgaattgaag ttgcagatat gggaacggct   1320
atatgatgga agtaaaggca aggtgatatt agagacaaag agctcaatgg cagcagtgga   1380
gataggagga ggaccgtggt ttgggacatg gaaaggagat acgagcaaca cgcccgagct   1440
actaaaacag gctcttcagg tcccattgga tcttgaaagc gccttaggtt tggtcccttt   1500
cttcaagcca ccgggtctgt aacattgatg agtgttttgt ttgttgatag agacccatgt   1560
gatgaatgaa gccttagtca tgtcattgct agcttcacta ttatgtatgt atgattttag   1620
ttcgttcggt ccttgtggta aatgatacgg gccagtgtaa agt                     1663
```

<210> SEQ ID NO 110
<211> LENGTH: 488
<212> TYPE: PRT
<213> ORGANISM: Arabidopsis sp.

<400> SEQUENCE: 110

```
Met Glu Ile Arg Ser Leu Ile Val Ser Met Asn Pro Asn Leu Ser Ser
1               5                   10                  15

Phe Glu Leu Ser Arg Pro Val Ser Pro Leu Thr Arg Ser Leu Val Pro
                20                  25                  30

Phe Arg Ser Thr Lys Leu Val Pro Arg Ser Ile Ser Arg Val Ser Ala
            35                  40                  45

Ser Ile Ser Thr Pro Asn Ser Glu Thr Asp Lys Ile Ser Val Lys Pro
    50                  55                  60

Val Tyr Val Pro Thr Ser Pro Asn Arg Glu Leu Arg Thr Pro His Ser
65                  70                  75                  80

Gly Tyr His Phe Asp Gly Thr Pro Arg Lys Phe Glu Gly Trp Tyr
                85                  90                  95

Phe Arg Val Ser Ile Pro Glu Lys Arg Glu Ser Phe Cys Phe Met Tyr
            100                 105                 110

Ser Val Glu Asn Pro Ala Phe Arg Gln Ser Leu Ser Pro Leu Glu Val
        115                 120                 125

Ala Leu Tyr Gly Pro Arg Phe Thr Gly Val Gly Ala Gln Ile Leu Gly
    130                 135                 140

Ala Asn Asp Lys Tyr Leu Cys Gln Tyr Glu Gln Asp Ser His Asn Phe
145                 150                 155                 160
```

-continued

```
Trp Gly Asp Arg His Glu Leu Val Leu Gly Asn Thr Phe Ser Ala Val
                165                 170                 175

Pro Gly Ala Lys Ala Pro Asn Lys Glu Val Pro Pro Glu Glu Phe Asn
            180                 185                 190

Arg Arg Val Ser Glu Gly Phe Gln Ala Thr Pro Phe Trp His Gln Gly
        195                 200                 205

His Ile Cys Asp Asp Gly Arg Thr Asp Tyr Ala Glu Thr Val Lys Ser
    210                 215                 220

Ala Arg Trp Glu Tyr Ser Thr Arg Pro Val Tyr Gly Trp Gly Asp Val
225                 230                 235                 240

Gly Ala Lys Gln Lys Ser Thr Ala Gly Trp Pro Ala Ala Phe Pro Val
                245                 250                 255

Phe Glu Pro His Trp Gln Ile Cys Met Ala Gly Gly Leu Ser Thr Gly
            260                 265                 270

Trp Ile Glu Trp Gly Gly Glu Arg Phe Glu Phe Arg Asp Ala Pro Ser
        275                 280                 285

Tyr Ser Glu Lys Asn Trp Gly Gly Phe Pro Arg Lys Trp Phe Trp
    290                 295                 300

Val Gln Cys Asn Val Phe Glu Gly Ala Thr Gly Glu Val Ala Leu Thr
305                 310                 315                 320

Ala Gly Gly Leu Arg Gln Leu Pro Gly Leu Thr Glu Thr Tyr Glu
                325                 330                 335

Asn Ala Ala Leu Val Cys Val His Tyr Asp Gly Lys Met Tyr Glu Phe
            340                 345                 350

Val Pro Trp Asn Gly Val Val Arg Trp Glu Met Ser Pro Trp Gly Tyr
        355                 360                 365

Trp Tyr Ile Thr Ala Glu Asn Glu Asn His Val Val Glu Leu Glu Ala
    370                 375                 380

Arg Thr Asn Glu Ala Gly Thr Pro Leu Arg Ala Pro Thr Thr Glu Val
385                 390                 395                 400

Gly Leu Ala Thr Ala Cys Arg Asp Ser Cys Tyr Gly Glu Leu Lys Leu
                405                 410                 415

Gln Ile Trp Glu Arg Leu Tyr Asp Gly Ser Lys Gly Lys Val Ile Leu
            420                 425                 430

Glu Thr Lys Ser Ser Met Ala Ala Val Glu Ile Gly Gly Pro Trp
        435                 440                 445

Phe Gly Thr Trp Lys Gly Asp Thr Ser Asn Thr Pro Glu Leu Leu Lys
    450                 455                 460

Gln Ala Leu Gln Val Pro Leu Asp Leu Glu Ser Ala Leu Gly Leu Val
465                 470                 475                 480

Pro Phe Phe Lys Pro Pro Gly Leu
                485

<210> SEQ ID NO 111
<211> LENGTH: 246
<212> TYPE: PRT
<213> ORGANISM: Arabidopsis sp.

<400> SEQUENCE: 111

Met Ser Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
            20                  25                  30

Pro Ala Ser Ser Asn Pro Leu Phe Leu Gly Gly Ala Gly Val Arg Gly
```

```
                35                  40                  45
Leu Asp Ile Gln Gly Lys Phe Val Ile Phe Thr Val Ile Gly Val Tyr
 50                  55                  60
Leu Glu Gly Asn Ala Val Pro Ser Leu Ser Val Lys Trp Lys Gly Lys
 65                  70                  75                  80
Thr Thr Glu Glu Leu Thr Glu Ser Ile Pro Phe Phe Arg Glu Ile Val
                 85                  90                  95
Thr Gly Ala Phe Glu Lys Phe Ile Lys Val Thr Met Lys Leu Pro Leu
                100                 105                 110
Thr Gly Gln Gln Tyr Ser Glu Lys Val Thr Glu Asn Cys Val Ala Ile
                115                 120                 125
Trp Lys Gln Leu Gly Leu Tyr Thr Asp Cys Glu Ala Lys Ala Val Glu
        130                 135                 140
Lys Phe Leu Glu Ile Phe Lys Glu Glu Thr Phe Pro Pro Gly Ser Ser
145                 150                 155                 160
Ile Leu Phe Ala Leu Ser Pro Thr Gly Ser Leu Thr Val Ala Phe Ser
                165                 170                 175
Lys Asp Asp Ser Ile Pro Glu Thr Gly Ile Ala Val Ile Glu Asn Lys
                180                 185                 190
Leu Leu Ala Glu Ala Val Leu Glu Ser Ile Ile Gly Lys Asn Gly Val
                195                 200                 205
Ser Pro Gly Thr Arg Leu Ser Val Ala Glu Arg Leu Ser Gln Leu Met
        210                 215                 220
Met Lys Asn Lys Asp Glu Lys Glu Val Ser Asp His Ser Leu Glu Glu
225                 230                 235                 240
Lys Leu Ala Lys Glu Asn
                245

<210> SEQ ID NO 112
<211> LENGTH: 3115
<212> TYPE: DNA
<213> ORGANISM: Arabidopsis sp.

<400> SEQUENCE: 112
cacacgttct cgtcctttc ttcttcctct ctgcattctt cacagagttt gtcaccacca    60
acaccaaaca cacaatttca cattcttttg catatttctt cttcttcttc cattatggag   120
atacggagct tgattgtttc tatgaaccct aatttatctt cctttgagct ctctcgccct   180
gtatctcctc tcactcgctc actagttccg ttccgatcga ctaaactagt tccccgctcc   240
atttctaggg tttcggcgtc gatctccacc ccgaatagtg aaactgacaa gatctccgtt   300
aaacctgttt acgtcccgac gtctcccaat cgcgaactcc ggactcctca cagtgggtaa   360
attgatccat tccattccat ttctcttctc ttgtttgttt tattaagctc caatttcagt   420
ttcgtctttt aatttatatg ttcttcttac gatcagtggg acttaaaaaa ttgctccttt   480
aaatgcttca gtatgttttg agtattacaa agttgtaaga ttttattttt attcatttgg   540
tggctcacca ttcgacgact acttttgaat ttgagttttt gaaaaatgca atttaacatc   600
agagagtttt tttttttatg gttgataact tattgtttaa cttttgaaaa atgcagatac   660
catttcgatg gaacacctcg gaagttcttc gagggatggt atttcagggt ttccatccca   720
gagaagaggg agagtttttg ttttatgtat tctgtgagaa atcctgcatt tcggcagagt   780
ttgtcaccat ggaagtggc tctatatgga cctagattca ctggtgttgg agctcagatt   840
cttggcgcta atgataaata tttatgccaa tacgaacaag actctcacaa tttctgggga   900
```

-continued

```
ggtaactcct tgacccttaa aatgctgtgt catgacaata agaaatcata tctgagtctt    960
ttctctactt ctagtactaa tgttcgttat tgttgttaaa gatctaagtc ttatctgaat   1020
tttgttacat tttggttctg gtgctttctc aacatgaatt tgtatatatg actttaaaga   1080
ttgcttacct aaagttttta ctcatgcata gatcgacatg agctagtttt ggggaatact   1140
tttagtgctg tgccaggcgc aaaggctcca acaaggagg ttccaccaga ggttctcact    1200
cctcccttgt tggttacttt gttatctgtt aaatagtttt ccaattgtat ccggatagtg   1260
ttctacttct ccttgtagaa aatctcaagt ttttgttact cttgctattc tcttggatgt   1320
tgatttgtaa agcatgtcgt tttattgtag gaatttaaca agagagtgtc cgaagggttc   1380
caagctactc cattttggca tcaaggtcac atttgcgatg atggccggta attatatgat   1440
tctatgcaca acaagaattc actatattat aaatattgga attgagtat ttttgttgaa    1500 aatttctgtg tttaaatctg acttgacttg ttttgtcagt actgactatg cggaaactgt   1560
gaaatctgct cgttgggagt atagtactcg tcccgtttac ggttggggtg atgttggggc   1620
caaacagaag tcaactgcag gctggcctgc agcttttcct gtatttgagc ctcattggca   1680
gatatgcatg gcaggaggcc tttccacagg tgtgagcttt gcttgattga cttaaagtta   1740
ataaatagac ggttaagttt acttgcctag tactaacaga aaattaagaa agaaaccacc   1800
ctctttctat cagcagaaac tgctattgta gttcttattt tttctcttgt atttgcaggg   1860
tggatagaat ggggcggtga aaggtttgag tttcgggatg caccttctta ttcagagaag   1920
aattggggtg gaggcttccc aagaaaatgg tttttgggta aacatttcat ccttttgcta   1980
catttcttgt tgcagacttt agttagctag tggacctgtg tatacaccca catgtagtat   2040
acttgtttga tagctttatt tgtcaatgtc tctttacagg tccagtgtaa tgtctttgaa   2100
ggggcaactg gagaagttgc tttaaccgca ggtggcgggt tgaggcaatt gcctggattg   2160
actgagacct atgaaaatgc tgcactggta tgcacttata agatcttctt aagcaatgac   2220
agtgagtatt agaaggcaga tagtttacaa aagctctggg cccttgtaaa tctgcaggtt   2280
tgtgtacact atgatggaaa aatgtacgag tttgttcctt ggaatggtgt tgttagatgg   2340
gaaatgtctc cctggggtta ttggtatata actgcagaga acgaaaacca tgtggtaaat   2400
ttgttttact agtttcattc agttttactt ttgacatcat atcattccct tatggctaga   2460
ttccaacacc cgatgaatgt cttgtgacag gtggaactag aggcaagaac aaatgaagcg   2520
ggtacacctc tgcgtgctcc taccacagaa gttgggctag ctacggcttg cagagatagt   2580
tgttacggtg aattgaagtt gcagatatgg gaacggctat atgatggaag taaaggcaag   2640
gtatgtatgc taatgtgatc caatccctgt agttaaaagt cttaacaaat cctaaggcag   2700
tgaaagaaga ttatgaacgt tgttatggt taacaatgat gcaggtgata ttagagacaa    2760
agagctcaat ggcagcagtg gagataggag gaggaccgtg gtttgggaca tggaaaggag   2820
atacgagcaa cacgcccgag ctactaaaac aggctcttca ggtcccattg gatcttgaaa   2880
gcgccttagg tttggtccct ttcttcaagc caccgggtct gtaacattga tgagtgtttt   2940
gtttgttgat agagacccat gtgatgaatg aagccttagt catgtcattg ctagcttcac   3000
tattatgtat gtatgatttt agttcgttcg gtccttgtgg taaatgatac gggccagtgt   3060
aaagtctagt tcaataaaag ccttgagtcg cataatttca atttcaaatt gcatc         3115
```

<210> SEQ ID NO 113
<211> LENGTH: 536
<212> TYPE: DNA
<213> ORGANISM: Arabidopsis sp.

<400> SEQUENCE: 113

```
cacccccaaac atcacaattt cacattcttt tgcatatttc ttcttcttct tccattatgg      60
agatacggag cttgattgtt tctatgaacc ctaatttatc ttcctttgag ctctctcgcc     120
ctgtatctcc tctcactcgc tcactagttc cgttccgatc gactaaacta gttccccgct     180
ccatttctag ggtttcggcg tcgatctcca ccccgaatag tgaaactgac aagatctccg     240
ttaaacctgt ttacgtcccg acgtctccca atcgcgaact ccggactcct cacagtggat     300
accatttcga tggaacacct cggaagttct tcgaggatg gtatttcagg gtttccatcc     360
cagagaagag ggagagtttt tgttttatgt attctgtgga gaatcctgca tttcggcaga     420
gtttgtcacc attggaagtg gctctatatg gacctagatt cactggtgtt ggagctcaga     480
ttcttggcgc taatgataaa tatttatgcc aatacgaaca agactctcac aatttc         536
```

<210> SEQ ID NO 114
<211> LENGTH: 411
<212> TYPE: PRT
<213> ORGANISM: Arabidopsis sp.
<220> FEATURE:
<223> OTHER INFORMATION: Peptide PIR: TO4448 shown in Figure 31

<400> SEQUENCE: 114

```
Pro Glu Lys Arg Glu Ser Phe Cys Phe Met Tyr Ser Val Glu Asn Pro
  1               5                  10                  15

Ala Phe Arg Gln Ser Leu Ser Pro Leu Glu Val Ala Leu Tyr Gly Pro
             20                  25                  30

Arg Phe Thr Gly Val Gly Ala Gln Ile Leu Gly Ala Asn Asp Lys Tyr
         35                  40                  45

Leu Cys Gln Tyr Glu Gln Asp Ser His Asn Phe Trp Gly Asp Arg His
     50                  55                  60

Glu Leu Val Leu Gly Asn Thr Phe Ser Ala Val Pro Gly Ala Lys Ala
 65                  70                  75                  80

Pro Asn Lys Glu Val Pro Pro Glu Glu Phe Asn Arg Arg Val Ser Glu
                 85                  90                  95

Gly Phe Gln Ala Thr Pro Phe Trp His Gln Gly His Ile Cys Asp Asp
            100                 105                 110

Gly Arg Thr Asp Tyr Ala Glu Thr Val Lys Ser Ala Arg Trp Glu Tyr
        115                 120                 125

Ser Thr Arg Pro Val Tyr Gly Trp Gly Asp Val Gly Ala Lys Gln Lys
    130                 135                 140

Ser Thr Ala Gly Trp Pro Ala Ala Phe Pro Val Phe Glu Pro His Trp
145                 150                 155                 160

Gln Ile Cys Met Ala Gly Gly Leu Ser Thr Gly Trp Ile Glu Trp Gly
                165                 170                 175

Gly Glu Arg Phe Glu Phe Arg Asp Ala Pro Ser Tyr Ser Glu Lys Asn
            180                 185                 190

Trp Gly Gly Gly Phe Pro Arg Lys Trp Phe Trp Val Gln Cys Asn Val
        195                 200                 205

Phe Glu Gly Ala Thr Gly Glu Val Ala Leu Thr Ala Gly Gly Gly Leu
    210                 215                 220

Arg Gln Leu Pro Gly Leu Thr Glu Thr Tyr Glu Asn Ala Ala Leu Val
225                 230                 235                 240

Cys Val His Tyr Asp Gly Lys Met Tyr Glu Phe Val Pro Trp Asn Gly
                245                 250                 255
```

-continued

```
Val Val Arg Trp Glu Met Ser Pro Trp Gly Tyr Trp Tyr Ile Thr Ala
            260             265             270

Glu Asn Glu Asn His Val Val Glu Leu Glu Ala Arg Thr Asn Glu Ala
        275             280             285

Gly Thr Pro Leu Arg Ala Pro Thr Thr Glu Val Gly Leu Ala Thr Ala
    290             295             300

Cys Arg Asp Ser Cys Tyr Gly Glu Leu Lys Leu Gln Ile Trp Glu Arg
305             310             315             320

Leu Tyr Asp Gly Ser Lys Gly Lys Leu Lys Val Leu Thr Asn Pro Lys
            325             330             335

Ala Val Lys Glu Asp Tyr Glu Arg Leu Leu Trp Leu Thr Met Met Gln
            340             345             350

Val Ile Leu Glu Thr Lys Ser Ser Met Ala Ala Val Glu Ile Gly Gly
        355             360             365

Gly Pro Trp Phe Gly Thr Trp Lys Gly Asp Thr Ser Asn Thr Pro Glu
    370             375             380

Leu Leu Lys Gln Ala Leu Gln Val Pro Leu Asp Leu Glu Ser Ala Leu
385             390             395             400

Gly Leu Val Pro Phe Phe Lys Pro Pro Gly Leu
            405             410
```